United States Patent
Bottini et al.

(10) Patent No.: US 10,626,094 B2
(45) Date of Patent: Apr. 21, 2020

(54) INHIBITORS OF LOW MOLECULAR WEIGHT PROTEIN TYROSINE PHOSPHATASE AND USES THEREOF

(71) Applicants: La Jolla Institute of Allergy & Immunology, La Jolla, CA (US); Sanford Burnham Prebys Medical Discovery Institute, La Jolla, CA (US)

(72) Inventors: Nunzio Bottini, La Jolla, CA (US); Jiwen Zou, La Jolla, CA (US); Santhi R. Ganji, La Jolla, CA (US); Stephanie Stanford, La Jolla, CA (US); Anthony Pinkerton, La Jolla, CA (US); Thomas D. Y. Chung, La Jolla, CA (US); Michael Hedrick, La Jolla, CA (US); Robert Ardecky, La Jolla, CA (US)

(73) Assignees: SANFORD BURNHAM PREBYS MEDICAL DISCOVERY INSTITUTE, La Jolla, CA (US); LA JOLLA INSTITUTE OF ALLERGY & IMMUNOLOGY, La Jolla, CA (US)

( * ) Notice: Subject to any disclaimer, the term of this patent is extended or adjusted under 35 U.S.C. 154(b) by 0 days.

(21) Appl. No.: 15/518,331

(22) PCT Filed: Oct. 14, 2015

(86) PCT No.: PCT/US2015/055607
§ 371 (c)(1),
(2) Date: Apr. 11, 2017

(87) PCT Pub. No.: WO2016/061280
PCT Pub. Date: Apr. 21, 2016

(65) Prior Publication Data
US 2017/0247340 A1    Aug. 31, 2017

Related U.S. Application Data

(60) Provisional application No. 62/063,937, filed on Oct. 14, 2014.

(51) Int. Cl.
| | | |
|---|---|---|
| *A61K 31/4709* | (2006.01) | |
| *A61P 9/00* | (2006.01) | |
| *C07D 215/46* | (2006.01) | |
| *C07D 239/94* | (2006.01) | |
| *C07D 401/12* | (2006.01) | |
| *C07D 405/12* | (2006.01) | |
| *C07D 401/04* | (2006.01) | |
| *C07D 403/12* | (2006.01) | |
| *C07D 215/42* | (2006.01) | |
| *C07D 405/04* | (2006.01) | |
| *C07D 409/04* | (2006.01) | |

(52) U.S. Cl.
CPC .......... *C07D 239/94* (2013.01); *C07D 215/42* (2013.01); *C07D 215/46* (2013.01); *C07D 401/04* (2013.01); *C07D 401/12* (2013.01); *C07D 403/12* (2013.01); *C07D 405/04* (2013.01); *C07D 405/12* (2013.01); *C07D 409/04* (2013.01)

(58) Field of Classification Search
CPC .. C07D 239/94; C07D 405/12; C07D 215/46; C07D 401/12
See application file for complete search history.

(56) References Cited

U.S. PATENT DOCUMENTS

| | | | |
|---|---|---|---|
| 6,440,995 B1 | 8/2002 | Alanine et al. | |
| 7,169,797 B2 | 1/2007 | Xin et al. | |
| 7,402,696 B2 * | 7/2008 | Suzuki | A61K 31/167 549/493 |

(Continued)

FOREIGN PATENT DOCUMENTS

| | | | | |
|---|---|---|---|---|
| JP | 2007514759 A | | 6/2007 | |
| JP | 2008-179621 | * | 8/2008 | ........... C07D 211/58 |

(Continued)

OTHER PUBLICATIONS

Liu et al., Overcoming the Limitations of Directed C—H Functionalizations of Heterocycles, Nature, vol. 515, No. 7527, pp. 389-393. (Year: 2014).*
CAS printout of WO 2003/059886. (Year: 2003).*
Hamersak et al., Efficient Synthesis of Chiral Amides of 2-(2'-Carboxyphenyl)-4-Hydroxy-Quinoline, Synthesis, vol. 15, pp. 2174-2176. (Year: 2002).*
Ishihara et al., Synthesis of Isoindolo[2,1-a]quinoline Derivatives and Their Effects on N.sub.2-Induced Hypoxia, Chemical Pharmaceutical Bulletin, vol. 38, No. 11, pp. 3024-3030. (Year: 1990).*

(Continued)

*Primary Examiner* — Brenda L Coleman
(74) *Attorney, Agent, or Firm* — Wilson Sonsini Goodrich & Rosati

(57) ABSTRACT

Herein are provided, inter alia, compounds capable of modulating the level of activity of low molecular weight protein tyrosine phosphatase (LMPTP) and methods of using the same. In embodiments, the compound has a structure according to Formula (I-A).

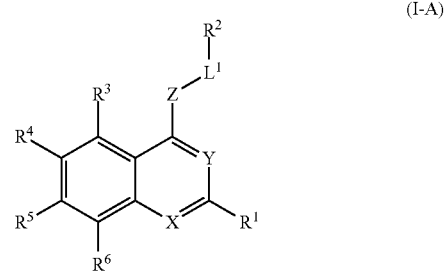

14 Claims, 16 Drawing Sheets

(56) References Cited

U.S. PATENT DOCUMENTS

| | | | | |
|---|---|---|---|---|
| 7,511,145 | B2* | 3/2009 | Schmitz | C07D 401/04 |
| | | | | 546/167 |
| 8,193,199 | B2* | 6/2012 | Chen | C07D 473/30 |
| | | | | 514/263.2 |
| 8,877,707 | B2* | 11/2014 | Zhong | C07D 401/10 |
| | | | | 514/4.3 |
| 8,901,145 | B2* | 12/2014 | Baldino | C07D 417/14 |
| | | | | 514/275 |
| 2006/0128702 | A1 | 6/2006 | Pal et al. | |
| 2008/0207614 | A1 | 8/2008 | Lee et al. | |
| 2009/0209536 | A1 | 8/2009 | Gahman et al. | |
| 2009/0306133 | A1* | 12/2009 | Blomberg | C07D 215/36 |
| | | | | 514/314 |

FOREIGN PATENT DOCUMENTS

| | | | |
|---|---|---|---|
| WO | WO-0076982 A1 | 12/2000 | |
| WO | WO-0192232 A1 | 12/2001 | |
| WO | WO-2004056352 A1 | 7/2004 | |
| WO | WO-2004081009 A1 | 9/2004 | |
| WO | WO-2004112710 A2 | 12/2004 | |
| WO | WO-2005035521 A1 * | 4/2005 | ........... C07D 401/04 |
| WO | WO-2005056552 A1 | 6/2005 | |
| WO | WO-2005108370 A1 | 11/2005 | |
| WO | WO-2011054433 A1 | 5/2011 | |
| WO | WO-2011127070 A2 * | 10/2011 | ........... A61K 31/343 |
| WO | WO-2014048532 A1 | 4/2014 | |
| WO | WO-2014147611 A1 | 9/2014 | |
| WO | WO-2014164749 A1 * | 10/2014 | ......... A61K 31/4965 |
| WO | WO-2014164767 A1 * | 10/2014 | ......... A61K 31/4965 |
| WO | WO-2015033228 A2 * | 3/2015 | ......... A61K 31/4709 |
| WO | WO-2016061280 A1 | 4/2016 | |
| WO | WO-2018204176 A1 | 11/2018 | |

OTHER PUBLICATIONS

Hanns et al., Quinoline Derivatives, XXXIV Derivatives of 2-Phenylquinoline-4-carboxylic acid and 2-Phenyl-4'-aminoquinoline, Journal fuer Praktische Chemie, vol. 133, pp. 13-18. (Year: 1932).*
STN printout of Registry No. 345341-94-8 (2001); 1789298-88-9 (2015); 1787785-59-4 (2015); 1787609-44-2 (2015); 1125451-90-2 (2009); 1125438-39-2 (2009); 1125418-33-8 (2009); 860724-06-7 (2005); 856096-27-0 (2005); and 753417-30-0 (2004).*
PCT/US2018/029749 International Search Report and Written Opinion dated Aug. 14, 2018.
Saeed et al. Synthesis of Benzo-Fused Six-Membered Aromatic Heterocycles . Der Chemica Sinica 2(1):66-69 (2011).
Stanford et al. Diabetes reversal by inhibition of the low-molecular-weight tyrosine phosphatase. Nat Chem Biol 13(6):624-632 (2017).
Chaires et al. Triplex Selective 2-(2-Naphthyl)quinoline Compounds: Origins of Affinity and New Design Principles. J Am Chem Soc 125(24):7272-7283 (2003).
Kireev et al. Molecular Modeling and Quantitative Structure-Activity Studies of Anti-HIV-1 2-Heteroarylquinoline-4-Amines. Eur J Med Chem 30(5):395-402 (1995).
Kumar et al. A Convenient Route to Biologically Important Quinazolines Using N-Arylamino-1,3-Diazabuta-1,3-Dienes. Synthesis 2005(18):3059-3062 (2005).
Mokrosz et al. Structure-activity relationship studies of CNS agents. Part 29. N-Methylpiperazino-substituted derivatives of quinazoline, phthalazine and quinoline as novel α1, 5-HT1A and 5-HT2A receptor ligands. Eur J Med Chem 31(12):973-980 (1996).
Mphahlele et al. One-Pot Palladium-Catalyzed Ci and Ch Bond Activation and Subsequent Suzukimiyaura Cross-Coupling of 2-Aryl-3-Iodo-4-(Phenylamino)Quinolines With Arylboronic Acids. Tetrahedron 67(25):4689-4695 (2011).
Paliakov et al. Boron Tribromide Mediated Debenzylation of Benzylamino and Benzyloxy Groups. Tetrahedron Letters 45(21):4093-4095 (2004).
Paliakov et al. Fujita-Ban QSAR Analysis and CoMFA Study of Quinoline Antagonists of Immunostimulatory CpG-Oligodeoxynucleotides. Bioorg Med Chem 15(1):324-332 (2006).
Rossi et al. Divergent Sequential Reactions of ß-(2-Aminophenyl)-α,ß-Ynones With Nitrogen Nucleophiles. Tetrahedron 60(50):11391-11398 (2004).
Rossi et al. Concise Synthesis of Fused Polycyclic Quinolines. Tetrahedron Let 42(22):3705-3708 (2001).
Say et al. Synthesis of 2-Phenylquinolin-4-Amines Substituted With Diverse Amino and Aminoalkyl Groups. Journal Heterocyclic Chemistry 43(6):1613-1620 (2006).
Strekowski et al. Structure-Activity Relationship Analysis of Substituted 4-Quinolinamines, Antagonists of Immunostimulatory CpG-Oligodeoxynucleotides. Bioorg Med Chem Lett 9(13):1819-1824 (1999).
Strekowski et al. Synthesis and Activity of Substituted 2-Phenylquinolin-4-Amines, Antagonists of Immunostimulatory Cpg-Oligodeoxynucleotides. J Med Chem 46(7):1242-1249 (2003).
Strekowski et al. Synthesis and Quantitative Structure-Activity Relationship Analysisof 2-(Aryl Or Heteroaryl)Quinolin-4-Amines, A New Class of Anti-HIV-1 Agents. J Med Chem 34(5):1739-1746 (2003).
Strekowski et al. Amination by Lithium Alkylamide Reagents of Ketimines Derived From 2-(Trifluoromethyl)Anilines and Methyl Halophenyl Ketones and Their Cyclization Products 2-(Halophenyl)Quinolin-4-Amines. Tetrahedron 52(9):3273-3282 (1996).
Wan et al. An Efficient Direct Amination of Cyclic Amides and Cyclic Ureas. Organic Letters (8):11:2425-2428 (2006).
Zhang et al. Pyridinylquinazolines Selectively Inhibit Human Methionine Aminopeptidase-1 in Cells. J Med Chem 56(10):3996-4016 (2013).
Von Hanns. Chinolinderivate, XXXIV. Derivate der 2-Phenyl-Chinolin-4'-Carbonsäure and 2-Phenyl-4'-Amino-Chinolin. Journal Fur Praktische Chemie : Practical Applications and Applied Chemistry : Covering All Aspects of Applied Chemistry 133(1-2):13-18 (1932) (Structures in English).
Berge et al. Pharmaceutical Salts. Journal of Pharmaceutical Sciences 66(1):1-19 (Jan. 1977).
Maccari et al. Low molecular weight phosphotyrosine protein phosphatases as emerging targets for the design of novel therapeutic agents. J Med Chem 55(1):2-22 (2012)
PCT/US2015/055607 International Preliminary Report on Patentability dated Apr. 27, 2017.
PCT/US2015/055607 International Search Report and Written Opinion dated Feb. 9, 2016.
PubChem CID 7047. (69 pgs.) (Created Sep. 16, 2004).
PubChem CID 73050850. (9 pgs.) (Created Mar. 10, 2014).
Wade et al. Deletion of low molecular weight protein tyrosine phosphatase (Acp1) protects against stress-induced cardiomyopathy. J Pathol 237(4):482-494 (2015).

* cited by examiner

INHIBITORS OF LOW MOLECULAR WEIGHT PROTEIN TYROSINE PHOSPHATASE AND USES THEREOF

CROSS-REFERENCES TO RELATED APPLICATIONS

This application is filed pursuant to 35 U.S.C. § 371 as a United States National Phase Application of International Application No. PCT/US15/55607 entitled "INHIBITORS OF LOW MOLECULAR WEIGHT PROTEIN TYROSINE PHOSPHATASE AND USES THEREOF" filed Oct. 14, 2015; which claims benefit of U.S. Patent Application No. 62/063,937, entitled "SMALL MOLECULE ALLOSTERIC INHIBITORS OF LOW MOLECULAR WEIGHT PROTEIN TYROSINE PHOSPHATASE AND USES OF SAME" filed on Oct. 14, 2014, all of which are hereby incorporated by reference in their entirety.

STATEMENT AS TO RIGHTS TO INVENTIONS MADE UNDER FEDERALLY SPONSORED RESEARCH AND DEVELOPMENT

This invention was made with government support under R03 DA033986 awarded by the National Institutes of Health. The government has certain rights in the invention.

BACKGROUND OF THE INVENTION

Obesity is frequently complicated by a constellation of metabolic and cardiovascular anomalies, called the metabolic syndrome, which significantly increases morbidity and mortality of affected individuals. Insulin resistance is an important component of the metabolic syndrome. Protein tyrosine phosphatases (PTPs) that regulate insulin signaling are in principle excellent therapeutic targets for insulin resistance syndromes, including low molecular weight protein tyrosine phosphatase (LMPTP), encoded by the ACP1 gene. LMPTP is highly expressed in liver, muscle, adipocytes, heart and other tissues. There is strong in vitro and in vivo evidence that LMPTP is a negative regulator of insulin signaling and a promising drug target in obesity and heart failure. Genetic association studies in humans support a negative role for LMPTP in insulin resistance and the metabolic complications of obesity. In vivo, partial knockdown of LMPTP expression by specific antisense oligonucleotides (ASOs) led to improved glycemic and lipid profiles and decreased insulin resistance in diet-induced obese C57BL/6 mice. Interestingly, anti-LMPTP ASOs did not induce any metabolic phenotype in lean mice. Additionally, global deletion of LMPTP in mice protected mice from cardiac hypertrophy, fibrosis, and heart failure.

It has been estimated that every year in the U.S. more than 70 billion dollars are spent for the treatment of obesity-related conditions and almost 300,000 deaths/year can be attributed to the complications of obesity. Obese patients often show multiple metabolic and cardiovascular anomalies known as "the metabolic syndrome", including glucose intolerance, hyperlipidemia (especially high triglycerides with low HDL), and hypertension.

BRIEF SUMMARY OF THE INVENTION

Herein are provided, inter alia, compounds capable of modulating the level of activity of low molecular weight protein tyrosine phosphatase (LMPTP) and methods of using the same.

In an aspect is provided a compound having the formula

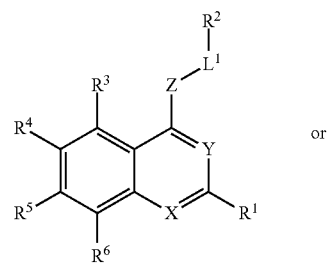

(I-A)

or

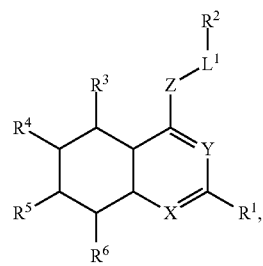

(I-B)

or a pharmaceutically acceptable salt thereof.

X is independently N or $CR^7$.

Y is independently N or $CR^8$.

Z is independently a covalent bond, —O—, —$NR^9$—, —$NR^9C(O)$—, —$C(O)NR^9$—, —O—C(O)—, or —C(O)—O—.

$L^1$ is independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ is independently hydrogen, —$NR^{10}R^{11}$, —$OR^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, —$CX^3_3$, —$CHX^3_2$, —$CH_2X^3$, —$OCX^3_3$, —$OCHX^3_2$, —$OCH_2X^3$, —CN, —$SO_{n3}R^{16}$, —$SO_{v3}NR^{13}R^{14}$, —$NHC(O)NR^{13}R^{14}$, —$N(O)_{m3}$, —$NR^{13}R^{14}$, —$C(O)R^{15}$, —$C(O)$—$OR^{15}$, —$C(O)NR^{13}R^{14}$, —$OR^{16}$, —$NR^{13}SO_2R^{16}$, —$NR^{13}C(O)R^{15}$, —$NR^{13}C(O)OR^{15}$, —$NR^{13}OR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is independently hydrogen, halogen, —$CX^4_3$, —$CHX^4_2$, —$CH_2X^4$, —$OCX^4_3$, —$OCHX^4_2$, —$OCH_2X^4$, —CN, —$SO_{n4}R^{20}$, —$SO_{v4}NR^{17}R^{18}$, —$NHC(O)NR^{17}R^{18}$, —$N(O)_{m4}$, —$NR^{17}R^{18}$, —$C(O)R^{19}$, —$C(O)$—$OR^{19}$, —$C(O)NR^{17}R^{18}$, —$OR^{20}$, —$NR^{17}SO_2R^{20}$, —$NR^{17}C(O)R^{19}$, —$NR^{17}C(O)OR^{19}$, —$NR^{17}OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently hydrogen, halogen, $-CX^5_3$, $-CHX^5_2$, $-CH_2X^5$, $-OCX^5_3$, $-OCHX^5_2$, $-OCH_2X^5$, $-CN$, $-SO_{n5}R^{24}$, $-SO_{v5}NR^{21}R^{22}$, $-NHC(O)NR^{21}R^{22}$, $-N(O)_{m5}$, $-NR^{21}R^{22}$, $-C(O)R^{23}$, $-C(O)-OR^{23}$, $-C(O)NR^{21}R^{22}$, $-OR^{24}$, $-NR^{21}SO_2R^{24}$, $-NR^{21}C(O)R^{23}$, $-NR^{21}C(O)OR^{23}$, $-NR^{21}OR^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is independently hydrogen, halogen, $-CX^6_3$, $-CHX^6_2$, $-CH_2X^6$, $-OCX^6_3$, $-OCHX^6_2$, $-OCH_2X^6$, $-CN$, $-SO_{n6}R^{28}$, $-SO_{v6}NR^{25}R^{26}$, $-NHC(O)NR^{25}R^{26}$, $-N(O)_{m6}$, $-NR^{25}R^{26}$, $-C(O)R^{27}$, $-C(O)-OR^{27}$, $-C(O)NR^{25}R^{26}$, $-OR^{28}$, $-NR^{25}SO_2R^{28}$, $-NR^{25}C(O)R^{27}$, $-NR^{25}C(O)OR^{27}$, $-NR^{25}OR^{27}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each of $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$ and $R^{11}$, $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl.

Each of $X^3$, $X^4$, $X^5$, and $X^6$ is independently $-F$, $-Cl$, $-Br$, or $-I$.

Each of m3, m4, m5, and m6 is independently 1 or 2.

Each of n3, n4, n5, and n6 is independently an integer from 0 to 3.

Each of v3, v4, v5, and v6 is independently 1 or 2.

In an aspect is provided a pharmaceutical composition including a compound described herein, or pharmaceutically acceptable salt thereof, and a pharmaceutically acceptable excipient.

In an aspect is provided a method of inhibiting low molecular weight protein tyrosine phosphatase (LMPTP) activity including contacting the low molecular weight protein tyrosine phosphatase (LMPTP) with a compound described herein.

In an aspect is provided a method of treating a disease or condition associated with low molecular weight protein tyrosine phosphatase (LMPTP) including administering to a subject in need thereof an effective amount of a compound described herein. In embodiments, the disease or condition is diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure), or metabolic syndrome.

BRIEF DESCRIPTION OF THE DRAWINGS

FIG. 2A shows weight curves over the course of the HFD. FIG. 2B shows intraperitoneal glucose tolerance test (IPGTT) was performed on mice at 2 months of age, prior to the start of the HFD. Mice were fasted overnight and injected with 1 g glucose/kg body weight, and blood glucose levels were measured at the indicated times. FIG. 2C shows IPGTT was performed on mice after 3 months HFD. FIG. 2D shows that fasting serum insulin levels were assessed by ELISA.

DETAILED DESCRIPTION OF THE INVENTION

I. Definitions

Figure 1:
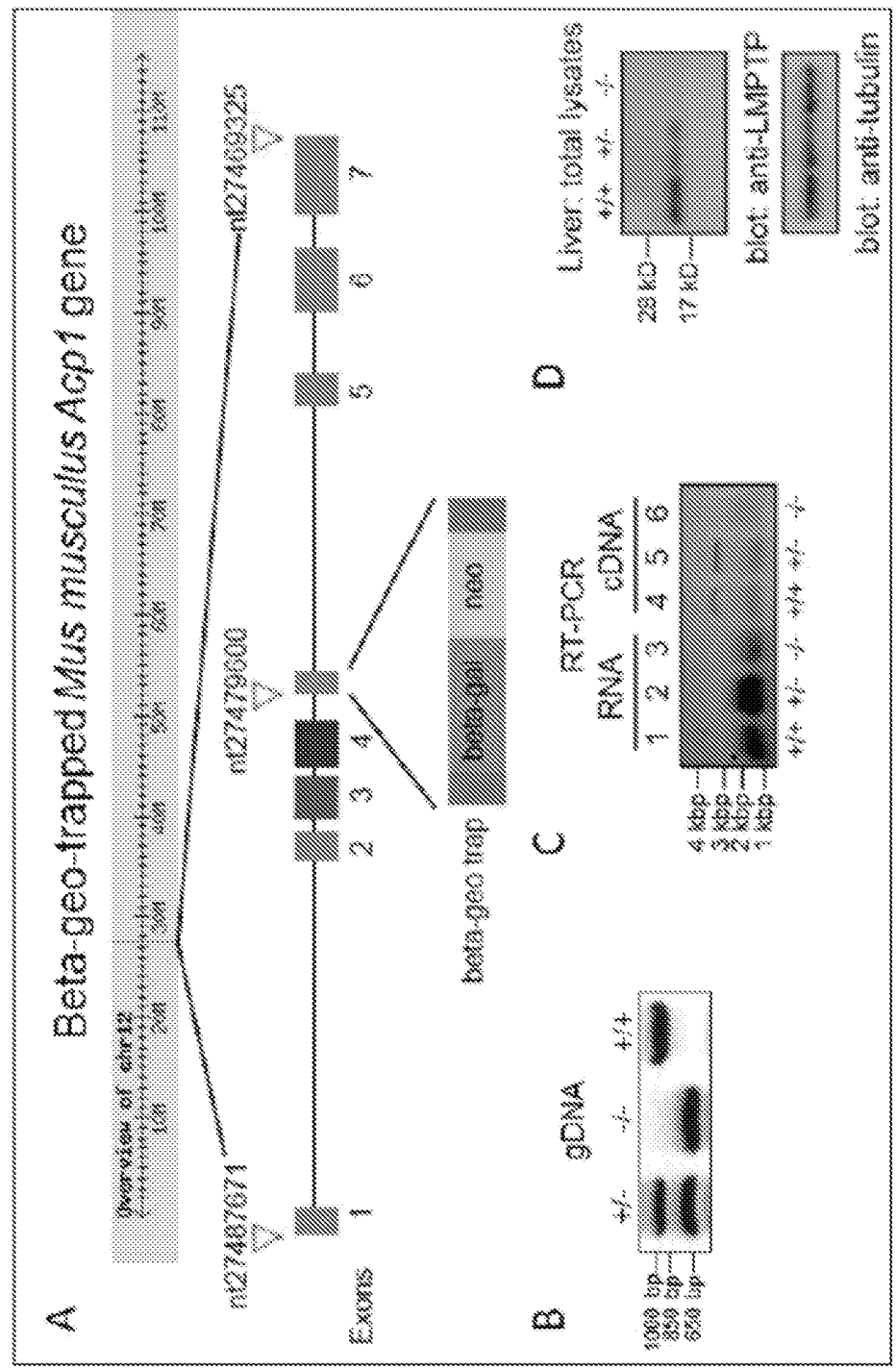
FIG. 1A shows localization of the gene-trap in the mouseAcp1 gene used to generate an LMPTP knockout mouse. Exon 3 and exon 4 are alternatively spliced to generate Lmptp-A and —B isoforms.
FIG. 1B shows PCR-based mouse genotyping using a forward primer located 5' to the gene-trap, a forward primer within the gene-trap, and a reverse primer located 3' to the gene-trap.
FIG. 1C shows RT-PCR with Lmptp primers on RNA extracted from the liver of a KO mouse and heterozygous and wild-type (WT) littermates.
FIG. 1D shows anti-Lmptp Western blot and control anti-tubulin blot of liver lysates of a KO mouse and heterozygous and WT littermates.
Figure 2:
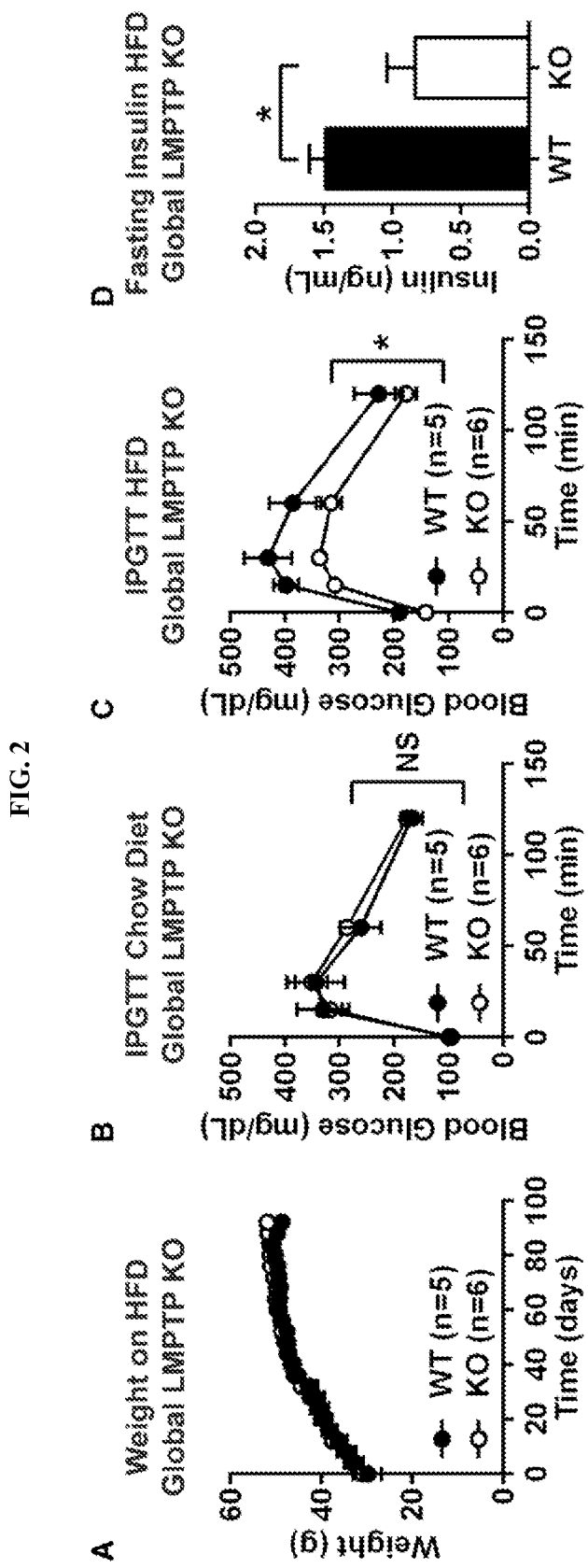
FIGS. 2A-2D show that LMPTP KO decreases diabetes of obese mice.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH₂—CH₂—O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH═CH—O—CH₃, —Si(CH₃)₃, —CH₂—CH═N—OCH₃, —CH═CH—N(CH₃)—CH₃, —O—CH₃, —O—CH₂—CH₃, and —CN. Up to two or three heteroatoms may be consecutive, such as, for example, —CH₂—NH—OCH₃ and —CH₂—O—Si(CH₃)₃.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ⌇⌇ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

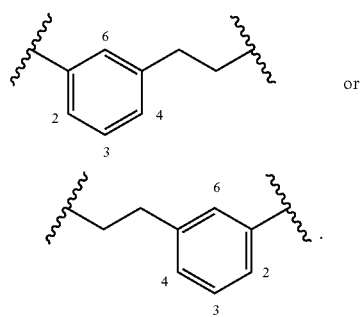

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —Cl$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "low molecular weight protein tyrosine phosphatase (LMPTP) inhibitor" or "LMPTP compound" or "LMPTP inhibitor" refers to a compound (e.g. compounds described herein) that reduces the activity of low molecular weight protein tyrosine phosphatase (LMPTP)."

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "low molecular weight protein tyrosine phosphatase (LMPTP) inhibitor" and "LMPTP inhibitor" is a compound that negatively affects (e.g. decreases) the activity or function of low molecular weight protein tyrosine phosphatase (LMPTP) relative to the activity or function of low molecular weight protein tyrosine phosphatase (LMPTP) in the absence of the inhibitor (e.g., wherein the LMPTP inhibitor binds LMPTP).

In embodiments, the low molecular weight protein tyrosine phosphatase (LMPTP) inhibitor is an allosteric inhibitor. As used herein, an allosteric inhibitor binds to an allosteric site other than the active site of the LMPTP, thereby inhibiting activity of the LMPTP.

The terms "low molecular weight protein tyrosine phosphatase" and "LMPTP" refer to a protein (including homologs, isoforms, and functional fragments thereof) with low molecular weight protein tyrosine phosphatase (LMPTP). The term includes any recombinant or naturally-occurring form of low molecular weight protein tyrosine phosphatase (LMPTP) or variants thereof that maintain low molecular weight protein tyrosine phosphatase (LMPTP) (e.g. within at least 30%, 40%, 50%, 60%, 70%, 80%, 90%, 95%, or 100% activity compared to wildtype low molecular weight protein tyrosine phosphatase (LMPTP)). In embodiments, the LMPTP is a human LMPTP.

The terms "disease" or "condition" refer to a state of being or health status of a patient or subject capable of being treated with the compounds or methods provided herein. In embodiments, the disease or condition is diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure), or metabolic syndrome.

The term "obesity" is generally defined as a body mass index (BMI) over 30, for purposes of this disclosure, any subject, including those with a body mass index of less than 30, who needs or wishes to reduce body weight or prevent body weight gain is included in the scope of "obese." Thus, subjects with a BMI of less than 30 and 25 and above (considered overweight) or below 25 are also included in the subjects of the invention. Morbid obesity refers to a BMI of 40 or greater.

In embodiments, the disease or condition is a metabolic disease or disorder including those which can be alleviated by control of plasma glucose levels, insulin levels, and/or insulin secretion, such as diabetes and diabetes-related conditions, and conditions and disorders including, but not limited to, hypertension, dyslipidemia, cardiovascular or heart disease, eating disorders, insulin-resistance, obesity, and diabetes mellitus of any kind, including type 1, type 2, and gestational diabetes.

By "metabolic syndrome" is meant that a subject has a condition characterized by at least two of increased triglycerides, reduced high-density lipoprotein (HDL), increased blood pressure, increased fasting plasma glucose or type 2 diabetes, or obesity.

By "cardiac hypertrophy" is meant any undesirable cardiac muscle growth, increase in cardiac chamber mass relative to body size, or increase in cardiac chamber wall thickness at normal or increased chamber volume.

The terms "heart disease" and "cardiovascular disease" refers to a disorder of the heart and blood vessels, and includes disorders of the arteries, veins, arterioles, venules, and capillaries. Heart disease includes: atherosclerosis; autoimmune myocarditis, chronic cardiac hypoxia, congestive heart failure, coronary artery disease, cardiomyopathy and cardiac cell dysfunction (e.g., aortic smooth muscle cell activation; cardiac cell apoptosis; and immunomodulation of cardiac cell function).

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of $liposomal$ formulations, intravenous infusion, transdermal patches, etc.

As used herein, the term "Co-administer" means that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a low molecular weight protein tyrosine phosphatase (LMPTP) associated disease modulator is a compound that reduces the severity of one or more symptoms of a disease associated with low molecular weight protein tyrosine phosphatase (LMPTP). A low molecular weight protein tyrosine phosphatase (LMPTP) modulator is a compound that increases or decreases the activity or function or level of activity or level of function of low molecular weight protein tyrosine phosphatase (LMPTP).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with low molecular weight protein tyrosine phosphatase (LMPTP) activity or a low molecular weight protein tyrosine phosphatase (LMPTP) associated disease or condition) means that the disease is caused by (in whole or in part), or a symptom of the disease is caused by (in whole or inpart) the substance or substance activity or function. For example, a disease or condition associated with low molecular weight protein tyrosine phosphatase (LMPTP) activity or function may be one that results (entirely or partially) from aberrant low molecular weight protein tyrosine phosphatase (LMPTP) function (e.g. enzyme activity, protein-protein interaction, signaling pathway) or a disease or condition wherein a particular symptom of the disease or condition is caused (entirely or partially) by aberrant low molecular weight protein tyrosine phosphatase (LMPTP) activity or function. As used herein, what is described as being associated with a disease, if a causative agent, could be a target for treatment of the disease. For example, a disease or condition associated with low molecular weight protein tyrosine phosphatase (LMPTP) activity or function or a low molecular weight protein tyrosine phosphatase (LMPTP) associated disease or condition, may be treated with a low molecular weight protein tyrosine phosphatase (LMPTP) modulator or low molecular weight protein tyrosine phosphatase (LMPTP) inhibitor, in the instance where increased low molecular weight protein tyrosine phosphatase (LMPTP) activity or function causes the disease or condition.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a low molecular weight protein tyrosine phosphatase (LMPTP) with a compound as described herein may reduce the level of a product of the low molecular weight protein tyrosine phosphatase (LMPTP) catalyzed reaction or the level of a downstream derivative of the product or binding may reduce the interactions between the low molecular weight protein tyrosine phosphatase (LMPTP) enzyme or a low molecular weight protein tyrosine phosphatase (LMPTP) reaction product and downstream effectors or signaling pathway components, resulting in changes in cell growth, proliferation, or survival.

II. Compounds

Disclosed herein is a collection of small-molecule inhibitors of the low molecular weight protein tyrosine phosphatase (LMPTP). The assays utilized in the primary and secondary screening were designed to identify allosteric inhibitors of LMPTP. All of these compounds inhibit LMPTP in vitro, and show poor inhibition of two other protein tyrosine phosphatases, the lymphoid phosphatase (LYP) and the VH1-related phosphatase (VHR). The structure of the compounds was further optimized to generate a series of inhibitors of LMPTP-A isoform, with high selectivity over the LMPTP-B isoform, LYP and VHR, and with cellular activity. In an aspect is provided a compound having the formula:

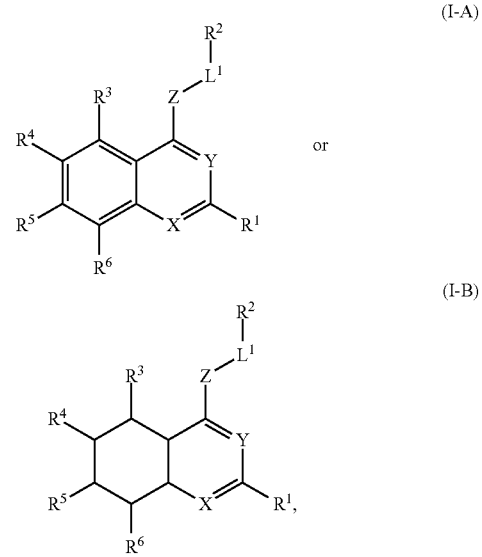

or a pharmaceutically acceptable salt thereof.

X is independently N or $CR^7$.

Y is independently N or $CR^8$.

Z is independently a covalent bond, —O—, —$NR^9$—, —$NR^9C(O)$—, —$C(O)NR^9$—, —O—C(O)—, or —C(O)—O—.

$L^1$ is independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ is independently hydrogen, —$NR^{10}R^{11}$, —$OR^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, $-OR^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, $-CX^3_3$, $-CHX^3_2$, $-CH_2X^3$, $-OCX^3_3$, $-OCHX^3_2$, $-OCH_2X^3$, $-CN$, $-SO_{n3}R^{16}$, $-SO_{v3}NR^{13}R^{14}$, $-NHC(O)NR^{13}R^{14}$, $-N(O)_{m3}$, $-NR^{13}R^{14}$, $-C(O)R^{15}$, $-C(O)-OR^{15}$, $-C(O)NR^{13}R^{14}$, $-OR^{16}$, $-NR^{13}SO_2R^{15}$, $-NR^{13}C(O)R^{15}$, $-NR^{13}C(O)OR^{15}$, $-NR^{13}OR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is independently hydrogen, halogen, $-CX^4_3$, $-CHX^4_2$, $-CH_2X^4$, $-OCX^4_3$, $-OCHX^4_2$, $-OCH_2X^4$, $-CN$, $-SO_{n4}R^{20}$, $-SO_{v4}NR^{17}R^{18}$, $-NHC(O)NR^{17}R^{18}$, $-N(O)_{m4}$, $-NR^{17}R^{18}$, $-C(O)R^{19}$, $-C(O)-OR^{19}$, $-C(O)NR^{17}R^{18}$, $-OR^{20}$, $-NR^{17}SO_2R^{20}$, $-NR^{17}C(O)R^{19}$, $-NR^{17}C(O)OR^{19}$, $-NR^{17}OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently hydrogen, halogen, $-CX^5_3$, $-CHX^5_2$, $-CH_2X^5$, $-OCX^5_3$, $-OCHX^5_2$, $-OCH_2X^5$, $-CN$, $-SO_{n5}R^{24}$, $-SO_{v5}NR^{21}R^{22}$, $-NHC(O)NR^{21}R^{22}$, $-N(O)_{m5}$, $-NR^{21}R^{22}$, $-C(O)R^{23}$, $-C(O)-OR^{23}$, $-C(O)NR^{21}R^{22}$, $-OR^{24}$, $-NR^{21}SO_2R^{24}$, $-NR^{21}C(O)R^{23}$, $-NR^{21}C(O)OR^{23}$, $-NR^{21}OR^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is independently hydrogen, halogen, $-CX^6_3$, $-CHX^6_2$, $-CH_2X^6$, $-OCX^6_3$, $-OCHX^6_2$, $-OCH_2X^6$, $-CN$, $-SO_{n6}R^{28}$, $-SO_{v6}NR^{25}R^{26}$, $-NHC(O)NR^{25}R^{26}$, $-N(O)_{m6}$, $-NR^{25}R^{26}$, $-C(O)R^{27}$, $-C(O)-OR^{27}$, $-C(O)NR^{25}R^{26}$, $-OR^{28}$, $-NR^{25}SO_2R^{28}$, $-NR^{25}C(O)R^{27}$, $-NR^{25}C(O)OR^{27}$, $-NR^{25}OR^{27}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2B}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each of $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$ and $R^{11}$, $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl.

Each of $X^3$, $X^4$, $X^5$, and $X^6$ is independently $-F$, $-Cl$, $-Br$, or $-I$.

Each of m3, m4, m5, and m6 is independently 1 or 2.

Each of n3, n4, n5, and n6 is independently an integer from 0 to 3.

Each of v3, v4, v5, and v6 is independently 1 or 2.

In embodiments X is independently N. In embodiments, X is independently $CR^7$.

In embodiments, Y is independently N. In embodiments, Y is independently $CR^8$.

In embodiments, X is N, and Y is $CR^8$. In embodiments, X and Y are each N.

In embodiments, the compound has a structure according to formula (I-A).

In embodiments, the compound has a structure according to formula (I-B).

In embodiments, when X and Y are each N, Z is $-NH-$, $R^3-R^6$ are each hydrogen, $L^1$ is substituted or unsubstituted $C_{1-3}$ alkylene, and $R^2$ is unsubstituted morpholine, unsubstituted pyridine, unsubstituted phenyl, unsubstituted imidazole, unsubstituted tetrahydrofuran, unsubstituted cyclopentane, or dimethoxybenzene, then $R^1$ is not $-C_6H_5$, 3-$CH_3C_6H_4$, 4-$CH_3C_6H_4$, 2-$FC_6H_4$, or 4-$O^iPrC_6H_4$. In embodiments, when X and Y are each N, Z is $-NH-$, $R^3-R^6$ are each hydrogen, $L^1$ is substituted or unsubstituted $C_{1-6}$ alkylene, and $R^2$ is unsubstituted morpholine, unsubstituted pyridine, unsubstituted phenyl, unsubstituted imidazole, unsubstituted tetrahydrofuran, unsubstituted cyclopentane, or dimethoxybenzene, then $R^1$ is not $-C_6H_5$, 3-$CH_3C_6H_4$, 4-$CH_3C_6H_4$, 2-$FC_6H_4$, or 4-$O^iPrC_6H_4$. In embodiments, when X and Y are each N, Z is $-NH-$, $R^3-R^6$ are each hydrogen, $L^1$ is substituted or unsubstituted $C_{1-6}$ alkylene, $R^2$ is unsubstituted morpholine, unsubstituted pyridine, unsubstituted phenyl, unsubstituted imidazole, unsubstituted tetrahydrofuran, unsubstituted cyclopentane, or dimethoxybenzene, and $R^1$ is aryl, then $R^1$ is not unsubstituted phenyl or a phenyl group substituted only by 1 or 2 groups selected from halogen, unsubstituted alkyl, or unsubstituted alkoxy. In embodiments, when X and Y are each N, Z is $-NH-$, $R^3-R^6$ are each hydrogen, $L^1$ is substituted or unsubstituted $C_{1-6}$ alkylene (e.g., unsubstituted $C_{1-3}$ alkylene), $R^2$ is unsubstituted morpholine, unsubstituted pyridine, unsubstituted phenyl, unsubstituted imidazole, unsubstituted tetrahydrofuran, unsubstituted cyclopentane, or dimethoxybenzene, and $R^1$ is aryl (e.g., phenyl), then $R_1$ comprises an amide substituent (e.g., $-C(O)NR^{1C}R^{1D}$ as described herein).

In embodiments, when X and Y are each N, Z is NH, $R^3-R^6$ are each hydrogen, $L^1$ is a bond, and $R^2$ is $-C_6H_4CO_2H$ or unsubstituted cyclopentane, then $R^1$ is not unsubstituted phenyl or 4-$NO_2C_6H_4$. In embodiments, when X and Y are each N, Z is NH, $R^3-R^6$ are each hydrogen, $L^1$ is a bond or substituted or unsubstituted alkylene, and $R^2$ is $-C_6H_4CO_2H$ or unsubstituted cyclopentane, then $R^1$ is not unsubstituted phenyl or 4-$NO_2C_6H_4$. In embodiments, when X and Y are each N, Z is NH, $R^3-R^6$ are each hydrogen, $L^1$ is a bond or substituted or unsubstituted alkylene, and $R^2$ is $-C_6H_4CO_2H$ or unsubstituted cyclopentane, and $R^1$ is phenyl, then $R^1$ comprises two or more substituents.

In embodiments, when X and Y are each N, Z is NH, $R^3-R^6$ are each hydrogen, and -$L^1$-$R^2$ is $-(CH_2)_3O(^iPr)$, $-(CH_2)_6CO_2H$, or $-(CH_2)_3OCH_2CH_3$, then $R^1$ is not unsubstituted phenyl. In embodiments, when X and Y are each N, Z is NH, $R^3-R^6$ are each hydrogen, -$L^1$-$R^2$ is $-(CH_2)_3O(^iPr)$, $-(CH_2)_6CO_2H$, or $-(CH_2)_3OCH_2CH_3$, and $R^1$ is phenyl, then $R^1$ comprises 2 or more substituents. In embodiments, when X and Y are each N, Z is NH, $R^3-R^6$ are each hydrogen, -$L^1$-$R^2$ combine to form an unsubstituted heteroalkylene, and $R^1$ is phenyl, then $R^1$ comprises 1 or more (e.g., 1 or more or 2 or more) substituents. In embodiments, when X and Y are each N, Z is NH, $R^3$—$R^6$ are each hydrogen, -$L^1$-$R^2$ combine to form an alkyl having a carboxylic acid or carboxylic ester substituent, and $R^1$ is phenyl, then $R^1$ comprises 1 or more (e.g., 1 or more or 2 or more) substituents.

In embodiments, when X is N, Y is CH, $R^3$—$R^6$ are each H, and —Z-$L^1$-$R^2$ is

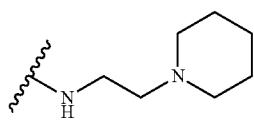 [SMILES: *NCCN1CCCCC1]

(—NH(CH$_2$)$_2$N(CH$_2$)$_5$) or

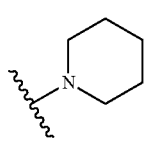

(—N(CH$_2$)$_5$), then $R^1$ is not unsubstituted phenyl. In embodiments, when X is N, Y is CH, $R^3$—$R^6$ are each H, and $R^2$ is unsubstituted piperidine, then $R^1$ is not unsubstituted phenyl. In embodiments, when X is N, Y is CH, $R^3$—$R^6$ are each H, and $R^2$ is unsubstituted piperidine, then $R^1$ is not unsubstituted phenyl. In embodiments, when X is N, Y is CH, $R^3$—$R^6$ are each H, $R^2$ is unsubstituted piperidine, and $R^1$ is aryl (e.g., phenyl), then $R_1$ comprises an amide substituent (e.g., —C(O)NR$^{1C}$R$^{1D}$ as described herein).

In embodiments, Z is a bond, —O—, or —NR$^9$—.

In embodiments, Z is —NH—, $L^1$ is substituted or unsubstituted $C_1$-$C_6$ alkylene, and $R^2$ is selected from:

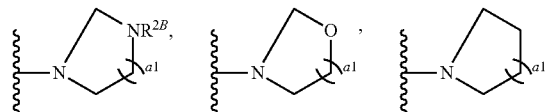

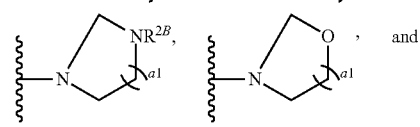

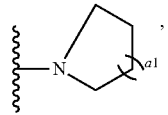

wherein a1 is 0, 1, 2, or 3; and $R^{2B}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, —Z-$L^1$-$R^2$ is selected from:

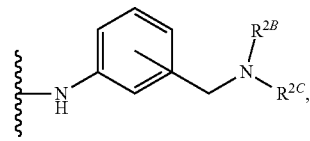

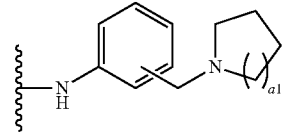

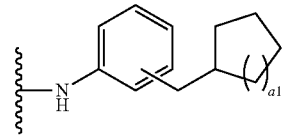

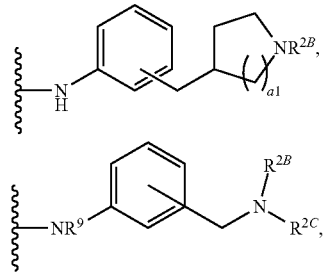

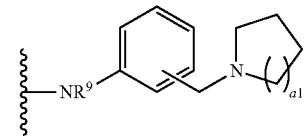

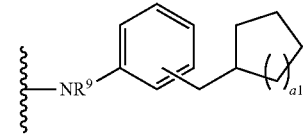

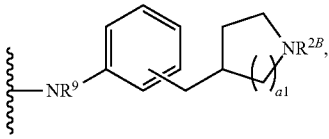

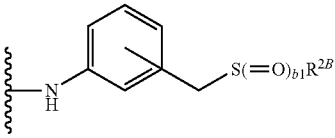

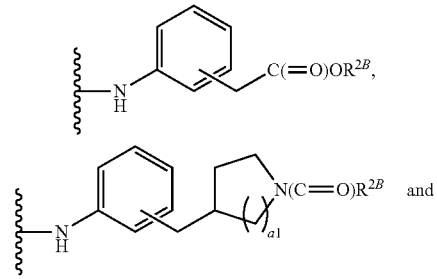

and

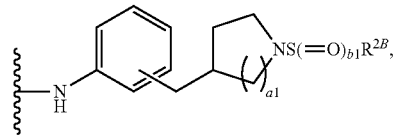

wherein a1 is 0, 1, 2, or 3; b1 is 0, 1, or 2; and $R^{2B}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, —Z-$L^1$-$R^2$ is —C(O)NR$^{2B}$R$^{2C}$ or —C(O)OR$^2$.

In embodiments, $R^1$ is unsubstituted phenyl. In embodiments, $R^1$ is phenyl comprising substituents (e.g., 1, 2, 3, 4 or 5 substituents) selected from F, Cl, Br, —CN, —NR$_4$R$_5$, —NO$_2$, —CF$_3$, —OCF$_3$, —OH, substituted or unsubstituted $C_1$-$C_6$alkyl, and —O(substituted or unsubstituted $C_1$-$C_6$alkyl). In embodiments, $R^1$ is -(substituted or unsubstituted $C_1$-$C_6$alkyl)(O)(CF$_3$), -(substituted or unsubstituted $C_1$-$C_6$alkyl)(O)-(substituted or unsubstituted $C_1$-$C_6$alkyl), -(substituted or unsubstituted $C_1$-$C_6$alkyl)NH(substituted or unsubstituted $C_1$-$C_6$alkyl), -(substituted or unsubstituted $C_1$-$C_6$alkyl)N R$^{1B}$R$^{1C}$, —C(=O) (substituted or unsubstituted $C_1$-$C_6$alkyl), (substituted or unsubstituted cycloalkyl)-$C_1$-$C_6$alkyl, CO$_2$H, —C(=O)—O—R$^{1B}$, C(=O)NH$_2$, C(=O)NR$^{1B}$R$^{1C}$, or two groups on adjacent carbon atoms of the phenyl group are combined with the adjacent carbon atoms to form a —O(CH$_2$)$_{c1}$O— ring. In embodiments, $R^1$ is C(=O)[(CH$_2$)$_{d1}$] NR$^{1B}$R$^{1C}$, C(=O)[(CH$_2$)$_{d1}$]piperidine, C(=O)[(CH$_2$)$_{d1}$] morpholine, or C(=O)[(CH$_2$)$_{d1}$]piperazine, wherein d1 is 0, 1, 2, 3, 4, 5, or 6. In embodiments, $R^1$ is selected from

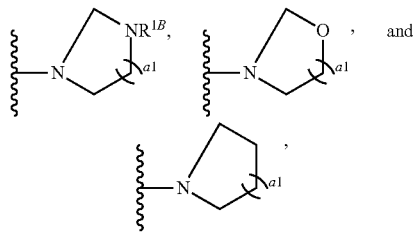

and, wherein a1 is 0, 1, 2, or 3. In embodiments, R1 is selected from

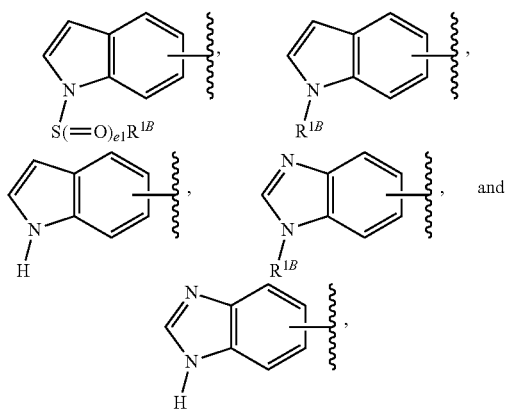

wherein e1 is 0, 1, or 2. In embodiments, $R^1$ is selected from S(=O)$_{e1}$R$^{1B}$, NHC(=O)R$^{1B}$, NR$^{1B}$C(=O)R$^{1C}$, NR$^{1B}$C(=O)N(R$^{1C}$)$_2$, NHC(=O)NR$^{1B}$R$^{1C}$.

In embodiments, $R^1$ is 5- or 6-membered unsubstituted heteroaryl. In embodiments, $R^1$ is an optionally substituted 5- or 6-membered heteroaryl comprising a substituent (e.g., 1, 2, or 3 substituents) selected from h F, Cl, Br, —CN, —NR$_4$R$_5$, —NO$_2$, —CF$_3$, —OCF$_3$, —OH, —$C_1$-$C_6$alkyl, or —OC$_1$-$C_6$alkyl. In embodiments, $R^1$ is optionally substituted bicyclic heteroaryl ring (e.g., benzothiophene, benzofuran, indole, oxindole, or benzimidazole). In embodiments, $R^1$ is substituted or unsubstituted alkyl, substituted or unsubstituted cycloalkyl, or substituted or unsubstituted heterocycloalkyl. In embodiments, $R^1$ is substituted or unsubstituted alkoxy. In embodiments, $R^1$ is haloalkyl, or haloalkoxy.

In embodiments, $R^2$ is selected from the group consisting of substituted or unsubstituted phenyl, substituted or unsubstituted 5- or 6-membered heteroaryl, substituted or unsubstituted alkyl, substituted or unsubstituted cycloalkyl, and substituted or unsubstituted heterocycloalkyl. In embodiments, $R^2$ is —O(substituted or unsubstituted alkyl). In embodiments, $R^2$ is haloalkyl, or haloalkoxy.

In embodiments, $R^3$ is independently hydrogen, F, Cl, Br, —CN, —CF$_3$, —OCF$_3$, or —OH. In embodiments, $R^3$ is substituted or unsubstituted $C_1$-$C_6$ alkyl, —O-substituted or unsubstituted $C_1$-$C_6$ alkyl), —C(=O)(substituted or unsubstituted $C_1$-$C_6$ alkyl), or CO$_2$H. In embodiments, $R^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is —NR$^{13}$R$^{14}$, —OR$^{16}$, —C(O)NR$^{13}$R$^{14}$, or —C(O)—OR$^{15}$.

In embodiments, $R^4$ is independently hydrogen, F, Cl, Br, —CN, —CF$_3$, —OCF$_3$, or —OH. In embodiments, $R^4$ is substituted or unsubstituted $C_1$-$C_6$ alkyl, —O-substituted or unsubstituted $C_1$-$C_6$ alkyl), —C(=O)(substituted or unsubstituted $C_1$-$C_6$ alkyl), or CO$_2$H. In embodiments, $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is —NR$^{17}$R$^{18}$, —OR$^{20}$, —C(O)NR$^{17}$R$^{18}$, or —C(O)—OR$^{19}$.

In embodiments, $R^5$ is independently hydrogen, F, Cl, Br, —CN, —CF$_3$, —OCF$_3$, or —OH. In embodiments, $R^5$ is substituted or unsubstituted $C_1$-$C_6$ alkyl, —O-substituted or unsubstituted $C_1$-$C_6$ alkyl), —C(=O)(substituted or unsubstituted $C_1$-$C_6$ alkyl), or CO$_2$H. In embodiments, $R^5$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is —NR$^{21}$R$^{22}$, —OR$^{24}$, —C(O)NR$^{21}$R$^{22}$, or —C(O)—OR$^{23}$.

In embodiments, $R^6$ is independently hydrogen, F, Cl, Br, —CN, —CF$_3$, —OCF$_3$, or —OH. In embodiments, $R^6$ is substituted or unsubstituted $C_1$-$C_6$ alkyl, —O-substituted or unsubstituted $C_1$-$C_6$ alkyl), —C(=O)(substituted or unsubstituted $C_1$-$C_6$ alkyl), or CO$_2$H. In embodiments, $R^6$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is —NR$^{25}$R$^{26}$, —OR$^{28}$, —C(O)NR$^{25}$R$^{26}$, or —C(O)—OR$^{27}$.

In embodiments, the compound has a structure according to the formula,

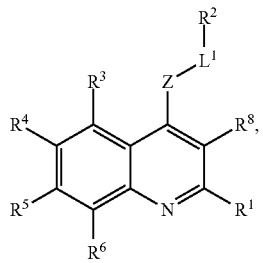

(II)

or a pharmaceutically acceptable salt thereof.

Z is independently a covalent bond, —O—, —NR$^9$—, —NR$^9$C(O)—, —C(O)NR$^9$—, —O—C(O)—, or —C(O)—O—.

L$^1$ is independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

R$^1$ is independently hydrogen, —NR$^{10}$R$^{11}$, —OR$^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^2$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^3$ is independently hydrogen, halogen, —CX$^3{}_3$, —CHX$^3{}_2$, —CH$_2$X$^3$, —OCX$^3{}_3$, —OCHX$^3{}_2$, —OCH$_2$X$^3$, —CN, —SO$_{n3}$R$^{16}$, —SO$_{v3}$NR$^{13}$R$^{14}$, —NHC(O)NR$^{13}$R$^{14}$, —N(O)$_{m3}$, —NR$^{13}$R$^{14}$, —C(O)R$^{15}$, —C(O)—OR$^{15}$, —C(O)NR$^{13}$R$^{14}$, —OR$^{16}$, —NR$^{13}$SO$_2$R$^{16}$, —NR$^{13}$C(O)R$^{15}$, —NR$^{13}$C(O)OR$^{15}$, —NR$^{13}$OR$^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^4$ is independently hydrogen, halogen, —CX$^4{}_3$, —CHX$^4{}_2$, —CH$_2$X$^4$, —OCX$^4{}_3$, —OCHX$^4{}_2$, —OCH$_2$X$^4$, —CN, —SO$_{14}$R$^{20}$, —SO$_{v4}$NR$^{17}$R$^{18}$, —NHC(O)NR$^{17}$R$^{18}$, —N(O)$_{m4}$, —NR$^{17}$R$^{18}$, —C(O)R$^{19}$, —C(O)—OR$^{19}$, —C(O)NR$^{17}$R$^{18}$, —OR$^{20}$, —NR$^{17}$SO$_2$R$^{20}$, —NR$^{17}$C(O)R$^{19}$, —NR$^{17}$C(O)OR$^{19}$, —NR$^{17}$OR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^5$ is independently hydrogen, halogen, —CX$^5{}_3$, —CHX$^5{}_2$, —CH$_2$X$^5$, —OCX$^5{}_3$, —OCHX$^5{}_2$, —OCH$_2$X$^5$, —CN, —SO$_{n5}$R$^{24}$, —SO$_{v5}$NR$^{21}$R$^{22}$, —NHC(O)NR$^{21}$R$^{22}$, —N(O)$_{m6}$, —NR$^{21}$R$^{22}$, —C(O)R$^{23}$, —C(O)—OR$^{23}$, —C(O)NR$^{21}$R$^{22}$, —OR$^{24}$, —NR$^{21}$SO$_2$R$^{24}$, —NR$^{21}$C(O)R$^{23}$, —NR$^{21}$C(O)OR$^{23}$, —NR$^{21}$OR$^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^6$ is independently hydrogen, halogen, —CX$^6{}_3$, —CHX$^6{}_2$, —CH$_2$X$^6$, —OCX$^6{}_3$, —OCHX$^6{}_2$, —OCH$_2$X$^6$, —CN, —SO$_{n6}$R$^{28}$, —SO$_{v6}$NR$^{25}$R$^{26}$, —NHC(O)NR$^{25}$R$^{26}$, —N(O)$_{m6}$, —NR$^{25}$R$^{26}$, —C(O)R$^{27}$, —C(O)—OR$^{27}$, —C(O)NR$^{25}$R$^{26}$, —OR$^{28}$, —NR$^{25}$SO$_2$R$^{28}$, —NR$^{25}$C(O)R$^{27}$, —NR$^{25}$C(O)OR$^{27}$, —NR$^{25}$OR$^{27}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, and R$^{28}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^6$ and R$^7$, R$^{10}$ and R$^{11}$, R$^{14}$ and R$^{15}$, and R$^{18}$ and R$^{19}$ substituents bonded to the same nitrogen atom may optionally be joined to form a substituted or unsubstituted heterocycloalkyl or substituted or unsubstituted heteroaryl.

Each X$^3$, X$^4$, X$^5$, and X$^6$ is independently —F, —Cl, —Br, or —I.

Each m3, m4, m5, and m6 is independently 1 or 2.

Each n3, n4, n5, and n6 is independently an integer from 0 to 3.

Each v3, v4, v5, and v6 is independently 1 or 2.

In embodiments, when R$^3$—R$^6$ are each H, and —Z-L$^1$-R$^2$ is

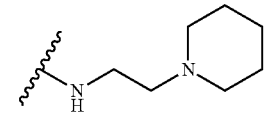 [SMILES: *NCCN1CCCCC1]

(—NH(CH$_2$)$_2$N(CH$_2$)$_5$) or

(—N(CH$_2$)$_5$), then R$^1$ is not unsubstituted phenyl. In embodiments, when X is N, Y is CH, R$^3$—R$^6$ are each H, and R$^2$ is unsubstituted piperidine, then R$^1$ is not unsubstituted phenyl. In embodiments, when X is N, Y is CH, R$^3$—R$^6$ are each H, and R$^2$ is unsubstituted piperidine, then R$^1$ is not unsubstituted phenyl. In embodiments, when X is N, Y is CH, R$^3$—R$^6$ are each H, R$^2$ is unsubstituted piperidine, and R$^1$ is aryl (e.g., phenyl), then R$_1$ comprises an amide substituent (e.g., —C(O)NR$^{1C}$R$^{1D}$ as described herein).

In embodiments, Z is independently a covalent bond or —NR$^9$—; L$^1$ is independently a bond, substituted or unsubstituted alkylene, substituted or unsubstituted heteroalkylene, substituted or unsubstituted arylene, or substituted or unsubstituted heteroarylene; and R$^2$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, Z is independently —NR$^9$—; L$^1$ is independently substituted or unsubstituted alkylene or substituted or unsubstituted arylene; and $R^2$ is independently substituted or unsubstituted alkyl or substituted or unsubstituted heterocycloalkyl.

In embodiments, Z is independently —NH—; $L^1$ is independently substituted or unsubstituted $C_3$-$C_6$ alkylene; and $R^2$ is substituted or unsubstituted heterocycloalkyl.

In embodiments, Z is independently —NH—; $L^1$ is independently substituted or unsubstituted arylene; $R^2$ is independently $C_1$-$C_3$ alkyl comprising a substituent group $R^{2A}$; $R^{2A}$ is independently —$NR^{2B}R^{2C}$, substituted or unsubstituted cycloalkyl, substituted or unsubstituted heterocycloalkyl, substituted or unsubstituted aryl, or substituted or unsubstituted heteroaryl; and each of $R^{2B}$ and $R^{2C}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein $R^{2B}$ and $R^{2C}$ combine to form a substituted or unsubstituted heterocycloalkyl.

In embodiments, $R^1$ is substituted or unsubstituted aryl or substituted or unsubstituted heteroaryl.

In embodiments, $R^1$ is aryl or heteroaryl comprising a substituent group $R^{1A}$; $R^{1A}$ is independently halogen, —CN, —$OR^{1B}$, —$SR^{1B}$, —$NR^{1C}R^{1D}$, —$NR^{1C}C(O)R^{1B}$, —$C(O)NR^{1C}R^{1D}$, —$CO_2R^{1B}$, substituted or unsubstituted alkyl, or substituted or unsubstituted heteroalkyl; each of $R^{1B}$ and $R^{1C}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1D}$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{1C}$ and $R^{1D}$ attached to the same nitrogen atom optionally combine to form a substituted or unsubstituted heterocycloalkyl.

In embodiments, $R^1$ is phenyl comprising a substituent group —$C(O)NR^{1C}R^{1D}$.

In embodiments, the compound has a structure according to the formula,

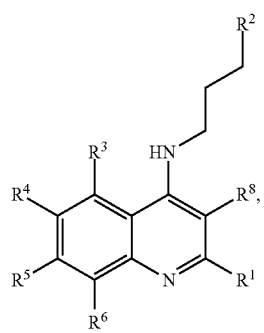

(II-A)

or a pharmaceutically acceptable salt thereof.

$R^1$ is substituted or unsubstituted heteroaryl or phenyl comprising a substituent group $R^{1A}$.

$R^2$ is substituted or unsubstituted cycloalkyl or substituted or unsubstituted heterocycloalkyl.

$R^{1A}$ is independently halogen, —CN, —$OR^{1B}$, —$SR^{1B}$, —$NR^{1C}R^{1D}$, —$NR^{1C}C(O)R^{1B}$, —$C(O)NR^{1C}R^{1D}$, —$CO_2R^{1B}$, substituted or unsubstituted alkyl, or substituted or unsubstituted heteroalkyl.

Each of $R^{1B}$ and $R^{1C}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1D}$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{1C}$ and $R^{1D}$ attached to the same nitrogen atom optionally combine to form a substituted or unsubstituted heterocycloalkyl.

In embodiments, the compound has a structure according to the formula,

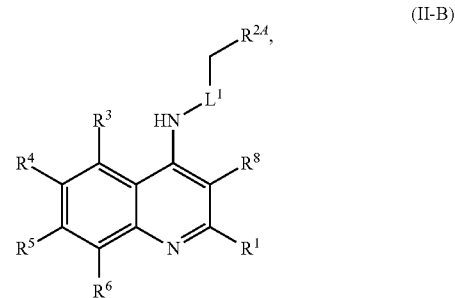

(II-B)

or a pharmaceutically acceptable salt thereof.

$R^1$ is substituted or unsubstituted heteroaryl or phenyl comprising a substituent group $R^{1A}$.

$L^1$ is independently substituted or unsubstituted arylene.

$R^{1A}$ is independently halogen, —CN, —$OR^{1B}$, —$SR^{1B}$, —$NR^{1C}R^{1D}$, —$NR^{1C}C(O)R^{1B}$, —$C(O)NR^{1C}R^{1D}$, —$CO_2R^{1B}$, substituted or unsubstituted alkyl, or substituted or unsubstituted heteroalkyl.

Each of $R^{1B}$ and $R^{1C}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1D}$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{1C}$ and $R^{1D}$ attached to the same nitrogen atom optionally combine to form a substituted or unsubstituted heterocycloalkyl.

$R^{2A}$ is independently —$NR^{2B}R^{2C}$, substituted or unsubstituted cycloalkyl, substituted or unsubstituted heterocycloalkyl, substituted or unsubstituted aryl, or substituted or unsubstituted heteroaryl.

Each of $R^{2B}$ and $R^{2C}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein $R^{2B}$ and $R^{2C}$ combine to form a substituted or unsubstituted heterocycloalkyl.

In embodiments, $R^1$ is phenyl comprising a substituent group $R^{1A}$; and $R^{1A}$ is —$C(O)NR^{1C}R^{1D}$.

In embodiments, $R^{1A}$ is para to the carbon attached to the quinoline moiety.

In embodiments, the compound has a structure according to the formula,

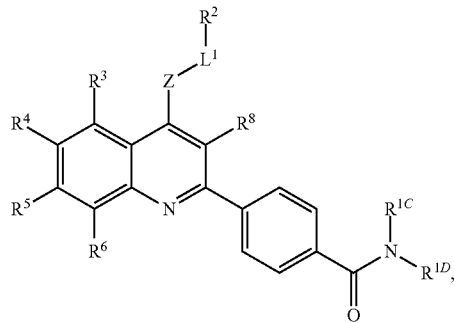

(II-C)

or a pharmaceutically acceptable salt thereof.

$R^{1C}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1D}$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein $R^{1C}$ and $R^{1D}$ attached to the same nitrogen atom optionally combine to form a substituted or unsubstituted heterocycloalkyl.

In embodiments, Z is independently —$NR^9$—; and $L^1$ is independently substituted or unsubstituted alkylene or substituted or unsubstituted arylene.

In embodiments, each of $R^3$, $R^4$, $R^5$, $R^6$, and $R^8$ is hydrogen.

In embodiments, the compound has a structure according to the formula,

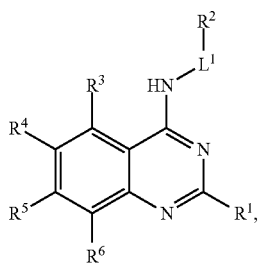

(III)

or a pharmaceutically acceptable salt thereof.

X is independently N or $CR^7$.

Y is independently N or $CR^8$.

Z is independently a covalent bond, —O—, —$NR^9$—, —$NR^9C(O)$—, —$C(O)NR^9$—, —O—C(O)—, or —C(O)—O—.

$L^1$ is a bond, and $R^2$ is unsubstituted alkyl or substituted or unsubstituted heterocycloalkyl; or $L^1$ is substituted or unsubstituted $C_2$-$C_6$ alkylene, and $R^2$ is or substituted or unsubstituted heterocycloalkyl, where said heterocycloalkyl is not unsubstituted morpholine.

$R^1$ is independently hydrogen, —$NR^{10}R^{11}$, —$OR^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, —$CX^3_3$, —$CHX^3_2$, —$CH_2X^3$, —$OCX^3_3$, —$OCHX^3_2$, —$OCH_2X^3$, —CN, —$SO_{n3}R^{16}$, —$SO_{v3}NR^{13}R^{14}$, —$NHC(O)NR^{13}R^{14}$, —$N(O)_{m3}$, —$NR^{13}R^{14}$, —$C(O)R^{15}$, —C(O)—$OR^1$, —C(O)$NR^{13}R^{14}$, —$OR^{16}$, —$NR^{13}SO_2R^{16}$, —$NR^{13}C(O)R^{15}$, —$NR^{13}C(O)OR^{15}$, —$NR^{13}OR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is independently hydrogen, halogen, —$CX^4_3$, —$CHX^4_2$, —$CH_2X^4$, —$OCX^4_3$, —$OCHX^4_2$, —$OCH_2X^4$, —CN, —$SO_{n4}R^{20}$, —$SO_{v4}NR^{17}R^{18}$, —$NHC(O)NR^{17}R^{18}$, —$N(O)_{m4}$, —$NR^{17}R^{18}$, —$C(O)R^{19}$, —C(O)—$OR^{19}$, —$C(O)NR^{17}R^{18}$, —$OR^{20}$, —$NR^{17}SO_2R^{20}$, —$NR^{17}C(O)R^{19}$, —$NR^{17}C(O)OR^{19}$, —$NR^{17}OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently hydrogen, halogen, —$CX^5_3$, —$CHX^5_2$, —$CH_2X^5$, —$OCX^5_3$, —$OCHX^5_2$, —$OCH_2X^5$, —CN, —$SO_{n5}R^{24}$, —$SO_{v5}NR^{21}R^{22}$, —$NHC(O)NR^{21}R^{22}$, —$N(O)_{m5}$, —$NR^{21}R^{22}$, —$C(O)R^{23}$, —C(O)—$OR^{23}$, —$C(O)NR^{21}R^{22}$, —$OR^{24}$, —$NR^{21}SO_2R^{24}$, —$NR^{21}C(O)R^{23}$, —$NR^{21}C(O)OR^{23}$, —$NR^{21}OR^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is independently hydrogen, halogen, —$CX^6_3$, —$CHX^6_2$, —$CH_2X^6$, —$OCX^6_3$, —$OCHX^6_2$, —$OCH_2X^6$, —CN, —$SO_{n6}R^{28}$, —$SO_{v6}NR^{25}R^{26}$, —$NHC(O)NR^{25}R^{26}$, —$N(O)_{m6}$, —$NR^{25}R^{26}$, —$C(O)R^{27}$, —C(O)—$OR^{27}$, —$C(O)NR^{25}R^{26}$, —$OR^{28}$, —$NR^{25}SO_2R^{28}$, —$NR^{25}C(O)R^{27}$, —$NR^{25}C(O)OR^{27}$, —$NR^{25}OR^{27}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each $R^7$, $R^8$, $R^9$, $R^{10}$, $R^{11}$, $R^{12}$, $R^{13}$, $R^{14}$, $R^1$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$ and $R^{11}$, $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl.

Each $X^3$, $X^4$, $X^5$, and $X^6$ is independently —F, —Cl, —Br, or —I.

Each m3, m4, m5, and m6 is independently 1 or 2.

Each n3, n4, n5, and n6 is independently an integer from 0 to 3.

Each v3, v4, v5, and v6 is independently 1 or 2.

In embodiments, each of $R^3$, $R^4$, $R^5$, $R^6$, and $R^8$ is hydrogen.

In embodiments, Z is independently a covalent bond. In embodiments, Z is independently —O—. In embodiments, Z is independently —$NR^9$—. In embodiments, Z is independently —$NR^9C(O)$—. In embodiments, Z is independently —$C(O)NR^9$—. In embodiments, Z is independently —O—C(O)—. In embodiments, Z is independently —C(O)—O—.

In embodiments, $L^1$ is independently a bond. In embodiments, $L^1$ is independently substituted or unsubstituted alkylene. In embodiments, $L^1$ is independently substituted or unsubstituted heteroalkylene. In embodiments, $L^1$ is independently substituted or unsubstituted cycloalkylene. In embodiments, $L^1$ is independently substituted or unsubstituted heterocycloalkylene. In embodiments, $L^1$ is independently substituted or unsubstituted arylene. In embodiments, $L^1$ is independently substituted or unsubstituted heteroarylene. In embodiments, $L^1$ is independently substituted alkylene. In embodiments, $L^1$ is independently substituted heteroalkylene. In embodiments, $L^1$ is independently substituted cycloalkylene. In embodiments, $L^1$ is independently substituted heterocycloalkylene. In embodiments, $L^1$ is independently substituted arylene. In embodiments, $L^1$ is independently substituted heteroarylene. In embodiments, $L^1$ is independently unsubstituted alkylene. In embodiments, $L^1$ is independently unsubstituted heteroalkylene. In embodiments, $L^1$ is independently unsubstituted cycloalkylene. In embodiments, $L^1$ is independently unsubstituted heterocycloalkylene. In embodiments, $L^1$ is independently unsubstituted arylene. In embodiments, $L^1$ is independently unsubstituted heteroarylene. In embodiments, $L^1$ is independently substituted or unsubstituted $C_1$-$C_6$ alkylene. In embodiments, $L^1$ is independently substituted or unsubstituted 2 to 6 membered heteroalkylene. In embodiments, $L^1$ is independently substituted or unsubstituted $C_3$-$C_8$ cycloalkylene. In embodiments, $L^1$ is independently substituted or unsubstituted 3 to 8 membered heterocycloalkylene. In embodiments, $L^1$ is independently substituted or unsubstituted $C_6$ arylene. In embodiments, $L^1$ is independently substituted or unsubstituted 5 to 6 membered heteroarylene. In embodiments, $L^1$ is independently substituted $C_1$-$C_6$ alkylene. In embodiments, $L^1$ is independently substituted 2 to 6 membered heteroalkylene. In embodiments, $L^1$ is independently substituted $C_3$-$C_8$ cycloalkylene. In embodiments, $L^1$ is independently substituted 3 to 8 membered heterocycloalkylene. In embodiments, $L^1$ is independently substituted $C_6$ arylene. In embodiments, $L^1$ is independently substituted 5 to 6 membered heteroarylene. In embodiments, $L^1$ is independently unsubstituted $C_1$-$C_6$ alkylene. In embodiments, $L^1$ is independently unsubstituted 2 to 6 membered heteroalkylene. In embodiments, $L^1$ is independently unsubstituted $C_3$-$C_8$ cycloalkylene. In embodiments, $L^1$ is independently unsubstituted 3 to 8 membered heterocycloalkylene. In embodiments, $L^1$ is independently unsubstituted $C_6$ arylene. In embodiments, $L^1$ is independently unsubstituted 5 to 6 membered heteroarylene.

In embodiments, $R^1$ is independently hydrogen. In embodiments, $R^1$ is independently —$NR^{10}R^{11}$. In embodiments, $R^1$ is independently —$OR^{12}$. In embodiments, $R^1$ is independently substituted or unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently substituted or unsubstituted heterocycloalkyl. In embodiments, $R^1$ is independently substituted or unsubstituted aryl. In embodiments, $R^1$ is independently or substituted or unsubstituted heteroaryl. In embodiments, $R^1$ is independently substituted alkyl. In embodiments, $R^1$ is independently substituted heteroalkyl. In embodiments, $R^1$ is independently substituted cycloalkyl. In embodiments, $R^1$ is independently substituted heterocycloalkyl. In embodiments, $R^1$ is independently substituted aryl. In embodiments, $R^1$ is independently substituted heteroaryl. In embodiments, $R^1$ is independently unsubstituted alkyl. In embodiments, $R^1$ is independently unsubstituted heteroalkyl. In embodiments, $R^1$ is independently unsubstituted cycloalkyl. In embodiments, $R^1$ is independently unsubstituted heterocycloalkyl. In embodiments, $R^1$ is independently unsubstituted aryl. In embodiments, $R^1$ is independently unsubstituted heteroaryl. In embodiments, $R^1$ is independently substituted or unsubstituted $C_1$-$C_6$ alkyl. In embodiments, $R^1$ is independently substituted or unsubstituted 2 to 6 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$ aryl. In embodiments, $R^1$ is independently substituted or unsubstituted 5 to 6 membered heteroaryl. In embodiments, $R^1$ is independently substituted $C_1$-$C_6$ alkyl. In embodiments, $R^1$ is independently substituted 2 to 6 membered heteroalkyl. In embodiments, $R^1$ is independently substituted $C_3$-$C_8$ cycloalkyl. In embodiments, $R^1$ is independently substituted 3 to 8 membered heterocycloalkyl. In embodiments, $R^1$ is independently substituted $C_6$ aryl. In embodiments, $R^1$ is independently substituted 5 to 6 membered heteroaryl. In embodiments, $R^1$ is independently unsubstituted $C_1$-$C_6$ alkyl. In embodiments, $R^1$ is independently unsubstituted 2 to 6 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$ aryl. In embodiments, $R^1$ is independently unsubstituted 5 to 6 membered heteroaryl.

In embodiments, $R^2$ is independently hydrogen. In embodiments, $R^2$ is independently substituted or unsubstituted alkyl. In embodiments, $R^2$ is independently substituted or unsubstituted heteroalkyl. In embodiments, $R^2$ is independently substituted or unsubstituted cycloalkyl. In embodiments, $R^2$ is independently substituted or unsubstituted heterocycloalkyl. In embodiments, $R^2$ is independently substituted or unsubstituted aryl. In embodiments, $R^2$ is independently substituted or unsubstituted heteroaryl. In embodiments, $R^2$ is independently substituted alkyl. In embodiments, $R^2$ is independently substituted heteroalkyl. In embodiments, $R^2$ is independently substituted cycloalkyl. In embodiments, $R^2$ is independently substituted heterocycloalkyl. In embodiments, $R^2$ is independently substituted aryl. In embodiments, $R^2$ is independently substituted heteroaryl. In embodiments, $R^2$ is independently unsubstituted alkyl. In embodiments, $R^2$ is independently unsubstituted heteroalkyl. In embodiments, $R^2$ is independently unsubstituted cycloalkyl. In embodiments, $R^2$ is independently unsubstituted heterocycloalkyl. In embodiments, $R^2$ is independently unsubstituted aryl. In embodiments, $R^2$ is independently unsubstituted heteroaryl. In embodiments, $R^2$ is independently substituted or unsubstituted $C_1$-$C_6$ alkyl. In embodiments, $R^2$ is independently substituted or unsubstituted 2 to 6 membered heteroalkyl. In embodiments, $R^2$ is independently substituted or unsubstituted $C_3$-$C_8$ cycloalkyl. In embodiments, $R^2$ is independently substituted or unsubstituted 3 to 8 membered heterocycloalkyl. In embodiments, $R^2$ is independently substituted or unsubstituted $C_6$ aryl. In embodiments, $R^2$ is independently substituted or unsubstituted 5 to 6 membered heteroaryl. In embodiments, $R^2$ is independently substituted $C_1$-$C_6$ alkyl. In embodiments, $R^2$ is independently substituted 2 to 6 membered heteroalkyl. In embodiments, $R^2$ is independently substituted $C_3$-$C_8$ cycloalkyl. In embodiments, $R^2$ is independently substituted 3 to 8 membered heterocycloalkyl. In embodiments, $R^2$ is independently substituted $C_6$ aryl. In embodiments, $R^2$ is independently substituted 5 to 6 membered heteroaryl. In embodiments, $R^2$ is independently unsubstituted $C_1$-$C_6$ alkyl. In embodiments, $R^2$ is independently unsubstituted 2 to 6 membered heteroalkyl. In embodiments, $R^2$ is independently unsubstituted $C_3$-$C_8$ cycloalkyl. In embodiments, $R^2$ is independently unsubstituted 3 to 8 membered heterocycloalkyl. In embodiments, $R^2$ is independently unsubstituted $C_6$ aryl. In embodiments, $R^2$ is independently unsubstituted 5 to 6 membered heteroaryl.

In embodiments, $R^3$ is independently hydrogen. In embodiments, $R^3$ is independently halogen. In embodiments, $R^3$ is independently —$CX^3_3$. In embodiments, $R^3$ is independently —$CHX^3_2$. In embodiments, $R^3$ is independently —$CH_2X^3$. In embodiments, $R^3$ is independently —$OCX^3_3$. In embodiments, $R^3$ is independently —$OCHX^3_2$. In embodiments, $R^3$ is independently —$OCH_2X^3$. In embodiments, $R^3$ is independently —CN, —$SO_{n3}R^{16}$. In embodiments, $R^3$ is independently —$SO_{v3}NR^{13}R^{14}$. In embodiments, $R^3$ is independently —$NHC(O)NR^{13}R^{14}$. In embodiments, $R^3$ is independently —$N(O)_{m3}$. In embodiments, $R^3$ is independently —$NR^{13}R^{14}$, —$C(O)R^{15}$. In embodiments, $R^3$ is independently —$C(O)$—$OR^{15}$. In embodiments, $R^3$ is independently —$C(O)NR^{13}R^{14}$. In embodiments, $R^3$ is independently —$OR^6$. In embodiments, $R^3$ is independently —$NR^{13}SO_2R^{16}$. In embodiments, $R^3$ is independently —$NR^{13}C(O)R^{15}$. In embodiments, $R^3$ is independently —$NR^{13}C(O)OR^{15}$. In embodiments, $R^3$ is independently —$NR^{13}OR^{15}$. In embodiments, $R^3$ is independently substituted or unsubstituted alkyl. In embodiments, $R^3$ is independently substituted or unsubstituted heteroalkyl. In embodiments, $R^3$ is independently substituted or unsubstituted cycloalkyl. In embodiments, $R^3$ is independently substituted or unsubstituted heterocycloalkyl. In embodiments, $R^3$ is independently substituted or unsubstituted aryl. In embodiments, $R^3$ is independently substituted or unsubstituted heteroaryl. In embodiments, $R^3$ is independently substituted alkyl. In embodiments, $R^3$ is independently substituted heteroalkyl. In embodiments, $R^3$ is independently substituted cycloalkyl. In embodiments, $R^3$ is independently substituted heterocycloalkyl. In embodiments, $R^3$ is independently substituted aryl. In embodiments, $R^3$ is independently substituted heteroaryl. In embodiments, $R^3$ is independently unsubstituted alkyl. In embodiments, $R^3$ is independently unsubstituted heteroalkyl. In embodiments, $R^3$ is independently unsubstituted cycloalkyl. In embodiments, $R^3$ is independently unsubstituted heterocycloalkyl. In embodiments, $R^3$ is independently unsubstituted aryl. In embodiments, $R^3$ is independently unsubstituted heteroaryl. In embodiments, $R^3$ is independently substituted or unsubstituted $C_1$-$C_6$ alkyl. In embodiments, $R^3$ is independently substituted or unsubstituted 2 to 6 membered heteroalkyl. In embodiments, $R^3$ is independently substituted or unsubstituted $C_3$-$C_8$ cycloalkyl. In embodiments, $R^3$ is independently substituted or unsubstituted 3 to 8 membered heterocycloalkyl. In embodiments, $R^3$ is independently substituted or unsubstituted $C_6$ aryl. In embodiments, $R^3$ is independently substituted or unsubstituted 5 to 6 membered heteroaryl. In embodiments, $R^3$ is independently substituted $C_1$-$C_6$ alkyl. In embodiments, $R^3$ is independently substituted 2 to 6 membered heteroalkyl. In embodiments, $R^3$ is independently substituted $C_3$-$C_8$ cycloalkyl. In embodiments, $R^3$ is independently substituted 3 to 8 membered heterocycloalkyl. In embodiments, $R^3$ is independently substituted $C_6$ aryl. In embodiments, $R^3$ is independently substituted 5 to 6 membered heteroaryl. In embodiments, $R^3$ is independently unsubstituted $C_1$-$C_6$ alkyl. In embodiments, $R^3$ is independently unsubstituted 2 to 6 membered heteroalkyl. In embodiments, $R^3$ is independently unsubstituted $C_3$-$C_8$ cycloalkyl. In embodiments, $R^3$ is independently unsubstituted 3 to 8 membered heterocycloalkyl. In embodiments, $R^3$ is independently unsubstituted $C_6$ aryl. In embodiments, $R^3$ is independently unsubstituted 5 to 6 membered heteroaryl.

In embodiments, $R^4$ is independently hydrogen. In embodiments, $R^4$ is independently halogen. In embodiments, $R^4$ is independently —$CX^4_3$. In embodiments, $R^4$ is independently —$CHX^4_2$. In embodiments, $R^4$ is independently —$CH_2X^4$. In embodiments, $R^4$ is independently —$OCX^4_3$. In embodiments, $R^4$ is independently —$OCHX^4_2$. In embodiments, $R^4$ is independently —$OCH_2X^4$. In embodiments, $R^4$ is independently —CN. In embodiments, $R^4$ is independently —$SO_{n4}R^{20}$. In embodiments, $R^4$ is independently —$SO_{v4}NR^{17}R^{18}$. In embodiments, $R^4$ is independently —$NHC(O)NR^{17}R^{18}$. In embodiments, $R^4$ is independently —$N(O)_{m4}$. In embodiments, $R^4$ is independently —$NR^{17}R^{18}$. In embodiments, $R^4$ is independently —$C(O)R^{19}$. In embodiments, $R^4$ is independently —$C(O)$—$OR^{19}$. In embodiments, $R^4$ is independently —$C(O)NR^{17}R^{18}$. In embodiments, $R^4$ is independently —$OR^{20}$. In embodiments, $R^4$ is independently —$NR^7SO_2R^{20}$. In embodiments, $R^4$ is independently —$NR^{17}C(O)R^{19}$. In embodiments, $R^4$ is independently —$NR^{17}C(O)OR^{19}$. In embodiments, $R^4$ is independently —$NR^{17}OR^{19}$. In embodiments, $R^4$ is independently substituted or unsubstituted alkyl. In embodiments, $R^4$ is independently substituted or unsubstituted heteroalkyl. In embodiments, $R^4$ is independently substituted or unsubstituted cycloalkyl. In embodiments, $R^4$ is independently substituted or unsubstituted heterocycloalkyl. In embodiments, $R^4$ is independently substituted or unsubstituted aryl. In embodiments, $R^4$ is independently or substituted or unsubstituted heteroaryl. In embodiments, $R^4$ is independently substituted alkyl. In embodiments, $R^4$ is independently substituted heteroalkyl. In embodiments, $R^4$ is independently substituted cycloalkyl. In embodiments, $R^4$ is independently substituted heterocycloalkyl. In embodiments, $R^4$ is independently substituted aryl. In embodiments, $R^4$ is independently substituted heteroaryl. In embodiments, $R^4$ is independently unsubstituted alkyl. In embodiments, $R^4$ is independently unsubstituted heteroalkyl. In embodiments, $R^4$ is independently unsubstituted cycloalkyl. In embodiments, $R^4$ is independently unsubstituted heterocycloalkyl. In embodiments, $R^4$ is independently unsubstituted aryl. In embodiments, $R^4$ is independently unsubstituted heteroaryl. In embodiments, $R^4$ is independently substituted or unsubstituted $C_1$-$C_6$ alkyl. In embodiments, $R^4$ is independently substituted or unsubstituted 2 to 6 membered heteroalkyl. In embodiments, $R^4$ is independently substituted or unsubstituted $C_3$-$C_8$ cycloalkyl. In embodiments, $R^4$ is independently substituted or unsubstituted 3 to 8 membered heterocycloalkyl. In embodiments, $R^4$ is independently substituted or unsubstituted $C_6$ aryl. In embodiments, $R^4$ is independently substituted or unsubstituted 5 to 6 membered heteroaryl. In embodiments, $R^4$ is independently substituted $C_1$-$C_6$ alkyl. In embodiments, $R^4$ is independently substituted 2 to 6 membered heteroalkyl. In embodiments, $R^4$ is independently substituted $C_3$-$C_8$ cycloalkyl. In embodiments, $R^4$ is independently substituted 3 to 8 membered heterocycloalkyl. In embodiments, $R^4$ is independently substituted $C_6$ aryl. In embodiments, $R^4$ is independently substituted 5 to 6 membered heteroaryl. In embodiments, $R^4$ is independently unsubstituted $C_1$-$C_6$ alkyl. In embodiments, $R^4$ is independently unsubstituted 2 to 6 membered heteroalkyl. In embodiments, $R^4$ is independently unsubstituted $C_3$-$C_8$ cycloalkyl. In embodiments, $R^4$ is independently unsubstituted 3 to 8 membered heterocycloalkyl. In embodiments, $R^4$ is independently unsubstituted $C_6$ aryl. In embodiments, $R^4$ is independently unsubstituted 5 to 6 membered heteroaryl.

In embodiments, $R^5$ is independently hydrogen. In embodiments, $R^5$ is independently halogen. In embodiments, $R^5$ is independently —$CX^5_3$. In embodiments, $R^5$ is independently —$CHX^5_2$. In embodiments, $R^5$ is independently —$CH_2X^5$. In embodiments, $R^5$ is independently —$OCX^5_3$. In embodiments, $R^5$ is independently —$OCHX^{52}$. In embodiments, $R^5$ is independently —$OCH_2X^5$. In embodiments, $R^5$ is independently —CN. In embodiments, $R^5$ is independently —$SO_{n5}R^{24}$. In embodiments, $R^5$ is independently —$SO_{v5}NR^{21}R^{22}$. In embodiments, $R^5$ is independently —$NHC(O)NR^{21}R^{22}$. In embodiments, $R^5$ is independently -N(O)$_{m5}$. In embodiments, $R^5$ is independently —$NR^{21}R^{22}$. In embodiments, $R^5$ is independently —$C(O)R^{23}$. In embodiments, $R^5$ is independently —C(O)—$OR^{23}$. In embodiments, $R^5$ is independently —$C(O)NR^{21}R^{22}$. In embodiments, $R^5$ is independently —$OR^{24}$. In embodiments, $R^5$ is independently —$NR^{21}SO_2R^{24}$. In embodiments, $R^5$ is independently —$NR^{21}C(O)R^{23}$. In embodiments, $R^5$ is independently —$NR^{21}C(O)OR^{23}$. In embodiments, $R^5$ is independently —$NR^{21}OR^2$. In embodiments, $R^5$ is independently substituted or unsubstituted alkyl. In embodiments, $R^5$ is independently substituted or unsubstituted heteroalkyl. In embodiments, $R^5$ is independently substituted or unsubstituted cycloalkyl. In embodiments, $R^5$ is independently substituted or unsubstituted heterocycloalkyl. In embodiments, $R^5$ is independently substituted or unsubstituted aryl. In embodiments, $R^5$ is independently or substituted or unsubstituted heteroaryl. In embodiments, $R^5$ is independently substituted alkyl. In embodiments, $R^5$ is independently substituted heteroalkyl. In embodiments, $R^5$ is independently substituted cycloalkyl. In embodiments, $R^5$ is independently substituted heterocycloalkyl. In embodiments, $R^5$ is independently substituted aryl. In embodiments, $R^5$ is independently substituted heteroaryl. In embodiments, $R^5$ is independently unsubstituted alkyl. In embodiments, $R^5$ is independently unsubstituted heteroalkyl. In embodiments, $R^5$ is independently unsubstituted cycloalkyl. In embodiments, $R^5$ is independently unsubstituted heterocycloalkyl. In embodiments, $R^5$ is independently unsubstituted aryl. In embodiments, $R^5$ is independently unsubstituted heteroaryl. In embodiments, $R^5$ is independently substituted or unsubstituted $C_1$-$C_6$ alkyl. In embodiments, $R^5$ is independently substituted or unsubstituted 2 to 6 membered heteroalkyl. In embodiments, $R^5$ is independently substituted or unsubstituted $C_3$-$C_8$ cycloalkyl. In embodiments, $R^5$ is independently substituted or unsubstituted 3 to 8 membered heterocycloalkyl. In embodiments, $R^5$ is independently substituted or unsubstituted $C_6$ aryl. In embodiments, $R^5$ is independently substituted or unsubstituted 5 to 6 membered heteroaryl. In embodiments, $R^5$ is independently substituted $C_1$-$C_6$ alkyl. In embodiments, $R^5$ is independently substituted 2 to 6 membered heteroalkyl. In embodiments, $R^5$ is independently substituted $C_3$-$C_8$ cycloalkyl. In embodiments, $R^5$ is independently substituted 3 to 8 membered heterocycloalkyl. In embodiments, $R^5$ is independently substituted $C_6$ aryl. In embodiments, $R^5$ is independently substituted 5 to 6 membered heteroaryl. In embodiments, $R^5$ is independently unsubstituted $C_1$-$C_6$ alkyl. In embodiments, $R^5$ is independently unsubstituted 2 to 6 membered heteroalkyl. In embodiments, $R^5$ is independently unsubstituted $C_3$-$C_8$ cycloalkyl. In embodiments, $R^5$ is independently unsubstituted 3 to 8 membered heterocycloalkyl. In embodiments, $R^5$ is independently unsubstituted $C_6$ aryl. In embodiments, $R^5$ is independently unsubstituted 5 to 6 membered heteroaryl.

In embodiments, $R^6$ is independently hydrogen. In embodiments, $R^6$ is independently halogen. In embodiments, $R^6$ is independently —$CX^6_3$. In embodiments, $R^6$ is independently —$CHX^6_2$. In embodiments, $R^6$ is independently —$CH_2X^6$. In embodiments, $R^6$ is independently —$OCX^6_3$. In embodiments, $R^6$ is independently —$OCHX^6_2$. In embodiments, $R^6$ is independently —$OCH_2X^6$. In embodiments, $R^6$ is independently —CN. In embodiments, $R^6$ is independently —$SO_{n6}R^{28}$. In embodiments, $R^6$ is independently —$SO_{v6}NR^{25}R^{26}$. In embodiments, $R^6$ is independently —$NHC(O)NR^{25}R^{26}$. In embodiments, $R^6$ is independently —N(O)$_{m6}$. In embodiments, $R^6$ is independently —$NR^{25}R^{26}$. In embodiments, $R^6$ is independently —$C(O)R^{27}$. In embodiments, $R^6$ is independently —C(O)—$OR^{27}$. In embodiments, $R^6$ is independently —$C(O)NR^{25}R^{26}$. In embodiments, $R^6$ is independently —$OR^{28}$. In embodiments, $R^6$ is independently —$NR^{25}SO_2R^{28}$. In embodiments, $R^6$ is independently —$NR^{25}C(O)R^{27}$. In embodiments, $R^6$ is independently —$NR^{25}C(O)OR^{27}$. In embodiments, $R^6$ is independently —$NR^{25}OR^{27}$. In embodiments, $R^6$ is independently substituted or unsubstituted alkyl. In embodiments, $R^6$ is independently substituted or unsubstituted heteroalkyl. In embodiments, $R^6$ is independently substituted or unsubstituted cycloalkyl. In embodiments, $R^6$ is independently substituted or unsubstituted heterocycloalkyl. In embodiments, $R^6$ is independently substituted or unsubstituted aryl. In embodiments, $R^6$ is independently or substituted or unsubstituted heteroaryl. In embodiments, $R^6$ is independently substituted alkyl. In embodiments, $R^6$ is independently substituted heteroalkyl. In embodiments, $R^6$ is independently substituted cycloalkyl. In embodiments, $R^6$ is independently substituted heterocycloalkyl. In embodiments, $R^6$ is independently substituted aryl. In embodiments, $R^6$ is independently substituted heteroaryl. In embodiments, $R^6$ is independently unsubstituted alkyl. In embodiments, $R^6$ is independently unsubstituted heteroalkyl. In embodiments, $R^6$ is independently unsubstituted cycloalkyl. In embodiments, $R^6$ is independently unsubstituted heterocycloalkyl. In embodiments, $R^6$ is independently unsubstituted aryl. In embodiments, $R^6$ is independently unsubstituted heteroaryl. In embodiments, $R^6$ is independently substituted or unsubstituted $C_1$-$C_6$ alkyl. In embodiments, $R^6$ is independently substituted or unsubstituted 2 to 6 membered heteroalkyl. In embodiments, $R^6$ is independently substituted or unsubstituted $C_3$-$C_8$ cycloalkyl. In embodiments, $R^6$ is independently substituted or unsubstituted 3 to 8 membered heterocycloalkyl. In embodiments, $R^6$ is independently substituted or unsubstituted $C_6$ aryl. In embodiments, $R^6$ is independently substituted or unsubstituted 5 to 6 membered heteroaryl. In embodiments, $R^6$ is independently substituted $C_1$-$C_6$ alkyl. In embodiments, $R^6$ is independently substituted 2 to 6 membered heteroalkyl. In embodiments, $R^6$ is independently substituted $C_3$-$C_8$ cycloalkyl. In embodiments, $R^6$ is independently substituted 3 to 8 membered heterocycloalkyl. In embodiments, $R^6$ is independently substituted $C_6$ aryl. In embodiments, $R^6$ is independently substituted 5 to 6 membered heteroaryl. In embodiments, $R^6$ is independently unsubstituted $C_1$-$C_6$ alkyl. In embodiments, $R^6$ is independently unsubstituted 2 to 6 membered heteroalkyl. In embodiments, $R^6$ is independently unsubstituted $C_3$-$C_8$ cycloalkyl. In embodiments, $R^6$ is independently unsubstituted 3 to 8 membered heterocycloalkyl. In embodiments, $R^6$ is independently unsubstituted $C_6$ aryl. In embodiments, $R^6$ is independently unsubstituted 5 to 6 membered heteroaryl.

In embodiments, each $R^7$ is independently hydrogen. In embodiments, each $R^7$ is independently —$CX_3$. In embodiments, each $R^7$ is independently —CN. In embodiments, each $R^7$ is independently —COOH. In embodiments, each $R^7$ is independently —$CONH_2$. In embodiments, each $R^7$ is independently —$CHX_2$. In embodiments, each $R^7$ is independently —$CH_2X$. In embodiments, each $R^7$ is independently substituted or unsubstituted alkyl. In embodiments, each $R^7$ is independently substituted or unsubstituted heteroalkyl. In embodiments, each $R^7$ is independently substituted or unsubstituted cycloalkyl. In embodiments, each $R^7$ is independently substituted or unsubstituted heterocycloalkyl. In embodiments, each $R^7$ is independently substituted or unsubstituted aryl. In embodiments, each $R^7$ is independently or substituted or unsubstituted heteroaryl. In embodiments, $R^7$ is independently substituted alkyl. In embodiments, $R^7$ is independently substituted heteroalkyl. In embodiments, $R^7$ is independently substituted cycloalkyl. In embodiments, $R^7$ is independently substituted heterocycloalkyl. In embodiments, $R^7$ is independently substituted aryl. In embodiments, $R^7$ is independently substituted heteroaryl. In embodiments, $R^7$ is independently unsubstituted alkyl. In embodiments, $R^1$ is independently unsubstituted heteroalkyl. In embodiments, $R^7$ is independently unsubstituted cycloalkyl. In embodiments, $R^1$ is independently unsubstituted heterocycloalkyl. In embodiments, $R^7$ is independently unsubstituted aryl. In embodiments, $R^7$ is independently unsubstituted heteroaryl. In embodiments, $R^7$ is independently substituted or unsubstituted $C_1$-$C_6$ alkyl. In embodiments, $R^7$ is independently substituted or unsubstituted 2 to 6 membered heteroalkyl. In embodiments, $R^7$ is independently substituted or unsubstituted $C_3$-$C_8$ cycloalkyl. In embodiments, $R^7$ is independently substituted or unsubstituted 3 to 8 membered heterocycloalkyl. In embodiments, $R^7$ is independently substituted or unsubstituted $C_6$ aryl. In embodiments, $R^7$ is independently substituted or unsubstituted 5 to 6 membered heteroaryl. In embodiments, $R^7$ is independently substituted $C_1$-$C_6$ alkyl. In embodiments, $R^7$ is independently substituted 2 to 6 membered heteroalkyl. In embodiments, $R^7$ is independently substituted $C_3$-$C_8$ cycloalkyl. In embodiments, $R^7$ is independently substituted 3 to 8 membered heterocycloalkyl. In embodiments, $R^7$ is independently substituted $C_6$ aryl. In embodiments, $R^7$ is independently substituted 5 to 6 membered heteroaryl. In embodiments, $R^7$ is independently unsubstituted $C_1$-$C_6$ alkyl. In embodiments, $R^7$ is independently unsubstituted 2 to 6 membered heteroalkyl. In embodiments, $R^7$ is independently unsubstituted $C_3$-$C_8$ cycloalkyl. In embodiments, $R^7$ is independently unsubstituted 3 to 8 membered heterocycloalkyl. In embodiments, $R^7$ is independently unsubstituted $C_6$ aryl. In embodiments, $R^7$ is independently unsubstituted 5 to 6 membered heteroaryl.

In embodiments, each $R^8$ is independently hydrogen. In embodiments, each $R^8$ is independently —$CX_3$. In embodiments, each $R^8$ is independently —CN. In embodiments, each $R^8$ is independently —COOH. In embodiments, each $R^8$ is independently —$CONH_2$. In embodiments, each $R^8$ is independently —$CHX_2$. In embodiments, each $R^8$ is independently —$CH_2X$. In embodiments, each $R^8$ is independently substituted or unsubstituted alkyl. In embodiments, each $R^8$ is independently substituted or unsubstituted heteroalkyl. In embodiments, each $R^8$ is independently substituted or unsubstituted cycloalkyl. In embodiments, each $R^8$ is independently substituted or unsubstituted heterocycloalkyl. In embodiments, each $R^8$ is independently substituted or unsubstituted aryl. In embodiments, each $R^8$ is independently or substituted or unsubstituted heteroaryl. In embodiments, $R^8$ is independently substituted alkyl. In embodiments, $R^8$ is independently substituted heteroalkyl. In embodiments, $R^8$ is independently substituted cycloalkyl. In embodiments, $R^8$ is independently substituted heterocycloalkyl. In embodiments, $R^8$ is independently substituted aryl. In embodiments, $R^8$ is independently substituted heteroaryl. In embodiments, $R^8$ is independently unsubstituted alkyl. In embodiments, $R^8$ is independently unsubstituted heteroalkyl. In embodiments, $R^8$ is independently unsubstituted cycloalkyl. In embodiments, $R^8$ is independently unsubstituted heterocycloalkyl. In embodiments, $R^8$ is independently unsubstituted aryl. In embodiments, $R^8$ is independently unsubstituted heteroaryl. In embodiments, $R^8$ is independently substituted or unsubstituted $C_1$-$C_6$ alkyl. In embodiments, $R^8$ is independently substituted or unsubstituted 2 to 6 membered heteroalkyl. In embodiments, $R^8$ is independently substituted or unsubstituted $C_3$-$C_8$ cycloalkyl. In embodiments, $R^8$ is independently substituted or unsubstituted 3 to 8 membered heterocycloalkyl. In embodiments, $R^8$ is independently substituted or unsubstituted $C_6$ aryl. In embodiments, $R^8$ is independently substituted or unsubstituted 5 to 6 membered heteroaryl. In embodiments, $R^8$ is independently substituted $C_1$-$C_6$ alkyl. In embodiments, $R^8$ is independently substituted 2 to 6 membered heteroalkyl. In embodiments, $R^8$ is independently substituted $C_3$-$C_8$ cycloalkyl. In embodiments, $R^8$ is independently substituted 3 to 8 membered heterocycloalkyl. In embodiments, $R^8$ is independently substituted $C_6$ aryl. In embodiments, $R^8$ is independently substituted 5 to 6 membered heteroaryl. In embodiments, $R^8$ is independently unsubstituted $C_1$-$C_6$ alkyl. In embodiments, $R^8$ is independently unsubstituted 2 to 6 membered heteroalkyl. In embodiments, $R^8$ is independently unsubstituted $C_3$-$C_8$ cycloalkyl. In embodiments, $R^8$ is independently unsubstituted 3 to 8 membered heterocycloalkyl. In embodiments, $R^8$ is independently unsubstituted $C_6$ aryl. In embodiments, $R^8$ is independently unsubstituted 5 to 6 membered heteroaryl.

In embodiments, each $R^9$ is independently hydrogen. In embodiments, each $R^9$ is independently —$CX_3$. In embodiments, each $R^9$ is independently —CN. In embodiments, each $R^9$ is independently —COOH. In embodiments, each $R^9$ is independently —$CONH_2$. In embodiments, each $R^9$ is independently —$CHX_2$. In embodiments, each $R^9$ is independently —$CH_2X$. In embodiments, each $R^9$ is independently substituted or unsubstituted alkyl. In embodiments, each $R^9$ is independently substituted or unsubstituted heteroalkyl. In embodiments, each $R^9$ is independently substituted or unsubstituted cycloalkyl. In embodiments, each $R^9$ is independently substituted or unsubstituted heterocycloalkyl. In embodiments, each $R^9$ is independently substituted or unsubstituted aryl. In embodiments, each $R^9$ is independently or substituted or unsubstituted heteroaryl. In embodiments, $R^9$ is independently substituted alkyl. In embodiments, $R^9$ is independently substituted heteroalkyl. In embodiments, $R^9$ is independently substituted cycloalkyl. In embodiments, $R^9$ is independently substituted heterocycloalkyl. In embodiments, $R^9$ is independently substituted aryl. In embodiments, $R^9$ is independently substituted heteroaryl. In embodiments, $R^9$ is independently unsubstituted alkyl. In embodiments, $R^9$ is independently unsubstituted heteroalkyl. In embodiments, $R^9$ is independently unsubstituted cycloalkyl. In embodiments, $R^9$ is independently unsubstituted heterocycloalkyl. In embodiments, $R^9$ is independently unsubstituted aryl. In embodiments, $R^9$ is independently unsubstituted heteroaryl. In embodiments, $R^9$ is independently substituted or unsubstituted $C_1$-$C_6$ alkyl. In embodiments, $R^9$ is independently substituted or unsubstituted 2 to 6 membered heteroalkyl. In embodiments, $R^9$ is independently substituted or unsubstituted $C_3$-$C_8$ cycloalkyl. In embodiments, $R^9$ is independently substituted or unsubstituted 3 to 8 membered heterocycloalkyl. In embodiments, $R^9$ is independently substituted or unsubstituted $C_6$ aryl. In embodiments, $R^9$ is independently substituted or unsubstituted 5 to 6 membered heteroaryl. In embodiments, $R^9$ is independently substituted $C_1$-$C_6$ alkyl. In embodiments, $R^9$ is independently substituted 2 to 6 membered heteroalkyl. In embodiments, $R^9$ is independently substituted $C_3$-$C_8$ cycloalkyl. In embodiments, $R^9$ is independently substituted 3 to 8 membered heterocycloalkyl. In embodiments, $R^9$ is independently substituted $C_6$ aryl. In embodiments, $R^9$ is independently substituted 5 to 6 membered heteroaryl. In embodiments, $R^9$ is independently unsubstituted $C_1$-$C_6$ alkyl. In embodiments, $R^9$ is independently unsubstituted 2 to 6 membered heteroalkyl. In embodiments, $R^9$ is independently unsubstituted $C_3$-$C_8$ cycloalkyl. In embodiments, $R^9$ is independently unsubstituted 3 to 8 membered heterocycloalkyl. In embodiments, $R^9$ is independently unsubstituted $C_6$ aryl. In embodiments, $R^9$ is independently unsubstituted 5 to 6 membered heteroaryl.

In embodiments, each $R^{10}$ is independently hydrogen. In embodiments, each $R^{10}$ is independently —$CX_3$. In embodiments, each $R^{10}$ is independently —CN. In embodiments, each $R^{10}$ is independently —COOH. In embodiments, each $R^{10}$ is independently —$CONH_2$. In embodiments, each $R^{10}$ is independently —$CHX_2$. In embodiments, each $R^{10}$ is independently —$CH_2X$. In embodiments, each $R^{10}$ is independently substituted or unsubstituted alkyl. In embodiments, each $R^{10}$ is independently substituted or unsubstituted heteroalkyl. In embodiments, each $R^{10}$ is independently substituted or unsubstituted cycloalkyl. In embodiments, each $R^{10}$ is independently substituted or unsubstituted heterocycloalkyl. In embodiments, each $R^{10}$ is independently substituted or unsubstituted aryl. In embodiments, each $R^{10}$ is independently or substituted or unsubstituted heteroaryl. In embodiments, $R^{10}$ is independently substituted alkyl. In embodiments, $R^{10}$ is independently substituted heteroalkyl. In embodiments, $R^{10}$ is independently substituted cycloalkyl. In embodiments, $R^{10}$ is independently substituted heterocycloalkyl. In embodiments, $R^{10}$ is independently substituted aryl. In embodiments, $R^{10}$ is independently substituted heteroaryl. In embodiments, $R^{10}$ is independently unsubstituted alkyl. In embodiments, $R^{10}$ is independently unsubstituted heteroalkyl. In embodiments, $R^{10}$ is independently unsubstituted cycloalkyl. In embodiments, $R^{10}$ is independently unsubstituted heterocycloalkyl. In embodiments, $R^{10}$ is independently unsubstituted aryl. In embodiments, $R^{10}$ is independently unsubstituted heteroaryl. In embodiments, $R^{10}$ is independently substituted or unsubstituted $C_1$-$C_6$ alkyl. In embodiments, $R^{10}$ is independently substituted or unsubstituted 2 to 6 membered heteroalkyl. In embodiments, $R^{10}$ is independently substituted or unsubstituted $C_3$-$C_8$ cycloalkyl. In embodiments, $R^{10}$ is independently substituted or unsubstituted 3 to 8 membered heterocycloalkyl. In embodiments, $R^{10}$ is independently substituted or unsubstituted $C_6$ aryl. In embodiments, $R^{10}$ is independently substituted or unsubstituted 5 to 6 membered heteroaryl. In embodiments, $R^{10}$ is independently substituted $C_1$-$C_6$ alkyl. In embodiments, $R^{10}$ is independently substituted 2 to 6 membered heteroalkyl. In embodiments, $R^{10}$ is independently substituted $C_3$-$C_8$ cycloalkyl. In embodiments, $R^{10}$ is independently substituted 3 to 8 membered heterocycloalkyl. In embodiments, $R^{10}$ is independently substituted $C_6$ aryl. In embodiments, $R^{10}$ is independently substituted 5 to 6 membered heteroaryl. In embodiments, $R^{10}$ is independently unsubstituted $C_1$-$C_6$ alkyl. In embodiments, $R^9$ is independently unsubstituted 2 to 6 membered heteroalkyl. In embodiments, $R^{10}$ is independently unsubstituted $C_3$-$C_8$ cycloalkyl. In embodiments, $R^{10}$ is independently unsubstituted 3 to 8 membered heterocycloalkyl. In embodiments, $R^{10}$ is independently unsubstituted $C_6$ aryl. In embodiments, $R^{10}$ is independently unsubstituted 5 to 6 membered heteroaryl.

In embodiments, each $R^{11}$ is independently hydrogen. In embodiments, each $R^{11}$ is independently —$CX_3$. In embodiments, each $R^{11}$ is independently —CN. In embodiments, each $R^{11}$ is independently —COOH. In embodiments, each $R^{11}$ is independently —$CONH_2$. In embodiments, each $R^{11}$ is independently —$CHX_2$. In embodiments, each $R^{11}$ is independently —$CH_2X$. In embodiments, each $R^{11}$ is independently substituted or unsubstituted alkyl. In embodiments, each $R^{11}$ is independently substituted or unsubstituted heteroalkyl. In embodiments, each $R^{11}$ is independently substituted or unsubstituted cycloalkyl. In embodiments, each $R^{11}$ is independently substituted or unsubstituted heterocycloalkyl. In embodiments, each $R^{11}$ is independently substituted or unsubstituted aryl. In embodiments, each $R^{11}$ is independently or substituted or unsubstituted heteroaryl. In embodiments, $R^{11}$ is independently substituted alkyl. In embodiments, $R^{11}$ is independently substituted heteroalkyl. In embodiments, $R^{11}$ is independently substituted cycloalkyl. In embodiments, $R^{11}$ is independently substituted heterocycloalkyl. In embodiments, $R^{11}$ is independently substituted aryl. In embodiments, $R^{11}$ is independently substituted heteroaryl. In embodiments, $R^{11}$ is independently unsubstituted alkyl. In embodiments, $R^{11}$ is independently unsubstituted heteroalkyl. In embodiments, $R^{11}$ is independently unsubstituted cycloalkyl. In embodiments, $R^{11}$ is independently unsubstituted heterocycloalkyl. In embodiments, $R^{11}$ is independently unsubstituted aryl. In embodiments, $R^{11}$ is independently unsubstituted heteroaryl. In embodiments, $R^{11}$ is independently substituted or unsubstituted $C_1$-$C_6$ alkyl. In embodiments, $R^{11}$ is independently substituted or unsubstituted 2 to 6 membered heteroalkyl. In embodiments, $R^{11}$ is independently substituted or unsubstituted $C_3$-$C_8$ cycloalkyl. In embodiments, $R^{11}$ is independently substituted or unsubstituted 3 to 8 membered heterocycloalkyl. In embodiments, $R^1$ is independently substituted or unsubstituted $C_6$ aryl. In embodiments, $R^{11}$ is independently substituted or unsubstituted 5 to 6 membered heteroaryl. In embodiments, $R^{11}$ is independently substituted $C_1$-$C_6$ alkyl. In embodiments, $R^{11}$ is independently substituted 2 to 6 membered heteroalkyl. In embodiments, $R^{11}$ is independently substituted $C_3$-$C_8$ cycloalkyl. In embodiments, $R^{11}$ is independently substituted 3 to 8 membered heterocycloalkyl. In embodiments, $R^{11}$ is independently substituted $C_6$ aryl. In embodiments, $R^{11}$ is independently substituted 5 to 6 membered heteroaryl. In embodiments, $R^{11}$ is independently unsubstituted $C_1$-$C_6$ alkyl. In embodiments, $R^{11}$ is independently unsubstituted 2 to 6 membered heteroalkyl. In embodiments, $R^{11}$ is independently unsubstituted $C_3$-$C_8$ cycloalkyl. In embodiments, $R^{11}$ is independently unsubstituted 3 to 8 membered heterocycloalkyl. In embodiments, $R^{11}$ is independently unsubstituted $C_6$ aryl. In embodiments, $R^{11}$ is independently unsubstituted 5 to 6 membered heteroaryl.

In embodiments, each $R^{12}$ is independently hydrogen. In embodiments, each $R^{12}$ is independently —$CX_3$. In embodiments, each $R^{12}$ is independently —CN. In embodiments, each $R^{12}$ is independently —COOH. In embodiments, each $R^{12}$ is independently —CONH$_2$. In embodiments, each $R^{12}$ is independently —CHX$_2$. In embodiments, each $R^{12}$ is independently —CH$_2$X. In embodiments, each $R^{12}$ is independently substituted or unsubstituted alkyl. In embodiments, each $R^{12}$ is independently substituted or unsubstituted heteroalkyl. In embodiments, each $R^{12}$ is independently substituted or unsubstituted cycloalkyl. In embodiments, each $R^{12}$ is independently substituted or unsubstituted heterocycloalkyl. In embodiments, each $R^{12}$ is independently substituted or unsubstituted aryl. In embodiments, each $R^{12}$ is independently or substituted or unsubstituted heteroaryl. In embodiments, $R^{12}$ is independently substituted alkyl. In embodiments, $R^{12}$ is independently substituted heteroalkyl. In embodiments, $R^{12}$ is independently substituted cycloalkyl. In embodiments, $R^{12}$ is independently substituted heterocycloalkyl. In embodiments, $R^{12}$ is independently substituted aryl. In embodiments, $R^{12}$ is independently substituted heteroaryl. In embodiments, $R^{12}$ is independently unsubstituted alkyl. In embodiments, $R^{12}$ is independently unsubstituted heteroalkyl. In embodiments, $R^{12}$ is independently unsubstituted cycloalkyl. In embodiments, $R^{12}$ is independently unsubstituted heterocycloalkyl. In embodiments, $R^{12}$ is independently unsubstituted aryl. In embodiments, $R^{12}$ is independently unsubstituted heteroaryl. In embodiments, $R^{12}$ is independently substituted or unsubstituted $C_1$-$C_6$ alkyl. In embodiments, $R^{12}$ is independently substituted or unsubstituted 2 to 6 membered heteroalkyl. In embodiments, $R^{12}$ is independently substituted or unsubstituted $C_3$-$C_8$ cycloalkyl. In embodiments, $R^{12}$ is independently substituted or unsubstituted 3 to 8 membered heterocycloalkyl. In embodiments, $R^{12}$ is independently substituted or unsubstituted $C_6$ aryl. In embodiments, $R^{12}$ is independently substituted or unsubstituted 5 to 6 membered heteroaryl. In embodiments, $R^{12}$ is independently substituted $C_1$-$C_6$ alkyl. In embodiments, $R^{12}$ is independently substituted 2 to 6 membered heteroalkyl. In embodiments, $R^{12}$ is independently substituted $C_3$-$C_8$ cycloalkyl. In embodiments, $R^{12}$ is independently substituted 3 to 8 membered heterocycloalkyl. In embodiments, $R^{12}$ is independently substituted $C_6$ aryl. In embodiments, $R^{12}$ is independently substituted 5 to 6 membered heteroaryl. In embodiments, $R^{12}$ is independently unsubstituted $C_1$-$C_6$ alkyl. In embodiments, $R^{12}$ is independently unsubstituted 2 to 6 membered heteroalkyl. In embodiments, $R^{12}$ is independently unsubstituted $C_3$-$C_8$ cycloalkyl. In embodiments, $R^{12}$ is independently unsubstituted 3 to 8 membered heterocycloalkyl. In embodiments, $R^{12}$ is independently unsubstituted $C_6$ aryl. In embodiments, $R^{12}$ is independently unsubstituted 5 to 6 membered heteroaryl.

In embodiments, each $R^{13}$ is independently hydrogen. In embodiments, each $R^{13}$ is independently —CX$_3$. In embodiments, each $R^{13}$ is independently —CN. In embodiments, each $R^{13}$ is independently —COOH. In embodiments, each $R^{13}$ is independently —CONH$_2$. In embodiments, each $R^{13}$ is independently —CHX$_2$. In embodiments, each $R^{13}$ is independently —CH$_2$X. In embodiments, each $R^{13}$ is independently substituted or unsubstituted alkyl. In embodiments, each $R^{13}$ is independently substituted or unsubstituted heteroalkyl. In embodiments, each $R^{13}$ is independently substituted or unsubstituted cycloalkyl. In embodiments, each $R^{13}$ is independently substituted or unsubstituted heterocycloalkyl. In embodiments, each $R^{13}$ is independently substituted or unsubstituted aryl. In embodiments, each $R^{13}$ is independently or substituted or unsubstituted heteroaryl. In embodiments, $R^{13}$ is independently substituted alkyl. In embodiments, $R^{13}$ is independently substituted heteroalkyl. In embodiments, $R^{13}$ is independently substituted cycloalkyl. In embodiments, $R^{13}$ is independently substituted heterocycloalkyl. In embodiments, $R^{13}$ is independently substituted aryl. In embodiments, $R^{13}$ is independently substituted heteroaryl. In embodiments, $R^{13}$ is independently unsubstituted alkyl. In embodiments, $R^{13}$ is independently unsubstituted heteroalkyl. In embodiments, $R^{13}$ is independently unsubstituted cycloalkyl. In embodiments, $R^{13}$ is independently unsubstituted heterocycloalkyl. In embodiments, $R^{13}$ is independently unsubstituted aryl. In embodiments, $R^{13}$ is independently unsubstituted heteroaryl. In embodiments, $R^{11}$ is independently substituted or unsubstituted $C_1$-$C_6$ alkyl. In embodiments, $R^{13}$ is independently substituted or unsubstituted 2 to 6 membered heteroalkyl. In embodiments, $R^{13}$ is independently substituted or unsubstituted $C_3$-$C_8$ cycloalkyl. In embodiments, $R^{13}$ is independently substituted or unsubstituted 3 to 8 membered heterocycloalkyl. In embodiments, $R^{13}$ is independently substituted or unsubstituted $C_6$ aryl. In embodiments, $R^{13}$ is independently substituted or unsubstituted 5 to 6 membered heteroaryl. In embodiments, $R^{13}$ is independently substituted $C_1$-$C_6$ alkyl. In embodiments, $R^{13}$ is independently substituted 2 to 6 membered heteroalkyl. In embodiments, $R^{13}$ is independently substituted $C_3$-$C_8$ cycloalkyl. In embodiments, $R^{13}$ is independently substituted 3 to 8 membered heterocycloalkyl. In embodiments, $R^{13}$ is independently substituted $C_6$ aryl. In embodiments, $R^{13}$ is independently substituted 5 to 6 membered heteroaryl. In embodiments, $R^{13}$ is independently unsubstituted $C_1$-$C_6$ alkyl. In embodiments, $R^{13}$ is independently unsubstituted 2 to 6 membered heteroalkyl. In embodiments, $R^{13}$ is independently unsubstituted $C_3$-$C_8$ cycloalkyl. In embodiments, $R^{13}$ is independently unsubstituted 3 to 8 membered heterocycloalkyl. In embodiments, $R^{13}$ is independently unsubstituted $C_6$ aryl. In embodiments, $R^{13}$ is independently unsubstituted 5 to 6 membered heteroaryl.

In embodiments, each $R^{14}$ is independently hydrogen. In embodiments, each $R^{14}$ is independently —CX$_3$. In embodiments, each $R^{14}$ is independently —CN. In embodiments, each $R^{14}$ is independently —COOH. In embodiments, each $R^{14}$ is independently —CONH$_2$. In embodiments, each $R^{14}$ is independently —CHX$_2$. In embodiments, each $R^{14}$ is independently —CH$_2$X. In embodiments, each $R^{14}$ is independently substituted or unsubstituted alkyl. In embodiments, each $R^{14}$ is independently substituted or unsubstituted heteroalkyl. In embodiments, each $R^{14}$ is independently substituted or unsubstituted cycloalkyl. In embodiments, each $R^{14}$ is independently substituted or unsubstituted heterocycloalkyl. In embodiments, each $R^{14}$ is independently substituted or unsubstituted aryl. In embodiments, each $R^{14}$ is independently or substituted or unsubstituted heteroaryl. In embodiments, $R^{14}$ is independently substituted alkyl. In embodiments, $R^{14}$ is independently substituted heteroalkyl. In embodiments, $R^{14}$ is independently substituted cycloalkyl. In embodiments, $R^{14}$ is independently substituted heterocycloalkyl. In embodiments, $R^{14}$ is independently substituted aryl. In embodiments, $R^{14}$ is independently substituted heteroaryl. In embodiments, $R^{14}$ is independently unsubstituted alkyl. In embodiments, $R^{14}$ is independently unsubstituted heteroalkyl. In embodiments, $R^{14}$ is independently unsubstituted cycloalkyl. In embodiments, $R^{14}$ is independently unsubstituted heterocycloalkyl. In embodiments, $R^{14}$ is independently unsubstituted aryl. In embodiments, $R^{14}$ is independently unsubstituted heteroaryl. In embodiments, $R^{14}$ is independently substituted or unsubstituted $C_1$-$C_6$ alkyl. In embodiments, $R^{14}$ is independently substituted or unsubstituted 2 to 6 membered heteroalkyl. In embodiments, $R^{14}$ is independently substituted or unsubstituted $C_3$-$C_8$ cycloalkyl. In embodiments, $R^{14}$ is independently substituted or unsubstituted 3 to 8 membered heterocycloalkyl. In embodiments, $R^{14}$ is independently substituted or unsubstituted $C_6$ aryl. In embodiments, $R^{14}$ is independently substituted or unsubstituted 5 to 6 membered heteroaryl. In embodiments, $R^{14}$ is independently substituted $C_1$-$C_6$ alkyl. In embodiments, $R^{14}$ is independently substituted 2 to 6 membered heteroalkyl. In embodiments, $R^{14}$ is independently substituted $C_3$-$C_8$ cycloalkyl. In embodiments, $R^{14}$ is independently substituted 3 to 8 membered heterocycloalkyl. In embodiments, $R^{14}$ is independently substituted $C_6$ aryl. In embodiments, $R^{14}$ is independently substituted 5 to 6 membered heteroaryl. In embodiments, $R^{14}$ is independently unsubstituted $C_1$-$C_6$ alkyl. In embodiments, $R^{14}$ is independently unsubstituted 2 to 6 membered heteroalkyl. In embodiments, $R^{14}$ is independently unsubstituted $C_3$-$C_8$ cycloalkyl. In embodiments, $R^{14}$ is independently unsubstituted 3 to 8 membered heterocycloalkyl. In embodiments, $R^{14}$ is independently unsubstituted $C_6$ aryl. In embodiments, $R^{14}$ is independently unsubstituted 5 to 6 membered heteroaryl.

In embodiments, each $R^{15}$ is independently hydrogen. In embodiments, each $R^{15}$ is independently —$CX_3$. In embodiments, each $R^{15}$ is independently —CN. In embodiments, each $R^{15}$ is independently —COOH. In embodiments, each $R^{15}$ is independently —$CONH_2$. In embodiments, each $R^{15}$ is independently —$CHX_2$. In embodiments, each $R^{15}$ is independently —$CH_2X$. In embodiments, each $R^{15}$ is independently substituted or unsubstituted alkyl. In embodiments, each $R^{15}$ is independently substituted or unsubstituted heteroalkyl. In embodiments, each $R^{15}$ is independently substituted or unsubstituted cycloalkyl. In embodiments, each $R^{15}$ is independently substituted or unsubstituted heterocycloalkyl. In embodiments, each $R^{15}$ is independently substituted or unsubstituted aryl. In embodiments, each $R^{15}$ is independently or substituted or unsubstituted heteroaryl. In embodiments, $R^{15}$ is independently substituted alkyl. In embodiments, $R^{15}$ is independently substituted heteroalkyl. In embodiments, $R^{15}$ is independently substituted cycloalkyl. In embodiments, $R^{15}$ is independently substituted heterocycloalkyl. In embodiments, $R^{15}$ is independently substituted aryl. In embodiments, $R^{15}$ is independently substituted heteroaryl. In embodiments, $R^{15}$ is independently unsubstituted alkyl. In embodiments, $R^{15}$ is independently unsubstituted heteroalkyl. In embodiments, $R^{15}$ is independently unsubstituted cycloalkyl. In embodiments, $R^{15}$ is independently unsubstituted heterocycloalkyl. In embodiments, $R^{15}$ is independently unsubstituted aryl. In embodiments, $R^{15}$ is independently unsubstituted heteroaryl. In embodiments, $R^{15}$ is independently substituted or unsubstituted $C_1$-$C_6$ alkyl. In embodiments, $R^{15}$ is independently substituted or unsubstituted 2 to 6 membered heteroalkyl. In embodiments, $R^{15}$ is independently substituted or unsubstituted $C_3$-$C_8$ cycloalkyl. In embodiments, $R^{15}$ is independently substituted or unsubstituted 3 to 8 membered heterocycloalkyl. In embodiments, $R^{15}$ is independently substituted or unsubstituted $C_6$ aryl. In embodiments, $R^{15}$ is independently substituted or unsubstituted 5 to 6 membered heteroaryl. In embodiments, $R^{15}$ is independently substituted $C_1$-$C_6$ alkyl. In embodiments, $R^{15}$ is independently substituted 2 to 6 membered heteroalkyl. In embodiments, $R^{15}$ is independently substituted $C_3$-$C_8$ cycloalkyl. In embodiments, $R^{15}$ is independently substituted 3 to 8 membered heterocycloalkyl. In embodiments, $R^{15}$ is independently substituted $C_6$ aryl. In embodiments, $R^{15}$ is independently substituted 5 to 6 membered heteroaryl. In embodiments, $R^{15}$ is independently unsubstituted $C_1$-$C_6$ alkyl. In embodiments, $R^{15}$ is independently unsubstituted 2 to 6 membered heteroalkyl. In embodiments, $R^{15}$ is independently unsubstituted $C_3$-$C_8$ cycloalkyl. In embodiments, $R^{15}$ is independently unsubstituted 3 to 8 membered heterocycloalkyl. In embodiments, $R^{15}$ is independently unsubstituted $C_6$ aryl. In embodiments, $R^{15}$ is independently unsubstituted 5 to 6 membered heteroaryl.

In embodiments, each $R^{16}$ is independently hydrogen. In embodiments, each $R^{16}$ is independently —$CX_3$. In embodiments, each $R^{16}$ is independently —CN. In embodiments, each $R^{16}$ is independently —COOH. In embodiments, each $R^{16}$ is independently —$CONH_2$. In embodiments, each $R^{16}$ is independently —$CHX_2$. In embodiments, each $R^{16}$ is independently —$CH_2X$. In embodiments, each $R^{16}$ is independently substituted or unsubstituted alkyl. In embodiments, each $R^{16}$ is independently substituted or unsubstituted heteroalkyl. In embodiments, each $R^{16}$ is independently substituted or unsubstituted cycloalkyl. In embodiments, each $R^{16}$ is independently substituted or unsubstituted heterocycloalkyl. In embodiments, each $R^{16}$ is independently substituted or unsubstituted aryl. In embodiments, each $R^{16}$ is independently or substituted or unsubstituted heteroaryl. In embodiments, $R^{16}$ is independently substituted alkyl. In embodiments, $R^{16}$ is independently substituted heteroalkyl. In embodiments, $R^{16}$ is independently substituted cycloalkyl. In embodiments, $R^{16}$ is independently substituted heterocycloalkyl. In embodiments, $R^{16}$ is independently substituted aryl. In embodiments, $R^{16}$ is independently substituted heteroaryl. In embodiments, $R^{16}$ is independently unsubstituted alkyl. In embodiments, $R^{16}$ is independently unsubstituted heteroalkyl. In embodiments, $R^{16}$ is independently unsubstituted cycloalkyl. In embodiments, $R^{16}$ is independently unsubstituted heterocycloalkyl. In embodiments, $R^{16}$ is independently unsubstituted aryl. In embodiments, $R^{16}$ is independently unsubstituted heteroaryl. In embodiments, $R^{16}$ is independently substituted or unsubstituted $C_1$-$C_6$ alkyl. In embodiments, $R^{16}$ is independently substituted or unsubstituted 2 to 6 membered heteroalkyl. In embodiments, $R^{16}$ is independently substituted or unsubstituted $C_3$-$C_8$ cycloalkyl. In embodiments, $R^{16}$ is independently substituted or unsubstituted 3 to 8 membered heterocycloalkyl. In embodiments, $R^{16}$ is independently substituted or unsubstituted $C_6$ aryl. In embodiments, $R^{16}$ is independently substituted or unsubstituted 5 to 6 membered heteroaryl. In embodiments, $R^{16}$ is independently substituted $C_1$-$C_6$ alkyl. In embodiments, $R^{16}$ is independently substituted 2 to 6 membered heteroalkyl. In embodiments, $R^{16}$ is independently substituted $C_3$-$C_8$ cycloalkyl. In embodiments, $R^{16}$ is independently substituted 3 to 8 membered heterocycloalkyl. In embodiments, $R^{16}$ is independently substituted $C_6$ aryl. In embodiments, $R^{16}$ is independently substituted 5 to 6 membered heteroaryl. In embodiments, $R^{16}$ is independently unsubstituted $C_1$-$C_6$ alkyl. In embodiments, $R^{16}$ is independently unsubstituted 2 to 6 membered heteroalkyl. In embodiments, $R^{16}$ is independently unsubstituted $C_3$-$C_8$ cycloalkyl. In embodiments, $R^{16}$ is independently unsubstituted 3 to 8 membered heterocycloalkyl. In embodiments, $R^{16}$ is independently unsubstituted $C_6$ aryl. In embodiments, $R^{16}$ is independently unsubstituted 5 to 6 membered heteroaryl.

In embodiments, each $R^{17}$ is independently hydrogen. In embodiments, each $R^{17}$ is independently —$CX_3$. In embodiments, each $R^{17}$ is independently —CN. In embodiments, each $R^{17}$ is independently —COOH. In embodiments, each $R^{17}$ is independently —$CONH_2$. In embodiments, each $R^{17}$ is independently —CHX$_2$. In embodiments, each R$^{17}$ is independently —CH$_2$X. In embodiments, each R$^{17}$ is independently substituted or unsubstituted alkyl. In embodiments, each R$^{17}$ is independently substituted or unsubstituted heteroalkyl. In embodiments, each R$^{17}$ is independently substituted or unsubstituted cycloalkyl. In embodiments, each R$^{17}$ is independently substituted or unsubstituted heterocycloalkyl. In embodiments, each R$^{17}$ is independently substituted or unsubstituted aryl. In embodiments, each R$^{17}$ is independently or substituted or unsubstituted heteroaryl. In embodiments, R$^{17}$ is independently substituted alkyl. In embodiments, R$^{17}$ is independently substituted heteroalkyl. In embodiments, R$^{17}$ is independently substituted cycloalkyl. In embodiments, R$^{17}$ is independently substituted heterocycloalkyl. In embodiments, R$^{17}$ is independently substituted aryl. In embodiments, R$^{17}$ is independently substituted heteroaryl. In embodiments, R$^{17}$ is independently unsubstituted alkyl. In embodiments, R$^{17}$ is independently unsubstituted heteroalkyl. In embodiments, R$^{17}$ is independently unsubstituted cycloalkyl. In embodiments, R$^{17}$ is independently unsubstituted heterocycloalkyl. In embodiments, R$^{17}$ is independently unsubstituted aryl. In embodiments, R$^{17}$ is independently unsubstituted heteroaryl. In embodiments, R$^{17}$ is independently substituted or unsubstituted C$_1$-C$_6$ alkyl. In embodiments, R$^{17}$ is independently substituted or unsubstituted 2 to 6 membered heteroalkyl. In embodiments, R$^{17}$ is independently substituted or unsubstituted C$_3$-C$_8$ cycloalkyl. In embodiments, R$^{17}$ is independently substituted or unsubstituted 3 to 8 membered heterocycloalkyl. In embodiments, R$^{17}$ is independently substituted or unsubstituted C$_6$ aryl. In embodiments, R$^{17}$ is independently substituted or unsubstituted 5 to 6 membered heteroaryl. In embodiments, R$^{17}$ is independently substituted C$_1$-C$_6$ alkyl. In embodiments, R$^{17}$ is independently substituted 2 to 6 membered heteroalkyl. In embodiments, R$^{17}$ is independently substituted C$_3$-C$_8$ cycloalkyl. In embodiments, R$^{17}$ is independently substituted 3 to 8 membered heterocycloalkyl. In embodiments, R$^{17}$ is independently substituted C$_6$ aryl. In embodiments, R$^{17}$ is independently substituted 5 to 6 membered heteroaryl. In embodiments, R$^{17}$ is independently unsubstituted C$_1$-C$_6$ alkyl. In embodiments, R$^{17}$ is independently unsubstituted 2 to 6 membered heteroalkyl. In embodiments, R$^{17}$ is independently unsubstituted C$_3$-C$_8$ cycloalkyl. In embodiments, R$^{17}$ is independently unsubstituted 3 to 8 membered heterocycloalkyl. In embodiments, R$^{17}$ is independently unsubstituted C$_6$ aryl. In embodiments, R$^{17}$ is independently unsubstituted 5 to 6 membered heteroaryl.

In embodiments, each R$^{18}$ is independently hydrogen. In embodiments, each R$^{18}$ is independently —CX$_3$. In embodiments, each R$^{18}$ is independently —CN. In embodiments, each R$^{18}$ is independently —COOH. In embodiments, each R$^{18}$ is independently —CONH$_2$. In embodiments, each R$^{18}$ is independently —CHX$_2$. In embodiments, each R$^{18}$ is independently —CH$_2$X. In embodiments, each R$^{18}$ is independently substituted or unsubstituted alkyl. In embodiments, each R$^{18}$ is independently substituted or unsubstituted heteroalkyl. In embodiments, each R$^{18}$ is independently substituted or unsubstituted cycloalkyl. In embodiments, each R$^{18}$ is independently substituted or unsubstituted heterocycloalkyl. In embodiments, each R$^{18}$ is independently substituted or unsubstituted aryl. In embodiments, each R$^{18}$ is independently or substituted or unsubstituted heteroaryl. In embodiments, R$^{18}$ is independently substituted alkyl. In embodiments, R$^{18}$ is independently substituted heteroalkyl. In embodiments, R$^{18}$ is independently substituted cycloalkyl. In embodiments, R$^{18}$ is independently substituted heterocycloalkyl. In embodiments, R$^{18}$ is independently substituted aryl. In embodiments, R$^{18}$ is independently substituted heteroaryl. In embodiments, R$^{18}$ is independently unsubstituted alkyl. In embodiments, R$^{18}$ is independently unsubstituted heteroalkyl. In embodiments, R$^{18}$ is independently unsubstituted cycloalkyl. In embodiments, R$^{18}$ is independently unsubstituted heterocycloalkyl. In embodiments, R$^{18}$ is independently unsubstituted aryl. In embodiments, R$^{18}$ is independently unsubstituted heteroaryl. In embodiments, R$^{18}$ is independently substituted or unsubstituted C$_1$-C$_6$ alkyl. In embodiments, R$^{18}$ is independently substituted or unsubstituted 2 to 6 membered heteroalkyl. In embodiments, R$^{18}$ is independently substituted or unsubstituted C$_3$-C$_8$ cycloalkyl. In embodiments, R$^{18}$ is independently substituted or unsubstituted 3 to 8 membered heterocycloalkyl. In embodiments, R$^{18}$ is independently substituted or unsubstituted C$_6$ aryl. In embodiments, R$^{18}$ is independently substituted or unsubstituted 5 to 6 membered heteroaryl. In embodiments, R$^{18}$ is independently substituted C$_1$-C$_6$ alkyl. In embodiments, R$^{18}$ is independently substituted 2 to 6 membered heteroalkyl. In embodiments, R$^{18}$ is independently substituted C$_3$-C$_8$ cycloalkyl. In embodiments, R$^{18}$ is independently substituted 3 to 8 membered heterocycloalkyl. In embodiments, R$^{18}$ is independently substituted C$_6$ aryl. In embodiments, R$^{18}$ is independently substituted 5 to 6 membered heteroaryl. In embodiments, R$^{18}$ is independently unsubstituted C$_1$-C$_6$ alkyl. In embodiments, R$^{18}$ is independently unsubstituted 2 to 6 membered heteroalkyl. In embodiments, R$^{18}$ is independently unsubstituted C$_3$-C$_8$ cycloalkyl. In embodiments, R$^{18}$ is independently unsubstituted 3 to 8 membered heterocycloalkyl. In embodiments, R$^{18}$ is independently unsubstituted C$_6$ aryl. In embodiments, R$^{18}$ is independently unsubstituted 5 to 6 membered heteroaryl.

In embodiments, each R$^{19}$ is independently hydrogen. In embodiments, each R$^{19}$ is independently —CX$_3$. In embodiments, each R$^{19}$ is independently —CN. In embodiments, each R$^{19}$ is independently —COOH. In embodiments, each R$^{19}$ is independently —CONH$_2$. In embodiments, each R$^{19}$ is independently —CHX$_2$. In embodiments, each R$^{19}$ is independently —CH$_2$X. In embodiments, each R$^{19}$ is independently substituted or unsubstituted alkyl. In embodiments, each R$^{19}$ is independently substituted or unsubstituted heteroalkyl. In embodiments, each R$^{19}$ is independently substituted or unsubstituted cycloalkyl. In embodiments, each R$^{19}$ is independently substituted or unsubstituted heterocycloalkyl. In embodiments, each R$^{19}$ is independently substituted or unsubstituted aryl. In embodiments, each R$^{19}$ is independently or substituted or unsubstituted heteroaryl. In embodiments, R$^{19}$ is independently substituted alkyl. In embodiments, R$^{19}$ is independently substituted heteroalkyl. In embodiments, R$^{19}$ is independently substituted cycloalkyl. In embodiments, R$^{19}$ is independently substituted heterocycloalkyl. In embodiments, R$^{19}$ is independently substituted aryl. In embodiments, R$^{19}$ is independently substituted heteroaryl. In embodiments, R$^{19}$ is independently unsubstituted alkyl. In embodiments, R$^{19}$ is independently unsubstituted heteroalkyl. In embodiments, R$^{19}$ is independently unsubstituted cycloalkyl. In embodiments, R$^{19}$ is independently unsubstituted heterocycloalkyl. In embodiments, R$^{19}$ is independently unsubstituted aryl. In embodiments, R$^{19}$ is independently unsubstituted heteroaryl. In embodiments, R$^{19}$ is independently substituted or unsubstituted C$_1$-C$_6$ alkyl. In embodiments, R$^{19}$ is independently substituted or unsubstituted 2 to 6 membered heteroalkyl. In embodiments, R$^{19}$ is independently substituted or unsubstituted C$_3$-C$_8$ cycloalkyl. In embodiments, $R^{19}$ is independently substituted or unsubstituted 3 to 8 membered heterocycloalkyl. In embodiments, $R^{19}$ is independently substituted or unsubstituted $C_6$ aryl. In embodiments, $R^{19}$ is independently substituted or unsubstituted 5 to 6 membered heteroaryl. In embodiments, $R^{19}$ is independently substituted $C_1$-$C_6$ alkyl. In embodiments, $R^{19}$ is independently substituted 2 to 6 membered heteroalkyl. In embodiments, $R^{19}$ is independently substituted $C_3$-$C_8$ cycloalkyl. In embodiments, $R^{19}$ is independently substituted 3 to 8 membered heterocycloalkyl. In embodiments, $R^{19}$ is independently substituted $C_6$ aryl. In embodiments, $R^{19}$ is independently substituted 5 to 6 membered heteroaryl. In embodiments, $R^{19}$ is independently unsubstituted $C_1$-$C_6$alkyl. In embodiments, $R^{19}$ is independently unsubstituted 2 to 6 membered heteroalkyl. In embodiments, $R^{19}$ is independently unsubstituted $C_3$-$C_8$ cycloalkyl. In embodiments, $R^{19}$ is independently unsubstituted 3 to 8 membered heterocycloalkyl. In embodiments, $R^{19}$ is independently unsubstituted $C_6$ aryl. In embodiments, $R^{19}$ is independently unsubstituted 5 to 6 membered heteroaryl.

In embodiments, each $R^{20}$ is independently hydrogen. In embodiments, each $R^{20}$ is independently —$CX_3$. In embodiments, each $R^{20}$ is independently —CN. In embodiments, each $R^{20}$ is independently —COOH. In embodiments, each $R^{20}$ is independently —$CONH_2$. In embodiments, each $R^{20}$ is independently —$CHX_2$. In embodiments, each $R^{20}$ is independently —$CH_2X$. In embodiments, each $R^{20}$ is independently substituted or unsubstituted alkyl. In embodiments, each $R^{20}$ is independently substituted or unsubstituted heteroalkyl. In embodiments, each $R^{20}$ is independently substituted or unsubstituted cycloalkyl. In embodiments, each $R^{20}$ is independently substituted or unsubstituted heterocycloalkyl. In embodiments, each $R^{20}$ is independently substituted or unsubstituted aryl. In embodiments, each $R^{20}$ is independently or substituted or unsubstituted heteroaryl. In embodiments, $R^{20}$ is independently substituted alkyl. In embodiments, $R^{20}$ is independently substituted heteroalkyl. In embodiments, $R^{20}$ is independently substituted cycloalkyl. In embodiments, $R^{20}$ is independently substituted heterocycloalkyl. In embodiments, $R^{20}$ is independently substituted aryl. In embodiments, $R^{20}$ is independently substituted heteroaryl. In embodiments, $R^{20}$ is independently unsubstituted alkyl. In embodiments, $R^{20}$ is independently unsubstituted heteroalkyl. In embodiments, $R^{20}$ is independently unsubstituted cycloalkyl. In embodiments, $R^{20}$ is independently unsubstituted heterocycloalkyl. In embodiments, $R^{20}$ is independently unsubstituted aryl. In embodiments, $R^{20}$ is independently unsubstituted heteroaryl. In embodiments, $R^{20}$ is independently substituted or unsubstituted $C_1$-$C_6$ alkyl. In embodiments, $R^{20}$ is independently substituted or unsubstituted 2 to 6 membered heteroalkyl. In embodiments, $R^{20}$ is independently substituted or unsubstituted $C_3$-$C_8$ cycloalkyl. In embodiments, $R^{20}$ is independently substituted or unsubstituted 3 to 8 membered heterocycloalkyl. In embodiments, $R^{20}$ is independently substituted or unsubstituted $C_6$ aryl. In embodiments, $R^{20}$ is independently substituted or unsubstituted 5 to 6 membered heteroaryl. In embodiments, $R^{20}$ is independently substituted $C_1$-$C_6$ alkyl. In embodiments, $R^{20}$ is independently substituted 2 to 6 membered heteroalkyl. In embodiments, $R^{20}$ is independently substituted $C_3$-$C_8$ cycloalkyl. In embodiments, $R^{20}$ is independently substituted 3 to 8 membered heterocycloalkyl. In embodiments, $R^{20}$ is independently substituted $C_6$ aryl. In embodiments, $R^{20}$ is independently substituted 5 to 6 membered heteroaryl. In embodiments, $R^{20}$ is independently unsubstituted $C_1$-$C_6$ alkyl. In embodiments, $R^{20}$ is independently unsubstituted 2 to 6 membered heteroalkyl. In embodiments, $R^{20}$ is independently unsubstituted $C_3$-$C_8$ cycloalkyl. In embodiments, $R^{20}$ is independently unsubstituted 3 to 8 membered heterocycloalkyl. In embodiments, $R^{20}$ is independently unsubstituted $C_6$ aryl. In embodiments, $R^{20}$ is independently unsubstituted 5 to 6 membered heteroaryl.

In embodiments, each $R^{21}$ is independently hydrogen. In embodiments, each $R^{21}$ is independently —$CX_3$. In embodiments, each $R^{21}$ is independently —CN. In embodiments, each $R^{21}$ is independently —COOH. In embodiments, each $R^{21}$ is independently —$CONH_2$. In embodiments, each $R^{21}$ is independently —$CHX_2$. In embodiments, each $R^{21}$ is independently —$CH_2X$. In embodiments, each $R^{21}$ is independently substituted or unsubstituted alkyl. In embodiments, each $R^{21}$ is independently substituted or unsubstituted heteroalkyl. In embodiments, each $R^{21}$ is independently substituted or unsubstituted cycloalkyl. In embodiments, each $R^{21}$ is independently substituted or unsubstituted heterocycloalkyl. In embodiments, each $R^{21}$ is independently substituted or unsubstituted aryl. In embodiments, each $R^{21}$ is independently or substituted or unsubstituted heteroaryl. In embodiments, $R^{21}$ is independently substituted alkyl. In embodiments, $R^{21}$ is independently substituted heteroalkyl. In embodiments, $R^{21}$ is independently substituted cycloalkyl. In embodiments, $R^{21}$ is independently substituted heterocycloalkyl. In embodiments, $R^{21}$ is independently substituted aryl. In embodiments, $R^{21}$ is independently substituted heteroaryl. In embodiments, $R^{21}$ is independently unsubstituted alkyl. In embodiments, $R^{21}$ is independently unsubstituted heteroalkyl. In embodiments, $R^{21}$ is independently unsubstituted cycloalkyl. In embodiments, $R^{21}$ is independently unsubstituted heterocycloalkyl. In embodiments, $R^{21}$ is independently unsubstituted aryl. In embodiments, $R^{21}$ is independently unsubstituted heteroaryl. In embodiments, $R^{21}$ is independently substituted or unsubstituted $C_1$-$C_6$ alkyl. In embodiments, $R^{21}$ is independently substituted or unsubstituted 2 to 6 membered heteroalkyl. In embodiments, $R^{21}$ is independently substituted or unsubstituted $C_3$-$C_8$ cycloalkyl. In embodiments, $R^{21}$ is independently substituted or unsubstituted 3 to 8 membered heterocycloalkyl. In embodiments, $R^{21}$ is independently substituted or unsubstituted $C_6$ aryl. In embodiments, $R^{21}$ is independently substituted or unsubstituted 5 to 6 membered heteroaryl. In embodiments, $R^{21}$ is independently substituted $C_1$-$C_6$ alkyl. In embodiments, $R^{21}$ is independently substituted 2 to 6 membered heteroalkyl. In embodiments, $R^{21}$ is independently substituted $C_3$-$C_8$ cycloalkyl. In embodiments, $R^{21}$ is independently substituted 3 to 8 membered heterocycloalkyl. In embodiments, $R^{21}$ is independently substituted $C_6$ aryl. In embodiments, $R^{21}$ is independently substituted 5 to 6 membered heteroaryl. In embodiments, $R^{21}$ is independently unsubstituted $C_1$-$C_6$ alkyl. In embodiments, $R^{21}$ is independently unsubstituted 2 to 6 membered heteroalkyl. In embodiments, $R^{21}$ is independently unsubstituted $C_3$-$C_8$ cycloalkyl. In embodiments, $R^{21}$ is independently unsubstituted 3 to 8 membered heterocycloalkyl. In embodiments, $R^{21}$ is independently unsubstituted $C_6$ aryl. In embodiments, $R^{21}$ is independently unsubstituted 5 to 6 membered heteroaryl.

In embodiments, each $R^{22}$ is independently hydrogen. In embodiments, each $R^{22}$ is independently —$CX_3$. In embodiments, each $R^{22}$ is independently —CN. In embodiments, each $R^{22}$ is independently —COOH. In embodiments, each $R^{22}$ is independently —$CONH_2$. In embodiments, each $R^{22}$ is independently —$CHX_2$. In embodiments, each $R^{22}$ is independently —$CH_2X$. In embodiments, each $R^{22}$ is independently substituted or unsubstituted alkyl. In embodiments, each $R^{22}$ is independently substituted or unsubstituted heteroalkyl. In embodiments, each $R^{22}$ is independently substituted or unsubstituted cycloalkyl. In embodiments, each $R^{22}$ is independently substituted or unsubstituted heterocycloalkyl. In embodiments, each $R^{22}$ is independently substituted or unsubstituted aryl. In embodiments, each $R^{22}$ is independently or substituted or unsubstituted heteroaryl. In embodiments, $R^{22}$ is independently substituted alkyl. In embodiments, $R^{22}$ is independently substituted heteroalkyl. In embodiments, $R^{22}$ is independently substituted cycloalkyl. In embodiments, $R^{22}$ is independently substituted heterocycloalkyl. In embodiments, $R^{22}$ is independently substituted aryl. In embodiments, $R^{22}$ is independently substituted heteroaryl. In embodiments, $R^{22}$ is independently unsubstituted alkyl. In embodiments, $R^{22}$ is independently unsubstituted heteroalkyl. In embodiments, $R^{22}$ is independently unsubstituted cycloalkyl. In embodiments, $R^{22}$ is independently unsubstituted heterocycloalkyl. In embodiments, $R^{22}$ is independently unsubstituted aryl. In embodiments, $R^{22}$ is independently unsubstituted heteroaryl. In embodiments, $R^{22}$ is independently substituted or unsubstituted $C_1$-$C_6$ alkyl. In embodiments, $R^{22}$ is independently substituted or unsubstituted 2 to 6 membered heteroalkyl. In embodiments, $R^{22}$ is independently substituted or unsubstituted $C_3$-$C_8$ cycloalkyl. In embodiments, $R^{22}$ is independently substituted or unsubstituted 3 to 8 membered heterocycloalkyl. In embodiments, $R^{22}$ is independently substituted or unsubstituted $C_6$ aryl. In embodiments, $R^{22}$ is independently substituted or unsubstituted 5 to 6 membered heteroaryl. In embodiments, $R^{22}$ is independently substituted $C_1$-$C_6$ alkyl. In embodiments, $R^{22}$ is independently substituted 2 to 6 membered heteroalkyl. In embodiments, $R^{22}$ is independently substituted $C_3$-$C_8$ cycloalkyl. In embodiments, $R^{22}$ is independently substituted 3 to 8 membered heterocycloalkyl. In embodiments, $R^{22}$ is independently substituted $C_6$ aryl. In embodiments, $R^{22}$ is independently substituted 5 to 6 membered heteroaryl. In embodiments, $R^{22}$ is independently unsubstituted $C_1$-$C_6$ alkyl. In embodiments, $R^{22}$ is independently unsubstituted 2 to 6 membered heteroalkyl. In embodiments, $R^{22}$ is independently unsubstituted $C_3$-$C_8$ cycloalkyl. In embodiments, $R^{22}$ is independently unsubstituted 3 to 8 membered heterocycloalkyl. In embodiments, $R^{22}$ is independently unsubstituted $C_6$ aryl. In embodiments, $R^{22}$ is independently unsubstituted 5 to 6 membered heteroaryl.

In embodiments, each $R^{23}$ is independently hydrogen. In embodiments, each $R^{23}$ is independently —$CX_3$. In embodiments, each $R^{23}$ is independently —CN. In embodiments, each $R^{13}$ is independently —COOH. In embodiments, each $R^{23}$ is independently —$CONH_2$. In embodiments, each $R^{23}$ is independently —$CHX_2$. In embodiments, each $R^{23}$ is independently —$CH_2X$. In embodiments, each $R^{23}$ is independently substituted or unsubstituted alkyl. In embodiments, each $R^{23}$ is independently substituted or unsubstituted heteroalkyl. In embodiments, each $R^{23}$ is independently substituted or unsubstituted cycloalkyl. In embodiments, each $R^{23}$ is independently substituted or unsubstituted heterocycloalkyl. In embodiments, each $R^{23}$ is independently substituted or unsubstituted aryl. In embodiments, each $R^{23}$ is independently or substituted or unsubstituted heteroaryl. In embodiments, $R^{23}$ is independently substituted alkyl. In embodiments, $R^{23}$ is independently substituted heteroalkyl. In embodiments, $R^{23}$ is independently substituted cycloalkyl. In embodiments, $R^{23}$ is independently substituted heterocycloalkyl. In embodiments, $R^{23}$ is independently substituted aryl. In embodiments, $R^{23}$ is independently substituted heteroaryl. In embodiments, $R^{23}$ is independently unsubstituted alkyl. In embodiments, $R^{23}$ is independently unsubstituted heteroalkyl. In embodiments, $R^{23}$ is independently unsubstituted cycloalkyl. In embodiments, $R^{23}$ is independently unsubstituted heterocycloalkyl. In embodiments, $R^{23}$ is independently unsubstituted aryl. In embodiments, $R^{23}$ is independently unsubstituted heteroaryl. In embodiments, $R^{23}$ is independently substituted or unsubstituted $C_1$-$C_6$ alkyl. In embodiments, $R^{23}$ is independently substituted or unsubstituted 2 to 6 membered heteroalkyl. In embodiments, $R^{23}$ is independently substituted or unsubstituted $C_3$-$C_8$ cycloalkyl. In embodiments, $R^{23}$ is independently substituted or unsubstituted 3 to 8 membered heterocycloalkyl. In embodiments, $R^{23}$ is independently substituted or unsubstituted $C_6$ aryl. In embodiments, $R^{23}$ is independently substituted or unsubstituted 5 to 6 membered heteroaryl. In embodiments, $R^{23}$ is independently substituted $C_1$-$C_6$ alkyl. In embodiments, $R^{23}$ is independently substituted 2 to 6 membered heteroalkyl. In embodiments, $R^{23}$ is independently substituted $C_3$-$C_8$ cycloalkyl. In embodiments, $R^{23}$ is independently substituted 3 to 8 membered heterocycloalkyl. In embodiments, $R^{23}$ is independently substituted $C_6$ aryl. In embodiments, $R^{23}$ is independently substituted 5 to 6 membered heteroaryl. In embodiments, $R^{23}$ is independently unsubstituted $C_1$-$C_6$ alkyl. In embodiments, $R^{23}$ is independently unsubstituted 2 to 6 membered heteroalkyl. In embodiments, $R^{23}$ is independently unsubstituted $C_3$-$C_8$ cycloalkyl. In embodiments, $R^{23}$ is independently unsubstituted 3 to 8 membered heterocycloalkyl. In embodiments, $R^{23}$ is independently unsubstituted $C_6$ aryl. In embodiments, $R^{23}$ is independently unsubstituted 5 to 6 membered heteroaryl.

In embodiments, each $R^{24}$ is independently hydrogen. In embodiments, each $R^{24}$ is independently —$CX_3$. In embodiments, each $R^{24}$ is independently —CN. In embodiments, each $R^{24}$ is independently —COOH. In embodiments, each $R^{24}$ is independently —$CONH_2$. In embodiments, each $R^{24}$ is independently —$CHX_2$. In embodiments, each $R^{23}$ is independently —$CH_2X$. In embodiments, each $R^{24}$ is independently substituted or unsubstituted alkyl. In embodiments, each $R^{24}$ is independently substituted or unsubstituted heteroalkyl. In embodiments, each $R^{24}$ is independently substituted or unsubstituted cycloalkyl. In embodiments, each $R^{24}$ is independently substituted or unsubstituted heterocycloalkyl. In embodiments, each $R^{24}$ is independently substituted or unsubstituted aryl. In embodiments, each $R^{24}$ is independently or substituted or unsubstituted heteroaryl. In embodiments, $R^{24}$ is independently substituted alkyl. In embodiments, $R^{24}$ is independently substituted heteroalkyl. In embodiments, $R^{24}$ is independently substituted cycloalkyl. In embodiments, $R^{24}$ is independently substituted heterocycloalkyl. In embodiments, $R^{24}$ is independently substituted aryl. In embodiments, $R^{24}$ is independently substituted heteroaryl. In embodiments, $R^{24}$ is independently unsubstituted alkyl. In embodiments, $R^{24}$ is independently unsubstituted heteroalkyl. In embodiments, $R^{24}$ is independently unsubstituted cycloalkyl. In embodiments, $R^{24}$ is independently unsubstituted heterocycloalkyl. In embodiments, $R^{24}$ is independently unsubstituted aryl. In embodiments, $R^{24}$ is independently unsubstituted heteroaryl. In embodiments, $R^{24}$ is independently substituted or unsubstituted $C_1$-$C_6$ alkyl. In embodiments, $R^{24}$ is independently substituted or unsubstituted 2 to 6 membered heteroalkyl. In embodiments, $R^{24}$ is independently substituted or unsubstituted $C_3$-$C_8$ cycloalkyl. In embodiments, $R^{24}$ is independently substituted or unsubstituted 3 to 8 membered heterocycloalkyl. In embodiments, $R^{24}$ is independently substituted or unsubstituted $C_6$ aryl. In embodiments, $R^{24}$ is independently substituted or unsubstituted 5 to 6 membered heteroaryl. In embodiments, $R^{24}$ is independently substituted $C_1$-$C_6$ alkyl. In embodiments, $R^{24}$ is independently substituted 2 to 6 membered heteroalkyl. In embodiments, $R^{24}$ is independently substituted $C_3$-$C_8$ cycloalkyl. In embodiments, $R^{24}$ is independently substituted 3 to 8 membered heterocycloalkyl. In embodiments, $R^{24}$ is independently substituted $C_6$ aryl. In embodiments, $R^{24}$ is independently substituted 5 to 6 membered heteroaryl. In embodiments, $R^{24}$ is independently unsubstituted $C_1$-$C_6$ alkyl. In embodiments, $R^{24}$ is independently unsubstituted 2 to 6 membered heteroalkyl. In embodiments, $R^{24}$ is independently unsubstituted $C_3$-$C_8$ cycloalkyl. In embodiments, $R^{24}$ is independently unsubstituted 3 to 8 membered heterocycloalkyl. In embodiments, $R^{24}$ is independently unsubstituted $C_6$ aryl. In embodiments, $R^{24}$ is independently unsubstituted 5 to 6 membered heteroaryl.

In embodiments, each $R^{25}$ is independently hydrogen. In embodiments, each $R^{25}$ is independently —$CX_3$. In embodiments, each $R^{25}$ is independently —CN. In embodiments, each $R^{25}$ is independently —COOH. In embodiments, each $R^{25}$ is independently —$CONH_2$. In embodiments, each $R^{25}$ is independently —$CHX_2$. In embodiments, each $R^{25}$ is independently —$CH_2X$. In embodiments, each $R^{25}$ is independently substituted or unsubstituted alkyl. In embodiments, each $R^{25}$ is independently substituted or unsubstituted heteroalkyl. In embodiments, each $R^{25}$ is independently substituted or unsubstituted cycloalkyl. In embodiments, each $R^{25}$ is independently substituted or unsubstituted heterocycloalkyl. In embodiments, each $R^{25}$ is independently substituted or unsubstituted aryl. In embodiments, each $R^{25}$ is independently or substituted or unsubstituted heteroaryl. In embodiments, $R^{25}$ is independently substituted alkyl. In embodiments, $R^{25}$ is independently substituted heteroalkyl. In embodiments, $R^{25}$ is independently substituted cycloalkyl. In embodiments, $R^{25}$ is independently substituted heterocycloalkyl. In embodiments, $R^{25}$ is independently substituted aryl. In embodiments, $R^{25}$ is independently substituted heteroaryl. In embodiments, $R^{25}$ is independently unsubstituted alkyl. In embodiments, $R^{25}$ is independently unsubstituted heteroalkyl. In embodiments, $R^{25}$ is independently unsubstituted cycloalkyl. In embodiments, $R^{25}$ is independently unsubstituted heterocycloalkyl. In embodiments, $R^{25}$ is independently unsubstituted aryl. In embodiments, $R^{25}$ is independently unsubstituted heteroaryl. In embodiments, $R^{25}$ is independently substituted or unsubstituted $C_1$-$C_6$ alkyl. In embodiments, $R^{25}$ is independently substituted or unsubstituted 2 to 6 membered heteroalkyl. In embodiments, $R^{25}$ is independently substituted or unsubstituted $C_3$-$C_8$ cycloalkyl. In embodiments, $R^{25}$ is independently substituted or unsubstituted 3 to 8 membered heterocycloalkyl. In embodiments, $R^{25}$ is independently substituted or unsubstituted $C_6$ aryl. In embodiments, $R^{25}$ is independently substituted or unsubstituted 5 to 6 membered heteroaryl. In embodiments, $R^{25}$ is independently substituted $C_1$-$C_6$ alkyl. In embodiments, $R^{25}$ is independently substituted 2 to 6 membered heteroalkyl. In embodiments, $R^{25}$ is independently substituted $C_3$-$C_8$ cycloalkyl. In embodiments, $R^{25}$ is independently substituted 3 to 8 membered heterocycloalkyl. In embodiments, $R^{25}$ is independently substituted $C_6$ aryl. In embodiments, $R^{25}$ is independently substituted 5 to 6 membered heteroaryl. In embodiments, $R^{25}$ is independently unsubstituted $C_1$-$C_6$ alkyl. In embodiments, $R^{25}$ is independently unsubstituted 2 to 6 membered heteroalkyl. In embodiments, $R^{25}$ is independently unsubstituted $C_3$-$C_8$ cycloalkyl. In embodiments, $R^{25}$ is independently unsubstituted 3 to 8 membered heterocycloalkyl. In embodiments, $R^{25}$ is independently unsubstituted $C_6$ aryl. In embodiments, $R^{25}$ is independently unsubstituted 5 to 6 membered heteroaryl.

In embodiments, each $R^{26}$ is independently hydrogen. In embodiments, each $R^{26}$ is independently —$CX_3$. In embodiments, each $R^{26}$ is independently —CN. In embodiments, each $R^{26}$ is independently —COOH. In embodiments, each $R^{26}$ is independently —$CONH_2$. In embodiments, each $R^{26}$ is independently —$CHX_2$. In embodiments, each $R^{26}$ is independently —$CH_2X$. In embodiments, each $R^{26}$ is independently substituted or unsubstituted alkyl. In embodiments, each $R^{26}$ is independently substituted or unsubstituted heteroalkyl. In embodiments, each $R^{26}$ is independently substituted or unsubstituted cycloalkyl. In embodiments, each $R^{26}$ is independently substituted or unsubstituted heterocycloalkyl. In embodiments, each $R^{26}$ is independently substituted or unsubstituted aryl. In embodiments, each $R^{26}$ is independently or substituted or unsubstituted heteroaryl. In embodiments, $R^{26}$ is independently substituted alkyl. In embodiments, $R^{26}$ is independently substituted heteroalkyl. In embodiments, $R^{26}$ is independently substituted cycloalkyl. In embodiments, $R^{26}$ is independently substituted heterocycloalkyl. In embodiments, $R^{26}$ is independently substituted aryl. In embodiments, $R^{26}$ is independently substituted heteroaryl. In embodiments, $R^{26}$ is independently unsubstituted alkyl. In embodiments, $R^{26}$ is independently unsubstituted heteroalkyl. In embodiments, $R^{26}$ is independently unsubstituted cycloalkyl. In embodiments, $R^{26}$ is independently unsubstituted heterocycloalkyl. In embodiments, $R^{26}$ is independently unsubstituted aryl. In embodiments, $R^{26}$ is independently unsubstituted heteroaryl. In embodiments, $R^{26}$ is independently substituted or unsubstituted $C_1$-$C_6$ alkyl. In embodiments, $R^{26}$ is independently substituted or unsubstituted 2 to 6 membered heteroalkyl. In embodiments, $R^{26}$ is independently substituted or unsubstituted $C_3$-$C_8$ cycloalkyl. In embodiments, $R^{26}$ is independently substituted or unsubstituted 3 to 8 membered heterocycloalkyl. In embodiments, $R^{26}$ is independently substituted or unsubstituted $C_6$ aryl. In embodiments, $R^{26}$ is independently substituted or unsubstituted 5 to 6 membered heteroaryl. In embodiments, $R^{26}$ is independently substituted $C_1$-$C_6$ alkyl. In embodiments, $R^{26}$ is independently substituted 2 to 6 membered heteroalkyl. In embodiments, $R^{26}$ is independently substituted $C_3$-$C_8$ cycloalkyl. In embodiments, $R^{26}$ is independently substituted 3 to 8 membered heterocycloalkyl. In embodiments, $R^{26}$ is independently substituted $C_6$ aryl. In embodiments, $R^{26}$ is independently substituted 5 to 6 membered heteroaryl. In embodiments, $R^{26}$ is independently unsubstituted $C_1$-$C_6$ alkyl. In embodiments, $R^{26}$ is independently unsubstituted 2 to 6 membered heteroalkyl. In embodiments, $R^{26}$ is independently unsubstituted $C_3$-$C_8$ cycloalkyl. In embodiments, $R^{26}$ is independently unsubstituted 3 to 8 membered heterocycloalkyl. In embodiments, $R^{26}$ is independently unsubstituted $C_6$ aryl. In embodiments, $R^{26}$ is independently unsubstituted 5 to 6 membered heteroaryl.

In embodiments, each $R^{27}$ is independently hydrogen. In embodiments, each $R^{27}$ is independently —$CX_3$. In embodiments, each $R^{27}$ is independently —CN. In embodiments, each $R^{27}$ is independently —COOH. In embodiments, each $R^{27}$ is independently —$CONH_2$. In embodiments, each $R^{27}$ is independently —$CHX_2$. In embodiments, each $R^{27}$ is independently —$CH_2X$. In embodiments, each $R^{27}$ is independently substituted or unsubstituted alkyl. In embodiments, each $R^{27}$ is independently substituted or unsubstituted heteroalkyl. In embodiments, each $R^{27}$ is independently substituted or unsubstituted cycloalkyl. In embodiments, each $R^{27}$ is independently substituted or unsubstituted heterocycloalkyl. In embodiments, each $R^{27}$ is independently substituted or unsubstituted aryl. In embodiments, each $R^{27}$ is independently or substituted or unsubstituted heteroaryl. In embodiments, $R^{27}$ is independently substituted alkyl. In embodiments, $R^{27}$ is independently substituted heteroalkyl. In embodiments, $R^{27}$ is independently substituted cycloalkyl. In embodiments, $R^{27}$ is independently substituted heterocycloalkyl. In embodiments, $R^{27}$ is independently substituted aryl. In embodiments, $R^{27}$ is independently substituted heteroaryl. In embodiments, $R^{27}$ is independently unsubstituted alkyl. In embodiments, $R^{27}$ is independently unsubstituted heteroalkyl. In embodiments, $R^{27}$ is independently unsubstituted cycloalkyl. In embodiments, $R^{27}$ is independently unsubstituted heterocycloalkyl. In embodiments, $R^{27}$ is independently unsubstituted aryl. In embodiments, $R^{27}$ is independently unsubstituted heteroaryl. In embodiments, $R^{27}$ is independently substituted or unsubstituted $C_1$-$C_6$ alkyl. In embodiments, $R^{27}$ is independently substituted or unsubstituted 2 to 6 membered heteroalkyl. In embodiments, $R^{27}$ is independently substituted or unsubstituted $C_3$-$C_8$ cycloalkyl. In embodiments, $R^{27}$ is independently substituted or unsubstituted 3 to 8 membered heterocycloalkyl. In embodiments, $R^{27}$ is independently substituted or unsubstituted $C_6$ aryl. In embodiments, $R^{27}$ is independently substituted or unsubstituted 5 to 6 membered heteroaryl. In embodiments, $R^{27}$ is independently substituted $C_1$-$C_6$ alkyl. In embodiments, $R^{27}$ is independently substituted 2 to 6 membered heteroalkyl. In embodiments, $R^{27}$ is independently substituted $C_3$-$C_8$ cycloalkyl. In embodiments, $R^{27}$ is independently substituted 3 to 8 membered heterocycloalkyl. In embodiments, $R^{27}$ is independently substituted $C_6$ aryl. In embodiments, $R^{27}$ is independently substituted 5 to 6 membered heteroaryl. In embodiments, $R^{27}$ is independently unsubstituted $C_1$-$C_6$ alkyl. In embodiments, $R^{27}$ is independently unsubstituted 2 to 6 membered heteroalkyl. In embodiments, $R^{27}$ is independently unsubstituted $C_3$-$C_8$ cycloalkyl. In embodiments, $R^{27}$ is independently unsubstituted 3 to 8 membered heterocycloalkyl. In embodiments, $R^{27}$ is independently unsubstituted $C_6$ aryl. In embodiments, $R^{27}$ is independently unsubstituted 5 to 6 membered heteroaryl.

In embodiments, each $R^{28}$ is independently hydrogen. In embodiments, each $R^{28}$ is independently —$CX_3$. In embodiments, each $R^{28}$ is independently —CN. In embodiments, each $R^{28}$ is independently —COOH. In embodiments, each $R^{28}$ is independently —$CONH_2$. In embodiments, each $R^{28}$ is independently —$CHX_2$. In embodiments, each $R^{28}$ is independently —$CH_2X$. In embodiments, each $R^{28}$ is independently substituted or unsubstituted alkyl. In embodiments, each $R^{28}$ is independently substituted or unsubstituted heteroalkyl. In embodiments, each $R^{28}$ is independently substituted or unsubstituted cycloalkyl. In embodiments, each $R^{28}$ is independently substituted or unsubstituted heterocycloalkyl. In embodiments, each $R^{28}$ is independently substituted or unsubstituted aryl. In embodiments, each $R^{28}$ is independently or substituted or unsubstituted heteroaryl. In embodiments, $R^{28}$ is independently substituted alkyl. In embodiments, $R^{28}$ is independently substituted heteroalkyl. In embodiments, $R^{28}$ is independently substituted cycloalkyl. In embodiments, $R^{28}$ is independently substituted heterocycloalkyl. In embodiments, $R^{28}$ is independently substituted aryl. In embodiments, $R^{28}$ is independently substituted heteroaryl. In embodiments, $R^{28}$ is independently unsubstituted alkyl. In embodiments, $R^{28}$ is independently unsubstituted heteroalkyl. In embodiments, $R^{28}$ is independently unsubstituted cycloalkyl. In embodiments, $R^{28}$ is independently unsubstituted heterocycloalkyl. In embodiments, $R^{28}$ is independently unsubstituted aryl. In embodiments, $R^{28}$ is independently unsubstituted heteroaryl. In embodiments, $R^{28}$ is independently substituted or unsubstituted $C_1$-$C_6$ alkyl. In embodiments, $R^{28}$ is independently substituted or unsubstituted 2 to 6 membered heteroalkyl. In embodiments, $R^{28}$ is independently substituted or unsubstituted $C_3$-$C_8$ cycloalkyl. In embodiments, $R^{28}$ is independently substituted or unsubstituted 3 to 8 membered heterocycloalkyl. In embodiments, $R^{8}$ is independently substituted or unsubstituted $C_6$ aryl. In embodiments, $R^{28}$ is independently substituted or unsubstituted 5 to 6 membered heteroaryl. In embodiments, $R^{28}$ is independently substituted $C_1$-$C_6$ alkyl. In embodiments, $R^{28}$ is independently substituted 2 to 6 membered heteroalkyl. In embodiments, $R^{28}$ is independently substituted $C_3$-$C_8$ cycloalkyl. In embodiments, $R^{28}$ is independently substituted 3 to 8 membered heterocycloalkyl. In embodiments, $R^{28}$ is independently substituted $C_6$ aryl. In embodiments, $R^{28}$ is independently substituted 5 to 6 membered heteroaryl. In embodiments, $R^{28}$ is independently unsubstituted $C_1$-$C_6$ alkyl. In embodiments, $R^{28}$ is independently unsubstituted 2 to 6 membered heteroalkyl. In embodiments, $R^{28}$ is independently unsubstituted $C_3$-$C_8$ cycloalkyl. In embodiments, $R^{28}$ is independently unsubstituted 3 to 8 membered heterocycloalkyl. In embodiments, $R^{28}$ is independently unsubstituted $C_6$ aryl. In embodiments, $R^{28}$ is independently unsubstituted 5 to 6 membered heteroaryl.

In embodiments, $R^{1A}$ is independently halogen. In embodiments, $R^{1A}$ is independently —CN. In embodiments, $R^{1A}$ is independently —$OR^{1B}$. In embodiments, $R^{1A}$ is independently —$SR^{1B}$. In embodiments, $R^{1A}$ is independently —$NR^{1C}R^{1D}$. In embodiments, $R^{1A}$ is independently —$NR^{1C}C(O)R^{1B}$. In embodiments, $R^{1A}$ is independently —$C(O)NR^{1C}R^{1D}$. In embodiments, $R^{1A}$ is independently —$CO_2R^{1B}$. In embodiments, $R^{1A}$ is independently substituted or unsubstituted alkyl. In embodiments, $R^{1A}$ is independently substituted or unsubstituted heteroalkyl. In embodiments, $R^{1A}$ is independently substituted alkyl. In embodiments, $R^{1A}$ is independently substituted heteroalkyl. In embodiments, $R^{1A}$ is independently unsubstituted alkyl. In embodiments, $R^{1A}$ is independently unsubstituted heteroalkyl.

In embodiments, $R^{1B}$ is independently hydrogen. In embodiments, $R^{1B}$ is independently substituted or unsubstituted alkyl. In embodiments, $R^{1B}$ is independently substituted or unsubstituted heteroalkyl. In embodiments, $R^{1B}$ is independently substituted or unsubstituted cycloalkyl. In embodiments, $R^{1B}$ is independently substituted or unsubstituted heterocycloalkyl. In embodiments, $R^{1B}$ is independently substituted or unsubstituted aryl. In embodiments, $R^{1B}$ is independently substituted or unsubstituted heteroaryl. In embodiments, $R^{1B}$ is independently substituted alkyl. In embodiments, $R^{1B}$ is independently substituted heteroalkyl. In embodiments, $R^{1B}$ is independently substituted cycloalkyl. In embodiments, $R^{1B}$ is independently substituted heterocycloalkyl. In embodiments, $R^{1B}$ is independently substituted aryl. In embodiments, $R^{1B}$ is independently substituted heteroaryl. In embodiments, RIB is independently unsubstituted alkyl. In embodiments, $R^{1B}$ is independently unsubstituted heteroalkyl. In embodiments, $R^{1B}$ is independently unsubstituted cycloalkyl. In embodiments, $R^{1B}$ is independently unsubstituted heterocycloalkyl. In embodiments, $R^{1B}$ is independently unsubstituted aryl. In embodiments, $R^{1B}$ is independently unsubstituted heteroaryl.

In embodiments, $R^{1C}$ is independently hydrogen. In embodiments, $R^{1C}$ is independently substituted or unsubstituted alkyl. In embodiments, $R^{1C}$ is independently substituted or unsubstituted heteroalkyl. In embodiments, $R^{1C}$ is independently substituted or unsubstituted cycloalkyl. In embodiments, $R^{1C}$ is independently substituted or unsubstituted heterocycloalkyl. In embodiments, $R^{1C}$ is independently substituted or unsubstituted aryl. In embodiments, $R^{1C}$ is independently substituted or unsubstituted heteroaryl. In embodiments, $R^{1C}$ is independently substituted alkyl. In embodiments, $R^{1C}$ is independently substituted heteroalkyl. In embodiments, $R^{1C}$ is independently substituted cycloalkyl. In embodiments, $R^{1C}$ is independently substituted heterocycloalkyl. In embodiments, $R^{1C}$ is independently substituted aryl. In embodiments, $R^{1C}$ is independently substituted heteroaryl. In embodiments, $R^{1C}$ is independently unsubstituted alkyl. In embodiments, $R^{1C}$ is independently unsubstituted heteroalkyl. In embodiments, $R^{1C}$ is independently unsubstituted cycloalkyl. In embodiments, $R^{1C}$ is independently unsubstituted heterocycloalkyl. In embodiments, $R^{1C}$ is independently unsubstituted aryl. In embodiments, $R^{1C}$ is independently unsubstituted heteroaryl.

In embodiments, $R^{1D}$ is independently substituted or unsubstituted alkyl. In embodiments, $R^{1D}$ is independently substituted or unsubstituted heteroalkyl. In embodiments, $R^{1D}$ is independently substituted or unsubstituted cycloalkyl. In embodiments, $R^{1D}$ is independently substituted or unsubstituted heterocycloalkyl. In embodiments, $R^{1D}$ is independently substituted or unsubstituted aryl. In embodiments, $R^{1D}$ is independently or substituted or unsubstituted heteroaryl. In embodiments, $R^{1D}$ is independently substituted alkyl. In embodiments, $R^{1D}$ is independently substituted heteroalkyl. In embodiments, $R^{1D}$ is independently substituted cycloalkyl. In embodiments, $R^{1D}$ is independently substituted heterocycloalkyl. In embodiments, $R^{1D}$ is independently substituted aryl. In embodiments, $R^{1D}$ is independently substituted heteroaryl. In embodiments, $R^{1D}$ is independently unsubstituted alkyl. In embodiments, $R^{1D}$ is independently unsubstituted heteroalkyl. In embodiments, $R^{1D}$ is independently unsubstituted cycloalkyl. In embodiments, $R^{1D}$ is independently unsubstituted heterocycloalkyl. In embodiments, $R^{1D}$ is independently unsubstituted aryl. In embodiments, $R^{1D}$ is independently unsubstituted heteroaryl.

In embodiments, $R^{1C}$ and $R^{1D}$ attached to the same nitrogen atom optionally combine to form a substituted or unsubstituted heterocycloalkyl. In embodiments, $R^{1C}$ and $R^{1D}$ attached to the same nitrogen atom optionally combine to form a substituted heterocycloalkyl. In embodiments, $R^{1C}$ and $R^{1D}$ attached to the same nitrogen atom optionally combine to form an unsubstituted heterocycloalkyl.

In embodiments, $R^{2A}$ is independently —$NR^{2B}R^{2C}$. In embodiments, $R^{2A}$ is independently substituted or unsubstituted cycloalkyl. In embodiments, $R^{2A}$ is independently substituted or unsubstituted heterocycloalkyl. In embodiments, $R^{2A}$ is independently substituted or unsubstituted aryl. In embodiments, $R^{2A}$ is independently substituted or unsubstituted heteroaryl. In embodiments, $R^{2A}$ is independently substituted cycloalkyl. In embodiments, $R^{2A}$ is independently substituted heterocycloalkyl. In embodiments, $R^{2A}$ is independently substituted aryl. In embodiments, $R^{2A}$ is independently substituted heteroaryl. In embodiments, $R^{2A}$ is independently unsubstituted cycloalkyl. In embodiments, $R^{2A}$ is independently unsubstituted heterocycloalkyl. In embodiments, $R^{2A}$ is independently unsubstituted aryl. In embodiments, $R^{2A}$ is independently unsubstituted heteroaryl.

In embodiments, $R^{2B}$ is independently hydrogen. In embodiments, $R^{2B}$ is independently substituted or unsubstituted alkyl. In embodiments, $R^{2B}$ is independently substituted or unsubstituted heteroalkyl. In embodiments, $R^{2B}$ is independently substituted or unsubstituted cycloalkyl. In embodiments, $R^{2B}$ is independently substituted or unsubstituted heterocycloalkyl. In embodiments, $R^{2B}$ is independently substituted or unsubstituted aryl. In embodiments, $R^{2B}$ is independently substituted or unsubstituted heteroaryl. In embodiments, $R^{2B}$ is independently substituted alkyl. In embodiments, $R^{2B}$ is independently substituted heteroalkyl. In embodiments, $R^{2B}$ is independently substituted cycloalkyl. In embodiments, $R^{2B}$ is independently substituted heterocycloalkyl. In embodiments, $R^{2B}$ is independently substituted aryl. In embodiments, $R^{2B}$ is independently substituted heteroaryl. In embodiments, $R^{2B}$ is independently unsubstituted alkyl. In embodiments, $R^{2B}$ is independently unsubstituted heteroalkyl. In embodiments, $R^{2B}$ is independently unsubstituted cycloalkyl. In embodiments, $R^{2B}$ is independently unsubstituted heterocycloalkyl. In embodiments, $R^{2B}$ is independently unsubstituted aryl. In embodiments, $R^{2B}$ is independently unsubstituted heteroaryl.

In embodiments, $R^{2C}$ is independently hydrogen. In embodiments, $R^{2C}$ is independently substituted or unsubstituted alkyl. In embodiments, $R^{2C}$ is independently substituted or unsubstituted heteroalkyl. In embodiments, $R^{2C}$ is independently substituted or unsubstituted cycloalkyl. In embodiments, $R^{2C}$ is independently substituted or unsubstituted heterocycloalkyl. In embodiments, $R^{2C}$ is independently substituted or unsubstituted aryl. In embodiments, $R^{2C}$ is independently substituted or unsubstituted heteroaryl. In embodiments, $R^{2C}$ is independently substituted alkyl. In embodiments, $R^{2C}$ is independently substituted heteroalkyl. In embodiments, $R^{2C}$ is independently substituted cycloalkyl. In embodiments, $R^{2C}$ is independently substituted heterocycloalkyl. In embodiments, $R^{2C}$ is independently substituted aryl. In embodiments, $R^{2C}$ is independently substituted heteroaryl. In embodiments, $R^{2C}$ is independently unsubstituted alkyl. In embodiments, $R^{2C}$ is independently unsubstituted heteroalkyl. In embodiments, $R^{2C}$ is independently unsubstituted cycloalkyl. In embodiments, $R^{2C}$ is independently unsubstituted heterocycloalkyl. In embodiments, $R^{2C}$ is independently unsubstituted aryl. In embodiments, $R^{2C}$ is independently unsubstituted heteroaryl.

In embodiments, $R^{2B}$ and $R^{2C}$ combine to form a substituted or unsubstituted heterocycloalkyl. In embodiments, $R^{2B}$ and $R^{2C}$ combine to form a substituted heterocycloalkyl. In embodiments, $R^{2B}$ and $R^{2C}$ combine to form an unsubstituted heterocycloalkyl.

$R^6$ and $R^7$ substituents bonded to the same nitrogen atom may be joined to form a substituted or unsubstituted heterocycloalkyl. $R^6$ and $R^7$ substituents bonded to the same nitrogen atom may be joined to form a substituted or unsubstituted heteroaryl. $R^6$ and $R^7$ substituents bonded to the same nitrogen atom may be joined to form a substituted heterocycloalkyl. $R^6$ and $R^7$ substituents bonded to the same nitrogen atom may be joined to form a substituted heteroaryl. $R^6$ and $R^7$ substituents bonded to the same nitrogen atom may be joined to form an unsubstituted heterocycloalkyl. $R^6$ and $R^7$ substituents bonded to the same nitrogen atom may be joined to form an unsubstituted heteroaryl. $R^6$ and $R^7$ substituents bonded to the same nitrogen atom may be joined to form a substituted or unsubstituted 3 to 8 membered heterocycloalkyl. $R^6$ and $R^7$ substituents bonded to the same nitrogen atom may be joined to form a substituted or unsubstituted 5 to 6 membered heteroaryl. $R^6$ and $R^7$ substituents bonded to the same nitrogen atom may be joined to form a substituted 3 to 8 membered heterocycloalkyl. $R^6$ and $R^7$ substituents bonded to the same nitrogen atom may be joined to form a substituted 5 to 6 membered heteroaryl. $R^6$ and $R^7$ substituents bonded to the same nitrogen atom may be joined to form an unsubstituted 3 to 8 membered heterocycloalkyl. $R^6$ and $R^7$ substituents bonded to the same nitrogen atom may be joined to form an unsubstituted 5 to 6 membered heteroaryl.

$R^{10}$ and $R^{11}$ substituents bonded to the same nitrogen atom may be joined to form a substituted or unsubstituted heterocycloalkyl. $R^{10}$ and $R^{11}$ substituents bonded to the same nitrogen atom may be joined to form a substituted or unsubstituted heteroaryl. $R^{10}$ and $R^{11}$ substituents bonded to the same nitrogen atom may be joined to form a substituted heterocycloalkyl. $R^{10}$ and $R^{11}$ substituents bonded to the same nitrogen atom may be joined to form a substituted heteroaryl. $R^{10}$ and $R^{11}$ substituents bonded to the same nitrogen atom may be joined to form an unsubstituted heterocycloalkyl. $R^{10}$ and $R^{11}$ substituents bonded to the same nitrogen atom may be joined to form an unsubstituted heteroaryl. $R^{10}$ and $R^{11}$ substituents bonded to the same nitrogen atom may be joined to form a substituted or unsubstituted 3 to 8 membered heterocycloalkyl. $R^{10}$ and $R^{11}$ substituents bonded to the same nitrogen atom may be joined to form a substituted or unsubstituted 5 to 6 membered heteroaryl. $R^{10}$ and $R^{11}$ substituents bonded to the same nitrogen atom may be joined to form a substituted 3 to 8 membered heterocycloalkyl. $R^{10}$ and $R^{11}$ substituents bonded to the same nitrogen atom may be joined to form a substituted 5 to 6 membered heteroaryl. $R^{10}$ and $R^{11}$ substituents bonded to the same nitrogen atom may be joined to form an unsubstituted 3 to 8 membered heterocycloalkyl. $R^{10}$ and $R^{11}$ substituents bonded to the same nitrogen atom may be joined to form an unsubstituted 5 to 6 membered heteroaryl.

$R^{14}$ and $R^{15}$ substituents bonded to the same nitrogen atom may be joined to form a substituted or unsubstituted heterocycloalkyl. $R^{14}$ and $R^{15}$ substituents bonded to the same nitrogen atom may be joined to form a substituted or unsubstituted heteroaryl. $R^{14}$ and $R^{15}$ substituents bonded to the same nitrogen atom may be joined to form a substituted heterocycloalkyl. $R^{14}$ and $R^{15}$ substituents bonded to the same nitrogen atom may be joined to form a substituted heteroaryl. $R^{14}$ and $R^{15}$ substituents bonded to the same nitrogen atom may be joined to form an unsubstituted heterocycloalkyl. $R^{14}$ and $R^{15}$ substituents bonded to the same nitrogen atom may be joined to form an unsubstituted heteroaryl. $R^{14}$ and $R^{15}$ substituents bonded to the same nitrogen atom may be joined to form a substituted or unsubstituted 3 to 8 membered heterocycloalkyl. $R^{14}$ and $R^{15}$ substituents bonded to the same nitrogen atom may be joined to form a substituted or unsubstituted 5 to 6 membered heteroaryl. $R^{14}$ and $R^{15}$ substituents bonded to the same nitrogen atom may be joined to form a substituted 3 to 8 membered heterocycloalkyl. $R^{14}$ and $R^{15}$ substituents bonded to the same nitrogen atom may be joined to form a substituted 5 to 6 membered heteroaryl. $R^{14}$ and $R^{15}$ substituents bonded to the same nitrogen atom may be joined to form an unsubstituted 3 to 8 membered heterocycloalkyl. $R^{14}$ and $R^{15}$ substituents bonded to the same nitrogen atom may be joined to form an unsubstituted 5 to 6 membered heteroaryl.

$R^{18}$ and $R^{19}$ substituents bonded to the same nitrogen atom may be joined to form a substituted or unsubstituted heterocycloalkyl. $R^{18}$ and $R^{19}$ substituents bonded to the same nitrogen atom may be joined to form a substituted or unsubstituted heteroaryl. $R^{18}$ and $R^{19}$ substituents bonded to the same nitrogen atom may be joined to form a substituted heterocycloalkyl. $R^{18}$ and $R^{19}$ substituents bonded to the same nitrogen atom may be joined to form a substituted heteroaryl. $R^{18}$ and $R^{19}$ substituents bonded to the same nitrogen atom may be joined to form an unsubstituted heterocycloalkyl. $R^{18}$ and $R^{19}$ substituents bonded to the same nitrogen atom may be joined to form an unsubstituted heteroaryl. $R^{18}$ and $R^{19}$ substituents bonded to the same nitrogen atom may be joined to form a substituted or unsubstituted 3 to 8 membered heterocycloalkyl. $R^{18}$ and $R^{19}$ substituents bonded to the same nitrogen atom may be joined to form a substituted or unsubstituted 5 to 6 membered heteroaryl. $R^{18}$ and $R^{19}$ substituents bonded to the same nitrogen atom may be joined to form a substituted 3 to 8 membered heterocycloalkyl. $R^{18}$ and $R^{19}$ substituents bonded to the same nitrogen atom may be joined to form a substituted 5 to 6 membered heteroaryl. $R^{18}$ and $R^{19}$ substituents bonded to the same nitrogen atom may be joined to form an unsubstituted 3 to 8 membered heterocycloalkyl. $R^{18}$ and $R^{19}$ substituents bonded to the same nitrogen atom may be joined to form an unsubstituted 5 to 6 membered heteroaryl.

Each $X^3$ is independently —F. Each $X^3$ is independently —Cl. Each $X^3$ is independently —Br. Each $X^3$ is independently —I.

Each $X^4$ is independently —F. Each $X^4$ is independently —Cl. Each $X^4$ is independently —Br. Each $X^4$ is independently —I.

Each $X^5$ is independently —F. Each $X^5$ is independently —Cl. Each $X^5$ is independently —Br. Each $X^6$ is independently —I.

Each $X^6$ is independently —F. Each $X^6$ is independently —Cl. Each $X^6$ is independently —Br. Each $X^6$ is independently —I.

Each m3 is independently 1. Each m3 is independently 2. Each m4 is independently 1. Each m4 is independently 2. Each m5 is independently 1. Each m5 is independently 2. Each m6 is independently 1. Each m6 is independently 2.

Each n3 is independently 0. Each n3 is independently 1. Each n3 is independently 2. Each n3 is independently 3. Each n4 is independently 0. Each n4 is independently 1. Each n4 is independently 2. Each n4 is independently 3. Each n5 is independently 0. Each n5 is independently 1. Each n5 is independently 2. Each n5 is independently 3. Each n6 is independently 0. Each n6 is independently 1. Each n6 is independently 2. Each n6 is independently 3.

Each v3 is independently 1. Each v3 is independently 2. Each v4 is independently 1. Each v4 is independently 2. Each v5 is independently 1. Each v5 is independently 2. Each v6 is independently 1. Each v6 is independently 2.

In embodiments, $L^1$ is independently a bond, $R^{29}$-substituted or unsubstituted alkylene, $R^{29}$-substituted or unsubstituted heteroalkylene, $R^{29}$-substituted or unsubstituted cycloalkylene, $R^{29}$-substituted or unsubstituted heterocycloalkylene, $R^{29}$-substituted or unsubstituted arylene, or $R^{29}$-substituted or unsubstituted heteroarylene.

$R^{29}$ is independently oxo, halogen, —$CX^{29}{}_3$, —$CHX^{29}{}_2$, —$CH_2X^{29}$, —$OCX^{29}{}_3$, —$OCHX^{29}{}_2$, —$OCH_2X^{29}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. $X^{29}$ is halogen. In embodiments, $X^{29}$ is F.

$R^{30}$ is independently oxo, halogen, $-CX^{30}_3$, $-CHX^{30}_2$, $-CH_2X^{30}$, $-OCX^{30}_3$, $-OCHX^{30}_2$, $-OCH_2X^{30}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl. $X^{30}$ is halogen. In embodiments, $X^{30}$ is F.

In embodiments, $R^1$ is independently hydrogen, $-NR^{10}R^{11}$, $-OR^{12}$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

$R^{32}$ is independently oxo, halogen, $-CX^{32}_3$, $-CHX^{32}_2$, $-CH_2X^{32}$, $-OCX^{32}_3$, $-OCHX^{32}_2$, $-OCH_2X^{32}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$. $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. $X^{32}$ is halogen. In embodiments, $X^{32}$ is F.

$R^{33}$ is independently oxo, halogen, $-CX^{33}_3$, $-CHX^{33}_2$, $-CH_2X^{33}$, $-OCX^{33}_3$, $-OCHX^{33}_2$, $-OCH_2X^{33}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. $X^{33}$ is halogen. In embodiments, $X^{33}$ is F.

In embodiments, $R^2$ is independently hydrogen, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

$R^{35}$ is independently oxo, halogen, $-CX^{35}_3$, $-CHX^{35}_2$, $-CH_2X^{35}$, $-OCX^{35}_3$, $-OCHX^{35}_2$, $-OCH_2X^{35}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. $X^{35}$ is halogen. In embodiments, $X^{35}$ is F.

$R^{36}$ is independently oxo, halogen, $-CX^{36}_3$, $-CHX^{36}_2$, $-CH_2X^{36}$, $-OCX^{36}_3$, $-OCHX^{36}_2$, $-OCH_2X^{36}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl. $X^{36}$ is halogen. In embodiments, $X^{36}$ is F.

In embodiments, $R^3$ is independently hydrogen, halogen, $-CX^3_3$, $-CHX^3_2$, $-CH_2X^3$, $-OCX^3_3$, $-OCHX^3_2$, $-OCH_2X^3$, $-CN$, $-SO_{n3}R^{16}$, $-SO_{v3}NR^{13}R^{14}$, $-NHC(O)NR^{13}R^{14}$, $-N(O)_{m3}$, $-NR^{13}R^{14}$, $-C(O)R^{15}$, $-C(O)-OR^{15}$, $-C(O)NR^{13}R^{14}$, $-OR^{16}$, $-NR^{13}SO_2R^{16}$, $-NR^{13}C(O)R^{15}$, $-NR^{13}C(O)OR^{15}$, $-NR^{13}OR^{15}$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

In embodiments, $R^4$ is independently hydrogen, halogen, $-CX^4_3$, $-CHX^4_2$, $-CH_2X^4$, $-OCX^4_3$, $-OCHX^4_2$, $-OCH_2X^4$, $-CN$, $-SO_{n4}R^{20}$, $-SO_{v4}NR^{17}R^{18}$, $-NHC(O)NR^{17}R^{18}$, $-N(O)_{m4}$, $-NR^{17}R^{18}$, $-C(O)R^{19}$, $-C(O)-OR^{19}$, $-C(O)NR^{17}R^{18}$, $-OR^{20}$, $-NR^{17}SO_2R^{20}$, $-NR^{17}C(O)R^{19}$, $-NR^{17}C(O)OR^{19}$, $-NR^{17}OR^{19}$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl.

In embodiments, $R^5$ is independently hydrogen, halogen, $-CX^5_3$, $-CHX^5_2$, $-CH_2X^5$, $-OCX^5_3$, $-OCHX^5_2$, $-OCH_2X^5$, $-CN$, $-SO_{n5}R^{24}$, $-SO_{v5}NR^{21}R^{22}$, $-NHC(O)NR^{21}R^{22}$, $-N(O)_{m5}$, $-NR^{21}R^{22}$, $-C(O)R^{23}$, $-C(O)-OR^{23}$, $-C(O)NR^{21}R^{22}$, $-OR^{24}$, $-NR^{21}SO_2R^{24}$, $-NR^{21}C(O)R^{23}$, $-NR^{21}C(O)OR^{21}$, $-NR^{21}OR^{23}$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^6$ is independently hydrogen, halogen, $-CX^6_3$, $-CHX^6_2$, $-CH_2X^6$, $-OCX^6_3$, $-OCHX^6_2$, $-OCH_2X^6$, $-CN$, $-SO_{n6}R^{28}$, $-SO_{v6}NR^{25}R^{26}$, $-NHC(O)NR^{25}R^{26}$, $-N(O)_{m6}$, $-NR^{25}R^{26}$, $-C(O)R^{27}$, $-C(O)-OR^{27}$, $-C(O)NR^{25}R^{26}$, $-OR^{28}$, $-NR^{25}SO_2R^{28}$, $-NR^{25}C(O)R^{27}$, $-NR^{25}C(O)OR^{27}$, $-NR^{25}OR^{27}$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

In embodiments, each $R^7$ is independently hydrogen, $-CX_3$, $-CN$, $-COOH$, $-CONH_2$, $-CHX_2$, $-CH_2X$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl. Each X is independently $-F$, $-Cl$, $-Br$, or $-I$. In embodiments, X is $-F$.

$R^{42}$ is independently oxo, halogen, $-CX^{42}_3$, $-CHX^{42}_2$, $-CH_2X^{42}$, $-OCHX^{42}_2$, $-OCX^4_{23}$, $-OCH_2X^{42}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl. $X^{42}$ is halogen. In embodiments, $X^{42}$ is F.

$R^{43}$ is independently oxo, halogen, —$CX^{43}_3$, —$CHX^{43}_2$, —$CH_2X^{43}$, —$OCHX^{43}_2$, —$OCX^{43}_3$, —$OCH_2X^{43}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl. $X^{43}$ is halogen. In embodiments, $X^{43}$ is F.

In embodiments, each $R^8$ is independently hydrogen, —$CX_3$, —CN. —COOH, —$CONH_2$, —$CHX_2$, —$CH_2X$, $R^{45}$-substituted or unsubstituted alkyl, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl. Each X is independently —F, —Cl, —Br, or —I. In embodiments, X is —F.

$R^{45}$ is independently oxo, halogen, —$CX^{45}_3$, —$CHX^{45}_2$, —$CH_2X^{45}$, —$OCHX^{45}_2$, —$OCX^{45}_3$, —$OCH_2X^{45}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl. $X^{45}$ is halogen. In embodiments, $X^{45}$ is F.

$R^{46}$ is independently oxo, halogen, —$CX^{46}_3$, —$CHX^{46}_2$, —$CH_2X^{46}$, —$OCHX^{46}_2$, —$OCX^{46}_3$, —$OCH_2X^{46}$, —CN, —OH, —$NH_2$. —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl. $X^{46}$ is halogen. In embodiments, $X^{46}$ is F.

In embodiments, each $R^9$ is independently hydrogen, —$CX_3$, —CN, —COOH, —$CONH_2$, —$CHX_2$, —$CH_2X$, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl. Each X is independently —F, —Cl, —Br, or —I. In embodiments, X is —F.

$R^{48}$ is independently oxo, halogen, —$CX^{48}_3$, —$CHX^{48}_2$, —$CH_2X^{48}$, —$OCHX^{48}_2$, —$OCX^{48}_3$, —$OCH_2X^{48}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl. $X^{48}$ is halogen. In embodiments, $X^{48}$ is F.

$R^{49}$ is independently oxo, halogen, —$CX^{49}_3$, —$CHX^{49}_2$, —$CH_2X^{49}$, —$OCHX^{49}_2$, —$OCX^{49}_3$, —$OCH_2X^{49}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl. $X^{49}$ is halogen. In embodiments, $X^{49}$ is F.

In embodiments, each $R^{10}$ is independently hydrogen, —$CX_3$, —CN, —COOH, —$CONH_2$, —$CHX_2$, —$CH_2X$, $R^{51}$-substituted or unsubstituted alkyl, $R^{51}$-substituted or unsubstituted heteroalkyl, $R^{51}$-substituted or unsubstituted cycloalkyl, $R^{51}$-substituted or unsubstituted heterocycloalkyl, $R^{51}$-substituted or unsubstituted aryl, or $R^{51}$-substituted or unsubstituted heteroaryl. Each X is independently —F, —Cl, —Br, or —I. In embodiments, X is —F.

$R^{51}$ is independently oxo, halogen, —$CX^{51}_3$, —$CHX^{51}_2$, —$CH_2X^{51}$, —$OCHX^{51}_2$, —$OCX^{51}_3$, —$OCH_2X^{51}$, —CN, —OH, —$NH_2$. —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{52}$-substituted or unsubstituted alkyl, $R^{52}$-substituted or unsubstituted heteroalkyl, $R^{52}$-substituted or unsubstituted cycloalkyl, $R^{52}$-substituted or unsubstituted heterocycloalkyl, $R^{52}$-substituted or unsubstituted aryl, or $R^{52}$-substituted or unsubstituted heteroaryl. $X^{51}$ is halogen. In embodiments, $X^{52}$ is F.

$R^{52}$ is independently oxo, halogen, —$CX^{52}_3$, —$CHX^{52}_2$, —$CH_2X^{52}$, —$OCHX^{52}_2$, —$OCX^{53}_3$, —$OCH_2X^{52}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{53}$-substituted or unsubstituted alkyl, $R^{53}$-substituted or unsubstituted heteroalkyl, $R^{53}$-substituted or unsubstituted cycloalkyl, $R^{53}$-substituted or unsubstituted heterocycloalkyl, $R^{53}$-substituted or unsubstituted aryl, or $R^{53}$-substituted or unsubstituted heteroaryl. $X^{52}$ is halogen. In embodiments, $X^{52}$ is F.

In embodiments, each $R^{11}$ is independently hydrogen, —$CX_3$, —CN, —COOH, —$CONH_2$, —$CHX_2$, —$CH_2X$, $R^{54}$-substituted or unsubstituted alkyl, $R^{54}$-substituted or unsubstituted heteroalkyl, $R^{54}$-substituted or unsubstituted cycloalkyl, $R^{54}$-substituted or unsubstituted heterocycloalkyl, $R^{54}$-substituted or unsubstituted aryl, or $R^{54}$-substituted or unsubstituted heteroaryl. Each X is independently —F, —Cl, —Br, or —I. In embodiments, X is —F.

$R^{54}$ is independently oxo, halogen, —$CX^{54}_3$, —$CHX^{54}_2$, —$CH_2X^{44}$, —$OCHX^{54}_2$, —$OCX^{54}_3$, —$OCH_2X^{54}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl. $X^{54}$ is halogen. In embodiments, $X^{54}$ is F.

$R^{55}$ is independently oxo, halogen, —$CX^{55}_3$, —$CHX^{55}_2$, —$CH_2X^{55}$, —$OCHX^{55}_2$, —$OCX^{55}_3$, —$OCH_2X^{55}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl. $X^{55}$ is halogen. In embodiments, $X^{55}$ is F.

In embodiments, each $R^{12}$ is independently hydrogen, $-CX_3$, $-CN$, $-COOH$, $-CONH_2$, $-CHX_2$, $-CH_2X$, $R^{57}$-substituted or unsubstituted alkyl, $R^{57}$-substituted or unsubstituted heteroalkyl, $R^{57}$-substituted or unsubstituted cycloalkyl, $R^{57}$-substituted or unsubstituted heterocycloalkyl, $R^{57}$-substituted or unsubstituted aryl, or $R^{57}$-substituted or unsubstituted heteroaryl. Each X is independently $-F$, $-Cl$, $-Br$, or $-I$. In embodiments, X is $-F$.

$R^{57}$ is independently oxo, halogen, $-CX^{57}_3$, $-CHX^{57}_2$, $-CH_2X^{57}$, $-OCHX^{57}_2$, $-OCX^{57}_3$, $-OCH_2X^{57}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl. $X^{57}$ is halogen. In embodiments, $X^{57}$ is F.

$R^{58}$ is independently oxo, halogen, $-CX^{58}_3$, $-CHX^{58}_2$, $-CH_2X^{58}$, $-OCHX^{58}_2$, $-OCX^{58}_3$, $-OCH_2X^{58}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl. $X^{58}$ is halogen. In embodiments, $X^{58}$ is F.

In embodiments, each $R^{13}$ is independently hydrogen, $-CX_3$, $-CN$, $-COOH$, $-CONH_2$, $-CHX_2$, $-CH_2X$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl. Each X is independently $-F$, $-Cl$, $-Br$, or $-I$. In embodiments, X is $-F$.

$R^{60}$ is independently oxo, halogen, $-CX^{60}_3$, $-CHX^{60}_2$, $-CH_2X^{60}$, $-OCHX^{60}_2$, $-OCX^{60}_3$, $-OCH_2X^{60}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl. $X^{60}$ is halogen. In embodiments, $X^{60}$ is F.

$R^{61}$ is independently oxo, halogen, $-CX^{61}_3$, $-CHX^{61}_2$, $-CH_2X^{61}$, $-OCHX^{61}_2$, $-OCX^{61}_3$, $-OCH_2X^{61}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl. $X^{61}$ is halogen. In embodiments, $X^{60}$ is F.

In embodiments, each $R^{14}$ is independently hydrogen, $-CX_3$, $-CN$, $-COOH$, $-CONH_2$, $-CHX_2$, $-CH_2X$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl. Each X is independently $-F$, $-Cl$, $-Br$, or $-I$. In embodiments, X is $-F$.

$R^{63}$ is independently oxo, halogen, $-CX^{63}_3$, $-CHX^{63}_2$, $-CH_2X^{63}$, $-OCHX^{63}_2$, $-OCX^{63}_3$, $-OCH_2X^{63}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl. $X^6_3$ is halogen. In embodiments, $X^6_3$ is F.

$R^{64}$ is independently oxo, halogen, $-CX^{64}_3$, $-CHX^{64}_2$, $-CH_2X^{64}$, $-OCHX^{64}_2$, $-OCX^{64}_3$, $-OCH_2X^{64}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl. $X^{64}$ is halogen. In embodiments, $X^{64}$ is F.

In embodiments, each $R^{15}$ is independently hydrogen, $-CX_3$, $-CN$, $-COOH$, $-CONH_2$, $-CHX_2$, $-CH_2X$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl. Each X is independently $-F$, $-Cl$, $-Br$, or $-I$. In embodiments, X is $-F$.

$R^{66}$ is independently oxo, halogen, $-CX^{66}_3$, $-CHX^{66}_2$, $-CH_2X^{66}$, $-OCHX^{66}_2$, $-OCX^{66}_3$, $-OCH_2X^{66}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl. $X^{66}$ is halogen. In embodiments, $X^{66}$ is F.

$R^{67}$ is independently oxo, halogen, $-CX^{67}_3$, $-CHX^{67}_2$, $-CH_2X^{67}$, $-OCHX^{67}_2$, $-OCX^{67}_3$, $-OCH_2X^{67}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{68}$-substituted or unsubstituted alkyl, $R^{68}$-substituted or unsubstituted heteroalkyl, $R^{68}$-substituted or unsubstituted cycloalkyl, $R^{68}$-substituted or unsubstituted heterocycloalkyl, $R^{68}$-substituted or unsubstituted aryl, or $R^{68}$-substituted or unsubstituted heteroaryl. $X^{67}$ is halogen. In embodiments, $X^{67}$ is F.

In embodiments, each $R^{16}$ is independently hydrogen, $-CX_3$, $-CN$, $-COOH$, $-CONH_2$, $-CHX_2$, $-CH_2X$, $R^{69}$-substituted or unsubstituted alkyl, $R^{69}$-substituted or unsubstituted heteroalkyl, $R^{69}$-substituted or unsubstituted cycloalkyl, $R^{69}$-substituted or unsubstituted heterocycloalkyl, $R^{69}$-substituted or unsubstituted aryl, or $R^{69}$-substituted or unsubstituted heteroaryl. Each X is independently $-F$, $-Cl$, $-Br$, or $-I$. In embodiments, X is $-F$.

$R^{69}$ is independently oxo, halogen. $-CX^{69}_3$, $-CHX^{69}_2$, $-CH_2X^{69}$, $-OCHX^{69}_2$, $-OCX^{69}_3$, $-OCH_2X^{69}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, —NHC=(O)H, —NHC(O)—OH, —NHOH, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl. $X^{69}$ is halogen. In embodiments, $X^{69}$ is F.

$R^{70}$ is independently oxo, halogen, —$CX^{70}_3$, —$CHX^{70}_2$, —$CH_2X^{70}$, —$OCHX^{70}_2$, —$OCX^{70}_3$, —$OCH_2X^{70}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl. $X^{70}$ is halogen. In embodiments, $X^{70}$ is F.

In embodiments, each $R^{17}$ is independently hydrogen, —$CX_3$, —CN, —COOH, —$CONH_2$, —$CHX_2$, —$CH_2X$, $R^{72}$-substituted or unsubstituted alkyl, $R^{72}$-substituted or unsubstituted heteroalkyl, $R^{72}$-substituted or unsubstituted cycloalkyl, $R^{72}$-substituted or unsubstituted heterocycloalkyl, $R^{72}$-substituted or unsubstituted aryl, or $R^{72}$-substituted or unsubstituted heteroaryl. Each X is independently —F, —Cl, —Br, or —I. In embodiments, X is —F.

$R^{72}$ is independently oxo, halogen, —$CX^{72}_3$, —$CHX^{72}_2$, —$CH_2X^{72}$, —$OCHX^{72}_2$, —$OCX^{72}_3$, —$OCH_2X^{72}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl. $X^{72}$ is halogen. In embodiments, $X^{72}$ is F.

$R^{73}$ is independently oxo, halogen, —$CX^{73}_3$, —$CHX^{73}_2$, —$CH_2X^{73}$, —$OCHX^{73}_2$, —$OCX^{73}_3$, —$OCH_2X^{73}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{74}$-substituted or unsubstituted alkyl, $R^{74}$-substituted or unsubstituted heteroalkyl, $R^{74}$-substituted or unsubstituted cycloalkyl, $R^{74}$-substituted or unsubstituted heterocycloalkyl, $R^{74}$-substituted or unsubstituted aryl, or $R^{74}$-substituted or unsubstituted heteroaryl. $X^{73}$ is halogen. In embodiments, $X^{73}$ is F.

In embodiments, each $R^{18}$ is independently hydrogen, —$CX_3$, —CN, —COOH, —$CONH_2$, —$CHX_2$, —$CH_2X$, $R^{75}$-substituted or unsubstituted alkyl, $R^{75}$-substituted or unsubstituted heteroalkyl, $R^{75}$-substituted or unsubstituted cycloalkyl, $R^{75}$-substituted or unsubstituted heterocycloalkyl, $R^{75}$-substituted or unsubstituted aryl, or $R^{75}$-substituted or unsubstituted heteroaryl. Each X is independently —F, —Cl, —Br, or —I. In embodiments, X is —F.

$R^{75}$ is independently oxo, halogen, —$CX^{75}_3$, —$CHX^{75}_2$, —$CH_2X^{75}$, —$OCHX^{75}_2$, —$OCX^{75}_3$. —$OCH_2X^{75}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{76}$-substituted or unsubstituted alkyl, $R^{76}$-substituted or unsubstituted heteroalkyl, $R^{76}$-substituted or unsubstituted heterocycloalkyl, $R^{76}$-substituted or unsubstituted aryl, or $R^{76}$-substituted or unsubstituted heteroaryl. $X^{75}$ is halogen. In embodiments, $X^{75}$ is F.

$R^{76}$ is independently oxo, halogen, —$CX^{76}_3$, —$CHX^{76}_2$, —$CH_2X^{76}$, —$OCHX^{76}_2$, —$OCX^{76}_3$, —$OCH_2X^{76}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{77}$-substituted or unsubstituted alkyl, $R^{77}$-substituted or unsubstituted heteroalkyl, $R^{77}$-substituted or unsubstituted cycloalkyl, $R^{77}$-substituted or unsubstituted heterocycloalkyl, $R^{77}$-substituted or unsubstituted aryl, or $R^{77}$-substituted or unsubstituted heteroaryl. $X^{76}$ is halogen. In embodiments, $X^{76}$ is F.

In embodiments, each $R^{19}$ is independently hydrogen, —$CX_3$, —CN, —COOH, —$CONH_2$, —$CHX_2$, —$CH_2X$, $R^{78}$-substituted or unsubstituted alkyl, $R^{78}$-substituted or unsubstituted heteroalkyl, $R^{78}$-substituted or unsubstituted cycloalkyl, $R^{78}$-substituted or unsubstituted heterocycloalkyl, $R^{78}$-substituted or unsubstituted aryl, or $R^{78}$-substituted or unsubstituted heteroaryl. Each X is independently —F, —Cl, —Br, or —I. In embodiments, X is —F.

$R^{78}$ is independently oxo, halogen, —$CX^{78}_3$, —$CHX^{78}_2$, —$CH_2X^{78}$, —$OCHX^{78}_2$, —$OCX^{78}_3$, —$OCH_2X^{78}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl. $X^{78}$ is halogen. In embodiments, $X^{78}$ is F.

$R^{79}$ is independently oxo, halogen, —$CX^{79}_3$, —$CHX^{79}_2$, —$CH_2X^{79}$, —$OCHX^{79}_2$, —$OCX^{79}_3$, —$OCH_2X^{79}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{80}$-substituted or unsubstituted alkyl, $R^{80}$-substituted or unsubstituted heteroalkyl, $R^{80}$-substituted or unsubstituted cycloalkyl, $R^{80}$-substituted or unsubstituted heterocycloalkyl, $R^{80}$-substituted or unsubstituted aryl, or $R^{80}$-substituted or unsubstituted heteroaryl. $X^{79}$ is halogen. In embodiments, $X^{79}$ is F.

In embodiments, each $R^{20}$ is independently hydrogen, —$CX_3$, —CN, —COOH, —$CONH_2$, —$CHX_2$, —$CH_2X$, $R^{81}$-substituted or unsubstituted alkyl, $R^{81}$-substituted or unsubstituted heteroalkyl, $R^{81}$-substituted or unsubstituted cycloalkyl, $R^{81}$-substituted or unsubstituted heterocycloalkyl, $R^{81}$-substituted or unsubstituted aryl, or $R^{81}$-substituted or unsubstituted heteroaryl. Each X is independently —F, —Cl, —Br, or —I. In embodiments, X is —F.

$R^{81}$ is independently oxo, halogen, —$CX^{81}_3$, —$CHX^{81}_2$, —$CH_2X^{81}$, —$OCHX^{81}_2$, —$OCX^{81}_3$. —$OCH_2X^{81}$, —CN, —OH, —$NH_2$, —COOH, —$CONH_2$, —$NO_2$, —SH, —$SO_3H$, —$SO_4H$, —$SO_2NH_2$, —$NHNH_2$. —$ONH_2$, —NHC=(O)$NHNH_2$, —NHC=(O)$NH_2$, —$NHSO_2H$, —NHC=(O)H, —NHC(O)—OH, —NHOH, $R^{82}$-substituted or unsubstituted alkyl, $R^{82}$-substituted or unsubstituted heteroalkyl, $R^{82}$-substituted or unsubstituted cycloalkyl, $R^{82}$-substituted or unsubstituted heterocycloalkyl, $R^{82}$-substituted or unsubstituted aryl, or $R^{82}$-substituted or unsubstituted heteroaryl. $X^{81}$ is halogen. In embodiments, $X^{81}$ is F.

$R^{82}$ is independently oxo, halogen, —$CX^{82}_3$, —$CHX^{82}_2$, —$CH_2X^{82}$, —$OCHX^{82}_2$, —$OCX^{82}_3$, —$OCH_2X^{82}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{83}$-substituted or unsubstituted alkyl, $R^{83}$-substituted or unsubstituted heteroalkyl, $R^{83}$-substituted or unsubstituted cycloalkyl, $R^{83}$-substituted or unsubstituted heterocycloalkyl, $R^{83}$-substituted or unsubstituted aryl, or $R^{83}$-substituted or unsubstituted heteroaryl. $X^{82}$ is halogen. In embodiments, $X^{82}$ is F.

In embodiments, each $R^{21}$ is independently hydrogen, —$CX_3$, —CN, —COOH, —$CONH_2$, —$CHX_2$, —$CH_2X$, $R^{84}$-substituted or unsubstituted alkyl, $R^{84}$-substituted or unsubstituted heteroalkyl, $R^{84}$-substituted or unsubstituted cycloalkyl, $R^{84}$-substituted or unsubstituted heterocycloalkyl, $R^{84}$-substituted or unsubstituted aryl, or $R^{84}$-substituted or unsubstituted heteroaryl. Each X is independently —F, —Cl, —Br, or —I. In embodiments, X is —F.

$R^{84}$ is independently oxo, halogen, —$CX^{84}_3$, —$CHX^{84}_2$, —$CH_2X^{84}$, —$OCHX^{84}_2$, —$OCX^{84}_3$, —$OCH_2X^{84}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{85}$-substituted or unsubstituted alkyl, $R^{85}$-substituted or unsubstituted heteroalkyl, $R^{85}$-substituted or unsubstituted cycloalkyl, $R^{85}$-substituted or unsubstituted heterocycloalkyl, $R^{85}$-substituted or unsubstituted aryl, or $R^{85}$-substituted or unsubstituted heteroaryl. $X^{84}$ is halogen. In embodiments, $X^{84}$ is F.

$R^{85}$ is independently oxo, halogen, —$CX^{85}_3$, —$CHX^{85}_2$, —$CH_2X^{85}$, —$OCHX^{85}_2$, —$OCX^{85}_3$, —$OCH_2X^{85}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{86}$-substituted or unsubstituted alkyl, $R^{86}$-substituted or unsubstituted heteroalkyl, $R^{86}$-substituted or unsubstituted cycloalkyl, $R^{86}$-substituted or unsubstituted heterocycloalkyl, $R^{86}$-substituted or unsubstituted aryl, or $R^{86}$-substituted or unsubstituted heteroaryl. $X^{85}$ is halogen. In embodiments, $X^{85}$ is F.

In embodiments, each $R^{22}$ is independently hydrogen, —$CX_3$, —CN, —COOH, —$CONH_2$, —$CHX_2$, —$CH_2X$, $R^{87}$-substituted or unsubstituted alkyl, $R^{87}$-substituted or unsubstituted heteroalkyl, $R^{87}$-substituted or unsubstituted cycloalkyl, $R^{87}$-substituted or unsubstituted heterocycloalkyl, $R^{87}$-substituted or unsubstituted aryl, or $R^{87}$-substituted or unsubstituted heteroaryl. Each X is independently —F, —Cl, —Br, or —I. In embodiments, X is —F.

$R^{87}$ is independently oxo, halogen, —$CX^{87}_3$, —$CHX^{87}_2$, —$CH_2X^{87}$, —$OCHX^{87}_2$, —$OCX^{87}_3$, —$OCH_2X^{87}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{88}$-substituted or unsubstituted alkyl, $R^{88}$-substituted or unsubstituted heteroalkyl, $R^{88}$-substituted or unsubstituted cycloalkyl, $R^{88}$-substituted or unsubstituted heterocycloalkyl, $R^{88}$-substituted or unsubstituted aryl, or $R^{88}$-substituted or unsubstituted heteroaryl. $X^{87}$ is halogen. In embodiments, $X^{87}$ is F.

$R^{88}$ is independently oxo, halogen, —$CX^{88}_3$, —$CHX^{88}_2$, —$CH_2X^{88}$, —$OCHX^{88}_2$, —$OCX^{88}_3$, —$OCH_2X^{88}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{89}$-substituted or unsubstituted alkyl, $R^{89}$-substituted or unsubstituted heteroalkyl, $R^{89}$-substituted or unsubstituted cycloalkyl, $R^{89}$-substituted or unsubstituted heterocycloalkyl, $R^{89}$-substituted or unsubstituted aryl, or $R^{89}$-substituted or unsubstituted heteroaryl. $X^{88}$ is halogen. In embodiments, $X^{88}$ is F.

In embodiments, each $R^{23}$ is independently hydrogen, —$CX_3$, —CN, —COOH, —$CONH_2$, —$CHX_2$, —$CH_2X$, $R^{90}$-substituted or unsubstituted alkyl, $R^{90}$-substituted or unsubstituted heteroalkyl, $R^{90}$-substituted or unsubstituted cycloalkyl, $R^{90}$-substituted or unsubstituted heterocycloalkyl, $R^{90}$-substituted or unsubstituted aryl, or $R^{90}$-substituted or unsubstituted heteroaryl. Each X is independently —F, —Cl, —Br, or —I. In embodiments, X is —F.

$R^{90}$ is independently oxo, halogen, —$CX^{90}_3$, —$CHX^{90}_2$, —$CH_2X^{90}$, —$OCHX^{90}_2$, —$OCX^{90}_3$, —$OCH_2X^{90}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{91}$-substituted or unsubstituted alkyl, $R^{91}$-substituted or unsubstituted heteroalkyl, $R^{91}$-substituted or unsubstituted cycloalkyl, $R^{91}$-substituted or unsubstituted heterocycloalkyl, $R^{91}$-substituted or unsubstituted aryl, or $R^{91}$-substituted or unsubstituted heteroaryl. $X^{90}$ is halogen. In embodiments, $X^{90}$ is F.

$R^{91}$ is independently oxo, halogen, —$CX^{91}_3$, —$CHX^{91}_2$, —$CH_2X^{91}$, —$OCHX^{91}_2$, —$OCX^{91}_3$, —$OCH_2X^{91}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$. —NHC=(O)$NH_2$, —$NHSO_2H$, —NHC=(O)H, —NHC(O)—OH, —NHOH, $R^{92}$-substituted or unsubstituted alkyl, $R^{92}$-substituted or unsubstituted heteroalkyl, $R^{92}$-substituted or unsubstituted cycloalkyl, $R^{92}$-substituted or unsubstituted heterocycloalkyl, $R^{92}$-substituted or unsubstituted aryl, or $R^{92}$-substituted or unsubstituted heteroaryl. $X^{91}$ is halogen. In embodiments, $X^{91}$ is F.

In embodiments, each $R^{24}$ is independently hydrogen, —$CX_3$, —CN, —COOH, —$CONH_2$, —$CHX_2$, —$CH_2X$, $R^{93}$-substituted or unsubstituted alkyl, $R^{93}$-substituted or unsubstituted heteroalkyl, $R^{93}$-substituted or unsubstituted cycloalkyl, $R^{93}$-substituted or unsubstituted heterocycloalkyl, $R^{93}$-substituted or unsubstituted aryl, or $R^{93}$-substituted or unsubstituted heteroaryl. Each X is independently —F, —Cl, —Br, or —I. In embodiments, X is —F.

$R^{93}$ is independently oxo, halogen, —$CX^{93}_3$, —$CHX^{93}_2$, —$CH_2X^{93}$, —$OCHX^{93}_2$, —$OCX^{93}_3$, —$OCH_2X^{93}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{94}$-substituted or unsubstituted alkyl, $R^{94}$-substituted or unsubstituted heteroalkyl, $R^{94}$-substituted or unsubstituted cycloalkyl, $R^{94}$-substituted or unsubstituted heterocycloalkyl, $R^{94}$-substituted or unsubstituted aryl, or $R^{94}$-substituted or unsubstituted heteroaryl. $X^{93}$ is halogen. In embodiments, $X^{93}$ is F.

$R^{94}$ is independently oxo, halogen, —$CX^{94}_3$, —$CHX^{94}_2$, —$CH_2X^{94}$, —$OCHX^{94}_2$, —$OCX^{94}_3$, —$OCH_2X^{94}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{95}$-substituted or unsubstituted alkyl, $R^{95}$-substituted or unsubstituted heteroalkyl, $R^{95}$-substituted or unsubstituted cycloalkyl, $R^{95}$-substituted or unsubstituted heterocycloalkyl, $R^{95}$-substituted or unsubstituted aryl, or $R^{95}$-substituted or unsubstituted heteroaryl. $X^{94}$ is halogen. In embodiments, $X^{94}$ is F.

In embodiments, each $R^{25}$ is independently hydrogen, —$CX_3$, —CN, —COOH, —$CONH_2$, —$CHX_2$, —$CH_2X$, $R^{96}$-substituted or unsubstituted alkyl, $R^{96}$-substituted or unsubstituted heteroalkyl, $R^{96}$-substituted or unsubstituted cycloalkyl, $R^{96}$-substituted or unsubstituted heterocycloalkyl, $R^{96}$-substituted or unsubstituted aryl, or $R^{96}$-substituted or unsubstituted heteroaryl. Each X is independently —F, —Cl, —Br, or —I. In embodiments, X is —F.

$R^{96}$ is independently oxo, halogen, —$CX^{96}_3$, —$CHX^{96}_2$, —$CH_2X^{96}$, —$OCHX^{96}_2$, —$OCX^{96}_3$, —$OCH_2X^{96}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{97}$-substituted or unsubstituted alkyl, R$^{97}$-substituted or unsubstituted heteroalkyl, R$^{97}$-substituted or unsubstituted cycloalkyl, R$^{97}$-substituted or unsubstituted heterocycloalkyl, R$^{97}$-substituted or unsubstituted aryl, or R$^{97}$-substituted or unsubstituted heteroaryl. X$^{96}$ is halogen. In embodiments, X$^{96}$ is F.

R$^{97}$ is independently oxo, halogen, —CX$^{97}_3$, —CHX$^{97}_2$, —CH$_2$X$^{97}$, —OCHX$^{97}_2$, —OCX$^{97}_3$, —OCH$_2$X$^{97}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{98}$-substituted or unsubstituted alkyl, R$^{98}$-substituted or unsubstituted heteroalkyl, R$^{98}$-substituted or unsubstituted cycloalkyl, R$^{98}$-substituted or unsubstituted heterocycloalkyl, R$^{98}$-substituted or unsubstituted aryl, or R$^{98}$-substituted or unsubstituted heteroaryl. X$^{97}$ is halogen. In embodiments, X$^{97}$ is F.

In embodiments, each R$^{26}$ is independently hydrogen, —CX$_3$, —CN, —COOH, —CONH$_2$, —CHX$_2$, —CH$_2$X, R$^{99}$-substituted or unsubstituted alkyl, R$^{99}$-substituted or unsubstituted heteroalkyl, R$^{99}$-substituted or unsubstituted cycloalkyl, R$^{99}$-substituted or unsubstituted heterocycloalkyl, R$^{99}$-substituted or unsubstituted aryl, or R$^{99}$-substituted or unsubstituted heteroaryl. Each X is independently —F, —Cl, —Br, or —I. In embodiments, X is —F.

R$^{99}$ is independently oxo, halogen, —CX$^{99}_3$, —CHX$^{99}_2$, —CH$_2$X$^{99}$, —OCHX$^{99}_2$, —OCX$^{99}_3$, —OCH$_2$X$^{99}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{100}$-substituted or unsubstituted alkyl, R$^{100}$-substituted or unsubstituted heteroalkyl, R$^{100}$-substituted or unsubstituted cycloalkyl, R$^{100}$-substituted or unsubstituted heterocycloalkyl, R$^{100}$-substituted or unsubstituted aryl, or R$^{100}$-substituted or unsubstituted heteroaryl. X$^{99}$ is halogen. In embodiments, X$^{99}$ is F.

R$^{100}$ is independently oxo, halogen, —CX$^{100}_3$, —CHX$^{100}_2$, —CH$_2$X$^{100}$, —OCHX$^{100}_2$, —OCX$^{100}_3$, —OCH$_2$X$^{100}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{101}$-substituted or unsubstituted alkyl, R$^{101}$-substituted or unsubstituted heteroalkyl, R$^{101}$-substituted or unsubstituted cycloalkyl, R$^{101}$-substituted or unsubstituted heterocycloalkyl, R$^{101}$-substituted or unsubstituted aryl, or R$^{101}$-substituted or unsubstituted heteroaryl. X$^{100}$ is halogen. In embodiments, X$^{100}$ is F.

In embodiments, each R$^{27}$ is independently hydrogen, —CX$_3$, —CN, —COOH, —CONH$_2$, —CHX$_2$, —CH$_2$X, R$^{102}$-substituted or unsubstituted alkyl, R$^{102}$-substituted or unsubstituted heteroalkyl, R$^{102}$-substituted or unsubstituted cycloalkyl, R$^{102}$-substituted or unsubstituted heterocycloalkyl, R$^{102}$-substituted or unsubstituted aryl, or R$^{102}$-substituted or unsubstituted heteroaryl. Each X is independently —F, —Cl, —Br, or —I. In embodiments, X is —F.

R$^{102}$ is independently oxo, halogen, —CX$^{102}_3$, —CHX$^{102}_2$, —CH$_2$X$^{102}$, —OCHX$^{102}_2$, —OCX$^{102}_3$, —OCH$_2$X$^{102}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{103}$-substituted or unsubstituted alkyl, R$^{103}$-substituted or unsubstituted heteroalkyl, R$^{103}$-substituted or unsubstituted cycloalkyl, R$^{103}$-substituted or unsubstituted heterocycloalkyl, R$^{103}$-substituted or unsubstituted aryl, or R$^{103}$-substituted or unsubstituted heteroaryl. X$^{102}$ is halogen. In embodiments, X$^{102}$ is F.

R$^{103}$ is independently oxo, halogen, —CX$^{103}_3$, —CHX$^{103}_2$, —CH$_2$X$^{103}$, —OCHX$^{103}_2$, —OCX$^{103}_3$, —OCH$_2$X$^{103}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{104}$-substituted or unsubstituted alkyl, R$^{104}$-substituted or unsubstituted heteroalkyl, R$^{104}$-substituted or unsubstituted cycloalkyl, R$^{104}$-substituted or unsubstituted heterocycloalkyl, R$^{104}$-substituted or unsubstituted aryl, or R$^{104}$-substituted or unsubstituted heteroaryl. X$^{103}$ is halogen. In embodiments, X$^{103}$ is F.

In embodiments, each R$^{28}$ is independently hydrogen, —CX$_3$, —CN, —COOH, —CONH$_2$, —CHX$_2$, —CH$_2$X, R$^{105}$-substituted or unsubstituted alkyl, R$^{105}$-substituted or unsubstituted heteroalkyl, R$^{105}$-substituted or unsubstituted cycloalkyl, R$^{105}$-substituted or unsubstituted heterocycloalkyl, R$^{105}$-substituted or unsubstituted aryl, or R$^{105}$-substituted or unsubstituted heteroaryl. Each X is independently —F, —Cl, —Br, or —I. In embodiments, X is —F.

R$^{105}$ is independently oxo, halogen, —CX$^{105}_3$, —CHX$^{15}_2$, —CH$_2$X$^{105}$, —OCHX$^{105}_2$, —OCX$^{105}_3$, —OCH$_2$X$^{105}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{106}$-substituted or unsubstituted alkyl, R$^{106}$-substituted or unsubstituted heteroalkyl, R$^{106}$-substituted or unsubstituted cycloalkyl, R$^{106}$-substituted or unsubstituted heterocycloalkyl, R$^{106}$-substituted or unsubstituted aryl, or R$^{106}$-substituted or unsubstituted heteroaryl. X$^{105}$ is halogen. In embodiments, X$^{105}$ is F.

R$^{106}$ is independently oxo, halogen, —CX$^{106}_3$, —CHX$^{106}_2$, —CH$_2$X$^{106}$, —OCHX$^{106}_2$, —OCX$^{106}_3$, —OCH$_2$X$^{106}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{107}$-substituted or unsubstituted alkyl, R$^{107}$-substituted or unsubstituted heteroalkyl, R$^{107}$-substituted or unsubstituted cycloalkyl, R$^{107}$-substituted or unsubstituted heterocycloalkyl, R$^{107}$-substituted or unsubstituted aryl, or R$^{107}$-substituted or unsubstituted heteroaryl. X$^{106}$ is halogen. In embodiments, X$^{106}$ is F.

In embodiments, R$^{1A}$ is independently halogen, —CN, —OR$^{1B}$, —SR$^{1B}$, —NR$^{1C}$R$^{1D}$, NR$^{1C}$ C(O)R$^{1B}$, —C(O)NR$^{1C}$R$^{1D}$, —CO$_2$R$^{1B}$, R$^{108}$-substituted or unsubstituted alkyl, or R$^{108}$-substituted or unsubstituted heteroalkyl.

In embodiments, R$^{108}$ is independently oxo, halogen, —CX$^{108}_3$, —CHX$^{108}_2$, —CH$_2$X$^{108}$, —OCHX$^{108}_2$, —OCX$^{108}_3$, —OCH$_2$X$^{108}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{109}$-substituted or unsubstituted alkyl, R$^{109}$-substituted or unsubstituted heteroalkyl, R$^{109}$-substituted or unsubstituted cycloalkyl, R$^{109}$-substituted or unsubstituted heterocycloalkyl, R$^{109}$-substituted or unsubstituted aryl, or R$^{109}$-substituted or unsubstituted heteroaryl. X$^{108}$ is halogen. In embodiments, X$^{108}$ is F.

In embodiments, R$^{109}$ is independently oxo, halogen, —CX$^{109}_3$, —CHX$^{109}_2$, —CH$_2$X$^{109}$, —OCHX$^{109}_2$, —OCX$^{109}_3$, —OCH$_2$X$^{109}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{110}$-substituted or unsubstituted alkyl, R$^{110}$-substituted or unsubstituted heteroalkyl, R$^{110}$-substituted or unsubstituted cycloalkyl, R$^{110}$-substituted or unsubstituted heterocycloalkyl, R$^{110}$-substituted or unsubstituted aryl, or R$^{110}$-substituted or unsubstituted heteroaryl. X$^{109}$ is halogen. In embodiments, X$^{109}$ is F.

In embodiments, R$^{1B}$ is independently hydrogen, R$^{111}$-substituted or unsubstituted alkyl, R$^{111}$-substituted or unsubstituted heteroalkyl, R$^{111}$-substituted or unsubstituted cycloalkyl, R$^{111}$-substituted or unsubstituted heterocycloalkyl, R$^{111}$-substituted or unsubstituted aryl, or R$^{111}$-substituted or unsubstituted heteroaryl.

In embodiments, R$^{111}$ is independently oxo, halogen, —CX$^{111}_3$, —CHX$^{111}_2$, —CH$_2$X$^{111}$, —OCHX$^{111}_2$, —OCX$^{111}_3$, —OCH$_2$X$^{111}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H. —NHC(O)—OH, —NHOH, R$^{112}$-substituted or unsubstituted alkyl, R$^{112}$-substituted or unsubstituted heteroalkyl, R$^{112}$-substituted or unsubstituted cycloalkyl, R$^{112}$-substituted or unsubstituted heterocycloalkyl, R$^{112}$-substituted or unsubstituted aryl, or R$^{112}$-substituted or unsubstituted heteroaryl. X$^{111}$ is halogen. In embodiments, X$^{111}$ is F.

In embodiments, R$^{112}$ is independently oxo, halogen, —CX$^{112}_3$, —CHX$^{112}_2$, —CH$_2$X$^{112}$, —OCHX$^{112}_2$, —OCX$^{112}_3$, —OCH$_2$X$^{112}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{113}$-substituted or unsubstituted alkyl, R$^{113}$-substituted or unsubstituted heteroalkyl, R$^{113}$-substituted or unsubstituted cycloalkyl, R$^{113}$-substituted or unsubstituted heterocycloalkyl, R$^{113}$-substituted or unsubstituted aryl, or R$^{113}$-substituted or unsubstituted heteroaryl. X$^{112}$ is halogen. In embodiments, X$^{112}$ is F.

In embodiments, R$^{1C}$ is independently hydrogen, R$^{114}$-substituted or unsubstituted alkyl, R$^{114}$-substituted or unsubstituted heteroalkyl, R$^{114}$-substituted or unsubstituted cycloalkyl, R$^{114}$-substituted or unsubstituted heterocycloalkyl, R$^{114}$-substituted or unsubstituted aryl, or R$^{114}$-substituted or unsubstituted heteroaryl;

In embodiments, R$^{114}$ is independently oxo, halogen, —CX$^{114}_3$, —CHX$^{114}_2$, —CH$_2$X$^{114}$, —OCHX$^{114}_2$, —OCX$^{114}_3$, —OCH$_2$X$^{114}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{115}$-substituted or unsubstituted alkyl, R$^{115}$-substituted or unsubstituted heteroalkyl, R$^{115}$-substituted or unsubstituted cycloalkyl, R$^{115}$-substituted or unsubstituted heterocycloalkyl, R$^{115}$-substituted or unsubstituted aryl, or R$^{115}$-substituted or unsubstituted heteroaryl. X$^{114}$ is halogen. In embodiments, X$^{114}$ is F.

In embodiments, R$^{115}$ is independently oxo, halogen, —CX$^{115}_3$, —CHX$^{115}_2$, —CH$_2$X$^{115}$, —OCHX$^{115}_2$, —OCX$^{115}_3$, —OCH$_2$X$^{115}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{116}$-substituted or unsubstituted alkyl, R$^{116}$-substituted or unsubstituted heteroalkyl, R$^{116}$-substituted or unsubstituted cycloalkyl, R$^{116}$-substituted or unsubstituted heterocycloalkyl, R$^{116}$-substituted or unsubstituted aryl, or R$^{116}$-substituted or unsubstituted heteroaryl. X$^{115}$ is halogen. In embodiments, X$^{115}$ is F.

In embodiments, R$^{1D}$ is independently R$^{117}$-substituted or unsubstituted alkyl, R$^{117}$-substituted or unsubstituted heteroalkyl, R$^{117}$-substituted or unsubstituted cycloalkyl, R$^{117}$-substituted or unsubstituted heterocycloalkyl, R$^{117}$-substituted or unsubstituted aryl, or R$^{117}$-substituted or unsubstituted heteroaryl.

In embodiments, R$^{117}$ is independently oxo, halogen, —CX$^{117}_3$, —CHX$^{117}_2$, —CH$_2$X$^{117}$, —OCHX$^{117}_2$, —OCX$^{117}_3$, —OCH$_2$X$^{117}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{118}$-substituted or unsubstituted alkyl, R$^{118}$-substituted or unsubstituted heteroalkyl, R$^{118}$-substituted or unsubstituted cycloalkyl, R$^{118}$-substituted or unsubstituted heterocycloalkyl, R$^{118}$-substituted or unsubstituted aryl, or R$^{118}$-substituted or unsubstituted heteroaryl. X$^{117}$ is halogen. In embodiments, X$^{117}$ is F.

In embodiments, R$^{118}$ is independently oxo, halogen, —CX$^{118}_3$, —CHX$^{118}_2$, —CH$_2$X$^{118}$, —OCHX$^{118}_2$, —OCX$^{118}_3$, —OCH$_2$X$^{118}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{119}$-substituted or unsubstituted alkyl, R$^{119}$-substituted or unsubstituted heteroalkyl, R$^{119}$-substituted or unsubstituted cycloalkyl, R$^{119}$-substituted or unsubstituted heterocycloalkyl, R$^{119}$-substituted or unsubstituted aryl, or R$^{119}$-substituted or unsubstituted heteroaryl. X$^{118}$ is halogen. In embodiments, X$^{118}$ is F.

In embodiments, R$^{1C}$ and R$^{1D}$ attached to the same nitrogen atom optionally combine to form a R$^{120}$-substituted or unsubstituted heterocycloalkyl.

In embodiments, R$^{120}$ is independently oxo, halogen, —CX$^{120}_3$, —CHX$^{120}_2$, —CH$_2$X$^{120}$, —OCHX$^{120}_2$, —OCX$^{120}_3$, —OCH$_2$X$^{120}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{121}$-substituted or unsubstituted alkyl, R$^{121}$-substituted or unsubstituted heteroalkyl, R$^{121}$-substituted or unsubstituted cycloalkyl, R$^{121}$-substituted or unsubstituted heterocycloalkyl, R$^{121}$-substituted or unsubstituted aryl, or R$^{121}$-substituted or unsubstituted heteroaryl. X$^{120}$ is halogen. In embodiments, X$^{120}$ is F.

In embodiments, R$^{21}$ is independently oxo, halogen, —CX$^{121}_3$, —CHX$^{121}_2$, —CH$_2$X$^{121}$, —OCHX$^{121}_2$, —OCX$^{121}_3$, —OCH$_2$X$^{121}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{122}$-substituted or unsubstituted alkyl, R$^{122}$-substituted or unsubstituted heteroalkyl, R$^{122}$-substituted or unsubstituted cycloalkyl, R$^{122}$-substituted or unsubstituted heterocycloalkyl, R$^{122}$-substituted or unsubstituted aryl, or R$^{122}$-substituted or unsubstituted heteroaryl. X$^{121}$ is halogen. In embodiments, X$^{121}$ is F.

In embodiments, R$^{2A}$ is independently —NR$^{2B}$R$^{2C}$, R$^{123}$-substituted or unsubstituted cycloalkyl, R$^{123}$-substituted or unsubstituted heterocycloalkyl, R$^{123}$-substituted or unsubstituted aryl, or R$^{123}$-substituted or unsubstituted heteroaryl.

In embodiments, R$^{123}$ is independently oxo, halogen, —CX$^{123}_3$, —CHX$^{123}_2$, —CH$_2$X$^{123}$, —OCHX$^{123}_2$, —OCX$^{123}_3$, —OCH$_2$X$^{123}$, —CN, —OH, —NH$_2$, —CO OH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{124}$-substituted or unsubstituted alkyl, R$^{124}$-substituted or unsubstituted heteroalkyl, R$^{124}$-substituted or unsubstituted cycloalkyl, R$^{124}$-substituted or unsubstituted heterocycloalkyl, R$^{124}$-substituted or unsubstituted aryl, or R$^{124}$-substituted or unsubstituted heteroaryl. X$^{123}$ is halogen. In embodiments, X$^{123}$ is F.

In embodiments, R$^{124}$ is independently oxo, halogen, —CX$^{124}_3$, —CHX$^{124}_2$, —CH$_2$X$^{124}$, —OCHX$^{124}_2$, —OCX$^{124}_3$, —OCH$_2$X$^{124}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{125}$-substituted or unsubstituted alkyl, R$^{125}$-substituted or unsubstituted heteroalkyl, R$^{125}$-substituted or unsubstituted cycloalkyl, R$^{125}$-substituted or unsubstituted heterocycloalkyl, R$^{125}$-substituted or unsubstituted aryl, or R$^{125}$-substituted or unsubstituted heteroaryl. X$^{124}$ is halogen. In embodiments, X$^{124}$ is F.

In embodiments, R$^{2B}$ is independently hydrogen, R$^{126}$-substituted or unsubstituted alkyl, R$^{16}$-substituted or unsubstituted heteroalkyl, R$^{126}$-substituted or unsubstituted cycloalkyl, R$^{126}$-substituted or unsubstituted heterocycloalkyl, R$^{126}$-substituted or unsubstituted aryl, or R$^{126}$-substituted or unsubstituted heteroaryl.

In embodiments, R$^{126}$ is independently oxo, halogen, —CX$^{126}_3$, —CHX$^{126}_2$, —CH$_2$X$^{126}$, —OCHX$^{126}_2$, —OCX$^{126}_3$, —OCH$_2$X$^{126}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{127}$-substituted or unsubstituted alkyl, R$^{127}$-substituted or unsubstituted heteroalkyl, R$^{127}$-substituted or unsubstituted cycloalkyl, R$^{127}$-substituted or unsubstituted heterocycloalkyl, R$^{127}$-substituted or unsubstituted aryl, or R$^{127}$-substituted or unsubstituted heteroaryl. X$^{126}$ is halogen. In embodiments, X$^{126}$ is F.

In embodiments, R$^{127}$ is independently oxo, halogen, —CX$^{127}_3$, —CHX$^{127}_2$, —CH$_2$X$^{127}$, —OCHX$^{127}_2$, —OCX$^{127}_3$, —OCH$_2$X$^{127}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{128}$-substituted or unsubstituted alkyl, R$^{128}$-substituted or unsubstituted heteroalkyl, R$^{128}$-substituted or unsubstituted cycloalkyl, R$^{128}$-substituted or unsubstituted heterocycloalkyl, R$^{128}$-substituted or unsubstituted aryl, or R$^{128}$-substituted or unsubstituted heteroaryl. X$^{127}$ is halogen. In embodiments, X$^{127}$ is F.

In embodiments, R$^{2C}$ is independently hydrogen, R$^{126}$-substituted or unsubstituted alkyl, R$^{126}$-substituted or unsubstituted heteroalkyl, R$^{126}$-substituted or unsubstituted cycloalkyl, R$^{126}$-substituted or unsubstituted heterocycloalkyl, R$^{126}$-substituted or unsubstituted aryl, or R$^{126}$ substituted or unsubstituted heteroaryl.

In embodiments, R$^{126}$ is independently oxo, halogen, —CX$^{126}_3$, —CHX$^{126}_2$, —CH$_2$X$^{126}$, —OCHX$^{126}_2$, —OCX$^{126}_3$, —OCH$_2$X$^{126}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH. —NHOH, R$^{130}$-substituted or unsubstituted alkyl, R$^{130}$-substituted or unsubstituted heteroalkyl, R$^{130}$-substituted or unsubstituted cycloalkyl, R$^{130}$-substituted or unsubstituted heterocycloalkyl, R$^{130}$-substituted or unsubstituted aryl, or R$^{130}$-substituted or unsubstituted heteroaryl. X$^{129}$ is halogen. In embodiments, X$^{129}$ is F.

In embodiments, R$^{130}$ is independently oxo, halogen, —CX$^{130}_3$, —CHX$^{130}_2$, —CH$_2$X$^{130}$, —OCHX$^{130}_2$, —OCX$^{130}_3$, —OCH$_2$X$^{130}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{131}$-substituted or unsubstituted alkyl, R$^{131}$-substituted or unsubstituted heteroalkyl, R$^{131}$-substituted or unsubstituted cycloalkyl, R$^{131}$-substituted or unsubstituted heterocycloalkyl, R$^{131}$-substituted or unsubstituted aryl, or R$^{131}$-substituted or unsubstituted heteroaryl. X$^{130}$ is halogen. In embodiments, X$^{130}$ is F.

In embodiments, R$^{2B}$ and R$^{2C}$ attached to the same nitrogen atom optionally combine to form a R$^{132}$-substituted or unsubstituted heterocycloalkyl.

In embodiments, R$^{132}$ is independently oxo, halogen, —CX$^{132}_3$, —CHX$^{132}_2$, —CH$_2$X$^{132}$, —OCHX$^{132}_2$, —OCX$^{132}_3$, —OCH$_2$X$^{132}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{133}$-substituted or unsubstituted alkyl, R$^{133}$-substituted or unsubstituted heteroalkyl, R$^{133}$-substituted or unsubstituted cycloalkyl, R$^{133}$-substituted or unsubstituted heterocycloalkyl, R$^{133}$-substituted or unsubstituted aryl, or R$^{133}$-substituted or unsubstituted heteroaryl. X$^{132}$ is halogen. In embodiments, X$^{132}$ is F.

In embodiments, R$^{133}$ is independently oxo, halogen, —CX$^{133}_3$, —CHX$^{133}_2$, —CH$_2$X$^{133}$, —OCHX$^{133}_2$, —OCX$^{133}_3$, —OCH$_2$X$^{133}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{134}$-substituted or unsubstituted alkyl, R$^{134}$-substituted or unsubstituted heteroalkyl, R$^{134}$-substituted or unsubstituted cycloalkyl, R$^{134}$-substituted or unsubstituted heterocycloalkyl, R$^{134}$-substituted or unsubstituted aryl, or R$^{134}$-substituted or unsubstituted heteroaryl. X$^{133}$ is halogen. In embodiments, X$^{133}$ is F.

R$^{31}$, R$^{34}$, R$^{37}$, R$^{38}$, R$^{39}$, R$^{40}$, R$^{41}$, R$^{44}$, R$^{47}$, R$^{50}$, R$^{53}$, R$^{56}$, R$^{59}$, R$^{62}$, R$^{65}$, R$^{68}$, R$^{71}$, R$^{74}$, R$^{77}$, R$^{80}$, R$^{83}$, R$^{86}$, R$^{89}$, R$^{92}$, R$^{95}$, R$^{98}$, R$^{101}$, R$^{104}$, R$^{107}$, R$^{110}$, R$^{113}$, R$^{116}$, R$^{119}$, R$^{122}$, R$^{125}$, R$^{128}$, and R$^{131}$ are independently hydrogen, oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, a compound as described herein may include multiple instances of X and/or other variables. For example, where each X is different, they may be referred to as, for example, $X_a$, $X_b$, $X_c$, $X_d$, $X_e$, $X_f$, $X_g$, $X_h$, $X_i$, $X_j$, $X_k$, $X_l$, $X_m$, $X_n$, $X_o$, $X_p$, $X_q$, $X_r$, $X_s$, $X_t$, $X_u$, $X_v$, $X_w$, $X_x$, $X_y$, $X_z$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, $X_{ww}$, $X_{xx}$, $X_{yy}$, $X_{zz}$, $X_{aaa}$, $X_{bbb}$, $X_{ccc}$, $X_{ddd}$, $X_{eee}$, $X_{fff}$, $X_{ggg}$, $X_{hhh}$, $X_{iii}$, $X_{jjj}$, $X_{kkk}$, $X_{lll}$, $X_{mmm}$, and $X_{nnn}$, where the definition of X is assumed for each of $X_a$, $X_b$, $X_c$, $X_d$, $X_e$, $X_f$, $X_g$, $X_h$, $X_i$, $X_j$, $X_k$, $X_l$, $X_m$, $X_n$, $X_o$, $X_p$, $X_q$, $X_r$, $X_s$, $X_t$, $X_u$, $X_v$, $X_w$, $X_x$, $X_y$, $X_z$, $X_{aa}$, $X_{bb}$, $X_{cc}$, $X_{dd}$, $X_{ee}$, $X_{ff}$, $X_{gg}$, $X_{hh}$, $X_{ii}$, $X_{jj}$, $X_{kk}$, $X_{ll}$, $X_{mm}$, $X_{nn}$, $X_{oo}$, $X_{pp}$, $X_{qq}$, $X_{rr}$, $X_{ss}$, $X_{tt}$, $X_{uu}$, $X_{vv}$, $X_{ww}$, $X_{xx}$, $X_{yy}$, $X_{zz}$, $X_{aaa}$, $X_{bbb}$, $X_{ccc}$, $X_{ddd}$, $X_{eee}$, $X_{fff}$, $X_{ggg}$, $X_{hhh}$, $X_{iii}$ $X_{jjj}$, $X_{kkk}$, $X_{lll}$, $X_{mmm}$, and $X_{nnn}$. The variables used within a definition of X and/or other variables that appear at multiple instances and are different may similarly be appropriately labeled to distinguish each group for greater clarity.

In some embodiments, the compound is a compound described herein (e.g., in an aspect, embodiment, example, claim, table, scheme, drawing, or figure).

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, figure, table, scheme, or claim).

In embodiments, a compound as described herein may be obtained or used as a pharmaceutically acceptable salt, polymorph, solvate, tautomer, pharmaceutically acceptable prodrug or N-oxide thereof.

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic.

IV. Methods of Synthesis

In some embodiments, the syntheses of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FisherScientific (Fisher Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

V. Methods of Treatment

In an aspect is provided a method of treating a disease or condition including administering to a subject in need thereof an effective amount of a compound described herein.

In embodiments, the disease or condition is diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure) or metabolic syndrome.

In an aspect is provided a method of treating a disease associated with low molecular weight protein tyrosine phosphatase (LMPTP) activity including administering to a subject in need thereof an effective amount of a compound described herein. In embodiments, the disease is associated with aberrant low molecular weight protein tyrosine phosphatase (LMPTP) activity. For example, studies have shown that inhibition of low molecular weight protein tyrosine phosphatase (LMPTP) activity may be a target for cardiac diseases (e.g., heart failure). See, e.g., Wade et al., *J. Pathol.*, 2015, pages 1-13 (DOI: 10.1002/path.4594), which is hereby incorporated by reference in its entirety.

In embodiments, the method includes administering a second agent (e.g. therapeutic agent). In embodiments, the method includes administering a second agent (e.g. therapeutic agent) in a therapeutically effective amount. Examples of a second agent include therapeutic agents known in the art for the treatment of diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure) or metabolic syndrome. Thus, in embodiments, the method includes administering to a subject in need thereof an effective amount of a compound described herein in combination with a second therapeutic agent for the treatment of diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure) or metabolic syndrome.

VI. Methods of Inhibition

In an aspect is provided a method of inhibiting low molecular weight protein tyrosine phosphatase (LMPTP) activity including contacting the low molecular weight protein tyrosine phosphatase (LMPTP) with a compound described herein. In embodiments, the low molecular weight protein tyrosine phosphatase (LMPTP) is a human low molecular weight protein tyrosine phosphatase (LMPTP).

In embodiments, the inhibition is competitive inhibition. In embodiments, the inhibition is non-competitive inhibition. In embodiments, the inhibition is uncompetitive inhibition. In embodiments, the inhibition is irreversible. In embodiments, the inhibition is reversible.

In embodiments, the compound, or pharmaceutically acceptable salt thereof, is an allosteric inhibitor.

VII. Examples

In some embodiments, compounds described herein are prepared as shown in Scheme 1.

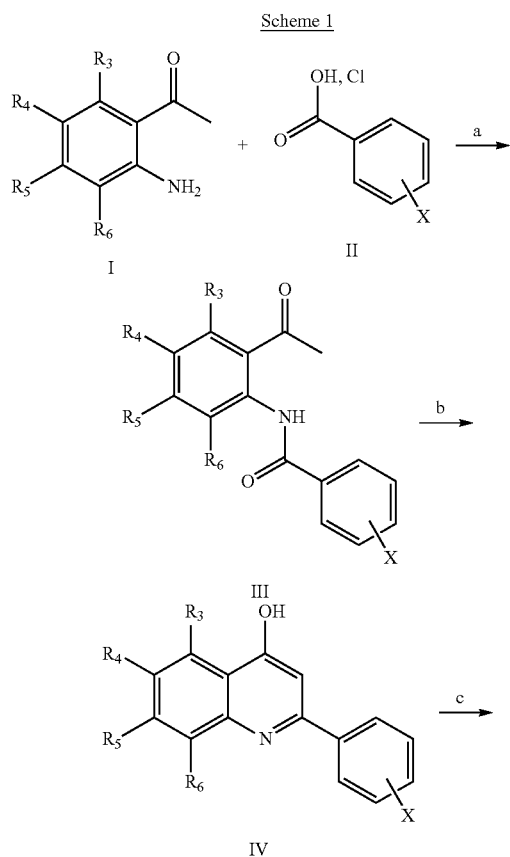

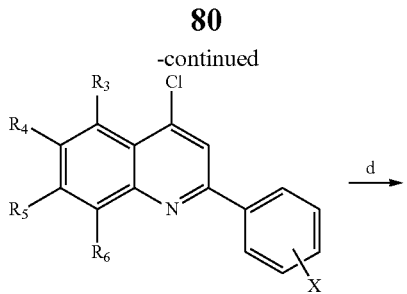

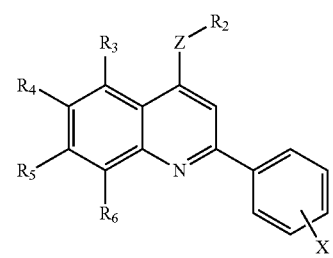

The synthesis of compound VI can be accomplished by the reactions illustrated in Scheme 1. Treatment of Compound I with an acid chloride II containing an amine base at temperatures between 0° C. and 50° C. in a solvent such as dichlormethane (DCM) produced compound III. Alternatively, activation of the carboxylic acid of formula II with a coupling reagent such as 1-Ethyl-3-(3-dimethylaminopropyl)carbodiimide (EDC) and Hydroxybenzotriazole (HOBt) in a solvent such as DMF or acetonitrile containing an amine base such as N,N-Diisopropylethyl amine, triethylamine or other organic bases followed by treatment of this mixture with compound I gives rise to compounds of formula III. Substitution of the coupling reagent EDC by 1-Propanephosphonic anhydride solution, 2,4,6-Tripropyl-1,3,5,2,4,6-trioxatriphosphorinane-2,4,6-trioxide (T3P), carbonyliimidazole, BOP reagent, dicyclohexylcarbodiimide (DCC), or HATU produces compound III.

Treatment of compound III with a strong base such as potassium t-butoxide, sodium hydride in a solvent such as tert-butanol, DMF or DMSO at temperatures between 0° C. and 100° C. produced compound IV. Compound IV when treated with phosphorus oxychloride or thionyl chloride at temperatures between 25° C. and 100° C. produced compound V. Finally, treatment compound V in an inert organic solvent such as THF, DMF, DMA containing an organic base such as triethylamine, or strong base such as potassium t-butoxide, sodium hydride or potassium hydride with an alcohol or amine compound of formula $HZR_2$ produces compounds of formula VI. The reaction is preferably carried out at temperatures between 25° C. and 150° C.

Preparation of Tert-Butyl Piperazine-1-Carboxylates Structure III

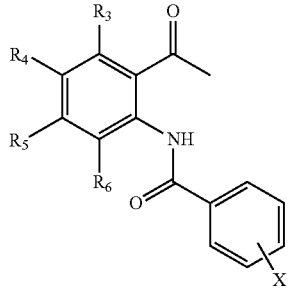

General Procedure A

Example A1: Preparation of N-(2-acetylphenyl)-4-methoxybenzamide

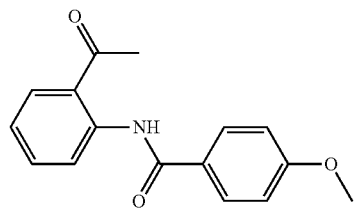 [SMILES: COc1ccc(C(=O)Nc2ccccc2C(C)=O)cc1]

To a solution of 1-(2-aminophenyl)ethanone (5.0 g, 37 mmol) and DIPEA (13 mL, 74 mmol) in 200 mL of THF in an ice bath was added 4-methoxybenzoyl chloride (7.5 mL, 56 mmol) dropwise. After 30 min at 0° C., the mixture was stirred at room temperature overnight and poured in 50 mL of ice water. The precipitate was collected and washed with water and then methanol. The solid was dried under vacuum to yield 8.0 g of N-(2-acetylphenyl)-4-methoxybenzamide (80% yield). MS (EI) m/z 270 [(M+I)+].

Preparation of Compounds of Structure IV

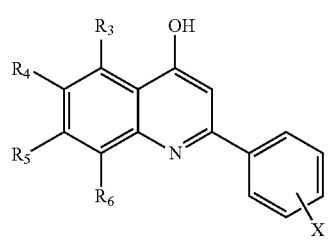

General Procedure B

Example B1: Preparation of 2-(4-methoxyphenyl)quinolin-4-ol

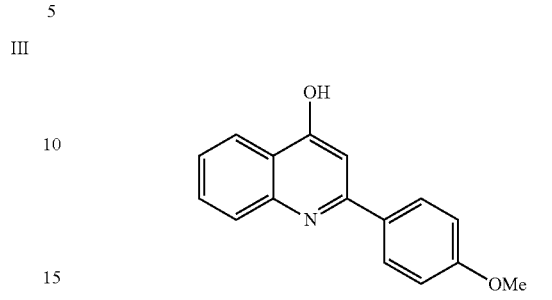

N-(2-acetylphenyl)-4-methoxybenzamide (4.0 g, 15 mmol) was suspended in 100 mL of tert-butyl alcohol. Potassium tert-butoxide (3.3 g, 30 mmol) was added. The mixture was heated at 75° C. overnight at nitrogen atmosphere. When the reaction was determined to be complete by HPLC, the reaction mixture was cooled and poured into 50 mL of ice water. 10% aqueous HCl was added until pH=6. The solid was collected and washed several times with water to afford 3.1 g of 2-(4-methoxyphenyl)quinolin-4-ol (84% yield). MS (EI) m/z 252 [(M+1)+].

Preparation of Compounds of Structure V

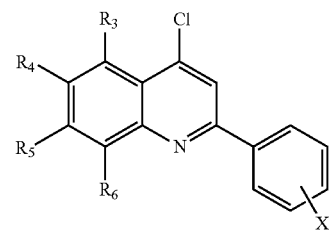

General Procedure C

Example C1: Preparation of 4-chloro-2-(4-methoxyphenyl)quinoline

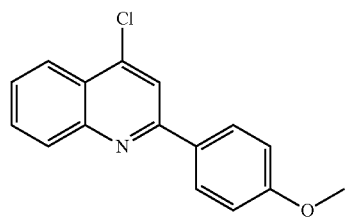 [SMILES: COc1ccc(-c2cc(Cl)c3ccccc3n2)cc1]

2-(4-methoxyphenyl)quinolin-4-ol (3.1 g, 12.4 mmol) was added to phosphorus oxychloride $POCl_3$ (50 mL, 540 mmol) to give an dark solution, then several drops of DMF was added. The reaction was heated at 90° C. overnight. When the reaction was determined to be complete by HPLC, the reaction mixture was cooled to room temperature and concentrated under reduced pressure. The resulting oil was basified with 1N NaOH solution, extracted with ethyl acetate and dried over magnesium sulfate. The organic layer was concentrated under reduced pressure to the crude product, which was chromatographed on silica gel and eluted with ethyl acetate and dichoromethane (0:100 to 30:70 gradient) to yield 2.0 g of product 4 (61% yield). $^1$H NMR (400 MHz, DMSO-d) δ 3.84 (s, 3H), 7.09 (m, 2H), 7.70 (m, 1H), 7.88 (m, 1H), 8.09 (m, 1H), 8.18 (m, 1H), 8.27 (m, 2H), 8.36 (m, 1H). MS (EI) m/z [(M+1)+].

Preparation of Compounds of Structure VI

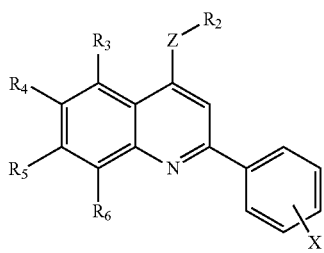

General Procedure D

Example D1: Preparation of 2-(4-methoxyphenyl)-N-(3-(piperidin-1-yl)propyl)quinolin-4-amine

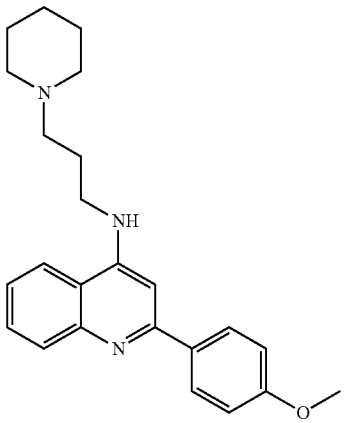 [SMILES: COc1ccc(-c2cc(NCCCN3CCCCC3)c3ccccc3n2)cc1]

Potassium tert-butoxide (50 mg, 0.5 mmol)) was added to a solution of 4-chloro-2-(4-methoxy-phenyl)quinoline 4 (1.0 g, 3.7 mmol) and 3-(Piperidin-1-yl)propan-1-amine (1.1 g, 7.7 mmol) in dry DMA (50 ml). The reaction was heated at 135° C. overnight at nitrogen atmosphere. When the reaction was determined to be complete by HPLC, the reaction mixture was cooled to room temperature and evaporated under vacuum to give a residue. 20 mL of water was added and extracted with chloroform. The organic layer was dried over magnesium sulfate and concentrated under reduced pressure to give the crude product, which was subjected to be purified by preparative HPLC to afford 0.8 g of 2-(4-methoxyphenyl)-N-(3-(piperidin-1-yl)propyl)quinolin-4-amine (57% yield). $^1$H NMR (400 MHz, DMSO-d) δ 1.44 (m, 2H), 1.60 (m, 4H), 1.97 (m, 2H), 2.72 (m, 6H), 3.45 (m, 2H), 3.82 (s, 3H), 4.94 (s, 2H), 6.91 (s, 1H), 7.04 (m, 2H), 7.39 (m, 2H), 7.61 (m, 1H), 7.82 (m, 1H), 8.13 (m, 3H), 8.26 (s, 2H). $^{13}$C NMR (400 MHz, DMSO-d) δ (ppm) 22.8, 23.7, 24.1, 53.0, 55.3, 94.5, 113.8, 117.7, 121.5, 123.6, 128.6, 129.3, 132.0, 147.7, 150.9, 156.0, 160.2, 164.4. MS (EI) m/z 376 [(M+1)+].

In some embodiments, compounds described herein are prepared as shown in Scheme 2.

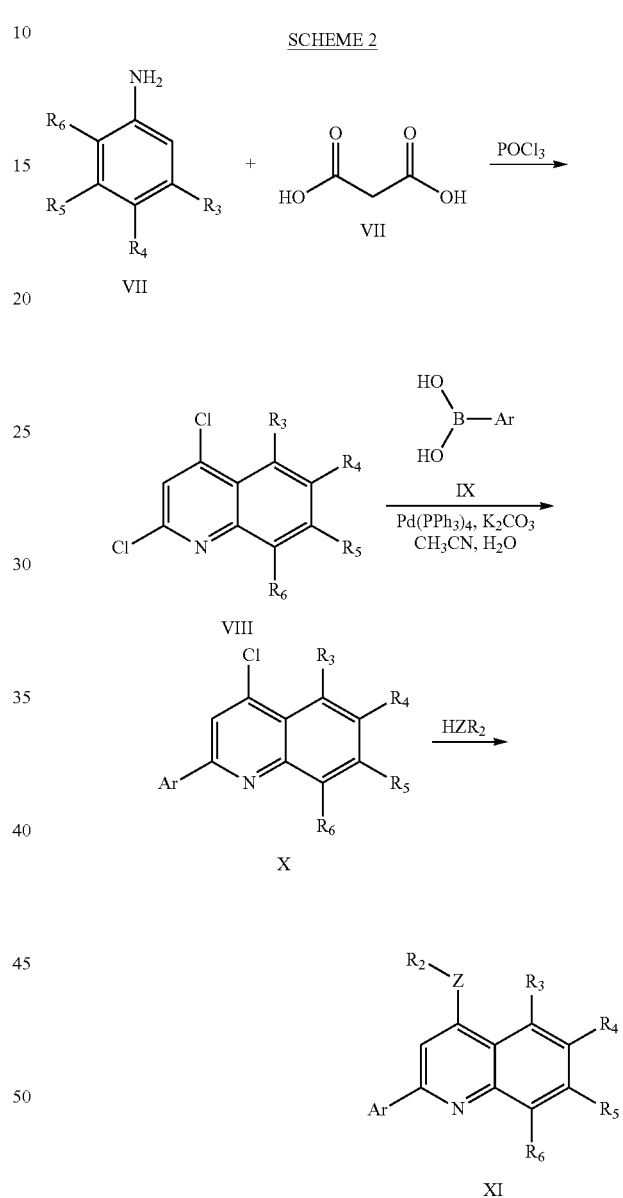

The synthesis of compound XI can be accomplished by the reactions illustrated in Scheme 2. A mixture of compound VII and compound VII when treated with phosphorus oxychloride or thionyl chloride at temperatures between 25° C. and 100° C. produced compound VIII. Suzuki coupling of compound VIII with an aromatic boronic acid IX employing standard Suzuki coupling conditions using a palladium zero species such as Pd(PPh$_3$)$_4$, with aqueous potassium carbonate or sodium carbonate in an inert solvent such as acetonitrile or toluene produces Compound X. The reaction is preferably carried out at temperatures between 25° C. and 150° C. The predominate isomer produced in this reaction is the C2 addition on the quinoline ring. Finally, treatment compound X in an inert organic solvent such as THF, DMF, DMA containing an organic base such as triethylamine, or strong base such as potassium t-butoxide, sodium hydride or potassium hydride with an alcohol or amine compound of formula $HZR_2$ produces compounds of formula XI. The reaction is preferably carried out at temperatures between 25° C. and 150° C.

Preparation of Compounds of Structure VIII

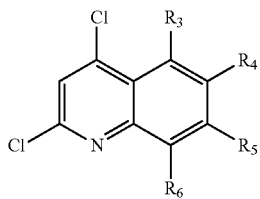

VIII

General Procedure E

Example E1: Preparation of 2,4-dichloroquinoline

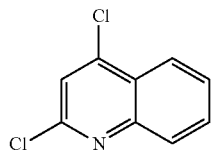

VIII

Aniline (10 g, 108 mmol) and malonic acid (11 g, 108 mmol) was suspended in $POCl_3$ (100 mL). The resulting mixture was stirred at 120° C. overnight. After cooling to room temperature, the mixture was poured into crushed ice while shaking. The mixture was partitioned between water (150 mL) and EA (150 mL). The aqueous phase was extracted with EA (200 mL×2). The combined organic phase was washed with water (250 mL×2) and brine (250 mL), and dried over $NaSO_4$. After filtration, the solvent was removed, and the residue was purified by silica gel column chromatography (PE/EA=50/1) to give 2,4-dichloroquinoline (4.3 g, yield: 20%) as a white solid. MS (EI): m/z 197.8 [(M+1)+].

Preparation of Compounds of Structure X

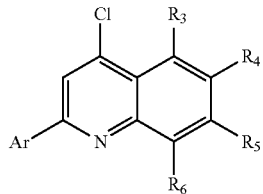

X

General Procedure F

Example F1: Preparation of 4-chloro-2-(2-trifluoromethyl-phenyl)-quinoline

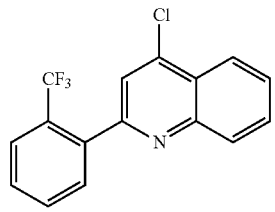 [SMILES: FC(F)(F)c1ccccc1-c1cc(Cl)c2ccccc2n1]

To a mixture of 2,4-dichloro-quinoline (300 mg, 1.51 mmol) in $CH_3CN$ (12 mL) and $H_2O$ (4 mL), was added 2-(trifluoromethyl)phenyboronic acid (232 mg, 1.66 mmol), $K_2CO_3$ (417 mg, 3.02 mmol) and $Pd(PPh_3)_4$ (36 mg, 0.03 mmol). The suspension was degassed under reduced pressure and purged with $N_2$ atmosphere for several times. The mixture was stirred at 80° C. overnight. The mixture was partitioned between water (30 mL) and EA (30 mL). The aqueous phase was extracted with EA (30 mL×2). The combined organic phase was washed with brine (80 mL×2) and dried over $NaSO_4$. After filtration, the solvent was removed, and the residue was purified by silica gel column chromatography (PE/EA=50/1) to give 4-chloro-2-(2-trifluoromethyl-phenyl)-quinoline (400 mg, yield: 86%) as a white solid. MS (EI): m/z 308.3 [(M+1)+].

Preparation of Compounds of Structure XI

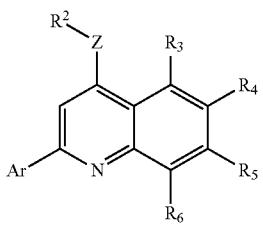

XI

General Procedure G

Example G1: Preparation of (3-piperidin-1-yl-propyl)-[2-(2-trifluoromethyl-phenyl)-quinolin-4-yl]-amine

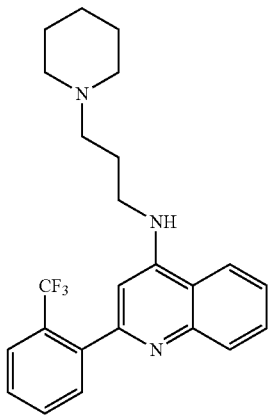

To a mixture of 4-chloro-2-(2-trifluoromethyl-phenyl)-quinoline (61 mg, 0.197 mmol) in DMA (2.5 mL), was added t-BuOK (1.3 mg, 0.012 mmol) and 3-piperidin-1-yl-propylamine (112 mg, 0.788 mmol). The resulting mixture was stirred for 4 hrs at 180° C. by microwave. The mixture was partitioned between water (30 mL) and EA (30 mL), extracted with EA (30 mL×2). The combined organic phase was washed with brine (60 mL×2) and dried over NaSO$_4$. After filtration, the solvent was removed, and the residue was purified by prep-HPLC and lyophilized with 2N HCl to afford (3-piperidin-1-yl-propyl)-[2-(2-trifluoromethyl-phenyl)-quinolin-4-yl]-amine (10 mg, yield: 23%) as a white solid.

$^1$H NMR (400 MHz, CD$_3$OD): δ=8.03 (d, J=8.0 Hz, 1H), 7.74 (t, J=6.8 Hz, 2H), 7.63-7.55 (m, 3H), 7.48 (d, J=7.6 Hz, 1H), 7.41-7.39 (m, 1H), 6.45 (s, 1H), 3.31 (t, J=6.8 Hz, 2H), 2.43-2.40 (m, 6H), 1.87-1.84 (m, 2H), 1.53-1.49 (m, 4H), 1.40-1.38 (m, 2H). MS (EI): m/z 414.2 [(M+1)+].

Example G2: (3-Piperidin-1-yl-propyl)-[2-(2-trifluoromethoxy-phenyl)-quinolin-4-yl]-amine

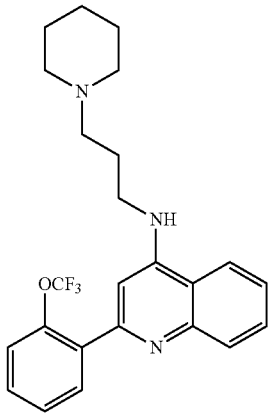

$^1$H NMR (400 MHz, CD$_3$OD): δ=8.47 (d, J=8.4 Hz, 1H), 7.93-7.90 (m, 1H), 7.82 (d, J=9.2 Hz, 2H), 7.73-7.67 (m, 2H), 7.60-7.53 (m, 2H), 6.97 (s, 1H), 3.68 (t, J=6.8 Hz, 2H), 3.51-3.46 (m, 2H), 3.21-3.16 (m, 2H), 2.90-2.84 (m, 2H), 2.23-2.16 (m, 2H). 1.86-1.79 (m, 2H), 1.77-1.73 (m, 3H), 1.44-1.41 (m, 1H). MS: m/z 430.2 [(M+1)+].

Example G3: (3-Piperidin-1-yl-propyl)-[2-(3-trifluoromethoxy-phenyl)-quinolin-4-yl]-amine

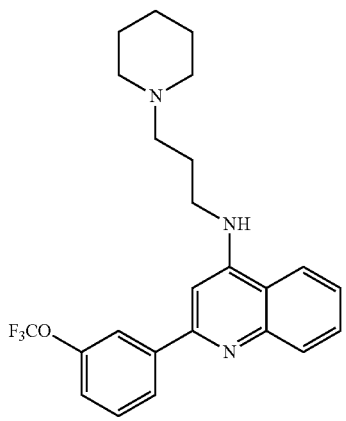

$^1$H NMR (400 MHz, CD$_3$OD): δ=8.42 (d, J=8.8 Hz, 1H), 7.94-7.88 (m, 3H), 7.86 (s, 1H), 7.72-7.64 (m, 2H), 7.55 (d, J=7.2 Hz, 1H), 7.03 (s, 1H), 3.74 (t, J=6.8 Hz, 2H), 3.50-3.47 (m, 2H), 3.21-3.17 (m, 2H), 2.89-2.84 (m, 2H), 2.26-2.18 (m, 2H). 1.86-1.69 (m, 5H), 1.44-1.40 (m, 1H). MS: m/z 430.2 [(M+1)+].

Example G4: (3-Piperidin-1-yl-propyl)-[2-(4-trifluoromethoxy-phenyl)-quinolin-4-yl]-amine

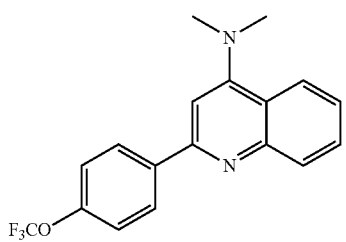 [SMILES: CN(C)c1cc(-c2ccc(OC(F)(F)F)cc2)nc2ccccc12]

$^1$H NMR (400 MHz, CD$_3$OD): δ=8.49 (d, J=8.4 Hz, 1H), 8.16 (dd, J=6.4, 2.4 Hz, 2H), 8.05-8.03 (m, 2H), 7.81-7.78 (m, 1H), 7.63 (d, J=8.4 Hz, 2H), 7.15 (s, 1H), 3.85 (t, J=7.2 Hz, 2H), 3.62-3.59 (m, 2H), 3.38-3.29 (m, 2H), 3.00-2.98 (m, 2H), 2.35-2.30 (m, 2H), 1.97-1.84 (m, 5H), 1.59-1.55 (m, 1H). MS: m/z 430.2 [(M+1)+].

Example G5: N,N-dimethyl-2-(4-(trifluoromethoxy)phenyl)quinolin-4-amine

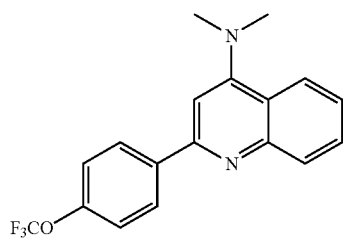

$^1$H NMR (400 MHz, CD$_3$OD): δ=8.35 (d, J=8.4 Hz, 1H), 7.98 (d, J=8.8 Hz, 2H), 7.91 (d, J=8.8 Hz, 1H), 7.87-7.85 (m, 1H), 7.60-7.56 (m, 1H), 7.49 (d, J=8.4 Hz, 2H), 7.02 (s, 1H), 3.49 (s, 6H). MS: m/z 333.1[(M+1)+].

Example G6: [2-(2-Fluoro-phenyl)-quinolin-4-yl]-(3-piperidin-1-yl-propyl)-amine

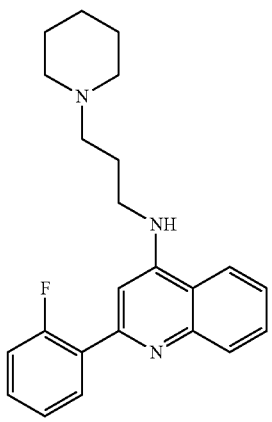 [SMILES: Fc1ccccc1-c1cc(NCCCN2CCCCC2)c2ccccc2n1]

$^1$H NMR (300 MHz, CDCl$_3$): δ=8.36 (d, J=8.4 Hz, 1H), 8.17 (d, J=8.1 Hz, 1H), 8.05-8.01 (m, 1H), 7.67 (t, J=7.5 Hz, 1H), 7.50 (t, J=7.5 Hz, 1H), 7.41-7.38 (m, 1H), 7.32-7.28 (m, 1H), 7.19-7.14 (m, 1H), 6.75 (s, 1H), 3.65-3.62 (m, 2H), 3.03-2.92 (m, 4H), 2.24-2.20 (m, 2H), 2.15-1.90 (m, 4H), 1.66-1.62 (m, 2H), 1.28-1.23 (m, 2H). MS: m/z 364.2 [(M+1)+].

Example G7: [2-(3-Fluoro-phenyl)-quinolin-4-yl]-(3-piperidin-1-yl-propyl)-amine

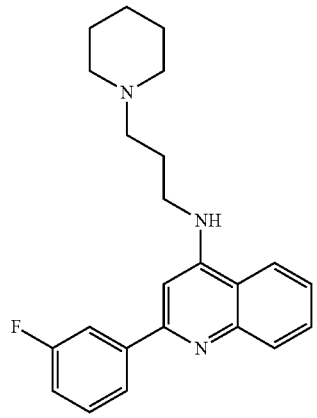 [SMILES: Fc1cccc(-c2cc(NCCCN3CCCCC3)c3ccccc3n2)c1]

$^1$H NMR (400 MHz, CD$_3$OD): δ=8.55 (d, J=8.0 Hz, 1H), 8.08-7.99 (m, 2H), 7.89-7.80 (m, 2H), 7.78-7.71 (m, 2H), 3.74 (td, J=8.8, 2.4 Hz, 1H), 7.16 (s, 1H), 3.87 (t, J=6.8 Hz, 2H), 3.63-3.60 (m, 2H), 3.34-3.31 (m, 2H), 3.03-2.97 (m, 2H), 2.39-2.34 (m, 2H). 1.99-1.87 (m, 5H), 1.57-1.54 (m, 1H). MS: m/z 364.2 [(M+1)+].

Example G8: [2-(4-Fluoro-phenyl)-quinolin-4-yl]-(3-piperidin-1-yl-propyl)-amine

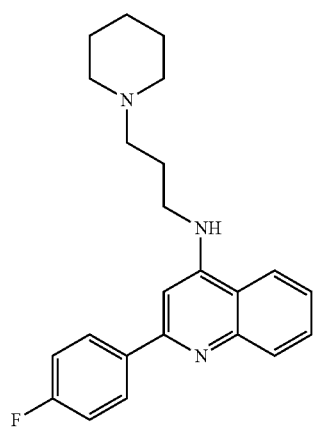 [SMILES: Fc1ccc(-c2cc(NCCCN3CCCCC3)c3ccccc3n2)cc1]

$^1$H NMR (400 MHz, CD$_3$OD): δ=8.53 (d, J=8.8 Hz, 1H), 8.13-8.10 (m, 2H), 8.07-8.01 (m, 2H), 7.77 (t, J=8.0 Hz, 1H), 7.46 (t, J=8.8 Hz, 2H), 7.13 (s, 1H), 3.86 (t, J=7.2 Hz, 2H), 3.63-3.60 (m, 2H), 3.34-3.31 (m, 2H), 3.03-2.97 (m, 2H), 2.37-2.33 (m, 2H), 1.99-1.87 (m, 5H), 1.60-1.50 (m, 1H). MS: m/z 364.2 [(M+1)+].

Example G9: (3-Piperidin-1-yl-propyl)-(2-m-tolyl-quinolin-4-yl)-amine

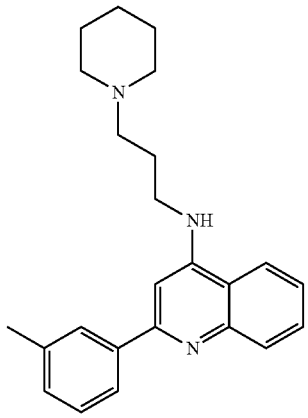 [SMILES: Cc1cccc(-c2cc(NCCCN3CCCCC3)c3ccccc3n2)c1]

¹H NMR (400 MHz, CDCl₃): δ=8.25 (d, J=8.4 Hz, 2H), 7.68 (s, 1H), 7.70 (d, J=7.6 Hz, 1H), 7.57 (t, J=8.0 Hz, 1H), 7.38 (t, J=7.6 Hz, 1H), 7.23 (t, J=7.6 Hz, 1H), 7.09 (d, J=7.6 Hz, 1H), 6.57 (s, 1H), 3.56-3.54 (m, 2H), 2.91-2.88 (m, 2H), 2.85-2.72 (m, 4H), 2.34 (s, 3H), 2.15-2.13 (m, 2H), 1.85-1.81 (m, 4H), 1.60-1.50 (m, 2H). MS: m/z 360.2 [(M+1)+].

Example G10: [2-(4-Dimethylamino-phenyl)-quinolin-4-yl]-(3-piperidin-1-yl-propyl)-amine

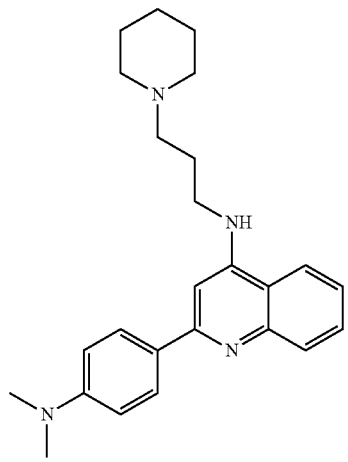 [SMILES: CN(C)c1ccc(-c2cc(NCCCN3CCCCC3)c3ccccc3n2)cc1]

¹H NMR (400 MHz, CD₃OD): δ=8.42 (d, J=8.4 Hz, 1H), 8.13 (d, J=8.4 Hz, 2H), 7.97 (d, J=8.4 Hz, 1H), 7.89-7.85 (m, 1H), 7.69-7.61 (m, 3H), 7.06 (s, 1H), 3.76 (t, J=6.8 Hz, 2H), 3.51-3.49 (m, 2H), 3.25-3.21 (m, 2H), 3.20 (s, 6H), 2.93-2.86 (m, 2H), 2.27-2.23 (m, 2H), 1.87-1.73 (m, 5H), 1.45-1.42 (m, 1H). MS: m/z 389.2 [(M+1)+].

Example G11: [2-(4-Dimethylamino-phenyl)-quinolin-4-yl]-dimethyl-amine

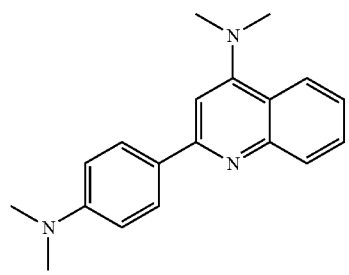 [SMILES: CN(C)c1ccc(-c2cc(N(C)C)c3ccccc3n2)cc1]

¹H NMR (400 MHz, CD₃OD): δ=8.45 (d, J=8.4 Hz, 1H), 8.19-8.15 (m, 2H), 8.08 (d, J=8.4, 1 Hz, 1H), 7.97 (t. J=8.0 Hz, 1H), 7.78-7.68 (m, 3H), 7.15 (s, 1H), 3.62 (s, 6H), 3.34 (s, 6H). MS: m/z 292.1 [(M+1)+].

Example G12: (2-Furan-2-yl-quinolin-4-yl)-(3-piperidin-1-yl-propyl)-amine

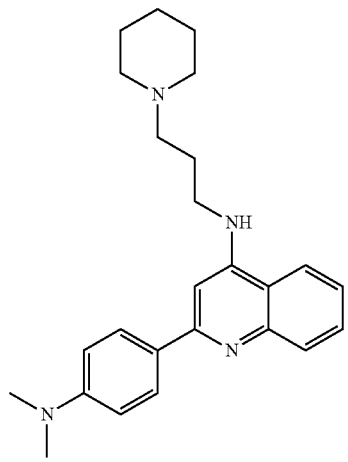 [SMILES: CN(C)c1ccc(-c2cc(NCCCN3CCCCC3)c3ccccc3n2)cc1]

¹H NMR (400 MHz, CD₃OD): δ=8.33 (d, J=8.4 Hz, 1H), 7.95-7.91 (m, 2H), 7.87-7.83 (m, 1H), 7.74 (d, J=3.6 Hz, 1H), 7.62-7.58 (m, 1H), 7.13 (s, 1H), 6.76-6.75 (m, 1H), 3.73 (t, J=6.8 Hz, 2H), 3.51-3.48 (m, 2H), 3.23-3.20 (m, 2H), 2.90-2.85 (m, 2H), 2.24-2.17 (m, 2H), 1.88-1.78 (m, 2H), 1.75-1.72 (m, 3H), 1.44-1.41 (m, 1H). MS: m/z 336.1 [(M+1)+].

Example G13: (2-Furan-2-yl-quinolin-4-yl)-dimethyl-amine

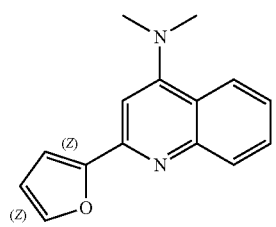 [SMILES: CN(C)c1cc(-c2ccco2)nc2ccccc12]

$^1$H NMR (400 MHz, CD$_3$OD): δ=8.39 (d, J=8.4 Hz, 1H), 8.07 (d, J=8.0 Hz, 1H), 8.01 (d, J=1.2 Hz, 1H), 7.95-7.91 (m, 1H), 7.76 (d, J=3.6 Hz, 1H), 7.68-7.64 (m, 1H), 7.27 (s, 1H), 6.86 (t, J=1.2 Hz, 1H), 3.59 (s, 6H). MS: m/z 239.1 [(M+1)+].

Example G14: (2-Furan-3-yl-quinolin-4-yl)-(3-piperidin-1-yl-propyl)-amine

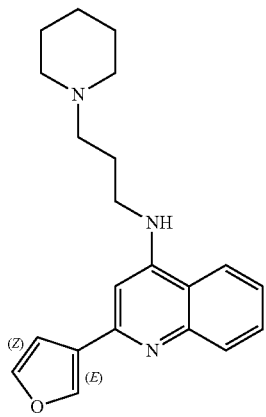 [SMILES: c1ccc2c(NCCCN3CCCCC3)cc(-c3ccoc3)nc2c1]

$^1$H NMR (400 MHz, CD$_3$OD): δ=8.63 (s, 1H), 8.35 (d, J=8.4 Hz, 1H), 7.93 (d, J=8.4 Hz, 1H), 7.84 (t, J=7.6 Hz, 1H), 7.82 (s, 1H), 7.60 (t, J=7.6 Hz, 1H), 7.25 (d, J=1.2 Hz, 1H), 7.03 (s, 1H), 3.73 (t, J=6.8 Hz, 2H), 3.51-3.48 (m, 2H), 3.23-3.20 (m, 2H), 2.92-2.86 (m, 2H), 2.23-2.20 (m, 2H), 1.87-1.75 (m, 5H), 1.48-1.40 (m, 1H). MS: m/z 336.2 [(M+1)+].

Example G15:
(2-Furan-3-yl-quinolin-4-yl)-dimethyl-amine

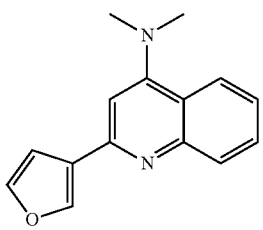 [SMILES: CN(C)c1cc(-c2ccoc2)nc2ccccc12]

(2-Furan-3-yl-quinolin-4-yl)-dimethyl-amine

The title compound was prepared using general procedure for 3-piperidin-1-yl-propyl)-[2-(2-trifluoromethyl-phenyl)-quinolin-4-yl]-amine.

$^1$H NMR (400 MHz, CD$_3$OD): δ=8.49 (s, 1H), 8.28 (d, J=8.4 Hz, 1H), 7.90 (d, J=8.4 Hz, 1H), 7.83-7.79 (m, 1H), 7.72 (t, J=1.2 Hz, 1H), 7.54 (td, J=8.4, 1.2 Hz, 1H), 7.15 (s, 1H), 7.03 (s, 1H), 3.46 (s, 6H). MS: m/z 239.1 [(M+1)+].

Example G16: (3-Piperidin-1-yl-propyl)-(2-thiophen-2-yl-quinolin-4-yl)-amine

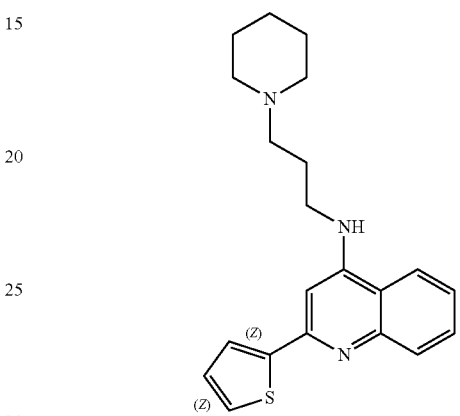

$^1$H NMR (400 MHz, CD$_3$OD): δ=8.35 (d, J=8.4 Hz, 1H), 8.03 (d, J=2.8 Hz, 1H), 7.94 (d, J=8.0 Hz, 1H), 7.88-7.85 (m, 2H), 7.84-7.60 (m, 1H), 7.28 (dd, J=5.2, 4.0 Hz, 1H), 6.95 (s, 1H), 3.71 (t, J=6.8 Hz, 2H), 3.53-3.48 (m, 2H), 3.26-3.20 (m, 2H), 2.91-2.85 (m, 2H), 2.25-2.17 (m, 2H), 1.90-1.68 (m, 5H), 1.44-1.41 (m, 1H). MS: m/z 352.1 [(M+1)+].

Example G17:
Dimethyl-(2-thiophen-2-yl-quinolin-4-yl)-amine

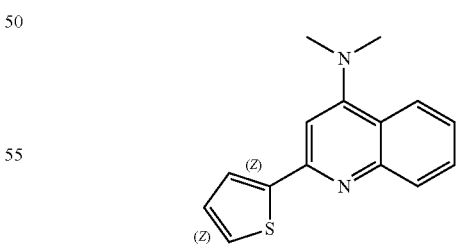

$^1$H NMR (400 MHz, CD$_3$OD): δ=8.29 (d, J=8.4 Hz, 1H), 7.98 (dd, J=3.6, 1.2 Hz, 1H), 7.94 (d, J=7.2 Hz, 1H), 7.84-7.80 (m, 2H), 7.57-7.53 (m, 1H), 7.26 (t, J=4.8 Hz, 1H), 6.98 (s, 1H), 3.47 (s, 6H). MS: m/z 255.1 (M+H+).

Example G18: [2-(1-Methyl-1H-pyrazol-4-yl)-quinolin-4-yl]-(3-piperidin-1-yl-propyl)-amine

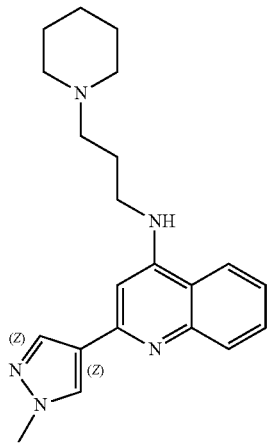 [SMILES: Cn1cc(-c2cc(NCCCN3CCCCC3)c3ccccc3n2)cn1]

¹H NMR (400 MHz, CD₃OD): δ=8.73 (d, J=6.8 Hz, 1H), 8.42-8.40 (m, 2H), 8.01-7.94 (m, 2H), 7.73-7.69 (m, 1H), 7.12 (s, 1H), 4.08 (s, 3H), 3.83 (t, J=6.8 Hz, 2H), 3.63-3.60 (m, 2H), 3.34-3.30 (m, 2H), 3.03-2.97 (m, 2H), 2.36-2.30 (m, 2H), 2.00-1.97 (m, 2H), 1.91-1.83 (m, 3H), 1.58-1.53 (m, 1H). MS: m/z 350.2 [(M+1)+].

Example G19: [2-(1-Methyl-1H-pyrazol-4-yl)-quinolin-4-yl]-(3-piperidin-1-yl-propyl)-amine

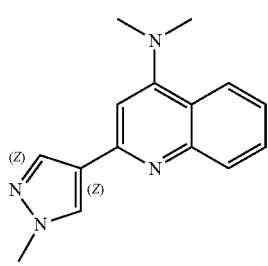 [SMILES: CN(C)c1cc(-c2cnn(C)c2)nc2ccccc12]

¹H NMR (400 MHz, CD₃OD): δ=8.50 (s, 1H), 8.26-8.23 (m, 2H), 7.92-7.87 (m, 1H), 7.79 (t, J=7.6 Hz, 1H), 7.52 (t, J=7.6 Hz, 1H), 7.01 (s, 1H), 3.94 (s, 3H), 3.44 (s, 6H). MS: m/z 253.1 [(M+1)+].

Example G20: [2-(1-Methyl-1H-pyrazol-4-yl)-quinolin-4-yl]-(3-piperidin-1-yl-propyl)-amine

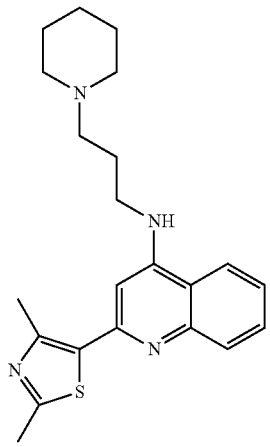 [SMILES: Cc1nc(C)c(-c2cc(NCCCN3CCCCC3)c3ccccc3n2)s1]

¹H NMR (400 MHz, CD₃OD): δ=8.55-8.53 (m, 1H), 8.05-8.01 (m, 1H), 7.96 (d, J=8.4 Hz, 1H), 7.80 (t, J=7.6 Hz, 1H), 7.05-7.04 (m, 1H), 3.80 (t, J=6.8 Hz, 2H), 3.62-3.59 (m, 2H), 3.31-3.29 (m, 2H), 3.03-2.97 (m, 2H), 2.87 (s, 3H), 2.62 (s, 3H), 2.35-2.29 (m, 2H), 2.00-1.97 (m, 2H), 1.92-1.86 (m, 3H), 1.58-1.53 (m, 1H). MS: m/z 381.1 [(M+1)+].

Example G21: [2-(2,4-Dimethyl-thiazol-5-yl)-quinolin-4-yl]-dimethyl-amine

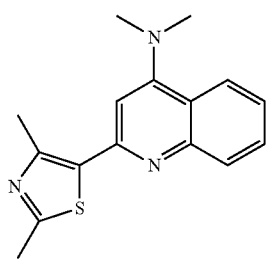 [SMILES: Cc1nc(C)c(-c2cc(N(C)C)c3ccccc3n2)s1]

¹H NMR (400 MHz, CD₃OD): δ=8.48 (d, J=8.4, 1H), 8.02-7.94 (m, 2H), 7.28-7.23 (m, 1H), 7.04 (s, 1H), 3.62 (s, 6H), 2.90 (s, 3H), 2.62 (s, 3H). MS: m/z 284.0 [(M+1)+].

Example G22: (3-Piperidin-1-yl-propyl)-[2-(1H-pyrrol-2-yl)-quinolin-4-yl]-amine

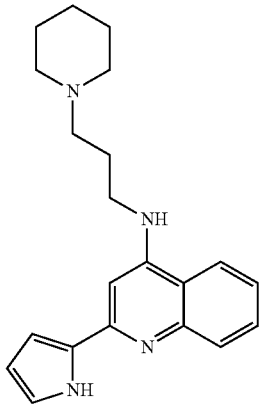 [SMILES: c1c[nH]c(-c2cc(NCCCN3CCCCC3)c3ccccc3n2)c1]

$^1$H NMR (400 MHz, CD$_3$OD): δ=8.35 (d, J=8.4 Hz, 1H), 7.98-7.92 (m, 2H), 7.66 (t, J=8.0 Hz, 1H), 7.41-7.40 (m, 1H), 7.31 (s, 1H), 7.18 (d, J=1.6 Hz, 1H), 6.49-6.47 (m, 1H), 3.83 (t, J=6.8 Hz, 2H), 3.63-3.60 (m, 2H), 3.36-3.33 (m, 2H), 3.02-2.98 (m, 2H), 2.34-2.31 (m, 2H), 1.97-1.85 (m, 5H), 1.59-1.51 (m, 1H). MS: m/z 335.2 [(M+1)+].

Example G23: Dimethyl-[2-(1H-pyrrol-2-yl)-quinolin-4-yl]-amine

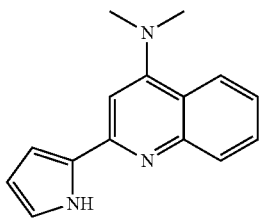 [SMILES: CN(C)c1cc(-c2ccc[nH]2)nc2ccccc12]

$^1$H NMR (400 MHz, CD$_3$OD): δ=8.19 (d, J=8.4 Hz, 1H), 7.86 (d, J=8.4 Hz, 1H), 7.77-7.73 (m, 1H), 7.49-7.45 (m, 1H), 7.25-7.24 (m, 1H), 7.15 (t, J=1.6 Hz, 1H), 7.02 (s, 1H), 6.34 (dd, J=3.6, 2.8 Hz, 1H), 3.41 (s, 6H). MS: m/z 238.2 [(M+1)+].

Example G24: [2-(4-methoxy-phenyl)-6-methyl-quinolin-4-yl]-(3-piperidin-1-yl-propyl)-amine

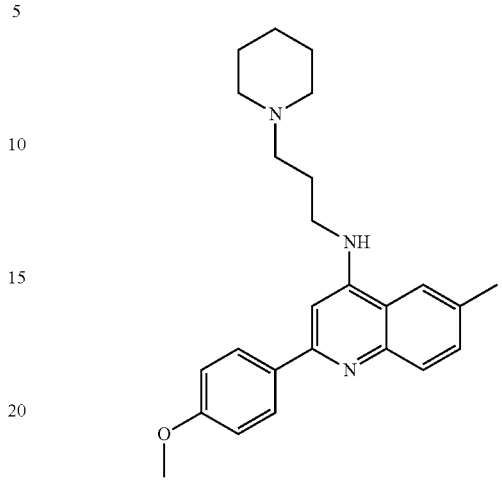

$^1$H NMR (400 MHz, CD$_3$OD): δ=8.30 (s, 1H), 8.02-7.99 (m, 2H), 7.94 (d, J=8.4 Hz, 1H), 7.84 (dd, J=8.8, 1.6 Hz, 1H), 7.23 (d, J=8.8 Hz, 2H), 7.05 (s, 1H), 3.96 (s, 3H), 3.83 (t, J=7.2 Hz, 2H), 3.63-3.60 (m, 2H), 3.43-3.30 (m, 2H), 3.02-2.99 (m, 2H), 2.63 (s, 3H), 2.35-2.31 (m, 2H), 2.00-1.85 (m, 5H), 1.60-1.49 (m, 1H). MS: m/z 390.2 [(M+1)+].

Example G25: [6-Methoxy-2-(4-methoxy-phenyl)-quinolin-4-yl]-(3-piperidin-1-yl-propyl)-amine

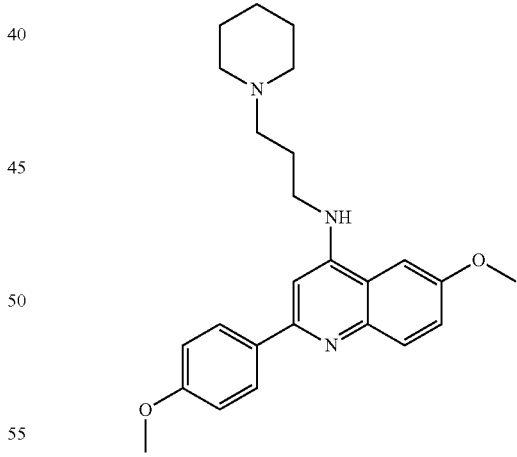

$^1$H NMR (400 MHz, CD$_3$OD): δ=7.88-7.84 (m, 3H), 7.77 (d, J=2.4 Hz, 1H), 7.48 (dd, J=9.2, 2.8 Hz, 1H), 7.10 (d, J=8.8 Hz, 2H), 6.91 (s, 1H), 3.93 (s, 3H), 3.82 (s, 3H), 3.71 (t, J=7.2 Hz, 2H), 3.50-3.48 (m, 2H), 3.22-3.19 (m, 2H), 2.90-2.84 (m, 2H), 2.26-2.20 (m, 2H), 1.87-1.73 (m, 5H), 1.46-1.40 (m, 1H). MS: m/z 406.2 [(M+1)+].

Example G26: [7-Methoxy-2-(4-methoxy-phenyl)-quinolin-4-yl]-(3-piperidin-1-yl-propyl)-amine

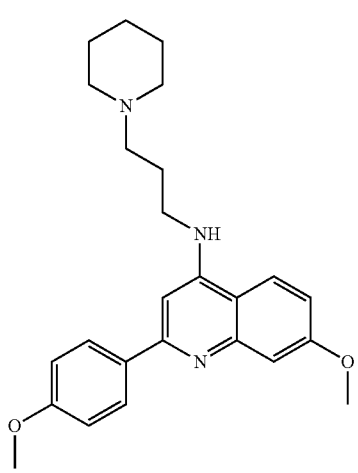 [SMILES: COc1ccc(-c2cc(NCCCN3CCCCC3)c3ccc(OC)cc3n2)cc1]

¹H NMR (400 MHz, CD₃OD): δ=8.37 (d, J=9.6 Hz, 1H), 8.00 (dd, J=12.0, 3.2 Hz, 2H), 7.44-7.42 (m, 1H), 7.34-7.31 (m, 1H), 7.23 (dd, J=12.0, 3.2 Hz, 2H), 6.98 (s, 1H), 4.03 (s, 3H), 3.96 (s, 3H), 3.81 (t, J=7.2 Hz, 2H), 3.62-3.59 (m, 2H), 3.43-3.30 (m, 2H), 3.03-2.97 (m, 2H), 2.35-2.27 (m, 2H), 2.01-1.82 (m, 5H), 1.60-1.52 (m, 1H). MS: m/z 406.2 [(M+1)+].

Example G27: [6-Chloro-2-(4-methoxy-phenyl)-quinolin-4-yl]-(3-piperidin-1-yl-propyl)-amine

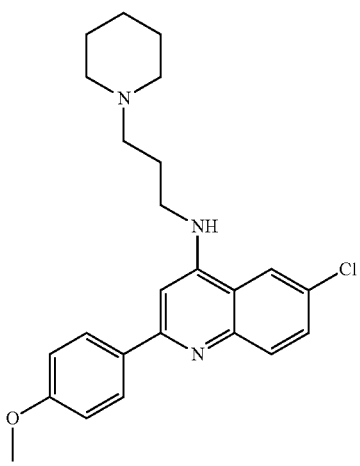 [SMILES: COc1ccc(-c2cc(NCCCN3CCCCC3)c3cc(Cl)ccc3n2)cc1]

¹H NMR (300 MHz, CDCl₃): δ=8.08-8.00 (m, 4H), 7.55 (dd, J=9.0, 1.8 Hz, 1H), 7.02 (d, J=8.7 Hz, 2H), 6.72 (s, 1H), 3.89 (s, 3H), 3.49-3.47 (m, 2H), 2.67-2.55 (m, 5H), 2.06-1.99 (m, 3H), 1.90-1.82 (m, 6H). MS: m/z 410.1 [(M+1)+].

Example G28: [2-(4-Methoxy-phenyl)-6-trifluoromethyl-quinolin-4-yl]-(3-piperidin-1-yl-propyl)-amine

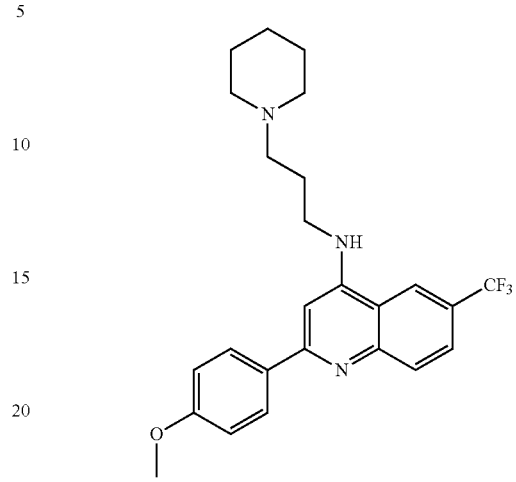

¹H NMR (400 MHz, CD₃OD): δ=8.95 (s, 1H), 8.23-8.20 (m, 2H), 8.07 (d, J=8.0 Hz, 2H), 7.25 (dd, J=6.8, 2.0 Hz, 2H), 7.19 (s, 1H), 3.97 (s, 3H), 3.87 (t, J=7.2 Hz, 2H), 3.63-3.60 (m, 2H), 3.53-3.31 (m, 2H), 3.03-2.96 (m, 2H), 2.37-2.33 (m, 2H), 1.96-1.87 (m, 5H), 1.60-1.51 (m, 1H). MS: m/z 444.2 [(M+1)+].

Example G29: [2-(4-Methoxy-phenyl)-6-nitro-quinolin-4-yl]-(3-piperidin-1-yl-propyl)-amine

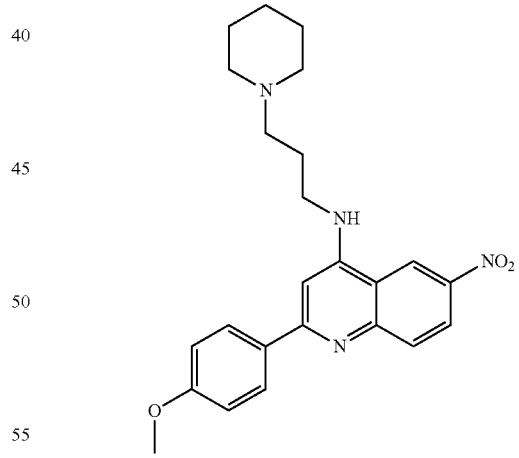

¹H NMR (400 MHz, CD₃OD): δ=9.41 (s, 1H), 8.60 (dd, J=9.2, 2.0 Hz, 1H), 8.08 (d, J=9.6 Hz, 1H), 7.96 (d, J=8.8 Hz, 2H), 7.13 (d, J=7.2 Hz, 2H), 7.08 (s, 1H), 3.84 (s, 3H), 3.80-3.74 (m, 2H), 3.56-3.47 (m, 2H), 3.21-3.20 (m, 2H), 2.90-2.84 (m, 2H), 2.25-2.23 (m, 2H), 1.87-1.74 (m, 5H), 1.50-1.41 (m, 1H). MS: m/z 421.2 [(M+1)+].

Example G30: [6-Fluoro-2-(4-methoxy-phenyl)-quinolin-4-yl]-(3-piperidin-1-yl-propyl)-amine

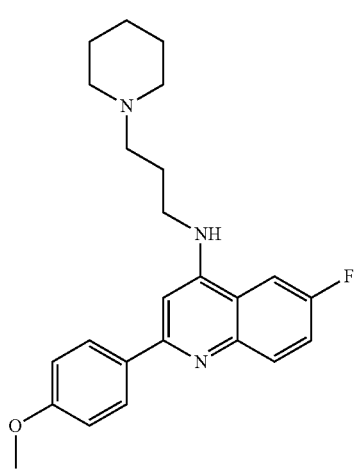 [SMILES: COc1ccc(-c2cc(NCCCN3CCCCC3)c3cc(F)ccc3n2)cc1]

¹H NMR (400 MHz, CD₃OD): δ=8.29 (dd, J=9.6, 2.8 Hz, 1H), 8.11 (dd, J=9.6, 4.8 Hz, 1H), 8.03 (dd, J=6.4, 2.4 Hz, 2H), 7.86-7.81 (m, 1H), 7.24 (d, J=8.0 Hz, 2H), 7.10 (s, 1H), 3.96 (s, 3H), 3.84 (t, J=7.2 Hz, 2H), 3.63-3.60 (m, 2H), 3.43-3.31 (m, 2H), 3.03-2.96 (m, 2H), 2.35-2.31 (m, 2H), 2.00-1.86 (m, 5H), 1.60-1.53 (m, 1H). MS: m/z 394.2 [(M+1)+].

Example G31: [2-(4-Methoxy-phenyl)-6-trifluoromethoxy-quinolin-4-yl]-(3-piperidin-1-yl-propyl)-amine

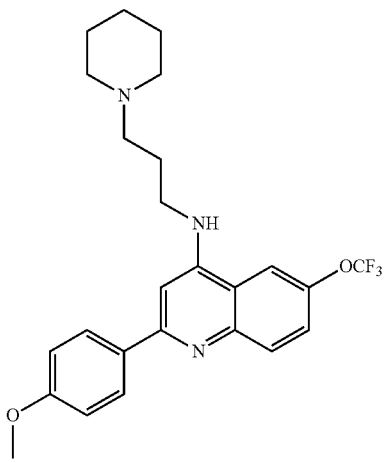 [SMILES: COc1ccc(-c2cc(NCCCN3CCCCC3)c3cc(OC(F)(F)F)ccc3n2)cc1]

¹H NMR (400 MHz, CD₃OD): δ=8.50 (s, 1H), 8.19-8.16 (m, 1H), 8.07-8.04 (m, 2H), 7.94 (dd, J=6.8, 1.6 Hz, 1H), 7.27-7.23 (m, 2H), 7.15 (s, 1H), 3.99 (s, 3H), 3.85 (t, J=6.8 Hz, 2H), 3.63-3.60 (m, 2H), 3.37-3.31 (m, 2H), 3.03-2.96 (m, 2H), 2.38-2.31 (m, 2H), 1.99-1.87 (m, 5H), 1.32-1.30 (m, 1H). MS: m/z 460.2 [(M+1)+].

Example G32: 3-[2-(2-Trifluoromethyl-phenyl)-quinolin-4-ylamino]-benzonitrile

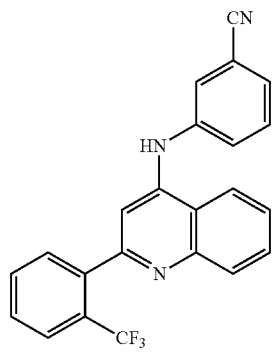 [SMILES: N#Cc1cccc(Nc2cc(-c3ccccc3C(F)(F)F)nc3ccccc23)c1]

¹H NMR (400 MHz, DMSO-d6): δ=9.35 (s, 1H), 8.40 (d, J=8.0 Hz, 1H), 7.95 (d, J=8.4 Hz, 1H), 7.85 (d, J=8.0 Hz, 1H), 7.81-7.52 (m, 9H), 7.09 (s, 1H). MS: m/z 390.1 [(M+1)+].

Example G33: Phenyl-[2-(2-trifluoromethyl-phenyl)-quinolin-4-yl]-amine

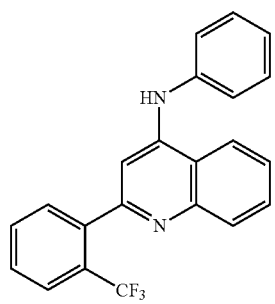 [SMILES: FC(F)(F)c1ccccc1-c1cc(Nc2ccccc2)c2ccccc2n1]

¹H NMR (400 MHz, DMSO-d6): δ=9.13 (s, 1H), 8.45 (d, J=8.0 Hz, 1H), 7.90 (d, J=8.0 Hz, 1H), 7.82 (d, J=7.6 Hz, 1H), 7.77-7.71 (m, 2H), 7.66-7.57 (m, 3H), 7.43-7.36 (m, 4H), 7.15-7.12 (m, 1H), 6.93 (s, 1H). MS: m/z 365.1 [(M+1)+].

Example G34: (4-Fluoro-phenyl)-[2-(2-trifluoromethyl-phenyl)-quinolin-4-yl]-amine

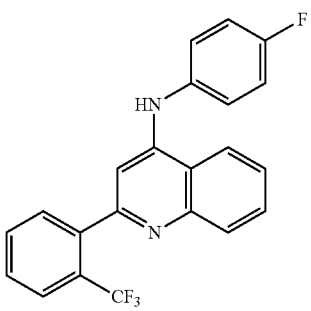 [SMILES: Fc1ccc(Nc2cc(-c3ccccc3C(F)(F)F)nc3ccccc23)cc1]

¹H NMR (400 MHz, DMSO-d6): δ=9.10 (s, 1H), 8.43 (d, J=8.4 Hz, 1H), 7.89 (d, J=8.4 Hz, 1H), 7.82 (d, J=7.6 Hz,

1H), 7.77-7.71 (m, 2H), 7.66-7.56 (m, 3H), 7.40-7.37 (m, 2H), 7.27-7.23 (m, 2H), 6.78 (s, 1H). MS: m/z 383.1 [(M+1)+].

Example G35: [2-(4-Methoxy-phenyl)-quinolin-4-yl]-phenyl-amine

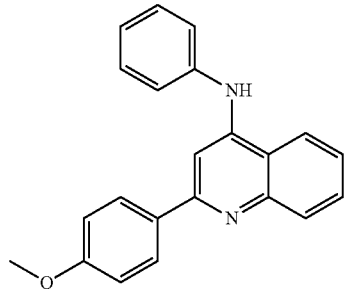 [SMILES: COc1ccc(-c2cc(Nc3ccccc3)c3ccccc3n2)cc1]

¹H NMR (400 MHz, DMSO-d6): δ=8.99 (s, 1H), 8.37 (d, J=8.0 Hz, 1H), 7.98-7.91 (m, 3H), 7.70 (t, J=8.0 Hz, J=1.2 Hz, 1H), 7.52-7.41 (m, 6H), 7.18-7.06 (m, 1H), 7.02 (d, J=2.8 Hz, 2H), 3.80 (s, 3H). MS: m/z 327.1 [(M+1)+].

Example G36: [2-(4-Methoxy-phenyl)-quinolin-4-yl]-(2-trifluoromethyl-phenyl)-amine

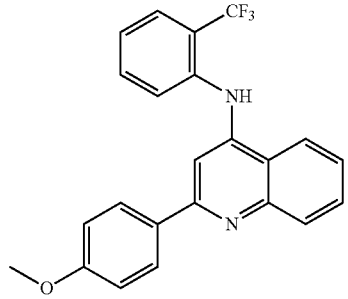 [SMILES: COc1ccc(-c2cc(Nc3ccccc3C(F)(F)F)c3ccccc3n2)cc1]

¹H NMR (400 MHz, CD₃OD): δ=8.46 (d, J=8.4 Hz, 1H), 8.02-7.90 (m, 3H), 7.82 (t, J=8.0 Hz, 1H), 7.75-7.65 (m, 2H), 7.63-7.59 (m, 3H), 7.02 (d, J=8.8 Hz, 2H), 6.29 (s, 1H), 3.78 (s, 3H). MS: m/z 395.1 [(M+1)+].

Example G37: [2-(4-Methoxy-phenyl)-quinolin-4-yl]-(3-trifluoromethyl-phenyl)-amine

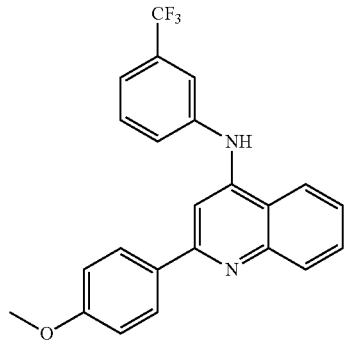 [SMILES: COc1ccc(-c2cc(Nc3cccc(C(F)(F)F)c3)c3ccccc3n2)cc1]

¹H NMR (400 MHz, DMSO-d6): δ=9.26 (s, 1H), 8.34 (d, J=8.0 Hz, 1H), 8.03 (d, J=8.8 Hz, 2H), 7.97 (d, J=8.4 Hz, 1H), 7.79-7.71 (m, 3H), 7.65 (t, J=8.0 Hz, 1H), 7.59 (s, 1H), 7.54 (t, J=8.0 Hz, 1H), 7.43 (d, 0.1=7.6 Hz, 1H), 7.05 (d, J=9.2 Hz, 2H), 3.82 (s, 3H). MS: m/z 395.1 [(M+1)+].

Example G38: 3-[2-(4-Methoxy-phenyl)-quinolin-4-ylamino]-benzonitrile

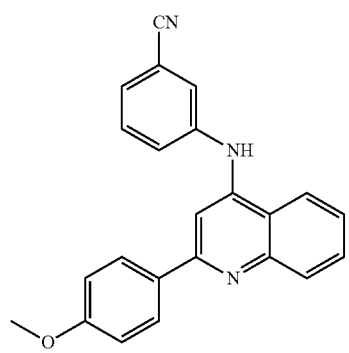 [SMILES: COc1ccc(-c2cc(Nc3cccc(C#N)c3)c3ccccc3n2)cc1]

¹H NMR (400 MHz, DMSO-d6): δ=9.20 (s, 1H), 8.31-8.29 (m, 1H), 8.06-8.03 (m, 2H), 7.98-7.95 (m, 1H), 7.79-7.71 (m, 3H), 7.64-7.52 (m, 4H), 7.05 (d, J=11.6 Hz, 2H), 3.83 (s, 3H). MS: m/z 352.1 [(M+1)+].

Example G63: [2-(4-Methoxy-phenyl)-quinolin-4-yl]-pyridin-2-yl-amine

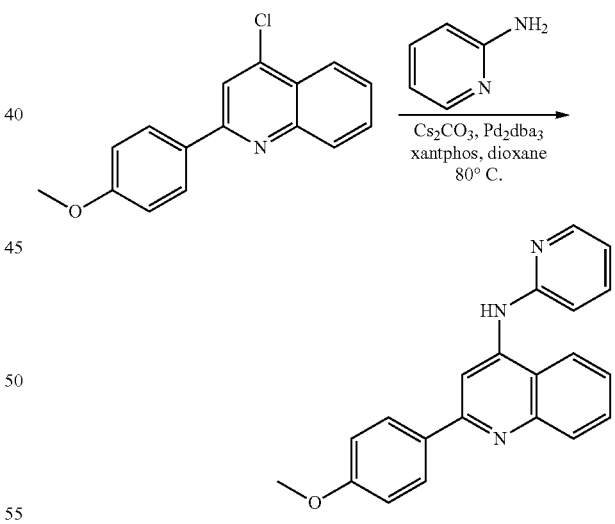

To a mixture of 4-chloro-2-(4-methoxy-phenyl)-quinoline (100 mg, 0.37 mmol), Pd₂(dba)₃ (34 mg, 0.04 mmol), xantphos (35 mg, 0.07 mmol), Cs₂CO₃ (241 mg, 0.74 mmol) in dioxane (5 mL) was added pyridin-2-ylamine (35 mg, 0.37 mmol) under N₂ atmosphere. The reaction mixture was stirred at 100° C. for 3 hrs. The mixture was concentrated under reduced pressure and the residue was partitioned between water (20 mL) and DCM (20 mL). It was extracted with DCM (20 mL×3). The combined organic phase was washed with brine, and dried over NaSO₄. After filtration, the solvent was removed, and the residue was purified by prep-HPLC to give [2-(4-methoxy-phenyl)-quinolin-4-yl]-pyridin-2-yl-amine (40 mg, yield: 33%) as a white solid. $^1$H NMR (400 MHz, DMSO-d6): δ=9.44 (s, 1H), 8.98 (s, 1H), 8.47 (d, J=8.0 Hz, 1H), 8.39-8.38 (m, 1H), 8.12 (d, J=8.8 Hz, 2H), 7.97 (d, J=8.0 Hz, 1H), 7.79-7.75 (m, 1H), 7.72 (t, J=7.2 Hz, 1H), 7.55 (t, J=7.2 Hz, 1H), 7.40 (d, J=8.4 Hz, 1H), 7.11-7.09 (m, 2H), 7.00-6.99 (m, 1H), 3.84 (s, 3H). MS: m/z 328.1 [(M+1)+].

Example G64: (4-Chloro-benzyl)-[2-(4-methoxy-phenyl)-quinolin-4-yl]-amine

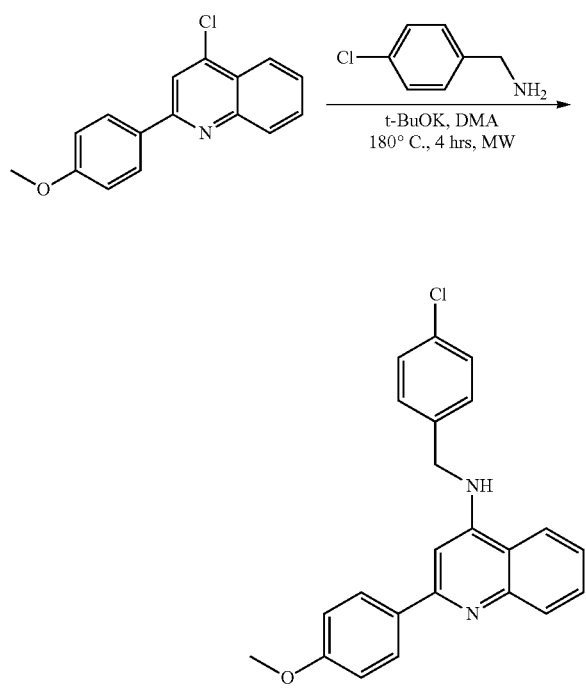

To a mixture of 4-cloro-2-(4-methoxy-phenyl)-quinoline (150 mg, 0.560 mmol) in DMA (2.5 mL), was added t-BuOK (3.7 mg, 0.034 mmol) and 4-chloro-benzylamine (316 mg, 2.240 mmol). The resulting mixture was stirred for 4 hrs at 180° C. by microwave. The mixture was partitioned between water (30 mL) and EA (30 mL), extracted with EA (30 mL×2). The combined organic phase was washed with brine (80 mL×2) and dried over NaSO$_4$. After filtration, the solvent was removed, and the residue was purified by silica gel column chromatography (PE/EA=2/1) to give (4-chloro-benzyl)-[2-(4-methoxy-phenyl)-quinolin-4-yl]-amine (34 mg, yield: 16%) as a white solid. $^1$H NMR (400 MHz, CDCl$_3$): δ=8.62 (d, J=8.0 Hz, 1H), 8.57 (d, J=6.8 Hz, 1H), 7.83 (d, J=8.0 Hz, 2H), 7.40-7.34 (m, 3H), 7.30-7.20 (m, 3H), 6.94 (d, J=8.0 Hz, 2H), 6.31 (s, 1H), 4.72 (d, J=5.2 Hz, 2H), 3.79 (s, 3H). MS: m/z 375.1 [(M+1)+]

In some embodiments, compounds described herein are prepared as shown in Scheme 3.

Scheme 3

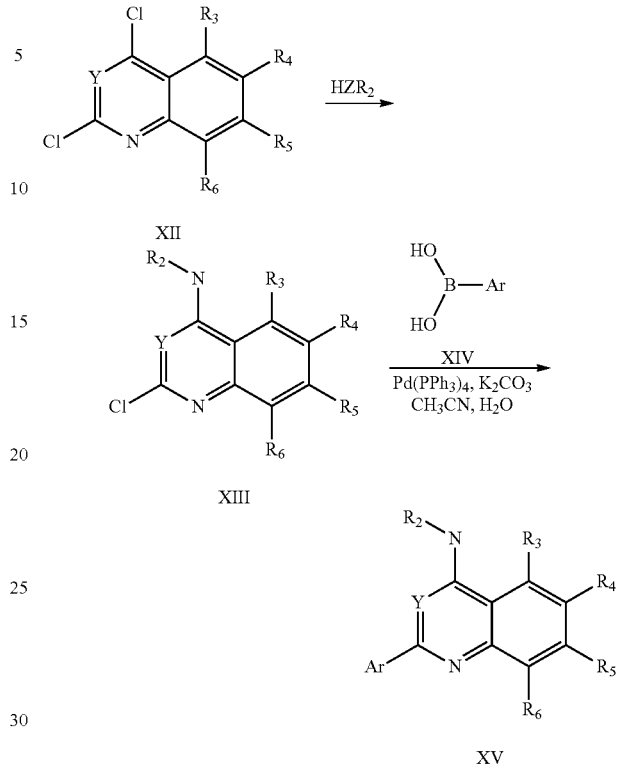

The synthesis of compound XV can be accomplished by the reactions illustrated in Scheme 3. Treatment compound XII in an inert organic solvent such as THF, DMF, DMA containing an organic base such as triethylamine, or strong base such as potassium t-butoxide, sodium hydride or potassium hydride with an alcohol or amine compound of formula HZR$_2$ produces compounds of formula XIII. The reaction is preferably carried out at temperatures between 25° C. and 150° C. The predominate isomer produced in this reaction is the C4 addition on the aromatic ring. Crystallization of the product of this reaction allows for the isolation of only the C4 isomer. Suzuki coupling of compound XIII with an aromatic boronic acid XIV employing standard Suzuki coupling conditions using a palladium zero species such as Pd(PPh$_3$)$_4$, with aqueous potassium carbonate or sodium carbonate in an inert solvent such as acetonitrile or toluene produces Compound XV. The reaction is preferably carried out at temperatures between 25° C. and 150° C.

Preparation of Compounds of Structure XIII

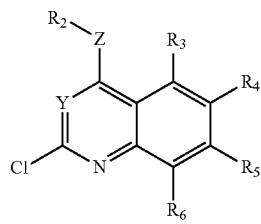

General Procedure H

Example H1: Preparation of 2-chloro-N-(3-(piperidin-1-yl)propyl)quinolin-4-amine To a mixture of 2,4-dichloroquinolne (5 g), 3-(piperidin-1-yl)propan-1-amine (3.5 g), potassium carbonate (6.96 g) was added DMA (100 ml). The reaction was heated for 20 hours, cooled and the solvent removed under vacuum. The residue was extracted with DCM/water and dried over sodium sulfate. The resulting solid was purified with silica gel eluted with 70% DCM/30% MeOH. The resulting solid was recrystallized from MeOH, to afford of 2-chloro-N-(3-(piperidin-1-yl)propyl)quinolin-4-amine (4 g, yield: 63%) as a white/tan solid, MS (EI): m/z 304 [(M+1)+].

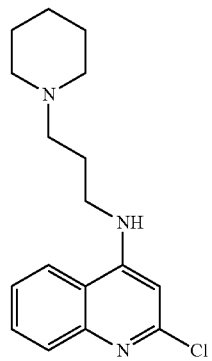 [SMILES: Clc1cc(NCCCN2CCCCC2)c2ccccc2n1]

Preparation of Compounds of Structure XV

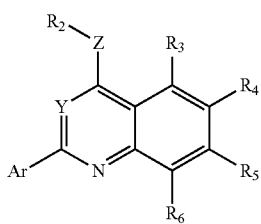

General Procedure I

Example I1: Preparation of N,N-diethyl-4-(4-((3-(piperidin-1-yl)propyl)amino)quinolin-2-yl)benzamide

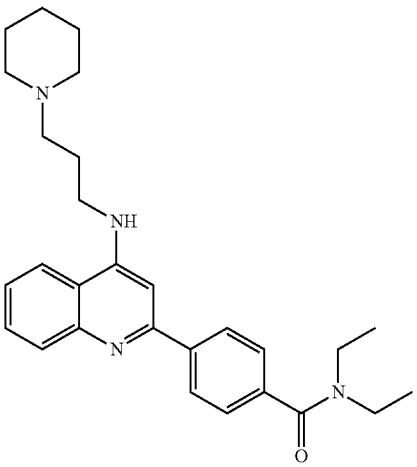 [SMILES: CCN(CC)C(=O)c1ccc(-c2cc(NCCCN3CCCCC3)c3ccccc3n2)cc1]

To a mixture of 2-chloro-N-(3-(piperidin-1-yl)propyl)quinolin-4-amine (1.72 g), 4-diethylaminoboronic acid (1.87 g) was added 10 ml of 2M sodium carbonate, 10 ml of toluene and 10 ml of EtOH. The reaction mixture was purged with nitrogen and then Pd (500 mg) was added and the reaction was heated to 85° C. for 6 hours. The reaction mixture was cooled and extracted with EtOAc/water. The organic layer was dried over sodium sulfate and the solvent removed under vacuum. The residue was purified using silica gel and eluted with a gradient of 70% DCM/30% MeOH to 30% DCM/70% MeOH, to afford N,N-diethyl-4-(4-((3-(piperidin-1-yl)propyl)amino)quinolin-2-yl)benzamide (1.1 g, yield: 33%) as a white/tan solid, MS (EI): m/z 445 [(M+1)+].

Example 2: LMPTP Primary Screening Protocol

This assay attempts to identify inhibitors of the LMPTP-A (Low Molecular Weight Protein Tyrosine Phosphatase-A) enzyme. It is run in 1536-well format and is measured via fluorescence intensity.

A listing of materials is provided:
Item, source, catalog no.
LMPTP-A Enzyme Stock Solution (4.22 mg/ml or 206.8 µM), SBMRI Protein Facility,
N/A
OMFP, Sigma, M2629-100MG
Bis-Tris pH 6.0, Fisher Sci, BP301-100
Triton-X 100, Sigma, T9284
DTT, Sigma, D9779
Mol. Grade Water, Mediatech, Inc., 46-000-CM
1536-well black High base opaque bottom plate, Nexus Biosystems, 00019120
Final assay conditions are:
0.625 nM LMPTP-A Enzyme
400 µM OMFP
50 mM Bis-Tris pH 6.0
1 mM DTT
0.01% Triton-X 100
20 µM test compound 3% DMSO (2% from substrate and 1% from compounds)
6 µL reaction volume
50 minutes incubation at room temp
Assay Procedure
1. Prepare Reagents as described in section F. Recipe.
2. Using LabCyte Echo, transfer 60 nL from 2 mM test compound source plate into assay plate Col. 5-48 (final concentration of test compounds is 20 µM). 60 nL of DMSO should be transferred to col. 1-4 for positive and negative control wells.
3. Spin plates at 1000 rpm for 1 minute in centrifuge.
4. Using the Beckman Coulter Bioraptr, add 3 µL/well of control buffer to columns 1 and 2.
5. Using the Bioraptr, add 3 µL/well of enzyme solution to col. 3-48.
6. Using the Bioraptr, add 3 µL/well of substrate solution to col. 1-48.
7. Spin plates at 1000 rpm for 1 minute in centrifuge.
8. Incubate plates in the dark at room temperature for 50 minutes.
9. Read plates on PerkinElmer Viewlux using a FI protocol.

Example 3

The following compounds were prepared using Procedures A-I of Example 1 described above, and the $IC_{50}$ values were obtained using the method of Example 2. $IC_{50}$ values are categorized according to the below scale.
A: $IC_{50}$>200 nM–<800 nM
B: $IC_{50}$>801 nM–<5000 nM
C: $IC_{50}$>5001 nM

TABLE A

| Compound | Name | MW (EI) [(M + 1)+] | IC50 (nM) |
|---|---|---|---|
| D1 | 2-(4-methoxyphenyl)-N-(3-(piperidin-1-yl)propyl)quinolin-4-amine: | 376 | B |
| D2 | N,N-dimethyl-2-(2-(trifluoromethyl)phenyl)quinolin-4-amine | 317 | B |
| G1 | (3-piperidin-1-yl-propyl)-[2-(2-trifluoromethyl-phenyl)-quinolin-4-yl]-amine | 414 | B |
| G2 | (3-piperidylpropyl){2-[2-(trifluoromethoxy)phenyl](4-quinolyl)}amine | 430 | A |
| G3 | (3-Piperidin-1-yl-propyl)-[2-(3-trifluoromethoxy-phenyl)-quinolin-4-yl]-amine | 430 | B |
| G4 | (3-Piperidin-1-yl-propyl)-[2-(4-trifluoromethoxy-phenyl)-quinolin-4-yl]-amine | 430 | B |
| G5 | N,N-dimethyl-2-(4-(trifluoromethoxy)phenyl)quinolin-4-amine | 317 | B |
| G6 | [2-(2-fluorophenyl)(4-quinolyl)](3-piperidylpropyl)amine | 364 | B |
| G7 | [2-(3-Fluoro-phenyl)-quinolin-4-yl]-(3-piperidin-1-yl-propyl)-amine364 | 364 | B |
| G8 | [2-(4-Fluoro-phenyl)-quinolin-4-yl]-(3-piperidin-1-yl-propyl)-amine | 364 | B |
| G9 | (3-Piperidin-1-yl-propyl)-(2-m-tolyl-quinolin-4-yl)-amine | 360 | B |
| G10 | [2-(4-Dimethylamino-phenyl)-quinolin-4-yl]-(3-piperidin-1-yl-propyl)-amine | 389 | B |
| G11 | [2-(4-Dimethylamino-phenyl)-quinolin-4-yl]-dimethyl-amine | 292 | C |
| G12 | (2-Furan-2-yl-quinolin-4-yl)-(3-piperidin-1-yl-propyl)-amine | 336 | B |
| G13 | (2-Furan-2-yl-quinolin-4-yl)-dimethyl-amine: | 239 | C |
| G14 | (2-Furan-3-yl-quinolin-4-yl)-(3-piperidin-1-yl-propyl)-amine | 336 | B |
| G15 | (2-Furan-3-yl-quinolin-4-yl)-dimethyl-amine | 239 | C |
| G16 | (3-Piperidin-1-yl-propyl)-(2-thiophen-2-yl-quinolin-4-yl)-amine | 352 | B |
| G17 | Dimethyl-(2-thiophen-2-yl-quinolin-4-yl)-amine | 255 | C |
| G18 | [2-(1-methylpyrazol-3-yl)(4-quinolyl)](3-piperidylpropyl)amine | 350 | C |
| G19 | Dimethyl[2-(1-methylpyrazol-4-yl)(4-quinolyl)]amine | 253 | C |
| G20 | [2-(2,4-dimethyl(1,3-thiazol-5-yl))(4-quinolyl)](3-piperidylpropyl)amine | 381 | B |
| G21 | [2-(2,4-Dimethyl-thiazol-5-yl)-quinolin-4-yl]-dimethyl-amine | 284 | C |
| G22 | (3-Piperidin-1-yl-propyl)-[2-(1H-pyrrol-2-yl)-quinolin-4-yl]-amine | 335 | B |
| G23 | Dimethyl-[2-(1H-pyrrol-2-yl)-quinolin-4-yl]-amine | 238 | C |
| G24 | [2-(4-methoxy-phenyl)-6-methyl-quinolin-4-yl]-(3-piperidin-1-yl-propyl)-amine | 390 | C |
| G25 | [6-Methoxy-2-(4-methoxy-phenyl)-quinolin-4-yl]-(3-piperidin-1-yl-propyl)-amine | 406 | C |
| G26 | [7-Methoxy-2-(4-methoxy-phenyl)-quinolin-4-yl]-(3-piperidin-1-yl-propyl)-amine | 406 | C |
| G27 | [6-Chloro-2-(4-methoxy-phenyl)-quinolin-4-yl]-(3-piperidin-1-yl-propyl)-amine | 410 | C |
| G28 | [2-(4-Methoxy-phenyl)-6-trifluoromethyl-quinolin-4-yl]-(3-piperidin-1-yl-propyl)-amine | 444 | C |

TABLE A-continued

| Compound | Name | MW (EI) [(M + 1)+] | IC50 (nM) |
|---|---|---|---|
| G29 | [2-(4-Methoxy-phenyl)-6-nitro-quinolin-4-yl]-(3-piperidin-1-yl-propyl)-amine | 421 | C |
| G30 | [6-Fluoro-2-(4-methoxy-phenyl)-quinolin-4-yl]-(3-piperidin-1-yl-propyl)-amine | 394 | B |
| G31 | [2-(4-Methoxy-phenyl)-6-trifluoromethoxy-quinolin-4-yl]-(3-piperidin-1-yl-propyl)-amine | 460 | C |
| G32 | 3-[2-(2-Trifluoromethyl-phenyl)-quinolin-4-ylamino]-benzonitrile | 390 | B |
| G33 | Phenyl-[2-(2-trifluoromethyl-phenyl)-quinolin-4-yl]-amine | 365 | C |
| G34 | (4-Fluoro-phenyl)-[2-(2-trifluoromethyl-phenyl)-quinolin-4-yl]-amine | 383 | B |
| G35 | [2-(4-Methoxy-phenyl)-quinolin-4-yl]-phenyl-amine | 327 | B |
| G36 | [2-(4-Methoxy-phenyl)-quinolin-4-yl]-(2-trifluoromethyl-phenyl)-amine | 395 | C |
| G37 | [2-(4-Methoxy-phenyl)-quinolin-4-yl]-(3-trifluoromethyl-phenyl)-amine | 395 | C |
| G38 | 3-[2-(4-Methoxy-phenyl)-quinolin-4-ylamino]-benzonitrile | 352 | A |
| G39 | (4-fluorophenyl)[2-(4-methoxyphenyl)(4-quinolyl)]amine | 345 | B |
| G40 | (4-chlorophenyl)[2-(4-methoxyphenyl)(4-quinolyl)]amine | 361 | B |
| G41 | (4-bromophenyl)[2-(4-methoxyphenyl)(4-quinolyl)]amine | 406 | B |
| G42 | [2-(4-methoxyphenyl)(4-quinolyl)][4-(trifluoromethyl)phenyl]amine | 395 | B |
| G43 | [2-(4-methoxyphenyl)(4-quinolyl)](4-methylphenyl)amine | 341 | B |
| G44 | [2-(4-methoxyphenyl)(4-quinolyl)][4-(methylethoxy)phenyl]amine | 385 | B |
| G45 | ethyl 4-{[2-(4-methoxyphenyl)-4-quinolyl]amino}benzoate | 399 | C |
| G46 | 2-(4-methoxyphenyl)(4-quinolyl)](1-methylpyrazol-3-yl)amine | 331 | B |
| G47 | 4-{[2-(4-methoxyphenyl)-4-quinolyl]amino}benzenecarbonitrile | 352 | A |
| G48 | (6-methoxy(3-pyridyl))[2-(4-methoxyphenyl)(4-quinolyl)]amine | 358 | A |
| G49 | (3-chloro-4-fluorophenyl)[2-(4-methoxyphenyl)(4-quinolyl)]amine | 379 | B |
| G50 | [2-(4-methoxyphenyl)(4-quinolyl)][3-(pyrrolidinylmethyl)phenyl]amine | 410 | A |
| G51 | 2-(4-methoxyphenyl)(4-quinolyl)][3-(pyrrolidinylmethyl)phenyl]amine | 410 | A |
| G52 | [2-(4-methoxyphenyl)(4-quinolyl)][4-(morpholin-4-ylmethyl)phenyl]amine | 426 | B |
| G53 | [2-(4-methoxyphenyl)(4-quinolyl)][3-(4-piperidylmethyl)phenyl]amine | 424 | B |
| G54 | [2-(4-methoxyphenyl)(4-quinolyl)][3-(piperidylmethyl)phenyl]amine | 424 | B |
| G55 | [2-(4-methoxyphenyl)(4-quinolyl)][3-(morpholin-4-ylmethyl)phenyl]amine | 426 | A |
| G56 | [2-(4-methoxyphenyl)(4-quinolyl)][3-(1,4-thiazaperhydroin-4-ylmethyl)phenyl]amine | 426 | A |
| G57 | [2-(4-methoxyphenyl)(4-quinolyl)]{3-[(4-methyl(1,4-diazaperhydroepinyl))methyl]phenyl}amine | 453 | A |
| G58 | [(3-{[2-(4-methoxyphenyl)(4-quinolyl)]amino}phenyl)methyl]dimethylamine | 384 | A |
| G59 | [2-(4-methoxyphenyl)(4-quinolyl)][3-(piperazinylmethyl)phenyl]amine | 425 | B |
| G60 | [2-(4-methoxyphenyl)(4-quinolyl)]{3-[(4-methylpiperazinyl)methyl]phenyl}amine | 439 | B |
| G61 | (3-Diethylaminomethyl-phenyl)-[2-(4-methoxy-phenyl)-quinolin-4-yl]-amine | 412 | B |
| G62 | 4-[(3-{[2-(4-methoxyphenyl)-4-quinolyl]amino}phenyl)methyl]-1,4-thiazaperhydroine-1,1-dione | 474 | B |
| G63 | [2-(4-methoxyphenyl)(4-quinolyl)]-2-pyridylamine | 328 | B |
| G64 | [2-(4-methoxyphenyl)(4-quinolyl)]-2-pyridylamine | 328 | B |
| G65 | [2-(4-methoxyphenyl)(4-quinolyl)]-4-pyridylamine | 328 | B |
| G66 | [2-(4-methoxyphenyl)(4-quinolyl)]pyrimidin-5-ylamine | 329 | B |
| G67 | [2-(4-methoxyphenyl)(4-quinolyl)](6-methyl(2-pyridyl))amine | 342 | B |

TABLE A-continued

| Compound | Name | MW (EI) [(M + 1)+] | IC50 (nM) |
|---|---|---|---|
| G68 | [2-(4-methoxyphenyl)(4-quinolyl)]-2-quinolylamine | 378 | B |
| G69 | 2-(4-methoxyphenyl)(4-quinolyl)]-8-quinolylamine | 378 | C |
| G70 | [2-(4-methoxyphenyl)(4-quinolyl)]pyrimidin-4-ylamine | 329 | B |
| G71 | [2-(4-methoxyphenyl)(4-quinolyl)]pyridazin-4-ylamine | 329 | B |
| G72 | [2-(4-methoxyphenyl)(4-quinolyl)]pyrimidin-2-ylamine | 329 | B |
| G73 | [2-(4-methoxyphenyl)(4-quinolyl)](6-methylpyrazin-2-yl)amine | 343 | B |
| G74 | [(4-chlorophenyl)methyl][2-(4-methoxyphenyl)(4-quinolyl)]amine | 375 | B |
| G75 | [2-(4-methoxyphenyl)(4-quinolyl)]benzylamine | 341 | B |
| G76 | [2-(4-methoxyphenyl)(4-quinolyl)](phenylethyl)amine | 355 | B |
| G77 | [2-(4-methoxyphenyl)(4-quinolyl)][(2-methoxyphenyl)methyl]amine | 371 | B |
| G78 | [2-(4-methoxyphenyl)(4-quinolyl)][(3-methoxyphenyl)methyl]amine | 371 | B |
| G79 | [2-(4-methoxyphenyl)(4-quinolyl)][(4-methoxyphenyl)methyl]amine | 371 | B |
| G80 | [2-(4-methoxyphenyl)(4-quinolyl)]{[2-(trifluoromethyl)phenyl]methyl}amine | 409 | B |
| G81 | [2-(4-methoxyphenyl)(4-quinolyl)]{[4-(trifluoromethyl)phenyl]methyl}amine | 409 | B |
| G82 | 3-({[2-(4-methoxyphenyl)-4-quinolyl]amino}methyl)benzenecarbonitrile | 366 | B |
| G83 | [2-(4-methoxyphenyl)(4-quinolyl)](2-phenylethyl)amine | 355 | B |
| G84 | [2-(4-chlorophenyl)ethyl][2-(4-methoxyphenyl)(4-quinolyl)]amine | 389 | B |
| G85 | [2-(4-methoxyphenyl)(4-quinolyl)][2-(4-methoxyphenyl)ethyl]amine | 385 | B |
| G86 | [2-(4-methoxyphenyl)(4-quinolyl)]{2-[4-(trifluoromethyl)phenyl]ethyl}amine | 423 | B |
| G87 | [2-(4-fluorophenyl)ethyl][2-(4-methoxyphenyl)(4-quinolyl)]amine | 373 | B |
| I1 | N,N-diethyl-4-(4-((3-(piperidin-1-yl)propyl)amino)quinolin-2-yl)benzamide | 445 | A |
| I2 | 2-(4-{[3-(pyrrolidinylmethyl)phenyl]amino}-2-quinolyl)benzenecarbonitrile | 405 | B |
| I3 | 4-(4-{[3-(4-piperidylmethyl)phenyl]amino}-2-quinolyl)benzamide | 437 | B |
| I4 | 4-[4-({3-[(dimethylamino)methyl]phenyl}amino)-2-quinolyl]benzamide | 397 | C |
| I5 | 4-(4-{[3-(pyrrolidinylmethyl)phenyl]amino}-2-quinolyl)benzamide | 423 | C |
| I6 | 4-(4-{[4-(piperidylmethyl)phenyl]amino}-2-quinolyl)benzamide | 437 | C |
| I7 | [2-(4-chloro-2-fluorophenyl)(4-quinolyl)][3-(4-piperidylmethyl)phenyl]amine | 446 | B |
| I8 | [2-(4-chloro-2-fluorophenyl)(4-quinolyl)][4-(piperidylmethyl)phenyl]amine | 446 | B |
| I9 | [(3-{[2-(4-chloro-2-fluorophenyl)(4-quinolyl)amino}methyl]dimethylamine | 406 | B |
| I10 | [2-(4-chloro-2-fluorophenyl)(4-quinolyl)][3-pyrrolidinylmethyl)phenyl]amine | 432 | B |
| I11 | [2-(3-chlorophenyl)(4-quinolyl)][4-(piperidylmethyl)phenyl]amine | 428 | B |
| I12 | [2-(3-chlorophenyl)(4-quinolyl)][3-(pyrrolidinylmethyl)phenyl]amine | 414 | B |
| I13 | (5-[(dimethylamino)methyl]-3-{[2-(3-chlorophenyl)(4-quinolyl)]amino}phenyl)methan-1-ol | 418 | B |
| I14 | (3-{[2-(3-chlorophenyl)(4-quinolyl)]amino}phenyl)dimethylamine | 374 | B |
| I15 | [2-(3-chlorophenyl)(4-quinolyl)][2-(1-methylpyrrolidin-2-yl)ethyl]amine | 366 | B |
| I16 | [(4-{[2-(3-chlorophenyl)(4-quinolyl)]amino}phenyl)methyl]dimethylamine | 388 | B |
| I17 | [2-(3-chlorophenyl)(4-quinolyl)](3-{[1-benzyl(4-piperidyl)]methyl}phenyl)amine | 519 | B |
| I18 | [2-(3-chlorophenyl)(4-quinolyl)]{3-[(1-methyl(4-piperidyl))methyl]phenyl}amine | 442 | B |
| I19 | [2-(3-chlorophenyl)(4-quinolyl)][3-(4-piperidylmethyl)phenyl]amine | 428 | B |

TABLE A-continued

| Compound | Name | MW (EI) [(M + 1)+] | IC50 (nM) |
|---|---|---|---|
| I20 | [2-(3-chlorophenyl)(4-quinolyl)][3-(4-piperidylmethyl)phenyl]amine | 428 | B |
| I21 | [2-(3-chlorophenyl)(4-quinolyl)][2-(4-piperidylmethyl)phenyl]amine | 428 | B |
| I22 | [(3-{[2-(3-chlorophenyl)(4-quinolyl)]amino}phenyl)methyl]dimethylamine | 388 | A |
| I23 | [2-(4-methoxyphenyl)(4-quinolyl)][4-(piperidylmethyl)phenyl]amine | 424 | B |
| I24 | [2-(4-methoxyphenyl)(4-quinolyl)][2-(1-methylpyrrolidin-2-yl)ethyl]amine | 362 | B |
| I25 | (3-{[2-(4-methoxyphenyl)(4-quinolyl)]amino}phenyl)dimethylamine | 370 | B |
| I26 | [(4-{[2-(4-methoxyphenyl)(4-quinolyl)]amino}phenyl)methyl]dimethylamine | 384 | B |
| I27 | [2-(4-methoxyphenyl)(4-quinolyl)][3-(2H-1,2,3,4-tetraazol-5-ylmethyl)phenyl]amine | 409 | B |
| I28 | 4-[(3-{[2-(4-methoxyphenyl)(4-quinolyl)]amino}phenyl)methyl]-1-(methylsulfonyl)piperidine | 502 | B |
| I29 | 1-acetyl-4-[(3-{[2-(4-methoxyphenyl)(4-quinolyl)]amino}phenyl)methyl]piperidine | 466 | A |
| I30 | {3-[(1-ethyl(4-piperidyl))methyl]phenyl}[2-(4-methoxyphenyl)(4-quinolyl)]amine | 452 | A |
| I31 | [2-(4-methoxyphenyl)(4-quinolyl)]{3-[(1-methyl-4-piperidyl))methyl]phenyl}amine | 438 | A |
| I32 | [2-(4-methoxyphenyl)(4-quinolyl)][4-(4-piperidylmethyl)phenyl]amine | 424 | B |
| I33 | {4-[(1-ethyl(4-piperidyl))methyl]phenyl}[2-(4-methoxyphenyl)(4-quinolyl)]amine | 452 | B |
| I34 | 1-acetyl-4-[(4-{[2-(4-methoxyphenyl)(4-quinolyl)]amino}phenyl)methyl]piperidine | 466 | B |
| I35 | 4-[(4-{[2-(4-methoxyphenyl)(4-quinolyl)]amino}phenyl)methyl]-1-(methylsulfonyl)piperidine | 502 | B |
| I36 | 2-(3-{[2-(4-methoxyphenyl)-4-quinolyl]amino}phenyl)ethanenitrile | 366 | B |
| I37 | [2-(4-methoxyphenyl)(4-quinolyl)]{2-[(1-methyl(4-piperidyl))methyl]phenyl}amine | 438 | C |
| I38 | [2-(4-methoxyphenyl)(4-quinolyl)][2-(4-piperidylmethyl)phenyl]amine | 424 | C |
| I39 | [(3-{[2-(4-methoxyphenyl)(4-quinolyl)]amino}phenyl)methyl]dimethylamine | 384 | B |
| I40 | {2-[2,5-bis(trifluoromethyl)phenyl](4-quinolyl)}(3-{[1-benzyl(4-piperidyl)]methyl}phenyl)amine | 620 | C |
| I41 | {2-[2,5-bis(trifluoromethyl)phenyl](4-quinolyl)}[3-(4-piperidylmethyl)phenyl]amine | 530 | B |
| I42 | {[3-({2-[3,5-bis(trifluoromethyl)phenyl](4-quinolyl)}amino)phenyl]methyl}dimethylamine | 490 | C |
| I43 | {2-[3,5-bis(trifluoromethyl)phenyl](4-quinolyl)}[4-(piperidylmethyl)phenyl]amine | 530 | C |
| I44 | {2-[3,5-bis(trifluoromethyl)phenyl](4-quinolyl)}[3-(pyrrolidinylmethyl)phenyl]amine | 516 | C |
| I45 | (5-[(dimethylamino)methyl]-3-{[2-(3-chlorophenyl)(4-quinolyl)]amino}phenyl)methan-1-ol | 418 | B |
| I46 | {2-[3,5-bis(trifluoromethyl)phenyl](4-quinolyl)}[2-(1-methylpyrrolidin-2-yl)ethyl]amine | 468 | C |
| I47 | {[4-({2-[3,5-bis(trifluoromethyl)phenyl](4-quinolyl)}amino)phenyl]methyl}dimethylamine | 490 | C |
| I48 | {2-[(1,1-dimethyl(4-piperidyl))methyl]phenyl} {2-[3,5-bis(trifluoromethyl)phenyl](4-quinolyl)}amine | 559 | C |
| I49 | {2-[3,5-bis(trifluoromethyl)phenyl](4-quinolyl)}[2-(4-piperidylmethyl)phenyl]amine | 530 | C |
| I50 | {2-[3,5-bis(trifluoromethyl)phenyl](4-quinolyl)}(3-{[1-benzyl(4-piperidyl)]methyl}phenyl)amine | 620 | C |
| I51 | {3-[(1,1-dimethyl(4-piperidyl))methyl]phenyl} {2-[3,5-bis(trifluoromethyl)phenyl](4-quinolyl)}amine | 559 | C |
| I52 | {2-[3,5-bis(trifluoromethyl)phenyl](4-quinolyl)}[3-(4-piperidylmethyl)phenyl]amine | 530 | C |
| I53 | {2-[2,4-bis(trifluoromethyl)phenyl](4-quinolyl)}[2-(1-methylpyrrolidin-2-yl)ethyl]amine | 468 | C |
| I54 | {[4-({2-[2,4-bis(trifluoromethyl)phenyl](4-quinolyl)}amino)phenyl]methyl}dimethylamine | 490 | C |
| I55 | {2-[2,4-bis(trifluoromethyl)phenyl](4-quinolyl)}[2-(4-piperidylmethyl)phenyl]amine | 530 | C |
| I56 | 2-methyl-N-(4-{4-[(3-piperidylpropyl)amino](2-quinolyl)}phenyl)propanamide | 431 | B |

TABLE A-continued

| Compound | Name | MW (EI) [(M + 1)+] | IC50 (nM) |
|---|---|---|---|
| I57 | phenyl-N-(4-{4-[(3-piperidylpropyl)amino](2-quinolyl)}phenyl)carboxamide | 465 | A |
| I58 | 3-[N-(4-{4-[(3-piperidylpropyl)amino]-2-quinolyl}phenyl)carbamoyl]propanoic acid | 461 | B |
| I59 | N-(2-cyanoethyl)(4-{4-[(3-piperidylpropyl)amino](2-quinolyl)}phenyl)carboxamide | 442 | A |
| I60 | N-ethyl-N-methyl(4-{4-[(3-piperidylpropyl)amino](2-quinolyl)}phenyl)carboxamide | 430 | B |
| I61 | N-(methylethyl)(4-{4-[(3-piperidylpropyl)amino](2-quinolyl)}phenyl)carboxamide | 431 | B |
| I62 | N-ethyl(4-{4-[(3-piperidylpropyl)amino](2-quinolyl)}phenyl)carboxamide | 417 | B |
| I63 | (4-{4-[(3-piperidylpropyl)amino](2-quinolyl)}phenyl)-N-(2,2,2-trifluoroethyl)carboxamide | 471 | B |
| I64 | N-(oxolan-2-ylmethyl)(4-{4-[(3-piperidylpropyl)amino](2-quinolyl)}phenyl)carboxamide | 473 | B |
| I65 | ethyl 2-[(4-{4-[(3-piperidylpropyl)amino]-2-quinolyl}phenyl)carbonylamino]acetate | 475 | A |
| I66 | N-[2-(dimethylamino)ethyl](4-{4-[(3-piperidylpropyl)amino](2-quinolyl)}phenyl)carboxamide | 460 | A |
| I67 | N-(3-hydroxypropyl)(4-{4-[(3-piperidylpropyl)amino](2-quinolyl)}phenyl)carboxamide | 447 | A |
| I68 | 2-[(4-{4-[(3-piperidylpropyl)amino]-2-quinolyl}phenyl)carbonylamino]acetic acid | 447 | B |
| I69 | methyl 2-[(4-{4-[(3-piperidylpropyl)amino]-2-quinolyl}phenyl)carbonylamino]acetate | 461 | B |
| I70 | N-cyclopropyl(4-{4-[(3-piperidylpropyl)amino](2-quinolyl)}phenyl)carboxamide | 430 | B |
| I71 | N,N-diethyl(4-{4-[(3-piperidylpropyl)amino](2-quinolyl)}phenyl)carboxamide | 445 | A |
| I72 | N,N-dimethyl(4-{4-[(3-piperidylpropyl)amino](2-quinolyl)}phenyl)carboxamide | 417 | B |
| I73 | N-methyl(4-{4-[(3-piperidylpropyl)amino](2-quinolyl)}phenyl)carboxamide | 403 | B |
| I74 | 4-{4-[(3-piperidylpropyl)amino]-2-quinolyl}benzamide | 389 | A |
| I75 | (2-{[2,4-bis(trifluoromethyl)phenyl]amino}(4-quinolyl))(3-piperidylpropyl)amine | 497 | C |
| I76 | {2-[(3-chlorophenyl)amino](4-quinolyl)}(3-piperidylpropyl)amine | 395 | C |
| I77 | N-(4-{4-[(3-piperidylpropyl)amino](2-quinolyl)}-2-(trifluoromethyl)phenyl)acetamide | 471 | B |
| I78 | (2-benzo[b]thiophen-6-yl(4-quinolyl))(3-piperidylpropyl)amine | 402 | A |
| I79 | 3-{4-[(3-piperidylpropyl)amino]-2-quinolyl}phenyl)methyl acetate | 418 | B |
| I80 | 3-amino-5-{4-[(3-piperidylpropyl)amino](2-quinolyl)}phenyl morpholin-4-yl ketone | 474 | B |
| I81 | 2-fluoro-4-{4-[(3-piperidylpropyl)amino](2-quinolyl)}benzamide | 407 | A |
| I82 | 2-chloro-4-{4-[(3-piperidylpropyl)amino](2-quinolyl)}benzamide | 423 | A |
| I83 | 3-methyl-5-{4-[(3-piperidylpropyl)amino](2-quinolyl)}pyridine-2-carbonitrile | 386 | B |
| I84 | 4-{4-[(3-piperidylpropyl)amino](2-quinolyl)}phenyl pyrrolidinyl ketone | 443 | B |
| I85 | [2-(3,5-difluorophenyl)(4-quinolyl)](3-piperidylpropyl)amine | 382 | B |
| I86 | (3-piperidylpropyl)[2-(2,4,5-trifluorophenyl)(4-quinolyl)]amine | 400 | B |
| I87 | (3-piperidylpropyl)(2-{6-[4-(trifluoromethyl)phenoxy](3-pyridyl)}(4-quinolyl))amine | 507 | B |
| I88 | {2-[3-chloro-2-(phenylmethoxy)(4-pyridyl)](4-quinolyl)}(3-piperidylpropyl)amine | 488 | B |
| I89 | [2-(5-bromo-2-methoxy(4-pyridyl))(4-quinolyl)](3-piperidylpropyl)amine | 456 | B |
| I90 | [2-(2,6-difluoro(3-pyridyl))(4-quinolyl)](3-piperidylpropyl)amine | 383 | B |

TABLE A-continued

| Compound | Name | MW (EI) [(M + 1)+] | IC50 (nM) |
|---|---|---|---|
| I91 | [2-(3-chloro-2-prop-2-enyloxy(4-pyridyl))(4-quinolyl)](3-piperidylpropyl)amine | 467 | C |
| I92 | [2-(5-methylthio(3-pyridyl))(4-quinolyl)](3-piperidylpropyl)amine | 393 | B |
| I93 | [2-(2-butoxy(3-pyridyl))(4-quinolyl)](3-piperidylpropyl)amine | 419 | B |
| I94 | [2-(3-fluoro(2-pyridyl))(4-quinolyl)](3-piperidylpropyl)amine | 365 | B |
| I95 | {2-[5-chloro-2-(cyclopropylmethoxy)(3-pyridyl)](4-quinolyl)}(3-piperidylpropyl)amine | 452 | B |
| I96 | [2-(2-ethoxy(3-pyridyl))(4-quinolyl)](3-piperidylpropyl)amine | 391 | B |
| I97 | [2-(6-fluoro(2-pyridyl))(4-quinolyl)](3-piperidylpropyl)amine | 365 | B |
| I98 | tert-butyl 2-{4-[(3-piperidylpropyl)amino]-2-quinolyl}indolecarboxylate | 485 | C |
| I99 | [2-(2-chloro(3-pyridyl))(4-quinolyl)](3-piperidylpropyl)amine | 381 | B |
| I100 | [2-(2,6-dichlorophenyl)(4-quinolyl)](3-piperidylpropyl)amine | 415 | C |
| I101 | 2-(3-bromo-4-chloro-2-fluorophenyl)(4-quinolyl)](3-piperidylpropyl)amine | 477 | B |
| I102 | [2-(2-chloro(4-pyridyl))(4-quinolyl)](3-piperidylpropyl)amine | 381 | B |
| I103 | [2-(2,4-dichlorophenyl)(4-quinolyl)](3-piperidylpropyl)amine | 415 | B |
| I104 | [2-(2-ethoxy(3-pyridyl))(4-quinolyl)](3-piperidylpropyl)amine | 391 | B |
| I105 | {2-[5-ethoxy-2-(trifluoromethyl)phenyl](4-quinolyl)}(3-piperidylpropyl)amine | 458 | B |
| I106 | dimethyl[(3-{4-[(3-piperidylpropyl)amino](2-quinolyl)}-4-(trifluoromethyl)phenyl)sulfonyl]amine | 521 | B |
| I107 | 2-(2,5-dimethylphenyl)(4-quinolyl)](3-piperidylpropyl)amine | 374 | B |
| I108 | [2-(3,4-dimethoxyphenyl)(4-quinolyl)](3-piperidylpropyl)amine | 406 | B |
| I109 | [2-(1-methylindol-5-yl)(4-quinolyl)](3-piperidylpropyl)amine | 399 | A |
| I110 | (2-indol-5-yl(4-quinolyl))(3-piperidylpropyl)amine | 385 | B |
| I111 | (2-benzimidazol-6-yl(4-quinolyl))(3-piperidylpropyl)amine | 386 | B |
| I112 | [2-(3,5-dimethylisoxazol-4-yl)(4-quinolyl)](3-piperidylpropyl)amine | 365 | C |
| I113 | [2-(4-(2H-3,4,5,6-tetrahydropyran-2-yloxy)phenyl)(4-quinolyl)](3-piperidylpropyl)amine | 446 | B |
| I114 | {2-[4-methylthio-2-(trifluoromethyl)phenyl](4-quinolyl)}(3-piperidylpropyl)amine | 460 | B |
| I115 | (3-piperidylpropyl)[2-(2,3,4-trifluorophenyl)(4-quinolyl)]amine | 400 | B |
| I116 | N-(2-{4-[(3-piperidylpropyl)amino]-2-quinolyl}phenyl)acetamide | 403 | C |
| I117 | N-(4-{4-[(3-piperidylpropyl)amino]-2-quinolyl}phenyl)acetamide | 403 | B |
| I118 | N-(3-{4-[(3-piperidylpropyl)amino]-2-quinolyl}phenyl)acetamide | 403 | B |
| I119 | {2-[4-chloro-2-(trifluoromethyl)phenyl](4-quinolyl)}(3-piperidylpropyl)amine | 448 | B |
| I120 | {2-[2-chloro-4-(trifluoromethyl)phenyl](4-quinolyl)}(3-piperidylpropyl)amine | 448 | B |
| I121 | 4-(methylsulfonyl)-1-{4-[(3-piperidylpropyl)amino](2-quinolyl)}-2-(trifluoromethyl)benzene | 492 | B |
| I122 | {2-[4-fluoro-2-(trifluoromethyl)phenyl](4-quinolyl)}(3-piperidylpropyl)amine | 432 | B |
| I123 | 3-{4-[(3-piperidylpropyl)amino]-2-quinolyl}benzamide | 389 | B |
| I124 | (2-indol-2-yl(4-quinolyl))(3-piperidylpropyl)amine | 385 | C |
| I125 | (2-(2H,3H-benzo[3,4-e]1,4-dioxin-6-yl)(4-quinolyl))(3-piperidylpropyl)amine | 404 | B |
| I126 | 2-(4-chloro-2-fluorophenyl)(4-quinolyl)](3-piperidylpropyl)amine | 398 | A |
| I127 | (3-piperidylpropyl)[2-(3,4,5-trifluorophenyl)(4-quinolyl)]amine | 399 | B |
| I128 | 3-{4-[(3-piperidylpropyl)amino]-2-quinolyl}benzoic acid | 390 | B |

TABLE A-continued

| Compound | Name | MW (EI) [(M + 1)+] | IC50 (nM) |
|---|---|---|---|
| I129 | dimethyl(3-{4-[(3-piperidylpropyl)amino](2-quinolyl)}phenyl)amine | 389 | B |
| I130 | [2-(2,6-difluorophenyl)(4-quinolyl)](3-piperidylpropyl)amine | 382 | B |
| I131 | (3-piperidylpropyl){2-[2-(2,2,2-trifluoroethoxy)phenyl](4-quinolyl)}amine | 444 | B |
| I132 | 4-(methylsulfonyl)-1-{4-[(3-piperidylpropyl)amino](2-quinolyl)}benzene | 424 | B |
| I133 | [2-(5-chloro-2-methoxyphenyl)(4-quinolyl)](3-piperidylpropyl)amine | 410 | B |
| I134 | [2-(4-chloro-2-methylphenyl)(4-quinolyl)](3-piperidylpropyl)amine | 394 | B |
| I135 | {2-[4-(methoxymethyl)phenyl](4-quinolyl)}(3-piperidylpropyl)amine | 390 | A |
| I136 | (3-piperidylpropyl)(2-(3-thienyl)(4-quinolyl))amine | 352 | C |
| I137 | ethyl 3-{4-[(3-piperidylpropyl)amino]-2-quinolyl}benzoate | 418 | B |
| I138 | [2-(3,4-dichlorophenyl)(4-quinolyl)](3-piperidylpropyl)amine | 415 | B |
| I139 | (3-piperidylpropyl)(2-(4-pyridyl)(4-quinolyl))amine | 347 | B |
| I140 | (2-benzo[b]thiophen-2-yl(4-quinolyl))(3-piperidylpropyl)amine | 402 | B |
| I141 | [2-(2,4-dimethoxypyrimidin-5-yl)(4-quinolyl)](3-piperidylpropyl)amine | 408 | B |
| I142 | [2-(5-chloro(2-thienyl))(4-quinolyl)](3-piperidylpropyl)amine | 386 | B |
| I143 | (3-piperidylpropyl)(2-pyrimidin-5-yl(4-quinolyl))amine | 348 | B |
| I144 | (3-piperidylpropyl)(2-(2-thienyl)(4-quinolyl))amine | 352 | B |
| I145 | {2-[3-(1,1-dimethyl-1-silaethyl)phenyl](4-quinolyl)}(3-piperidylpropyl)amine | 418 | B |
| I146 | 1-(methylsulfonyl)-3-{4-[(3-piperidylpropyl)amino](2-quinolyl)}benzene | 424 | B |
| I147 | (3-piperidylpropyl)(2-(3-pyridyl)(4-quinolyl))amine | 346 | B |
| I148 | {2-[4-(aminomethyl)phenyl](4-quinolyl)}(3-piperidylpropyl)amine | 375 | A |
| I149 | {2-[2,4-bis(trifluoromethyl)phenyl](4-quinolyl)}(3-piperidylpropyl)amine | 482 | A |
| I150 | 2-{4-[(3-piperidylpropyl)amino]-2-quinolyl}benzenecarbonitrile | 371 | A |
| I151 | (2-methyl(4-quinolyl))(3-piperidylpropyl)amine | 284 | C |
| I152 | {2-[5-nitro-2-(trifluoromethyl)phenyl](4-quinolyl)}(3-piperidylpropyl)amine | 459 | B |
| I153 | (3-piperidylpropyl){2-[2-(trifluoromethyl)(3-pyridyl)](4-quinolyl)}amine | 415 | B |
| I154 | [2-(2-methoxy(3-pyridyl))(4-quinolyl)](3-piperidylpropyl)amine | 377 | B |
| I155 | methyl 3-{4-[(3-piperidylpropyl)amino]-2-quinolyl}benzoate | 403 | B |
| I156 | [2-(6-methoxy(3-pyridyl))(4-quinolyl)](3-piperidylpropyl)amine | 377 | B |
| I157 | [2-(4-methylphenyl)(4-quinolyl)](3-piperidylpropyl)amine | 360 | B |
| I158 | [2-(2-methylthiophenyl)(4-quinolyl)](3-piperidylpropyl)amine | 392 | A |
| I159 | [2-(2-methylphenyl)(4-quinolyl)](3-piperidylpropyl)amine | 360 | B |
| I160 | 4-{4-[(3-piperidylpropyl)amino]-2-quinolyl}benzoic acid | 390 | B |
| I161 | [2-(2,3-dimethylphenyl)(4-quinolyl)](3-piperidylpropyl)amine | 374 | B |
| I162 | [2-(3-fluorophenyl)(4-quinolyl)](3-piperidylpropyl)amine | 364 | B |
| I163 | (2-phenyl(4-quinolyl))(3-piperidylpropyl)amine | 346 | B |
| I164 | [2-(2-fluoro-6-methoxyphenyl)(4-quinolyl)](3-piperidylpropyl)amine | 394 | B |
| I165 | [2-(3-methoxyphenyl)(4-quinolyl)](3-piperidylpropyl)amine | 376 | B |
| I166 | (3-piperidylpropyl){2-[2-(trifluoromethoxy)phenyl](4-quinolyl)}amine | 430 | A |
| I167 | (2-(2H-benzo[3,4-d]1,3-dioxolen-5-yl)(4-quinolyl))(3-piperidylpropyl)amine | 390 | B |

TABLE A-continued

| Compound | Name | MW (EI) [(M + 1)+] | IC50 (nM) |
|---|---|---|---|
| I168 | {2-[2,4-bis(trifluoromethyl)phenyl](4-quinolyl)}(3-piperidylpropyl)amine | 462 | A |
| I169 | 2-(4-methylthiophenyl)(4-quinolyl)](3-piperidylpropyl)amine | 392 | B |
| I170 | [2-(3,5-dichlorophenyl)(4-quinolyl)](3-piperidylpropyl)amine | 415 | B |
| I171 | 4-{4-[(3-piperidylpropyl)amino]-2-quinolyl}benzenecarbonitrile | 371 | B |
| I172 | [2-(2,6-dimethoxyphenyl)(4-quinolyl)](3-piperidylpropyl)amine | 406 | C |
| I173 | [2-(2,5-dimethoxyphenyl)(4-quinolyl)](3-piperidylpropyl)amine | 406 | B |
| I174 | [2-(2,4-dimethoxyphenyl)(4-quinolyl)](3-piperidylpropyl)amine | 406 | B |
| I175 | (3-piperidylpropyl)(2-pyrrol-2-yl(4-quinolyl))amine | 335 | B |
| I176 | [2-(2,4-dimethyl(1,3-thiazol-5-yl))(4-quinolyl)](3-piperidylpropyl)amine | 381 | B |
| I177 | (2-(3-furyl)(4-quinolyl))(3-piperidylpropyl)amine | 336 | B |
| I178 | [2-(1-methylpyrazol-3-yl)(4-quinolyl)](3-piperidylpropyl)amine | 350 | C |
| I179 | (3-morpholin-4-ylpropyl)(2-phenyl(4-quinolyl))amine | 348 | C |
| I180 | (2-morpholin-4-ylethyl)(2-phenyl(4-quinolyl))amine | 348 | B |
| I181 | (2-phenyl(4-quinolyl))(2-pyrrolidinylethyl)amine | 318 | C |
| I182 | (2-phenyl(4-quinolyl))(3-piperidylpropyl)amine | 346 | B |
| I183 | dimethyl{2-[(2-phenyl(4-quinolyl))amino]ethyl}amine | 292 | C |
| I184 | (2-morpholin-4-ylethyl)(2-phenylquinazolin-4-yl)amine | 335 | C |
| I185 | (2-phenylquinazolin-4-yl)(3-piperidylpropyl)amine | 347 | C |
| I186 | 2-phenyl-4-(3-piperidylpropoxy)quinoline | 347 | C |
| I887 | [2-(4-chlorophenyl)(4-quinolyl)](3-piperidylpropyl)amine | 380 | B |
| I188 | [2-(4-fluorophenyl)(4-quinolyl)](3-piperidylpropyl)amine | 364 | B |
| I189 | (4-{4-[(3-piperidylpropyl)amino](2-quinolyl)}phenyl)-N-(2-(4-pyridyl)ethyl)carboxamide | 494 | A |
| I190 | N-[3-(diethylamino)propyl](4-{4-[(3-piperidylpropyl)amino](2-quinolyl)}phenyl)carboxamide | 502 | A |
| I191 | N-(2-piperidylethyl)(4-{4-[(3-piperidylpropyl)amino](2-quinolyl)}phenyl)carboxamide | 500 | A |
| I192 | N-(3-morpholin-4-ylpropyl)(4-{4-[(3-piperidylpropyl)amino](2-quinolyl)}phenyl)carboxamide | 516 | A |
| I193 | piperazinyl 4-{4-[(3-piperidylpropyl)amino](2-quinolyl)}phenyl ketone | 458 | A |
| I194 | piperidyl 4-{4-[(3-piperidylpropyl)amino](2-quinolyl)}phenyl ketone | 457 | B |
| I195 | N-(3-aminopropyl)(4-{4-[(3-piperidylpropyl)amino](2-quinolyl)}phenyl)carboxamide | 446 | A |
| I196 | N-(4-piperidyl)(4-{4-[(3-piperidylpropyl)amino](2-quinolyl)}phenyl)carboxamide | 472 | A |
| I197 | N-(4-piperidylmethyl)(4-{4-[(3-piperidylpropyl)amino](2-quinolyl)}phenyl)carboxamide | 486 | A |
| I198 | N-(3-piperidylpropyl)(4-{4-[(3-piperidylpropyl)amino](2-quinolyl)}phenyl)carboxamide | 514 | A |
| I199 | [2-(4-methoxyphenyl)(4-quinolyl)](2-(2-pyridyl)ethyl)amine | 356 | B |
| I200 | [2-(4-methoxyphenyl)(4-quinolyl)](3-(4-pyridyl)propyl)amine | 370 | B |
| I201 | [2-(4-methoxyphenyl)(4-quinolyl)](2-(4-pyridyl)ethyl)amine | 356 | B |
| I202 | 2-(3-chlorophenyl)(4-quinolyl)](3-(3-pyridyl)propyl)amine | 374 | B |
| I203 | 2-(4-methoxyphenyl)(4-quinolyl)](3-(3-pyridyl)propyl)amine | 370 | B |
| I204 | [2-(4-chloro-2-fluorophenyl)(4-quinolyl)](3-(3-pyridyl)propyl)amine | 392 | B |

TABLE A-continued

| Compound | Name | MW (EI) [(M + 1)+] | IC50 (nM) |
|---|---|---|---|
| I205 | [2-(4-(1H-1,2,3,4-tetraazol-5-yl)phenyl)(4-quinolyl)](3-piperidylpropyl)amine | 414 | B |
| I206 | {4-[(4-ethylpiperazinyl)methyl]phenyl}[2-(4-methoxyphenyl)(4-5,6,7,8-tetrahydroquinolyl)]amine | 457 | B |
| I207 | [2-(4-methoxyphenyl)(4-5,6,7,8-tetrahydroquinolyl)][4-(piperidylmethyl)phenyl]amine | 430 | B |
| I208 | [2-(4-methoxyphenyl)(4-5,6,7,8-tetrahydroquinolyl)](3-piperidylpropyl)amine | 380 | B |
| I209 | [2-(4-methoxyphenyl)(4-5,6,7,8-tetrahydroquinolyl)][3-(pyrrolidinylmethyl)phenyl]amine | 414 | B |
| I210 | [2-(4-methoxyphenyl)(4-quinolyl)]{[4-(piperidylmethyl)phenyl]methyl}amine | 438 | B |
| I211 | [2-(4-methoxyphenyl)(4-quinolyl)]{[4-(morpholin-4-ylmethyl)phenyl]methyl}amine | 440 | B |
| I212 | 4-[4-({[4-(morpholin-4-ylmethyl)phenyl]methyl}amino)-2-quinolyl]benzamide | 453 | C |
| I213 | 4-[4-({[4-(piperidylmethyl)phenyl]methyl}amino)-2-quinolyl]benzamide | 451 | C |
| I214 | 4-{4-[({4-[(4-ethylpiperazinyl)methyl]phenyl}methyl)amino]-2-quinolyl}benzamide | 480 | C |
| I215 | 4-[4-({4-[(4-ethylpiperazinyl)methyl]phenyl}amino)-2-quinolyl]benzamide | 466 | C |
| I216 | 4-(4-{[4-(2-piperazinylethyl)phenyl]amino}-2-quinolyl)benzamide | 452 | C |
| I217 | 4-[4-({4-[2-(dimethylamino)ethyl]phenyl}amino)-2-quinolyl]benzamide | 411 | C |
| I218 | 4-(4-{[3-(diethylamino)propyl]amino}-2-quinolyl)benzamide | 377 | C |
| I219 | 4-{4-[(3-azaperhydroepinylpropyl)amino]-2-quinolyl}benzamide | 403 | C |
| I220 | 4-(4-{[4-(4-piperidylmethyl)phenyl]amino}-2-quinolyl)benzamide | 437 | C |
| I221 | 6-{4-[(3-piperidylpropyl)amino]-2-quinolyl}indolin-2-one | 401 | B |
| I222 | 4-(4-{4-[(4-aminophenyl)methyl]piperidyl}-2-quinolyl)benzamide | 437 | C |
| I223 | {2-[3-fluoro-2-(trifluoromethyl)phenyl](4-quinolyl)}(3-piperidylpropyl)amine | 432 | B |
| I224 | (2-benzothiazol-5-yl(4-quinolyl))(3-piperidylpropyl)amine | 403 | B |
| I225 | {2-[4-(4-fluorophenyl)phenyl](4-quinolyl)}(3-piperidylpropyl)amine | 440 | B |
| I226 | N-(2-methylpropyl)(4-{4-[(3-piperidylpropyl)amino](2-quinolyl)}phenyl)carboxamide | 445 | B |
| I227 | N-(2-hydroxyethyl)(4-{4-[(3-piperidylpropyl)amino](2-quinolyl)}phenyl)carboxamide | 433 | B |
| I228 | (2-fluoro-4-{4-[(3-piperidylpropyl)amino](2-quinolyl)}phenyl)-N-methylcarboxamide | 421 | B |
| I229 | N-ethyl(2-fluoro-4-{4-[(3-piperidylpropyl)amino](2-quinolyl)}phenyl)carboxamide | 435 | B |
| I230 | N-cyclohexyl(4-{4-[(3-piperidylpropyl)amino](2-quinolyl)}phenyl)carboxamide | 471 | B |
| I231 | N-(4-{4-[(3-piperidylpropyl)amino](2-quinolyl)}-2-(trifluoromethyl)phenyl)acetamide | 471 | B |
| I232 | N-(2-fluoro-4-{4-[(3-piperidylpropyl)amino](2-quinolyl)}phenyl)acetamide | 421 | B |
| I233 | 4-[(2-{4-[(3-piperidylpropyl)amino]-2-quinolyl}phenyl)sulfonyl]morpholine | 495 | C |
| I234 | morpholin-4-yl 4-{4-[(3-piperidylpropyl)amino](2-quinolyl)}phenyl ketone | 459 | A |
| I235 | 4-[(4-{4-[(3-piperidylpropyl)amino]-2-quinolyl}phenyl)sulfonyl]-1,4-thiazaperhydroine | 511 | A |
| I236 | 4-[(4-{4-[(3-piperidylpropyl)amino]-2-quinolyl}phenyl)sulfonyl]morpholine | 495 | A |
| I237 | N-{3-[4-({3-[(1-ethyl-4-piperidyl)methyl]phenyl}amino)-2-quinolyl]phenyl}acetamide | 479 | B |

TABLE A-continued

| Compound | Name | MW (EI) [(M + 1)+] | IC50 (nM) |
|---|---|---|---|
| I238 | [2-(3-chloro-2-fluorophenyl)(4-quinolyl)](3-piperidylpropyl)amine | 398 | B |
| I239 | [2-(5-bromo-3-chloro-2-fluorophenyl)(4-quinolyl)](3-piperidylpropyl)amine | 477 | B |
| I240 | diethyl[(2-{4-[(3-piperidylpropyl)amino](2-quinolyl)}phenyl)sulfonyl]amine | 481 | C |
| I241 | (2-(2-4,5-dihydrofuryl)(4-quinolyl))(3-piperidylpropyl)amine | 338 | C |
| I242 | diethyl[(4-methyl-3-{4-[(3-piperidylpropyl)amino](2-quinolyl)}phenyl)sulfonyl]amine | 495 | C |
| I243 | [2-(4-phenylphenyl)(4-quinolyl)](3-piperidylpropyl)amine | 422 | B |
| I244 | diethyl[(3-{4-[(3-piperidylpropyl)amino](2-quinolyl)}phenyl)sulfonyl]amine | 481 | C |
| I245 | {2-[3-(phenylmethylthio)phenyl](4-quinolyl)}(3-piperidylpropyl)amine | 468 | C |
| I246 | diethyl[(4-{4-[(3-piperidylpropyl)amino](2-quinolyl)}phenyl)sulfonyl]amine | 481 | B |
| I247 | (2-benzo[b]thiophen-5-yl(4-quinolyl))(3-piperidylpropyl)amine | 402 | A |
| I248 | 2-(2-methylbenzothiazol-6-yl)(4-quinolyl)](3-piperidylpropyl)amine | 417 | B |
| I249 | N-cyclopentyl(4-{4-[(3-piperidylpropyl)amino](2-quinolyl)}phenyl)carboxamide | 457 | A |
| I250 | 5-(acetylamino)-3-{4-[(3-piperidylpropyl)amino](2-quinolyl)}benzoic acid | 447 | B |
| I251 | (2-chloro-4-{4-[(3-piperidylpropyl)amino](2-quinolyl)}phenyl)-N-methylcarboxamide | 437 | A |
| I252 | 3-fluoro-4-{4-[(3-piperidylpropyl)amino](2-quinolyl)}benzamide | 407 | A |
| I253 | N-benzyl(4-{4-[(3-piperidylpropyl)amino](2-quinolyl)}phenyl)carboxamide | 479 | A |
| I254 | N-[2-(diethylamino)ethyl](4-{4-[3-piperidylpropyl)amino](2-quinolyl)}phenyl)carboxamide | 488 | A |
| I255 | N-[(4-{4-[(3-piperidylpropyl)amino]-2-quinolyl}phenyl)methyl]acetamide | 417 | A |
| I256 | (2-acenaphthen-4-yl(4-quinolyl))(3-piperidylpropyl)amine | 422 | A |
| I257 | (2-benzo[b]thiophen-6-yl(4-quinolyl))(3-piperidylpropyl)amine | 402 | A |
| I258 | (3-{4-[(3-piperidylpropyl)amino]-2-quinolyl}phenyl)methyl acetate | 418 | B |
| I259 | 3-amino-5-{4-[(3-piperidylpropyl)amino](2-quinolyl)}phenyl morpholin-4-yl ketone | 474 | B |
| I260 | 1-(phenylsulfonyl)-5-{4-[(3-piperidylpropyl)amino](2-quinolyl)}indole | 525 | B |
| I261 | 2-fluoro-4-{4-[(3-piperidylpropyl)amino](2-quinolyl)}benzamide | 407 | A |
| I262 | 2-methyl-N-(4-{4-[(3-piperidylpropyl)amino](2-quinolyl)}phenyl)propanamide | 431 | B |
| I263 | phenyl-N-(4-{4-[(3-piperidylpropyl)amino](2-quinolyl)}phenyl)carboxamide | 465 | A |
| I264 | 2-chloro-4-{4-[(3-piperidylpropyl)amino](2-quinolyl)}benzamide | 423 | A |
| I265 | N-(2-cyanoethyl)(4-{4-[3-piperidylpropyl)amino](2-quinolyl)}phenyl)carboxamide | 442 | A |
| I266 | N-ethyl-N-methyl(4-{4-[(3-piperidylpropyl)amino](2-quinolyl)}phenyl)carboxamide | 431 | B |
| I267 | N-(methylethyl)(4-{4-[(3-piperidylpropyl)amino](2-quinolyl)}phenyl)carboxamide | 431 | B |
| I268 | N-ethyl(4-{4-[(3-piperidylpropyl)amino](2-quinolyl)}phenyl)carboxamide | 417 | B |
| I269 | (4-{4-[(3-piperidylpropyl)amino](2-quinolyl)}phenyl)-N-(2,2,2-trifluoroethyl)carboxamide | 471 | B |
| I270 | N-(oxolan-2-ylmethyl)(4-{4-[(3-piperidylpropyl)amino](2-quinolyl)}phenyl)carboxamide | 473 | B |
| I271 | N-cyclopropyl(4-{4-[(3-piperidylpropyl)amino](2-quinolyl)}phenyl)carboxamide | 429 | B |
| I272 | 4-{4-[(3-piperidylpropyl)amino](2-quinolyl)}phenyl pyrrolidinyl ketone | 443 | B |

TABLE A-continued

| Compound | Name | MW (EI) [(M + 1)+] | IC50 (nM) |
|---|---|---|---|
| I273 | [2-(3,5-difluorophenyl)(4-quinolyl)](3-piperidylpropyl)amine | 382 | B |

Example 4.: SAR Analysis

Two initial compounds were selected (Scheme 4).

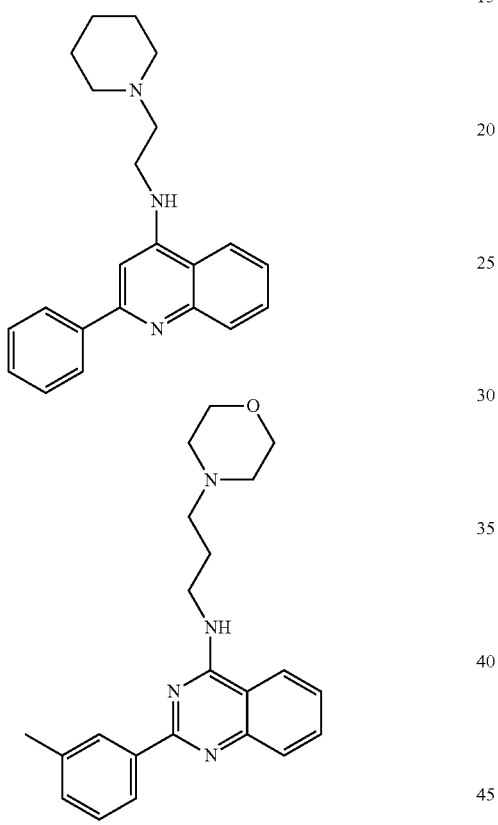

Scheme 4

The most potent scaffold discovered was the quinoline compound (IC$_{50}$=3.49 µM) The second scaffold identified was the quinazolinone compound (IC$_{50}$=7.12 µM).

Figure 15:
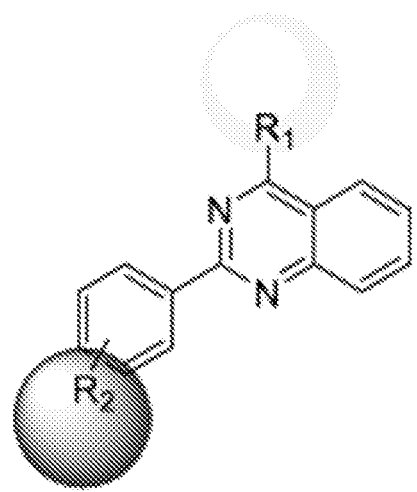
FIG. 15 describes an SAR strategy for the quinazolinone series.

The initial SAR strategy focused on the quinazolinone series. The SAR strategy for the quinazolinone series is outlined in FIG. 15.

First, at the R$_1$ position the inventors investigated the effects of changing the chain length, looking at the effects of branching on the chain, adding substituents on the chain, both aromatic and heteroaromatic, and the inventors investigated the substitution of cycloamino groups on the alkyl chain. For the R$_2$ group the inventors investigated the effects electron donating and electron withdrawing groups on the activity of the parent series. For all SAR tables shown below: P=purchased compounds, CP=cherry pick of 10 µM DMSO solutions from the NIH MLSMR library and S=synthesized compounds.

TABLE 1

Table 1 summarizes studies on the quinazoline series of compounds.
SAR explorations of the quinazoline core (Entries 1-7)

Core structure: 2-(R2-phenyl)-4-(R1)-quinazoline with R3 substituent on the benzo ring.

| Entry | P/S* | R₁ | R₂ | R₃ | LMPTP (OMFP) (IC₅₀) (μM) | n | SEM |
|---|---|---|---|---|---|---|---|
| 1 Screen hit | CP<br>P | —NH—(CH₂)₃—morpholine | 3-CH₃ | H | 7.12<br>13.5 | 3<br>4 | 0.72<br>0.71 |
| 2 | CP<br>P | —NH—(CH₂)₃—morpholine | 2-F | H | 22.0<br>13.0 | 3<br>4 | 2.31<br>3.31 |
| 3 | CP<br>P | —NH—(CH₂)₂—morpholine | 4-CH₃ | H | 16.0<br>18.8 | 3<br>4 | 1.02<br>0.93 |
| 4 | CP | —NH—(CH₂)₃—morpholine | H | H | 17 | 3 | 4.40 |
| 5 | CP<br>P | —NH—CH₂—(pyridin-3-yl) | H | H | 8.37<br>19.0 | 3<br>4 | 0.82<br>2.66 |
| 6 | CP<br>P | —NH—CH₂—(pyrimidin-5-yl) | 4-CH₃ | H | 8.04<br>12.9 | 3<br>4 | 0.46<br>1.74 |
| 7 | CP | —NH—CH(Ph)—CH₂OH | H | H | 17.0 | 4 | 3.85 |
| 8 | CP<br>P | —NH—(CH₂)₃—(imidazol-1-yl) | H | H | 13.9<br>17.8 | 3<br>4 | 2.01<br>1.09 |

TABLE 1-continued

Table 1 summarizes studies on the quinazoline series of compounds.
SAR explorations of the quinazoline core (Entries 1-7)

| Entry | P/S* | R₁ | R₂ | R₃ | LMPTP (OMFP) (IC$_{50}$) (µM) | n | SEM |
|---|---|---|---|---|---|---|---|
| 9 | CP | NH-CH(CH₃)-phenyl | H | H | 23.1 | 3 | 2.22 |
| 10 | CP<br>P | NH-CH₂CH₂-O-C(O)-(4-pyridyl) | H | H | 11.8<br>20.9 | 3<br>4 | 0.28<br>2.21 |
| 11 | CP<br>P | NH-CH₂CH₂-O-C(O)-(3-pyridyl) | H | H | 7.51<br>24.2 | 3<br>4 | 1.69<br>1.53 |
| 12 | CP | NH-CH₂-(tetrahydrofuran-2-yl) | 4-O(i-Pr) | H | 18.1 | 3 | 1.20 |
| 13 | CP | NH-CH₂-(3,4-dimethoxyphenyl) | H | H | 9.94 | 3 | 2.25 |
| 14 | CP | NH-CH(CH₃)-(2-pyridyl) | 2-F | H | 5.48 | 3 | 0.21 |
| 15 | CP | NH-cyclopentyl | H | H | 7.48 | 3 | 1.49 |
| 16 | P | NH-(4-CO₂H-phenyl) | 4-NO₂ | H | 10.9 | 3 | 2.84 |

TABLE 1-continued

Table 1 summarizes studies on the quinazoline series of compounds.
SAR explorations of the quinazoline core (Entries 1-7)

| Entry | P/S* | R₁ | R₂ | R₃ | LMPTP (OMFP) (IC₅₀) (µM) | n | SEM |
|---|---|---|---|---|---|---|---|
| 17 | CP | 2-(CO₂H)-anilino (NH-C₆H₄-CO₂H) | 4-NO₂ | H | >80 | 4 | — |
| 18 | P | NH-CH₂CH₂CH₂-O-iPr | H | H | 18.1 | 4 | 1.29 |
| 19 | CP | NH-(CH₂)₄-CO₂H | H | H | 12.0 | 3 | 0.49 |
| 20 | CP | NH-cyclopentyl | H | H | 10.0 | 3 | 0.65 |
|    | P  |                  |   |   | 21.1 | 4 | 2.02 |
| 21 | CP | NH-CH₂CH₂CH₂-O-Et | H | H | 12.3 | 3 | 2.04 |
| 22 | S | azepan-1-yl | H | H | 72.2 | 2 | 5.38 |
| 23 | S | 4-methylpiperidin-1-yl | H | H | >80 | 3 | — |
| 24 | S | morpholin-4-yl | H | H | >80 | 3 | — |

TABLE 1-continued

Table 1 summarizes studies on the quinazoline series of compounds.
SAR explorations of the quinazoline core (Entries 1-7)

| Entry | P/S* | R₁ | R₂ | R₃ | LMPTP (OMFP) (IC₅₀) (μM) | n | SEM |
|---|---|---|---|---|---|---|---|
| 25 | S | piperidinyl | H | H | >80 | 3 | — |
| 26 | S | pyrrolidinyl | H | H | >80 | 3 | — |
| 27 | S | N(Et)₂ | H | H | 53.1 | 4 | 1.27 |
| 28 | S | 4-methylpiperazinyl | H | H | >80 | 3 | — |
| 29 | S | NH-iBu | H | H | 14.5 | 4 | 0.98 |
| 30 | S | NH-nBu | H | H | 23.2 | 4 | 1.72 |
| 31 | S | NH-iPr | H | H | 15.0 | 4 | 1.04 |
| 32 | S | NH-cPr | H | H | 48.1 | 4 | 3.25 |
| 33 | S | thiomorpholinyl | H | H | >80 | 4 | — |

TABLE 1-continued

Table 1 summarizes studies on the quinazoline series of compounds.
SAR explorations of the quinazoline core (Entries 1-7)

| Entry | P/S* | R₁ | R₂ | R₃ | LMPTP (OMFP) (IC$_{50}$) (μM) | n | SEM |
|---|---|---|---|---|---|---|---|
| 34 | S | NH-cyclohexyl | H | H | 19.1 | 4 | 1.49 |
| 35 | S | NH-CH₂CH₂-piperidinyl | H | H | 64.3 | 4 | 6.90 |
| 36 | S | NH-CH₂CH₂-pyrrolidinyl | H | H | >80 | 4 | — |
| 37 | S | NH-(CH₂)₃-morpholinyl | H | H | 22.5 | 4 | 1.76 |
| 38 | S | NH-CH₂CH₂-morpholinyl | H | H | 25.4 | 4 | 2.29 |
| 39 | S | NH-(CH₂)₃-piperidinyl | H | H | 21.9 | 4 | 2.12 |
| 40 | S | NH-CH₂CH₂-N(CH₃)₂ | H | H | 58.1 | 3 | 7.04 |

P = compounds purchased from commercial sources
CP = "cherry pick" of 10 mM DMSO from NIH MLSMR
S = compound synthesized de novo by SBCCG The initial hit compound in Table 1, (Entry 1), was obtained and demonstrated similar potency to the solution screening sample (LMPTP (OMFP) IC$_{50}$=13.5 μM). The inventors found 20 additional analogs in the screening collection and synthesized an additional 18 analogs for the quinazolinone series. From these analogs, the inventors first tested four analogs where the R₁ group was fixed as a 3-morpholinopropan-1-amine and different R₂ substituents on the phenyl ring were examined. In general the substitution at the C-2 position of the phenyl is favored and an electron donating group at this position is also preferred (Entries 1-4). A similar observation was noted when the R₁ group was fixed and the C-2 position had a fluorine atom versus a hydrogen atom, the 2-F analogs were more potent. (Entry 9 and 14 and Entry 15 and 20). The inventors examined shorting the chain length at R₁ coupled with having an aromatic/heteroaromatic group on the chain; for these compounds the inventors observed little change in potency over the lead structure CID1566769. (Entries 5-7, 9, 13-14, 16-17). One interesting observation was when the cycloalkyl or cycloheteroalkyl group was attached directly to the ring with no carbon spacer the compounds were inactive. (Entries 22-26, 28, 33). When the R₁ group was an amine containing 2-4 carbon atoms, branched or straight chain, all the compounds had similar potencies (Entries 27, 29-31). Finally, when compounds with similar R₁ groups differing by only one carbon atom in the chain were compared the potencies were similar. (Entries 35 and 39, Entries 37 and 38).

TABLE 2

Table 2 summarizes studies on the quinolone series of compounds.
SAR explorations of the quinazoline core (Entries 1-7)

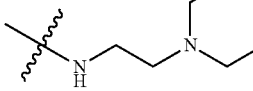

| Entry | P/S* | $R_1$ | $R_2$ | $R_3$ | LMPTP (OMFP) ($IC_{50}$) (μM) | n | SEM |
|---|---|---|---|---|---|---|---|
| 41 Screen hit | CP P S | 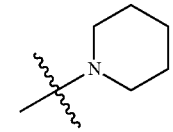 | H | H | 3.49 2.86 3.70 | 3 4 4 | 0.62 0.10 0.36 |
| 42 | CP P | 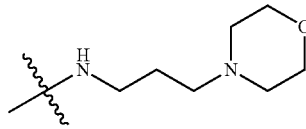 [SMILES: *NCCCN1CCCCC1] | H | H | 9.25 11.1 | 3 4 | 1.32 0.70 |
| 43 | S | 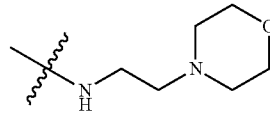 [SMILES: *NCCN1CCCCC1] | H | H | 7.68 | 4 | 0.71 |
| 44 | S | 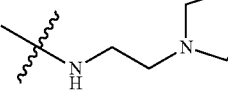 | H | H | 2.13 | 4 | 0.13 |
| 45 | S | 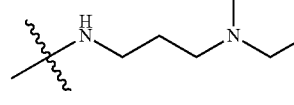 | H | H | 5.46 | 4 | 0.58 |
| 46 | S | 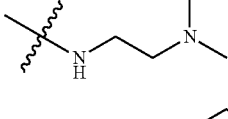 | H | H | 1.56 | 4 | 0.08 |
| 47 | S | 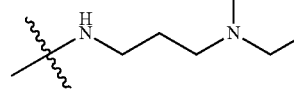 | H | H | 5.72 | 4 | 0.53 |
| 48 | S |  | 4-Cl | H | 1.54 | 4 | 0.06 |

TABLE 2-continued

Table 2 summarizes studies on the quinolone series of compounds.
SAR explorations of the quinazoline core (Entries 1-7)

| Entry | P/S* | R₁ | R₂ | R₃ | LMPTP (OMFP) (IC$_{50}$) (μM) | n | SEM |
|---|---|---|---|---|---|---|---|
| 49 | S | ⸺N(H)CH₂CH₂CH₂-piperidine | 4-F | H | 1.40 | 4 | 0.09 |
| 50 (Compound D1) (MLS-0472870) | S | ⸺N(H)CH₂CH₂CH₂-piperidine | 4-OCH₃ | H | 1.68 | 4 | 0.15 |
| 51 | S | ⸺N(H)CH₂CH₂CH₂-piperidine | CH₃ | H | 1.34 | 4 | 0.08 |
| 52 | S | ⸺N(H)CH₂CH₂CH₂-piperidine | 2-Cl | H | 11.6 | 4 | 0.41 |
| 53 | S | ⸺N(H)CH₂CH₂CH₂-piperidine | 3-Cl | H | 1.12 | 4 | 0.20 |
| 54 | S | ⸺N(H)CH₂CH₂CH₂-piperidine | 3-CF₃ | H | 2.66 | 4 | 0.14 |
| 55 | S | ⸺N(H)CH₂CH₂CH₂-piperidine | 2-OCH₃ | H | 2.87 | 4 | 0.11 |
| 56 | S | ⸺N(H)CH₂CH₂CH₂-piperidine | 3-F | H | 1.84 | 4 | 0.10 |

TABLE 2-continued

Table 2 summarizes studies on the quinolone series of compounds.
SAR explorations of the quinazoline core (Entries 1-7)

| Entry | P/S* | R₁ | R₂ | R₃ | LMPTP (OMFP) (IC$_{50}$) (μM) | n | SEM |
|---|---|---|---|---|---|---|---|
| 57 | S | (N-propyl-piperidine amine) | 3-OCH₃ | H | 2.21 | 4 | 0.15 |
| 58 | S | (N-propyl-piperidine amine) | H | 6-F | 22.0 | 4 | 7.35 |
| 59 | S | (N-propyl-piperidine amine) | H | 6-Br | >80 | 4 | — |
| 60 | S | (N-propyl-piperidine amine) | H | 6-CH₃ | >80 | 4 | — |
| 61 | S | (N-propyl-piperidine amine) | H | 6,7-di-OCH₃ | >80 | 4 | — |
| 62 | S | (cyclopentylamine) | H | H | 10.0 | 3 | 0.65 |
|    |   |                     |   |   | 21.1 | 4 | 2.02 |
| 63 | S | (O-propyl-piperidine) | H | H | 11.5 | 4 | 0.91 |
| 64 | S | (S-methyl, propyl-piperidine) | H | H | 66.9 | 3 | 5.77 |

Figure 16:
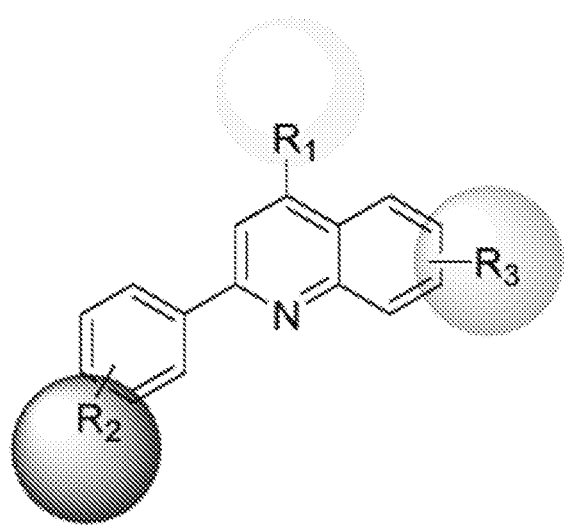
FIG. 16 describes an SAR strategy for the quinoline series.

P = compounds purchased from commercial sources
CP = "cherry pick" of 10 mM DMSO from NIH MLSMR
S = compound synthesized de novo by SBCCG A similar SAR strategy was applied to the quinolone series (FIG. 16).

For the $R_1$ group the inventors focused on either a 2 or 3 carbon spacer between the ring coupled nitrogen atom and the cycloalkyl or heterocycloalkyl tail groups. A limited number of $R_2$ groups were investigated and a small set of $R_3$ analogs were synthesized.

The screening hit CID2728458 (Entry 41) was independently purchased and synthesized and the activity of the purchased and synthesized compound was similar LMPTP (OMFP) $IC_{50}$=2.86 μM and LMPTP (OMFP) $IC_{50}$=3.70 μM respectively. Screening of Entry 42 showed that the potency was less than the screening hit.

Overall, the inventors synthesized 21 compounds in the quinoline series, to ultimately select Entry 50 (CID73050863) for SAR explorations.

For the first set of SAR analogs, the inventors choose to fix $R_2$ and $R_3$ as hydrogen atoms and vary the $R_1$ position. The most active member of this set of analogs (Entries 41-47) was the 3-(piperidin-1-yl)propan-1-amine analog, Entry 46. (LMPTP (OMFP) $IC_{50}$=1.56 μM). Next we fixed the $R_1$ group as the 3-(piperidin-1-yl)propan-1-amine moiety, the $R_3$ group as hydrogen atom and varied the $R_2$ substitution. Substitution around the phenyl substituent $R_2$ indicated little preference for electron withdrawing moieties over analogs containing electron donating groups, the respective LMPTP (OMFP) $IC_{50}$ values ranged from 1.12-2.86 μM range. (Table 2; entries 48-51, 53-57). In addition, no strong preference regarding position (ortho, meta, para) was determined with regards to potency, the notable exception being the 2-Cl analog Entry 52, LMPTP (OMFP) IC=11.2 μM. The third set of analogs fixed the $R_1$ group as the 3-(piperidin-1-yl)propan-1-amine moiety, the $R_2$ group as hydrogen atom and varied the $R_3$ substitution. The compounds synthesized had substituents at the C-6 or C-6, C-7 positions of the quinoline ring and all the compounds lost significant potency with these modifications. (Table 2; entries 58-61). Finally the inventors replaced the nitrogen atom attached directly to the quinoline ring of Entry 50 (Compound D1 of Example 1) with either an oxygen or sulfur atom and the compounds were inactive. (Entries 63-64).

Example 5: Cell Based Activity and Efficacy

Figure 7:
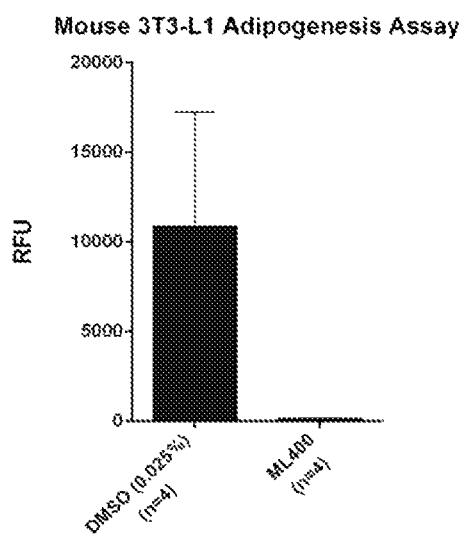
FIG. 7 shows that Compound D1 inhibits adipogenesis of 3T3-L1 cells.

The probe Compound D1 was also profiled in an insulin-based mouse 3T3-L1 adipogenesis assay. In this assay, 3T3-L1 pre-adipocytes are grown to 2-days post-confluence in DMEM with 10% bovine calf serum, and then induced to differentiate to adipocytes following stimulation for 2 days with an induction cocktail containing 1 μg/ml insulin, 1 μM dexamethasone, and 0.5 mM 3-isobutyl-1-methylxanthine in DMEM containing 10% fetal bovine serum (FBS).[44] 2 days later, the media is replaced with DMEM with 10% FBS and 1 μg/ml insulin, and after 2 additional days, the media is replaced with DMEM with 10% FBS for 2 additional days, at which point adipogenesis is measured using the AdipoRed Adipogenesis Assay Reagent from Lonza, according to the manufacturer's instructions. In brief, the assay reagent is added to the wells containing cells, where it partitions into the fat droplets of differentiated adipocytes, and emits fluorescence at 572 nm that can be detected with a plate-reader. To test the effect of probe Compound D1, cells were plated into 48-well plates and allowed to grow to confluence. Cells were then treated with 10 μM Compound D1 or 0.025% DMSO, and after 2 days induced to differentiate in the presence of 10 μM Compound D1 or 0.025% DMSO. Fresh compound or DMSO was added during each media replacement. As shown in the FIG. 7, it was found that treatment with 10 μM Compound D1 completely abolished 3T3-L1 adipogenesis.

ADME/T Profiling Assays

In the course of this investigation many compounds with similar potencies in the LMPTP (OMFP) assay were found. In order to determine which compound would be the best candidate for in vivo studies, an abbreviated ADME panel was ran on these compounds, a tabulation of the most interesting data on this set of compounds is illustrated in Table 3 below. From the hepatic microsome stability data the candidate selected for in vivo studies was Compound D1.

TABLE 3

Summary of in vitro ADME Properties of selected LMPTP inhibitors

| Compound ID (Entry) | Aqueous Solubility Pion's buffer (ug/mL) pH 5.0/6.2/7.4 | Plasma Stability % Remaining @ 3 hrs Human/Mouse | Hepatic Microsome Stability % Remaining @ 1 hr Human/Mouse |
|---|---|---|---|
| 41 | 111.8/95.7/54.5 | 70.08/62.25 | 26.54/0.38 |
| 48 | >113/>113/>113 | 100/59.47 | 23.10/15.38 |
| 50 (Compound D1) | >112/>112/>112 | 89.03/68.97 | 61.56/48.75 |
| 51 | >178/>178/>178 | 92.17/46.01 | 32.21/9.70 |
| 53 | >99/>99/>99 | 82.81/50.16 | 77.96/9.71 |
| 54 | 122.8/118.4/111.2 | 77.58/70.55 | 82.50/8.59 |
| 55 | >103/>103/>103 | 83.67/63.60 | 52.95/2.62 |

Figure 12:
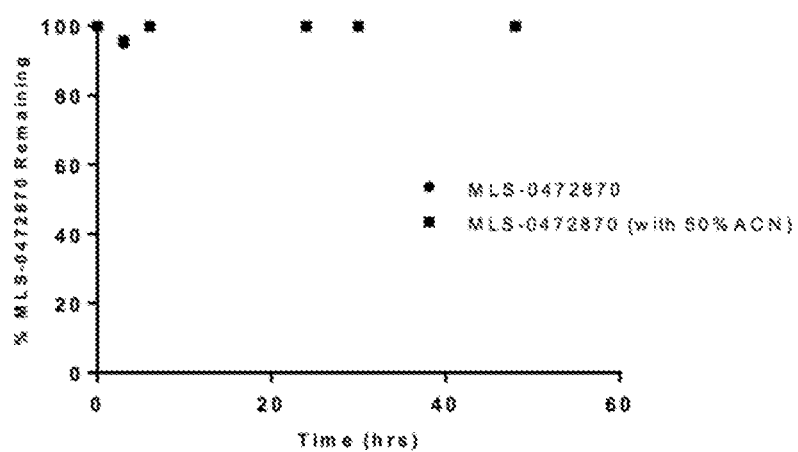
FIG. 12 shows the stability of Compound D1 in 1×PBS and 1:1 PBS:ACN at room temperature.

Compound D1 achieved very good concentrations 18-20× $IC_{50}$ in aqueous buffer between a pH range of 5.0-7.4. The solubility was comparable in PBS. See FIG. 12.

Plasma stability is a measure of the stability of small molecules and peptides in plasma and is an important parameter, which can strongly influence the in vivo efficacy of a test compound. Drug candidates are exposed to enzymatic processes (proteinases. esterases) in plasma, and they can undergo intramolecular rearrangement or bind irreversibly (covalently) to proteins. Compound D1 showed good stability in both human plasma and mouse plasma.

The microsomal stability assay is commonly used to rank compounds according to their metabolic stability. This assay addresses the pharmacologic question of how long the parent compound will remain circulating in plasma within the body. Compound D1 showed moderate stability in human and mouse liver microsomes after 1 hour.

Example 6: Rodent Pharmacokinetics

Figure 13:
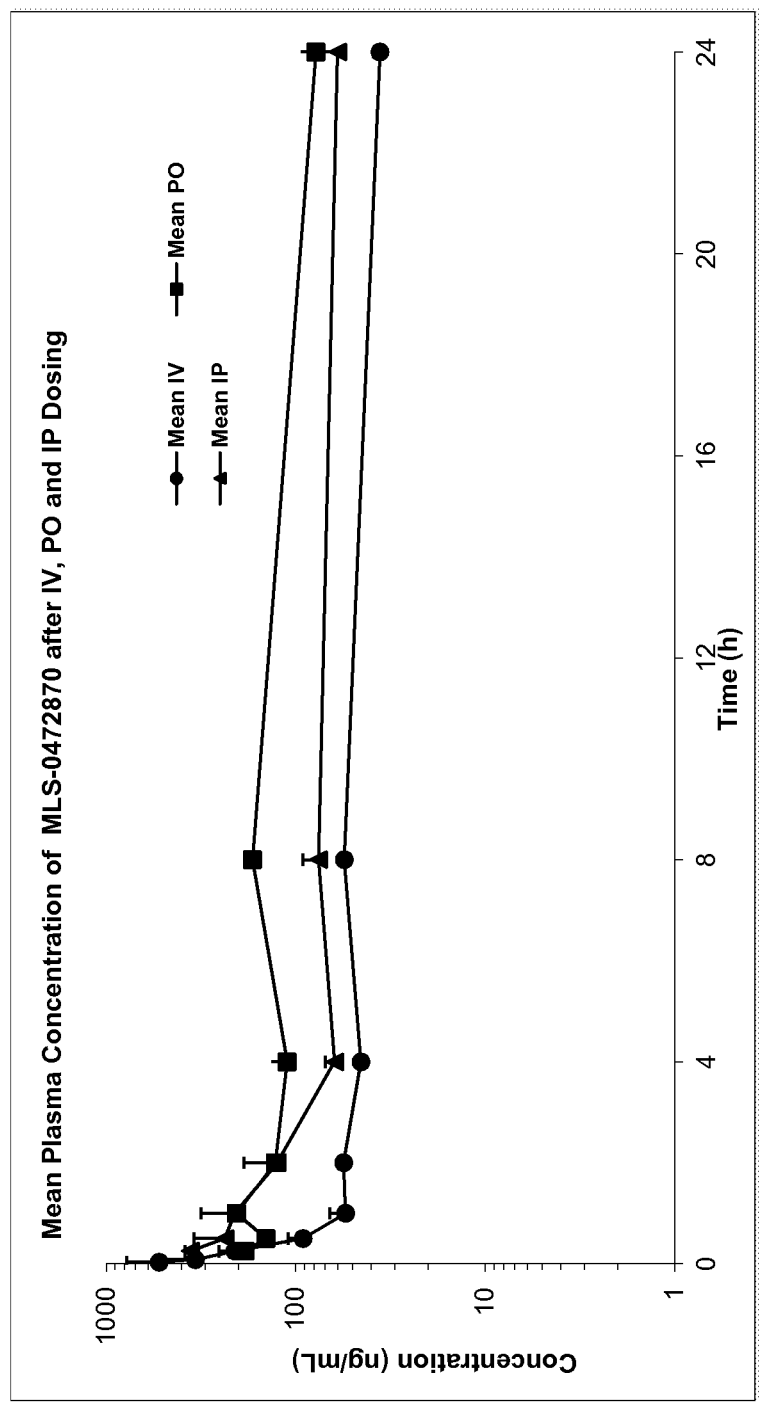
FIG. 13 shows mouse pharmacokinetics of Compound D1 after iv (5 mg/kg), ip (10 mg/kg) or po (30 mg/kg) dosing.

The inventors also examined ML400 (also described herein as MLS-0472870 or Compound D1) for its rodent pharmacokinetics. The probe Compound D1 was profiled in Male C57BL/6 Mice, with n=3 for each group studied (IV, IP and PO arms). The formulation used was 1.00 mg/mL in DMSO:Tween80:Water=5:5:90, which gave a clear solution. Low clearance and large volume of distribution were observed from IV arm and bioavailability was very good for PO and IP studies. Enterohepatic circulation was also observed for this compound. This compound has acceptable parameters for future in vivo studies (see Table 4 and FIG. 13).

TABLE 4

Summary of in vivo Properties of LMPTP
inhibitor probe Compound D1

| Parameter | Route of Adminstration | | |
|---|---|---|---|
| Study Group | IV | PO | IP |
| Administered Dose (mg/kg) | 4.89 | 29.6 | 9.69 |
| $t_{max}$ (h) | | 3.33 | 0.33 |
| $C_{max}$ (ng/mL) | | 3,210 | 365 |
| $t_{1/2}$ (h) | 39.6 | 29.2 | 32.5 |
| Cl (mL/min/kg) | 25.8 | | |
| Vdss (L/kg) | 83.1 | | |
| $AUC_{0-inf}$ (ng · h/mL) | 3,296 | 6,377 | 4,522 |
| Bioavailability (% F) | | 40.5 | 78 |

Example 7: Dose Response

Figure 14:
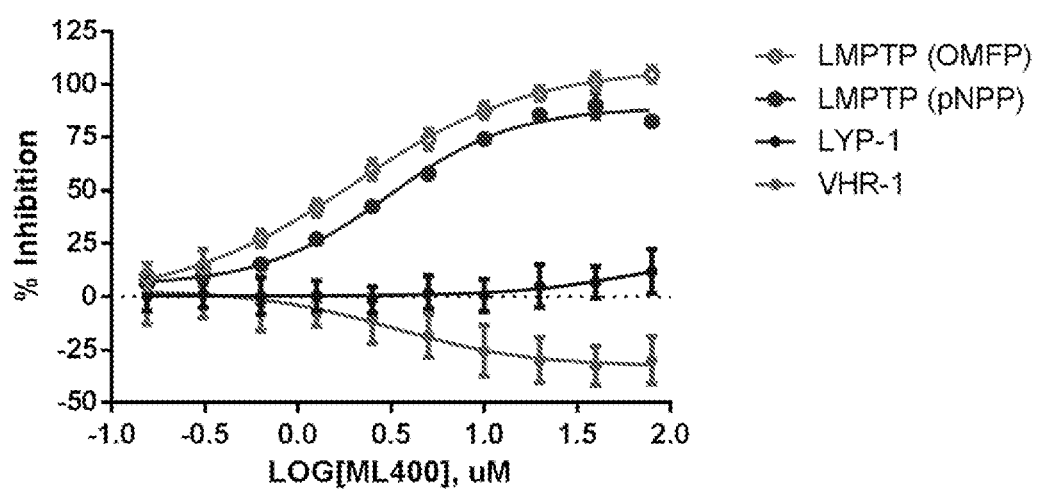
FIG. 14 shows dose response curves of Compound D1 in the LMPTP enzyme inhibition assays with OMFP and pNPP as substrates, as well as in the LYP-1 and VHR-1 phosphatase selectivity assays.

LYP-1 and VHR-1 dose response assays to assess selectivity of Compound D1 against these non-homologous phosphatases. This data are summarized in FIG. 14.

Example 8

Gene Trapping of the Acp1 Locus Abolishes Lmptp Expression

FIG. 1A shows localization of the gene-trap in the Acp1 gene. Exon 3 and exon 4 are alternatively spliced to generate Lmptp-A and -B isoforms. FIG. 1B shows PCR-based mouse genotyping using a forward primer located 5' to the gene-trap, a forward primer within the gene-trap, and a reverse primer located 3' to the gene-trap. FIG. 1C shows RT-PCR with Lmptp primers on RNA extracted from the liver of a KO mouse and heterozygous and wild-type (WT) littermates. FIG. 1D shows anti-Lmptp Western blot and control anti-tubulin blot of liver lysates of a KO mouse and heterozygous and WT littermates.

LMPTP KO Decreases Diabetes of Obese Mice

FIGS. 2A-2D show that genetic deletion of LMPTP attenuates diabetes of obese mice. (A-D) Male wild-type (WT) and LMPTP KO mice on C57BL/6 background were placed on high-fat diet (HFD; 60% kcal from fat) for 3 months starting at 2 months of age. (A) Weight curves over the course of the HFD. (B) Intraperitoneal glucose tolerance test (IPGTT) was performed on mice at 2 months of age, prior to the start of the HFD. Mice were fasted overnight and injected with 1 g glucose/kg body weight, and blood glucose levels were measured at the indicated times. (C) IPGTT was performed on mice after 3 months HFD. (D) Fasting serum insulin levels were assessed by ELISA. (A-D) Mean±SEM is shown. *p<0.05: NS, non-significant: Two-Way ANOVA (A, B, C) or Wilcoxon matched-pairs signed rank test (D).

LMPTP Knockdown Impairs Adipogenesis

Figure 3:
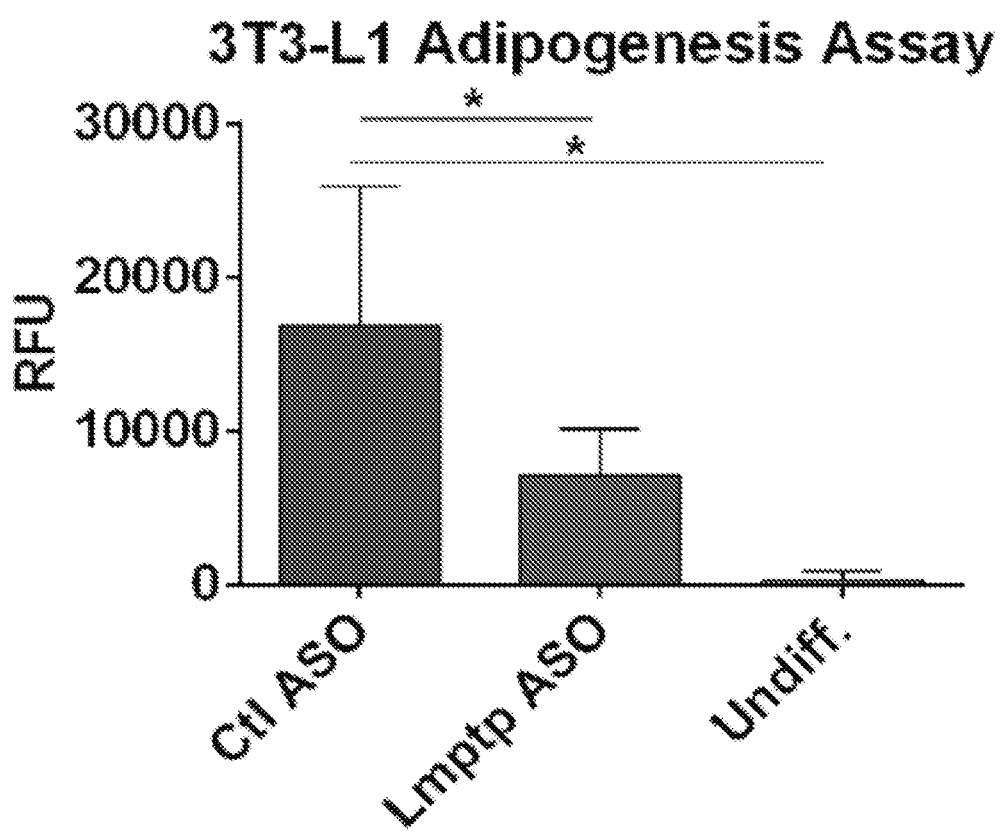
FIG. 3 shows that knockdown of Lmptp with antisense oligonucleotides (ASO) impairs adipogenesis of 3T3-L1 cells.

FIG. 3 shows that knockdown of Lmptp with antisense oligonucleotides (ASO) impairs adipogenesis of 3T3-L1 cells. 3T3-L1 cells were subjected to insulin-stimulated adipogenesis (as described in Example 5, describing cell based activity and efficacy) in the presence of 10 µM non-targeting (Ctl) or Lmptp ASO. Intracellular lipid accumulation was measured using the Lonza AdipoRed Assay Reagent. Mean±SD relative fluorescence units (RFU) are shown. *, p<0.05.

LMPTP-A Isoform Dephosphorylates Insulin Receptor (IR)

Figure 4:
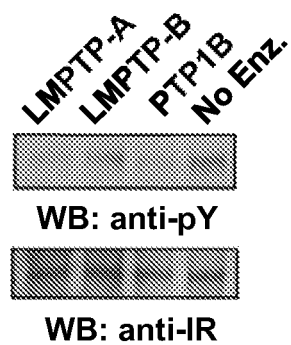
FIG. 4 shows that the LMPTP-A isoform dephosphorylates the IR.

The LMPTP-A isoform dephosphorylates the IR. The IR was immunoprecipitated from liver homogenates of mice subjected to 5 min stimulation with insulin (5 U intracardiac). Panels show WB of immunoprecipitates following incubation with 5 nM recombinant LMPTP-A, LMPTP-B or PTP1B or no enzyme for 30 min at 37° C. in 50 mM Bis-Tris, pH 6.0, 1 mM DTT. See FIG. 4.

Compound D1 Inhibits LMPTP with an Uncompetitive Mechanism of Action

Figure 5:
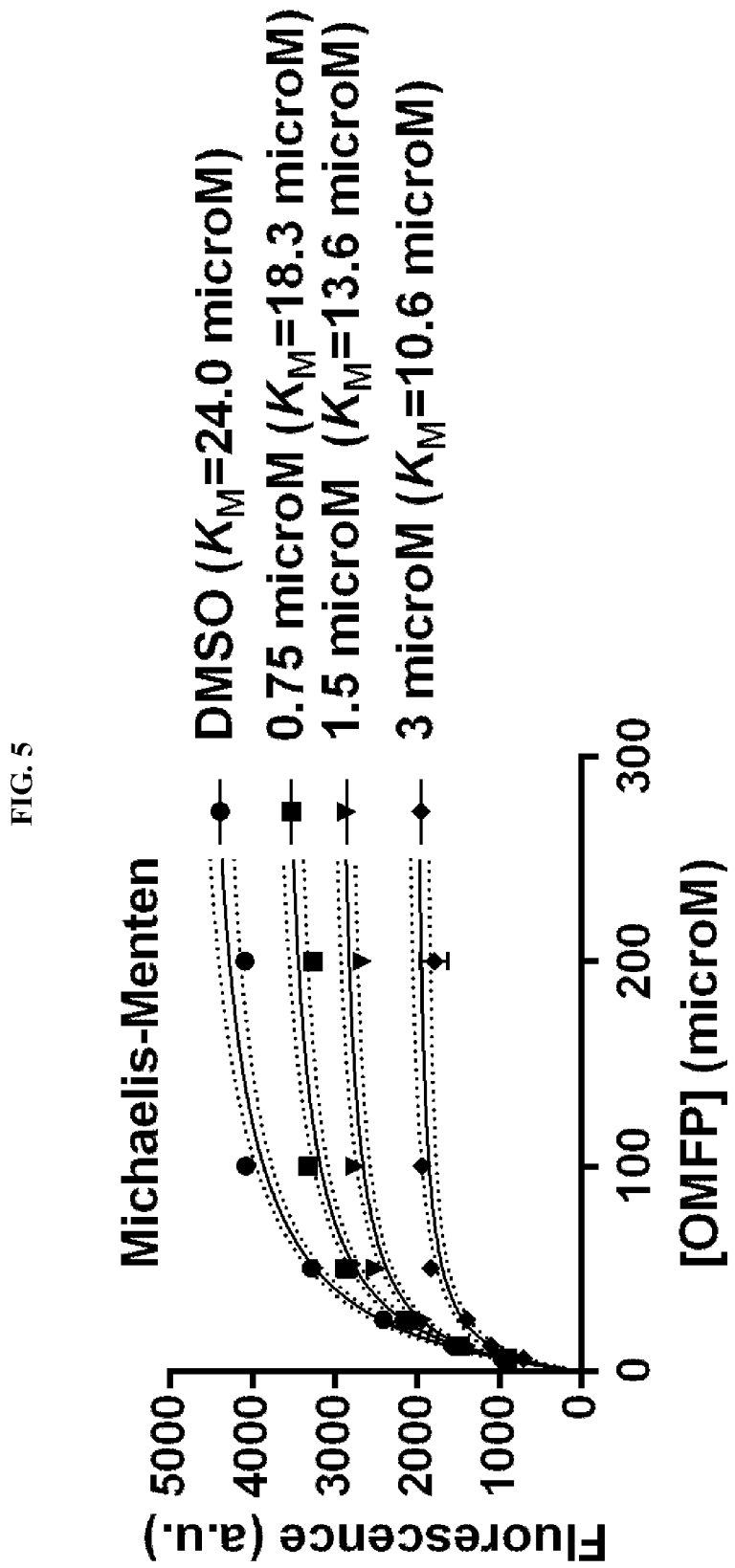
FIG. 5 shows that ML400 (Compound D1) inhibits LMPTP with an uncompetitive mechanism of action.

Compound D1 (ML400) inhibits LMPTP with an uncompetitive mechanism of action, lowering both Vmax and KM. Activity of 20 nM LMPTP on OMFP substrate in the presence of increasing concentrations of ML400. Reactions were conducted at 37° C. in 50 mM Bis-Tris, pH 6.0 with 1 mM DTT and 0.01% Triton X-100. Mean±SD is shown. Lines show fitting of data to the Michaelis-Menten equation. Note decrease in both Vmax and KM with increasing inhibitor concentration. See FIG. 5.

Figure 6:
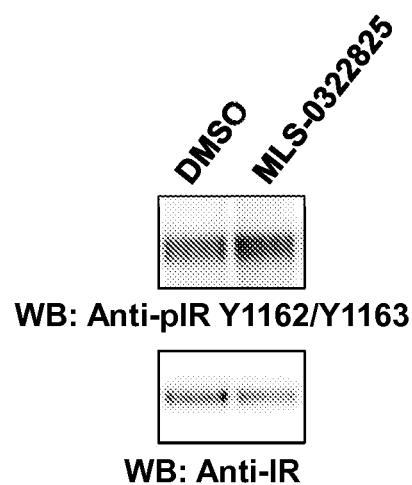
FIG. 6 shows that an LMPTP inhibitor (Entry 41 of Table 2) increases phosphorylation of the insulin receptor in HepG2 cells.

LMPTP Inhibitor Increases Phosphorylation of the Insulin Receptor in HepG2 Cells Compound 41 of Table 2 shows efficacy in cellular assays. WB of IR immunoprecipitation from human HepG2 hepatocytes incubated overnight in serum-starve culture media (containing 0.1% fetal bovine serum) in the presence of 10 microM of Compound 41 of Table 2 or DMSO. Cells were stimulated with 1.76 microM insulin for 5 min prior to lysis. See FIG. 6.

Compound D1 Treatment Improves Glucose Tolerance of Obese Mice

Figure 8:
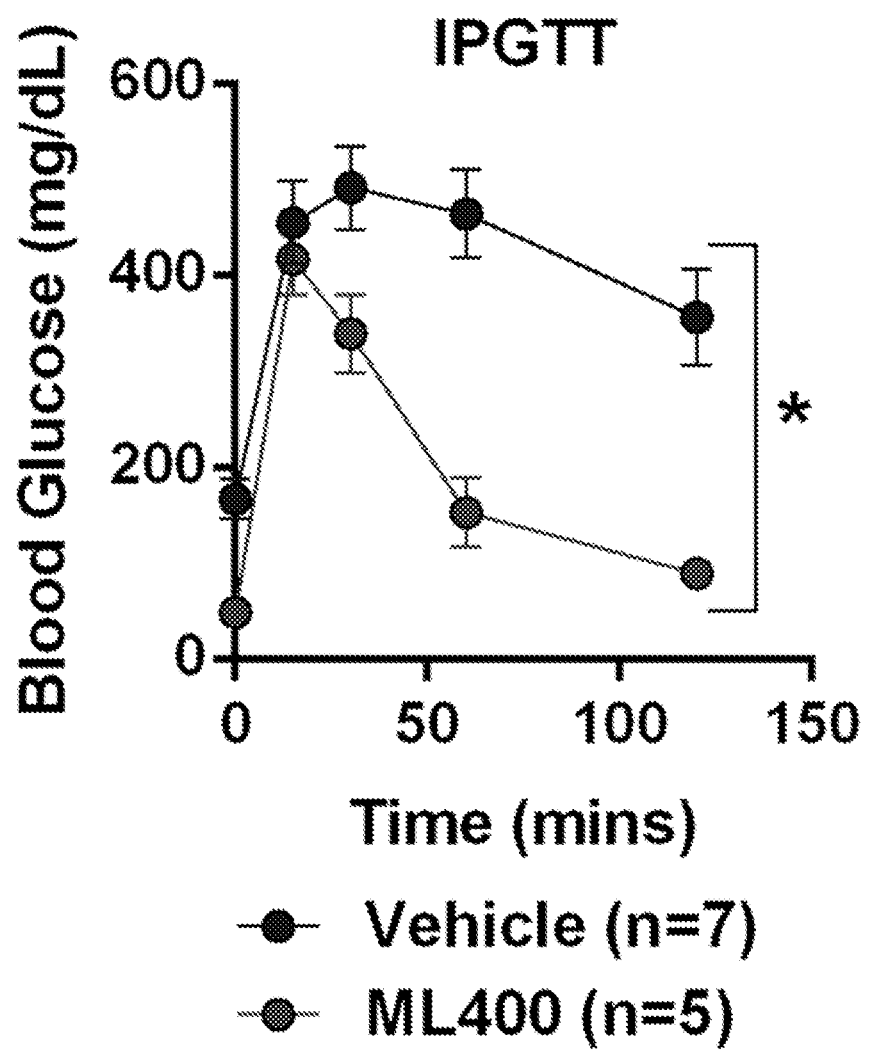
FIG. 8 shows that treatment with Compound D1 improves glucose tolerance of obese mice.

Male C57BL/6 mice were maintained on HFD containing 60 kcal % fat for 3 months, followed by daily IP administration of 30 mg/kg Compound D1 or vehicle. After 4 weeks, IPGTT were performed using 2 g glucose/kg body weight. Mean±SEM is shown. *, p<0.05, Two-way ANOVA. See FIG. 8.

Compound D1 Treatment does not Affect Kidney Function

Figure 9:
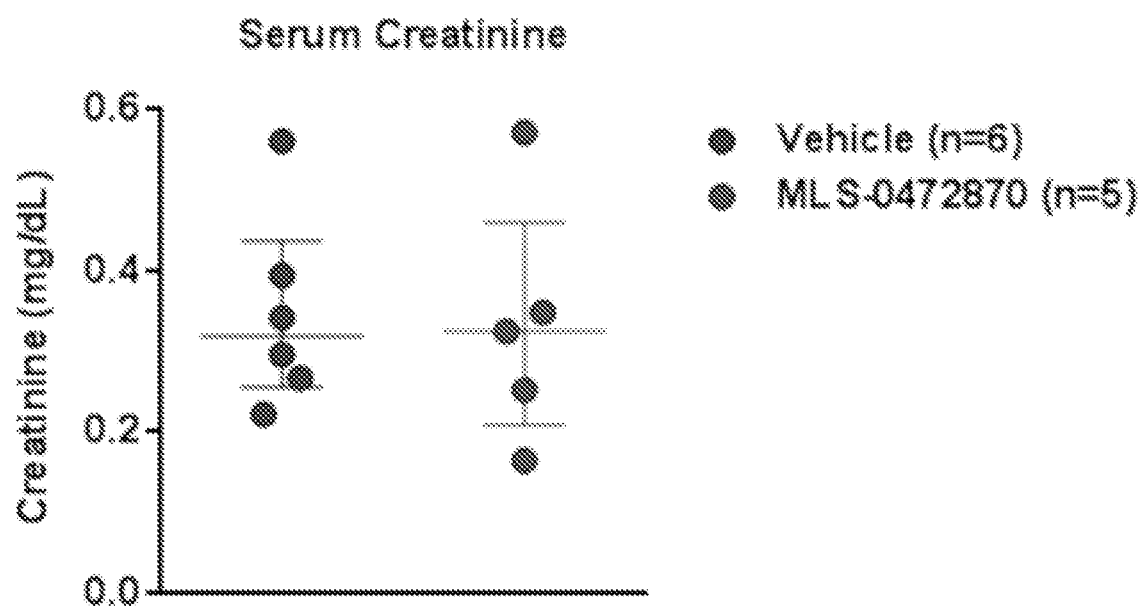
FIG. 9 shows that treatment with Compound D1 does not affect kidney function.

Serum creatinine levels from mice treated with Compound D1 (ML400) or vehicle (mice shown in FIG. 9) were assessed using the QuantiChrom Creatinine Assay Kit from BioAssay Systems.

Compound D1 Treatment does not Affect Liver Function

Figure 10:
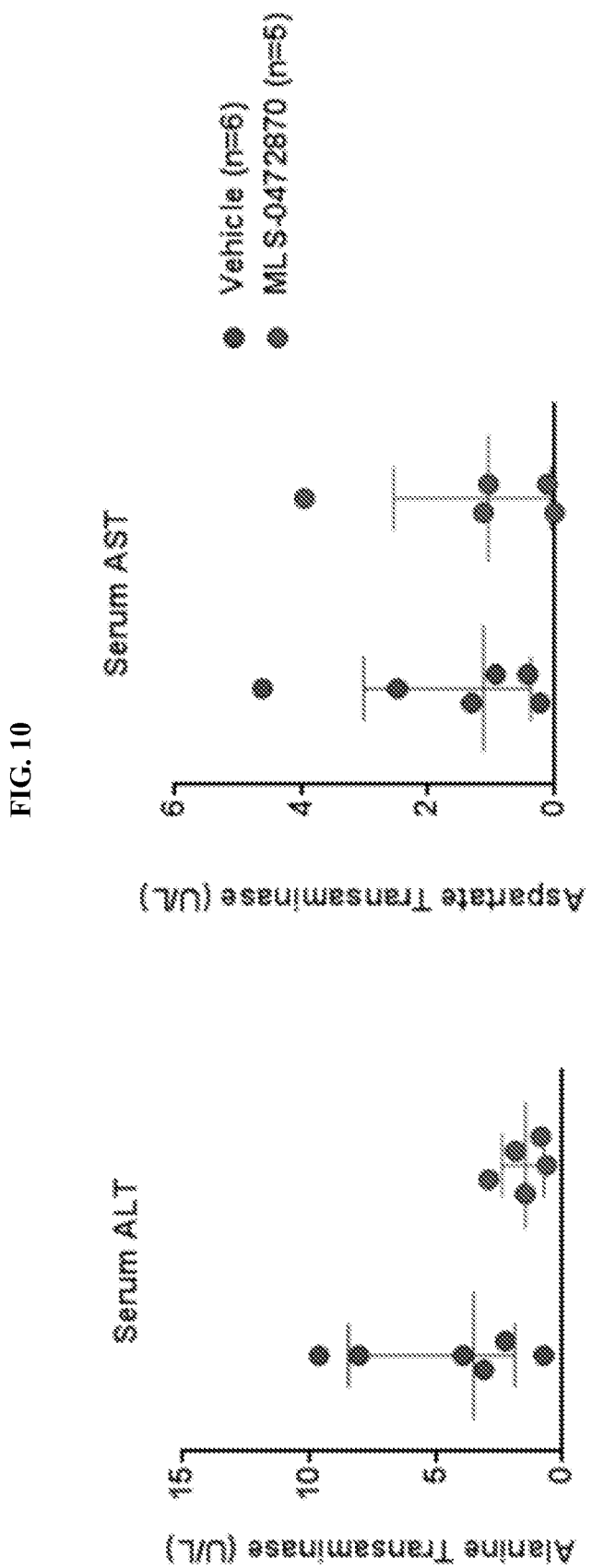
FIG. 10 shows that treatment with Compound D1 does not affect liver function.
Figure 11:
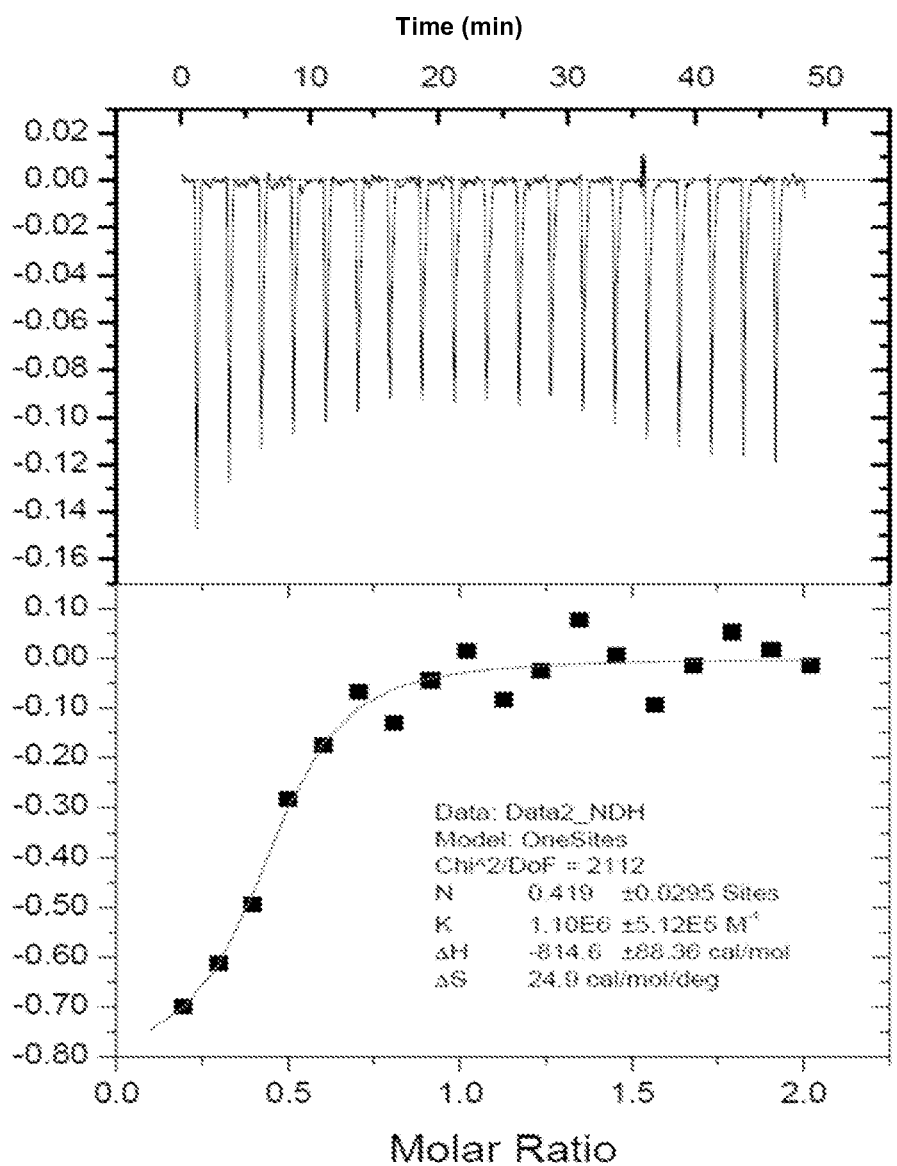
FIG. 11 shows that an LMPTP inhibitor (Compound G53) binds to LMPTP by isothermal calorimetry.

Serum alanine transaminase or aspartate transaminase levels from mice treated with Compound D1 (ML400) or vehicle (mice shown in FIG. 10) were assessed using EnzyChrom Assay Kits from BioAssay Systems.

The LMPTP Inhibitor Binds to LMPTP by Isothermal Calorimetry

ML400 analog G53 (Table A) binds to LMPTP. ITC was performed using recombinant human LMPTP-A and a derivative of Compound D1, G53. Kd=0.9 microM.

Example 9

Additional information is provided in Tables 5, 6, 7, and 8 (ML400=Compound D1).

TABLE 5

Table 1. Potency and selectivity characteristics for probe ML400

| CID/ML# | Target Name | IC$_{50}$ (nM) [SID, AID] | Anti-target Name(s) | IC$_{50}$ (µM) [SID, AID] | Fold-Selective | Secondary Assay(s) Names IC$_{50}$ (nM) [SID, AID] |
|---|---|---|---|---|---|---|
| CID 73050863 ML400 | LMPTP (low molecular weight protein tyrosine phosphatase) | 1680 ± 150 (n = 4) SID173019983 AID686962, AID743307 | LYP-1 (Lymphoid phosphatase, PTPN22) VHR-1 (Vaccinia Hf-related phosphatase) | >80 (n = 2) SID173019983 AID743309 >80 (n = 2) SID173019983 AID743310 | >60-fold >60-fold | LMPTP Orthogonal assay 3520 ± 330 (n = 2) SID173019983 AID 743308 |

TABLE 6

Table 2. Summary of Assays and AIDs

| PubChemBioAssay Name | AIDs | Probe Type | Assay Type | Assay Format | Assay Detection & well format | Center |
|---|---|---|---|---|---|---|
| Summary assay for small molecule inhibitors of Low Molecular Weight Protein Tyrosine Phosphatase, LMPTP | 651552 | Inhibitor | Summary | Bio-chemical | Fluorescence & 1536 well | SBCCG |
| uHTS identification of small molecule inhibitors of Low Molecular Weight Protein Tyrosine Phosphatase, LMPTP, via a fluorescence intensity assay | 651560 | Inhibitor | Primary | Bio-chemical | Fluorescence & 1536 well | SBCCG |
| Dose response confirmation of small molecule inhibitors of Low Molecular Weight Protein Tyrosine Phosphatase, LMPTP, via a fluorescence intensity assay | 651700 | Inhibitor | Confirmatory (DMSO Dose Response) | Bio-chemical | Fluorescence & 1536 well | SBCCG |
| Dose response confirmation of small molecule inhibitors of Low Molecular Weight Protein Tyrosine Phosphatase, LMPTP, in an orthogonal absorbance-based assay | 652005 | Inhibitor | Orthogonal (DMSO Dose Response) | Bio-chemical | Absorbance & 1536 well | SBCCG |
| Dose response confirmation of small molecule inhibitors of Low Molecular Weight Protein Tyrosine Phosphatase, LMPTP, in a fluorescence-based, Lymphoid Phosphatase, (PTPN22, LYP-1) selectivity Assay | 652006 | Inhibitor | Selectivity (DMSO Dose Response) | Bio-chemical | Fluorescence & 1536 well | SBCCG |
| Dose response confirmation of uHTS small molecule inhibitors of Low Molecular Weight Protein Tyrosine Phosphatase, LMPTP, in a fluorescence-based, VHR-1 (dual specificity phosphatase 3) selectivity assay | 686961 | Inhibitor | Selectivity (DMSO Dose Response) | Bio-chemical | Fluorescence & 1536 well | SBCCG |
| SAR confirmation of small molecule inhibitors of Low Molecular Weight Protein Tyrosine Phosphatase, LMPTP, via a fluorescence intensity assay | 686962 | Inhibitor | SAR (Dry Powder) | Bio-chemical | Fluorescence & 1536 well | SBCCG |
| SAR confirmation of small molecule inhibitors of Low Molecular Weight Protein Tyrosine Phosphatase, LMPTP, in an orthogonal absorbance-based assay | 686963 | Inhibitor | SAR (Dry Powder) | Bio-chemical | Absorbance & 1536 well | SBCCG |
| SAR confirmation of small molecule inhibitors of Low Molecular Weight Protein Tyrosine Phosphatase, LMPTP, via a fluorescence intensity assay, set 2 | 743307 | Inhibitor | SAR (Dry Powder) | Bio-chemical | Fluorescence & 1536 well | SBCCG |
| SAR confirmation of small molecule inhibitors of Low Molecular Weight Protein Tyrosine Phosphatase, LMPTP, in an orthogonal absorbance-based assay, set 2 | 743308 | Inhibitor | SAR (Dry Powder) | Bio-chemical | Fluorescence & 1536 well | SBCCG |
| SAR confirmation of small molecule inhibitors of Low Molecular Weight Protein Tyrosine Phosphatase, LMPTP, in a fluorescence-based, Lymphoid Phosphatase (PTPN22, LYP-1) selectivity Assay | 743309 | Inhibitor | SAR (Dry Powder) | Bio-chemical | Fluorescence & 1536 well | SBCCG |
| SAR confirmation of uHTS small molecule inhibitors of Low Molecular Weight Protein Tyrosine Phosphatase, LMPTP, in a fluorescence-based, VHR-1 (dual specificity phosphatase 3) selectivity assay | 743310 | Inhibitor | SAR (Dry Powder) | Bio-chemical | Fluorescence & 1536 well | SBCCG |

TABLE 7

Table 3. Calcutated Properties for ML400

| Calculated Property | ML400 CID73050863 |
|---|---|
| Molecular Weight | 421.53194 [g/mol] |
| Molecular Formula | $C_{25}H_{31}N_3O_3$ |
| H-Bond Donor | 2 |
| H-Bond Acceptor | 6 |
| Rotatable Bond Count | 7 |
| Exact Mass | 421.236542 |
| MonoIsotopic Mass | 421.236542 |
| Topological Polar Surface Area | 74.7 |

TABLE 7-continued

Table 3. Calcutated Properties for ML400

| Calculated Property | ML400 CID73050863 |
|---|---|
| Heavy Atom Count | 31 |
| Formal Charge | 0 |
| Complexity | 455 |
| Isotope Atom Count | 0 |
| Defined Atom StereoCenter Count | 0 |
| Undefined Atom StereoCenter Count | 0 |
| Defined Bond StereoCenter Count | 0 |
| Undefined Bond StereoCenter Count | 0 |
| Covalently-Bonded Unit Count | 2 |

TABLE 8

Table 4. Probe and Analog Submissions to MLSMR (Evotec) for Small Molecule Inhibitors of LMPTP Probe ML400 - CID73050863

| Probe/ Analog | MLS_ID (SBCCG) | MLS_ID (MLSMR) | CID | SID | Source | Amt (mg) | Date ordered/ Submitted |
|---|---|---|---|---|---|---|---|
| Probe ML400 | 0472870 | MLS005939925 | 73050863 | 173019983 | Synthesis | 27 | Apr. 15, 2014 |
| Analog 1 | 0322825 | MLS005939926 | 2728458 | 173019996 | Synthesis | 25.6 | Apr. 15, 2014 |
| Analog 2 | 0472782 | MLS005939927 | 73050855 | 173019979 | Synthesis | 24.7 | Apr. 15, 2014 |
| Analog 3 | 0472867 | MLS005939928 | 73050883 | 173019998 | Synthesis | 22.3 | Apr. 15, 2014 |
| Analog 4 | 0472866 | MLS005939929 | 73050881 | 173019997 | Synthesis | 22.8 | Apr. 15, 2014 |
| Analog 5 | 0472781 | MLS005939930 | 73050862 | 173019978 | Synthesis | 21.5 | Apr. 15, 2014 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the structure of formula (II):

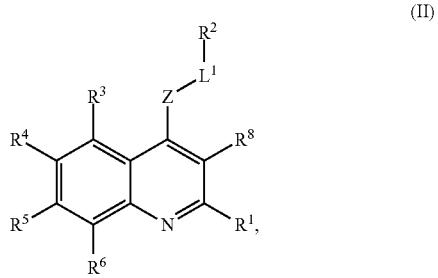

(II)

or a pharmaceutically acceptable salt thereof, wherein:

Z is —$NR^9$—, —$NR^9C(O)$—, or —O—C(O)—;

$L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is phenyl substituted with a substituent group —C(O)$NR^{1C}R^{1D}$;

$R^{1C}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1D}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or $R^{1C}$ and $R^{1D}$ and the nitrogen atom they are attached to may optionally combine to form a substituted or unsubstituted heterocycloalkyl;

$R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCHX^3_2$, —$OCH_2X^3$, —CN, —$SO_{n3}R^{16}$, —$SO_{v3}NR^{13}R^{14}$, —$NHC(O)NR^{13}R^{14}$, —$N(O)_{m3}$, —$NR^{13}R^{14}$, —$C(O)R^{15}$, —$C(O)$—$OR^{15}$, —$C(O)NR^{13}R^{14}$, —$OR^{16}$, —$NR^{13}SO_2R^{16}$, —$NR^{13}C(O)R^{15}$, —$NR^{13}C(O)OR^{15}$, —$NR^{13}OR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCHX^4_2$, —$OCH_2X^4$, —CN, —$SO_{n4}R^{20}$, —$SO_{v4}NR^{17}R^{18}$, —$NHC(O)NR^{17}R^{18}$, —$N(O)_{m4}$, —$NR^{17}R^{18}$, —$C(O)R^{19}$, —$C(O)$—$OR^{19}$, —$C(O)NR^{17}R^{18}$, —$OR^{20}$, —$NR^{17}SO_2R^{20}$, —$NR^{17}C(O)R^{19}$, —$NR^{17}C(O)OR^{19}$, —$NR^{17}OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCHX^5_2$, —$OCH_2X^5$, —CN, —$SO_{n5}R^{24}$, —$SO_{v5}NR^{21}R^{22}$, —$NHC(O)NR^{21}R^{22}$, —$N(O)_{m5}$, —$NR^{21}R^{22}$, —$C(O)R^{23}$, —$C(O)$—$OR^{23}$, —$C(O)NR^{21}R^{22}$, —$OR^{24}$, —$NR^{21}SO_2R^{24}$, —$NR^{21}C(O)R^{23}$, —$NR^{21}C(O)OR^{23}$, —$NR^{21}OR^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^6_3$, —$CHX^6_2$, —$CH_2X^6$, —$OCX^6_3$, —$OCHX^6_2$, —$OCH_2X^6$, —CN, —$SO_{n6}R^{28}$, —$SO_{v6}NR^{25}R^{26}$, —$NHC(O)NR^{25}R^{26}$, —$N(O)_{m6}$, —$NR^{25}R^{26}$, —$C(O)R^{27}$, —$C(O)$—$OR^{27}$, —C(O)NR²⁵R²⁶, —OR²⁸, —NR²⁵SO₂R²⁸, —NR²⁵C(O)R²⁷, —NR²⁵C(O)OR²⁷, —NR²⁵OR²⁷, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each R⁸, R⁹, R¹³, R¹⁴, R¹⁵, R¹⁶, R¹⁷, R¹⁸, R¹⁹, R²⁰, R²¹, R²², R²³, R²⁴, R²⁵, R²⁶, R²⁷, and R²⁸ is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each X is independently —F, —Cl, —Br, or —I;

each X³, X⁴, X⁵, and X⁶ is independently —F, —Cl, —Br, or —I;

each m3, m4, m5, and m6 is independently 1 or 2;

each n3, n4, n5, and n6 is independently an integer from 0 to 3; and each v3, v4, v5, and v6 is independently 1 or 2.

2. The compound of claim 1, or a pharmaceutically acceptable salt thereof, wherein
Z is —NR⁹—;
L¹ is a bond, substituted or unsubstituted alkylene, substituted or unsubstituted heteroalkylene, substituted or unsubstituted arylene, or substituted or unsubstituted heteroarylene; and
R² is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

3. The compound of claim 1, or a pharmaceutically acceptable salt thereof, wherein
Z is —NR⁹—;
L¹ is substituted or unsubstituted alkylene or substituted or unsubstituted arylene; and
R² is substituted or unsubstituted alkyl or substituted or unsubstituted heterocycloalkyl.

4. The compound of claim 2, or a pharmaceutically acceptable salt thereof, wherein
Z is —NH—;
L¹ is substituted or unsubstituted C₃-C₆ alkylene; and
R² is substituted or unsubstituted heterocycloalkyl.

5. The compound of claim 1, or a pharmaceutically acceptable salt thereof, wherein
Z is —NH—;
L¹ is substituted or unsubstituted arylene;
R² is C₁-C₃ alkyl substituted with substituent group R²ᴬ;
R²ᴬ is —NR²ᴮR²ᶜ, substituted or unsubstituted cycloalkyl, substituted or unsubstituted heterocycloalkyl, substituted or unsubstituted aryl, or substituted or unsubstituted heteroaryl; and
each of R²ᴮ and R²ᶜ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein R²ᴮ and R²ᶜ combine to form a substituted or unsubstituted heterocycloalkyl.

6. The compound of claim 1, having the structure of formula (II-A):

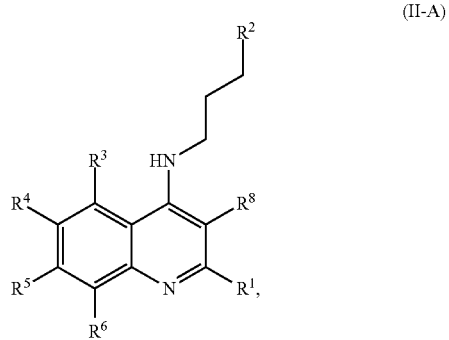

(II-A)

or a pharmaceutically acceptable salt thereof, wherein:
R² is substituted or unsubstituted cycloalkyl or substituted or unsubstituted heterocycloalkyl.

7. The compound of claim 1, having the structure of formula (II-B):

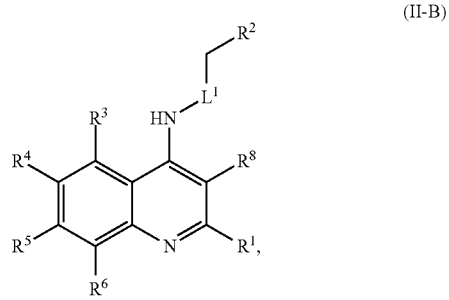

(II-B)

or a pharmaceutically acceptable salt thereof, wherein:
L¹ is substituted or unsubstituted arylene;
R²ᴬ is independently —NR²ᴮR²ᶜ, substituted or unsubstituted cycloalkyl, substituted or unsubstituted heterocycloalkyl, substituted or unsubstituted aryl, or substituted or unsubstituted heteroaryl; and
each of R²ᴮ and R²ᶜ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein R²ᴮ and R²ᶜ combine to form a substituted or unsubstituted heterocycloalkyl.

8. The compound of claim 6, or a pharmaceutically acceptable salt thereof, wherein
R¹ is phenyl substituted with substituent group R¹ᴬ; and
R¹ᴬ is —C(O)NR¹ᶜR¹ᴰ, wherein R¹ᴬ is para to the carbon attached to the quinoline moiety.

9. The compound of claim 1, having the structure of formula (II-C):

$$\text{(II-C)}$$

or a pharmaceutically acceptable salt thereof, wherein:
$R^{1C}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^{1D}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
or wherein $R^{1C}$ and $R^{1D}$ attached to the same nitrogen atom optionally combine to form a substituted or unsubstituted heterocycloalkyl.

10. The compound of claim 9, or a pharmaceutically acceptable salt thereof, wherein
Z is —$NR^9$—; and
$L^1$ is substituted or unsubstituted alkylene or substituted or unsubstituted arylene.

11. The compound of claim 10, or a pharmaceutically acceptable salt thereof, wherein each of $R^3$, $R^4$, $R^5$, $R^6$, and $R^8$ is hydrogen.

12. A compound that is:
N,N-diethyl-4-(4-((3-(piperidin-1-yl)propyl)amino)quinolin-2-yl)benzamide;
phenyl-N-(4-{4-[(3-piperidylpropyl)amino](2-quinolyl)}phenyl)carboxamide;
3-[N-(4-{4-[(3-piperidylpropyl)amino]-2-quinolyl}phenyl)carbamoyl]propanoic acid;
N-(2-cyanoethyl)(4-{4-[(3-piperidylpropyl)amino](2-quinolyl)}phenyl)carboxamide;
N-ethyl-N-methyl(4-{4-[(3-piperidylpropyl)amino](2-quinolyl)}phenyl)carboxamide;
N-(methylethyl)(4-{4-[(3-piperidylpropyl)amino](2-quinolyl)}phenyl)carboxamide;
N-ethyl(4-{4-[(3-piperidylpropyl)amino](2-quinolyl)}phenyl)carboxamide;
(4-{4-[(3-piperidylpropyl)amino](2-quinolyl)}phenyl)-N-(2,2,2-trifluoroethyl)carboxamide;
N-(oxolan-2-ylmethyl)(4-{4-[(3-piperidylpropyl)amino](2-quinolyl)}phenyl)carboxamide;
ethyl 2-[(4-{4-[(3-piperidylpropyl)amino]-2-quinolyl}phenyl)carbonylamino]acetate;
N-[2-(dimethylamino)ethyl](4-{4-[(3-piperidylpropyl)amino](2-quinolyl)}phenyl)carboxamide;
N-(3-hydroxypropyl)(4-{4-[(3-piperidylpropyl)amino](2-quinolyl)}phenyl)carboxamide;
2-[(4-{4-[(3-piperidylpropyl)amino]-2-quinolyl}phenyl)carbonylamino]acetic acid;
methyl 2-[(4-{4-[(3-piperidylpropyl)amino]-2-quinolyl}phenyl)carbonylamino]acetate;
N-cyclopropyl(4-{4-[(3-piperidylpropyl)amino](2-quinolyl)}phenyl)carboxamide;
N,N-dimethyl(4-{4-[(3-piperidylpropyl)amino](2-quinolyl)}phenyl)carboxamide;
N-methyl(4-{4-[(3-piperidylpropyl)amino](2-quinolyl)}phenyl)carboxamide;
3-amino-5-{4-[(3-piperidylpropyl)amino](2-quinolyl)}phenyl morpholin-4-yl ketone;
4-{4-[(3-piperidylpropyl)amino](2-quinolyl)}phenyl pyrrolidinyl ketone;
(4-{4-[(3-piperidylpropyl)amino](2-quinolyl)}phenyl)-N-(2-(4-pyridyl)ethyl)carboxamide;
N-[3-(diethylamino)propyl](4-{4-[(3-piperidylpropyl)amino](2-quinolyl)}phenyl)carboxamide;
N-(2-piperidylethyl)(4-{4-[(3-piperidylpropyl)amino](2-quinolyl)}phenyl)carboxamide;
N-(3-morpholin-4-ylpropyl)(4-{4-[(3-piperidylpropyl)amino](2-quinolyl)}phenyl)carboxamide;
piperazinyl 4-{4-[(3-piperidylpropyl)amino](2-quinolyl)}phenyl ketone;
piperidyl 4-{4-[(3-piperidylpropyl)amino](2-quinolyl)}phenyl ketone;
N-(3-aminopropyl)(4-{4-[(3-piperidylpropyl)amino](2-quinolyl)}phenyl)carboxamide;
N-(4-piperidyl)(4-{4-[(3-piperidylpropyl)amino](2-quinolyl)}phenyl)carboxamide;
N-(4-piperidylmethyl)(4-{4-[(3-piperidylpropyl)amino](2-quinolyl)}phenyl)carboxamide;
N-(3-piperidylpropyl)(4-{4-[(3-piperidylpropyl)amino](2-quinolyl)}phenyl)carboxamide;
N-(2-methylpropyl)(4-{4-[(3-piperidylpropyl)amino](2-quinolyl)}phenyl)carboxamide;
N-(2-hydroxyethyl)(4-{4-[(3-piperidylpropyl)amino](2-quinolyl)}phenyl)carboxamide;
(2-fluoro-4-{4-[(3-piperidylpropyl)amino](2-quinolyl)}phenyl)-N-methylcarboxamide;
N-ethyl(2-fluoro-4-{4-[(3-piperidylpropyl)amino](2-quinolyl)}phenyl)carboxamide;
N-cyclohexyl(4-{4-[(3-piperidylpropyl)amino](2-quinolyl)}phenyl)carboxamide;
morpholin-4-yl 4-{4-[(3-piperidylpropyl)amino](2-quinolyl)}phenyl ketone;
N-cyclopentyl(4-{4-[(3-piperidylpropyl)amino](2-quinolyl)}phenyl)carboxamide;
(2-chloro-4-{4-[(3-piperidylpropyl)amino](2-quinolyl)}phenyl)-N-methylcarboxamide;
N-benzyl(4-{4-[(3-piperidylpropyl)amino](2-quinolyl)}phenyl)carboxamide;
N-[2-(diethylamino)ethyl](4-{4-[(3-piperidylpropyl)amino](2-quinolyl)}phenyl)carboxamide;
or a pharmaceutically acceptable salt thereof.

13. A pharmaceutical composition comprising the compound of claim 1, or a pharmaceutically acceptable salt thereof, and a pharmaceutically acceptable excipient.

14. A method of treating a disease or condition, said method comprising administering to a subject in need thereof an effective amount of a compound of claim 1, or a pharmaceutically acceptable salt thereof, and
wherein said disease or condition is diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure or metabolic syndrome.

* * * * *

UNITED STATES PATENT AND TRADEMARK OFFICE
CERTIFICATE OF CORRECTION

PATENT NO. : 10,626,094 B2
APPLICATION NO. : 15/518331
DATED : April 21, 2020
INVENTOR(S) : Nunzio Bottini et al.

It is certified that error appears in the above-identified patent and that said Letters Patent is hereby corrected as shown below:

In the Specification

In Column 1, Lines 24 through 26, please replace:
"This invention was made with government support under R03 DA033986 awarded by the National Institutes of Health. The government has certain rights in the invention."

With:
"This invention was made with government support under R03 DA033986, and HG005033 awarded by the National Institutes of Health. The government has certain rights in the invention."

Signed and Sealed this
Twelfth Day of September, 2023

Katherine Kelly Vidal
Director of the United States Patent and Trademark Office